(12) United States Patent
Fox et al.

(10) Patent No.: US 10,214,758 B2
(45) Date of Patent: Feb. 26, 2019

(54) METHOD AND COMPOSITIONS FOR IMPROVED LIGNOCELLULOSIC MATERIAL HYDROLYSIS

(71) Applicants: Brian Grant Fox, Madison, WI (US); Taichi Takasuka, Madison, WI (US); Adam Joel Book, Madison, WI (US); Cameron Robert Currie, Madison, WI (US)

(72) Inventors: Brian Grant Fox, Madison, WI (US); Taichi Takasuka, Madison, WI (US); Adam Joel Book, Madison, WI (US); Cameron Robert Currie, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/709,971

(22) Filed: Dec. 10, 2012

(65) Prior Publication Data
US 2013/0189744 A1 Jul. 25, 2013

Related U.S. Application Data

(60) Provisional application No. 61/579,897, filed on Dec. 23, 2011, provisional application No. 61/579,301, filed on Dec. 22, 2011.

(51) Int. Cl.
| | | |
|---|---|---|
| *C12P 19/14* | (2006.01) | |
| *C12N 9/42* | (2006.01) | |
| *C12N 1/20* | (2006.01) | |
| *C12N 9/24* | (2006.01) | |
| *C12P 19/02* | (2006.01) | |
| *A23K 10/12* | (2016.01) | |

(52) U.S. Cl.
CPC ............ *C12P 19/14* (2013.01); *A23K 10/12* (2016.05); *C12N 1/20* (2013.01); *C12N 9/2434* (2013.01); *C12N 9/2437* (2013.01); *C12N 9/2491* (2013.01); *C12P 19/02* (2013.01); *C12Y 302/01004* (2013.01); *C12Y 302/01025* (2013.01); *C12Y 302/01091* (2013.01)

(58) Field of Classification Search
CPC . C12P 19/14; C12P 19/02; C12N 1/20; C12N 9/3491; C12N 9/92434; C12N 9/2437; A23K 10/12; C12Y 302/01091; C12Y 302/01004; C12Y 302/01025
See application file for complete search history.

(56) References Cited

U.S. PATENT DOCUMENTS

2010/0304405 A1* 12/2010 Fox et al. .................. 435/7.4
2013/0189744 A1 7/2013 Fox et al.

FOREIGN PATENT DOCUMENTS

WO 2010141604 A2 12/2010
WO WO/2010/141604 * 12/2010

OTHER PUBLICATIONS

Lim et al., Expression, purification and characterization of a functional carbohydrate-binding module from *Streptomyces* sp. SirexAA-E2014, Protein Expression and Purification (2014), vol. 98, pp. 1-9.*
Raisanen (2013), Basic Chemical Composition of the Biomass components fo Pine, Spruce and Birch., Finnish Forest Refine Research Institute. total 4 pages.*
All Things Pros; 2013. on the web at: allthingspros.blogspot.com/2013/01/board-appeals-derivation-declaration.html.*
Schlochtermeier, et al., The Gene Encoding the Cellulase (Avicelase) Cell From Streptomyces Reticuli and Analysis of Protein Domains, Molecular Microbiology, 1992, 6(23):3611-3621.
Adams, et al., Cellulose-degrading Bacteria Associated with the Invasive Woodwasp *Sirex noctilio*, The ISME Journal, 2011, 5:1323-1331.
Adav, et al., Quantitative iTRAQ Secretome Analysis of Cellulolytic Thermobifida Fusca, Journal of Proteome Research, 2010, 9:3016-3024.
Altschul, et al., Basic Local Alignment Search Tool, J. Mol. Biol, 1990, 215:403-410.
Anne, et al., Streptomyces Lividans as Host for Heterologous Protein Production, FEMS Microbiology Letters, 1993, 114(2):121-128.
Balan, et al., Lignocellulosic Biomass Pretreatment Using AFEX, Methods in Molecular Biology, 2009, 581:61-77.
Baldrian, et al., Degradation of Cellulose by Basidiomycetous Fungi, FEMS Microbiol. Rev., 2008, 32:501-521.
Bayer, et al., From Cellulosomes to Cellulosomics, The Chemical Record, 2008, 8(6):364-377.
Bergeron, et al., Putative Origin of Clonal Lineages of Amylostereum Areolatum, the Fungal Symbiont Associated with Sirex Noctilio, Retrieved from Pinus Sylvestris, in Eastern Canada, Fungal Biology, 2011, 115(8):750-758.
Bignell, et al., Isolation of Facultatively Aerobic Actinomycetes from the Gut, Parent Soil and Mound Materials of the Termites *Procubitermes aburiensis* and *Cubitermes severus*, FEMS Microbiology Ecology, 1991, 85:151-160.
Blommel, et al., Flexi Vector Cloning, Methods in Molecular Biology, 2009, 498:55-73.

(Continued)

*Primary Examiner* — Karen Cochrane Carlson
(74) *Attorney, Agent, or Firm* — Quarles & Brady LLP

(57) ABSTRACT

A method of digesting a lignocellulosic material is disclosed. In one embodiment, the method comprises the step of exposing the material to an effective amount of *Streptomyces* sp. ActE secretome such that at least partial lignocellulosic digestion occurs.

7 Claims, 70 Drawing Sheets
(22 of 70 Drawing Sheet(s) Filed in Color)
Specification includes a Sequence Listing.

(56) References Cited

OTHER PUBLICATIONS

Bradford, A Rapid and Sensitive Method for the Quantitation of Microgram Quantities of Protein Utilizing the Principle of Protein-Dye Binding, Analytical Biochemistry, 1976, 72(1-2):248-254.

Cantarel, et al., The Carbohydrate-Active EnZymes Database (CAZy): An Expert Resource for Glycogenomics, Nucleic Acids Research, 2009, 37:D233-D238.

Cereghino, et al., Production of Recombinant Proteins in Fermenter Cultures of the Yeast Pichia pastoris, Current Opinion in Biotechnology, 2002, 13(4):329-332.

Chater, et al., The Complex Extracellular Biology of Streptomyces, FEMS Microbiol. Rev., 2010, 34:171-198.

Chen, et al., Proteomic and Transcriptomic Analysis of Extracellular Proteins and mRNA Levels in Thermobifida Fusca Grown on Cellobiose and Glucose, Journal of Bacteriology, 2007, 189(17):6260-6265.

Cheng, et al. Transition of Cellulose Crystalline Structure and Surface Morphology of Biomass as a Function of Ionic Liquid Pretreatment and Its Relation to Enzymatic Hydrolysis, Biomacromolecules, 2011, 12(4):933-941.

Chundawat, et al., Restructuring the Crystalline Cellulose Hydrogen Bond Network Enhances Its Depolymerization Rate, J. Am. Chem. Soc., 2011, 133(29):11163-11174.

Crawford, Lignocellulose Decomposition by Selected Streptomyces Strains, Applied and Environmental Microbiology, 1978, 35(6):1041-1045.

Deboy, et al., Insights into Plant Cell Wall Degradation from the Genome Sequence of the Soil Bacterium Cellvibrio Japonicus, Journal of Bacteriology, 2008, 190(15):5455-5463.

Deng, et al., Development and Application of a PCR-Targeted Gene Disruption Method for Studying Ce1R Function in Thermobifida Fusca, Applied and Einvironmental Microbiology, 2010, 76(7):2098-2106.

Eastwood, et al., The Plant Cell Wall-Decomposing Machinery Underlies the Functional Diversity of Forest Fungi, Science, 2011, 333:762-765.

Forsberg, et al., Cleavage of Cellulose by a CBM33 Protein, Protein Science, 2011, 20:1479-1483.

Galm, et al., Comparative Analysis of the Biosynthetic Gene Clusters and Pathways for Three Structurally Related Antitumor Antibiotics Bleomycin, Tallysomycin and Zorbamycin, J. Nat. Prod., 2011, 74(3):526-536.

Goodfellow, et al., Ecology of Actinomycetes, Annual Review of Microbiology, 1983, 37:189-216.

Herpoel-Gimbert, et al., Comparative Secretome Analyses of Two Trichoderma Reesei RUT-C30 and CL847 Hypersecretory Strains, Biotechnology for Biofuels, 2008, 1:18, 12 pages.

Hess, et al., Metagenomic Discovery of Biomass-Degrading Genes and Genomes from Cow Rumen, Science, 2011, 331:463-467.

Hulcr, et al., Presence and Diversity of Streptomyces in Dendroctonus and Sympatric Bark Beetle Galleries Across North America, Microb. Ecol., 2011, 61:759-768.

Hyatt, et al., Prodigal: Prokaryotic Gene Recognition and Translation Initiation Site Identification, BMC Bioinformatics, 2010, 11:119.

Ishaque, et al., Cellulase Complex of a Mesophilic Streptomyces Strain, Canadian Journal of Microbiology, 1980, 26 (2):183-189.

Jarboe, et al., Metabolic Engineering for Production of Biorenewable Fuels and Chemicals: Contributions of Synthetic Biology, Journal of Biomedicine and Biotechnology, vol. 2010, Article ID 761042, 18 pages.

Kestler, et al., VennMaster: Area-Proportional Euler Diagrams for Functional GO Analysis of Microarrays, BMC Bioinformatics, 2008, 9:67, 12 pages.

Klepzig, et al., Symbioses: A Key Driver of Insect Physiological Processes, Ecological Interactions, Evolutionary Diversification, and Impacts on Humans, Environ. Entomol., 2009, 38(1):67-77.

Kukor, et al., Acquisition of Digestive Enzymes by Siricid Woodwasps from Their Fungal Symbiont, Science, 1983, 220:1161-1163.

Langston, et al., Oxidoreductive Cellulose Depolymerization by the Enzymes Cellobiose Dehydrogenase and Glycoside Hydrolase 61, Applied and Environmental Microbiology, 2011, 77(19)7007-7015.

Li, et al., Influence of Physico-Chemical Changes on Enzymatic Digestibility of Ionic Liquid and AFEX Pretreated Corn Stover, Bioresource Technology, 2011, 102(13):6928-6936.

Luyten, et al., Extensive Variation in Intracellular Symbiont Community Composition Among Members of a Single Population of the Wood-Boring Bivalve Lyrodus Pedicellatus (Bivalvia: Teredinidae), Applied and Environmental Microbiology, 2006, 72(1):412-417.

Lykidis, et al., Genome Sequence and Analysis of the Soil Cellulolytic Actinomycete Thermobifida Fusca YX, Journal of Bacteriology, 2007, 189(6):2477-2486.

Lynd, et al., Microbial Cellulose Utilization: Fundamentals and Biotechnology, Microbiology and Molecular Biology Reviews, 2002, 66(3):506-577.

Marushima, et al., CebR as a Master Regulator for Cellulose/Cellooligosaccharide Catabolism Affects Morphological Development in Streptomyces Griseus, Journal of Bacteriology, 2009, 191(19):5930-5940.

McCarthy, et al., Actinomycetes as Agents of Biodegradation in the Environment—A Review, Gene, 1992, 115 (1-2):189-192.

Medema, et al., antiSMASH: Rapid Identification, Annotation and Analysis of Secondary Metabolite Biosynthesis Gene Clusters in Bacterial and Fungal Genome Sequences, Nucleic Acids Research, 2011, 39:W339-W346.

Merino, et al., Progress and Challenges in Enzyme Development for Biomass Utilization, Adv. Biochem. Engin. Biotechnol., 2007, 108:95-120.

Miller, Use of Dinitrosalicylic Acid Reagent for Determination of Reducing Sugar, Analytical Chemistry, 1959, 31(3):426-428.

Natale, et al., Sec- and Tat-mediated Protein Secretion Across the Bacterial Cytoplasmic Membrane—Distinct Translocases and Mechanisms, Biochimica et Biophysica Acta, 2008, 1778:1735-1756.

Nijland, et al., Optimization of Protein Secretion by Bacillus Subtilis, Recent Patents on Biotechnology, 2008, 2(2):79-87.

Pasti, et al., Cellulolytic Activity of Actinomycetes Isolated from Termites (Termitidae) Gut, FEMS Microbiology Letters, 1985, 26(1):107-112.

Pasti, et al., Lignin-Solubilizing Ability of Actinomycetes Isolated from Termite (Termitidae) Gut, Applied and Environmental Microbiology, 1990, 56(7):2213-2218.

Peralta-Yahya, et al., Advanced Biofuel Production in Microbes, Biotechnol., J., 2010, 5:147-162.

Quinlan, et al., Insights into the Oxidative Degradation of Cellulose by a Copper Metalloenzyme that Exploits Biomass Components, PNAS, 2011, 108(37):15079-15084.

Raman, et al., Impact of Pretreated Switchgrass and Biomass Carbohydrates on Clostridium Thermocellum ATCC 27405 Cellulosome Composition: A Quantitative Proteomic Analysis, PLoS One, 2009, 4(4):e5271, 13 pages.

Book Adam J et al; "Cellulolytic Streptomyces Strains Associated with Herbiborous Insects Share a Phylogenetically Linked Capacity to Degrade Linocellulose", Appl. Environ. Microbiol. 2014, 80(15):4692-4701.

Riederer, et al., Global Gene Expression Patterns in Clostridium Thermocellum as Determined by Microarray Analysis of Chemostat Cultures on Cellulose or Cellobiose, Applied and Environmental Microbiology, 2011, 77(4):1243-1253.

Rutherford, et al., Artemis: Sequence Visualization and Annotation, Bioinformatics, 2000, 16(10):944-945.

Saloheimo, et al., The Cargo and the Transport System: Secreted Proteins and Protein Secretion in Trichoderma Reesei (Hypocrea Jecorina), Microbiology, 2012, 158:46-57.

Schafer, et al., Hemicellulose-Degrading Bacteria and Yeasts from the Termite Gut, Journal of Applied Bacteriology, 1996, 80(5):471-478.

Scharf, et al., Multiple Levels of Synergistic Collaboration in Termite Lignocellulose Digestion, PLoS One, 2011, 6(7):e21709, 7 pages.

Schlatter, et al., Resource Amendments Influence Density and Competitive Phenotypes of Streptomyces in Soil, Microb. Ecol., 2009, 57:413-420.

(56) References Cited

OTHER PUBLICATIONS

Schlochtermeier, et al., Biochemical and Electron Microscopic Studies of the Streptomyces Reticuli Cellulase (Avicelase) in Its Mycelium-Associated and Extracellular Forms, Applied and Environmental Microbiology, 1992, 58(10):3240-3248.

Schlochtermeier, et al., The Gene Encoding the Cellulase (Avicelase) Cel1 From Streptomyces Reticuli and Analysis of Protein Domains, Molecular Microbiology, 1992, 6(23):3611-3621.

Schuster, et al., Biology and Biotechnology of Trichoderma, Appl. Microbiol. Biotechnol., 2010, 87:787-799.

Semedo, et al., *Streptomyces drozdowiczii* sp. nov., a Novel Cellulolytic Streptomycete from Soil in Brazil, International Journal of Systematic and Evolutionary Microbiology, 2004, 54:1323-1328.

Shannon, et al., Cytoscape: A Software Environment for Integrated Models of Biomolecular Interaction Networks, Genome Research, 2003, 13:2498-2504.

Suen, et al., An Insect Herbivore Microbiome with High Plant Biomass-Degrading Capacity, PLoS Genetics, 2010, 6(9):e1001129, 14 pages.

Susi, et al., Biological Control of Wood Decay Against Fungal Infection, Journal of Environmental Management, 2011, 92(7):1681-1689.

Tabata, et al., Molecular Phylogeny of Species in the Genera *Amylostereum* and *Echinodontium*, Mycoscience, 2000, 41:585-593.

Teather, et al., Use of Congo Red-Polysaccharide Interactions in Enumeration and Characterization of Cellulolytic Bacteria from the Bovine Rumen, Applied and Environmental Microbiology, 1982, 43(4):777-780.

Tian, et al. Comparisons of SPORL and Dilute Acid Pretreatments for Sugar and Ethanol Productions from Aspen, Biotechnol. Prog., 2011, 27(2):419-427.

Tolonen, et al., Proteome-Wide Systems Analysis of a Cellulosic Biofuel-Producing Microbe, Molecular Systems Biology, 2011, 7:461, 12 pages.

Trop, et al., The Specificity of Proteinases from Streptomyces Griseus (Pronase), Biochem. J., 1970, 116:19-25.

Turini, et al., The Action of Phenylmethylsulfonyl Fluoride on Human Acetylcholinesterase, Chymotrypsin and Trypsin, Journal of Pharmacology and Experimental Therapeutics, 1969, 167(1):98-104.

Vaaje-Kolstad, An Oxidative Enzyme Boosting the Enzymatic Conversion of Recalcitrant Polysaccharides, Science, 2010, 330:219-222.

Vuong, et al., Glycoside Hydrolases: Catalytic Base/Nucleophile Diversity, Biotechnology and Bioengineering, 2010, 107(2):195-205.

Wachinger, et al., Identification of Mycelium-Associated Cellulase from Streptomyces Reticuli, Applied and Environmental Microbiology, 1989, 55(10):2653-2657.

Walter, et al., Physiological Studies of Cellulase (Avicelase) Synthesis in Streptomyces Reticuli, Applied and Environmental Microbiology, 1996, 62(3):1065-1069.

Walter, et al., The Synthesis of the Streptomyces Reticuli Cellulase (Avicelase) is Regulated by Both Activation and Repression Mechanisms, Mol. Gen. Genet, 1996, 251:186-195.

Wang, et al., Sulfite Pretreatment to Overcome Recalcitrance of Lignocellulose (SPORL) for Robust Enzymatic Saccharification of Hardwoods, Biotechnol. Prog., 2009, 25(4):1086-1092.

Wilson, Microbial Diversity of Cellulose Hydrolysis, Current Opinion in Microbiology, 2011, 14:1-5.

Wilson, Biochemistry and Genetics of Actinomycete Cellulases, Critical Reviews in Biotechnology, 1992, 12 (1-2):45-63.

Wood, et al., Production of Recombinant Bacterial Endoglucanase as a Co-Product with Ethanol During Fermentation Using Derivatives of *Escherichia coli* KO11, Biotechnology and Bioengineering, 1997, 55(3):547-555.

Zhang, et al., Extracellular Accumulation of Recombinant Proteins Fused to the Carrier Protein YebF in *Escherichia coli*, Nature Biotechnology, 2006, 24(1):100-104.

Zylstra, et al., Sirex Noctilio in North America: The Effect of Stem-Injection Timing on the Attractiveness and Suitability of Trap Trees, Agricultural and Forest Entomology, 2010, 12:243-250.

Adams, et al., Cellulolytic Associations of Sirex Noctilio Within the Context of a Multipartite Symbiosis, Department of Entomology, University of Wisconsin, Poster, 2008, 23 pages.

\* cited by examiner

Figure 1
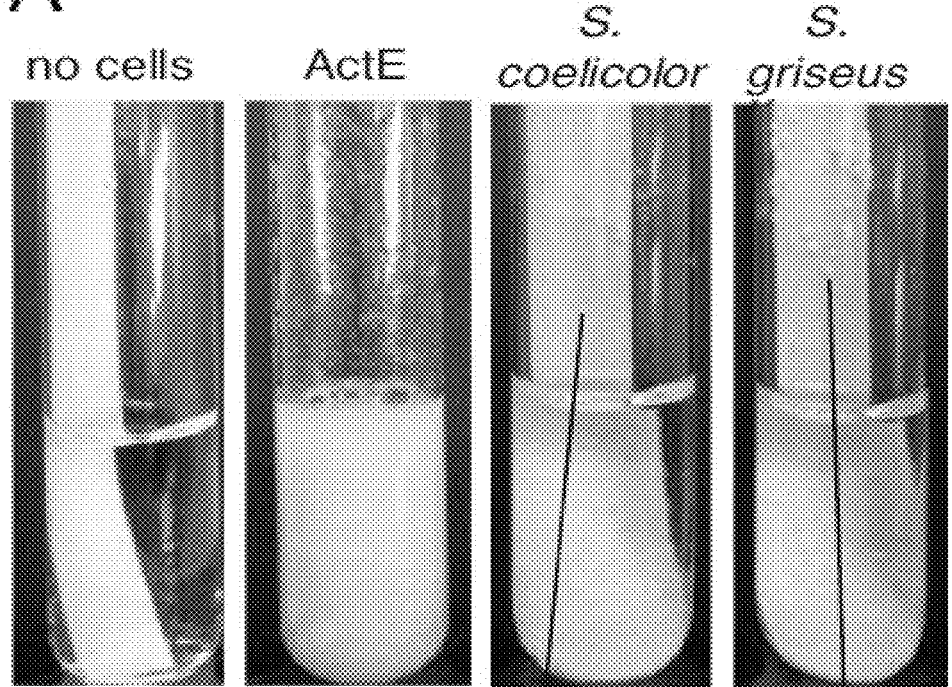
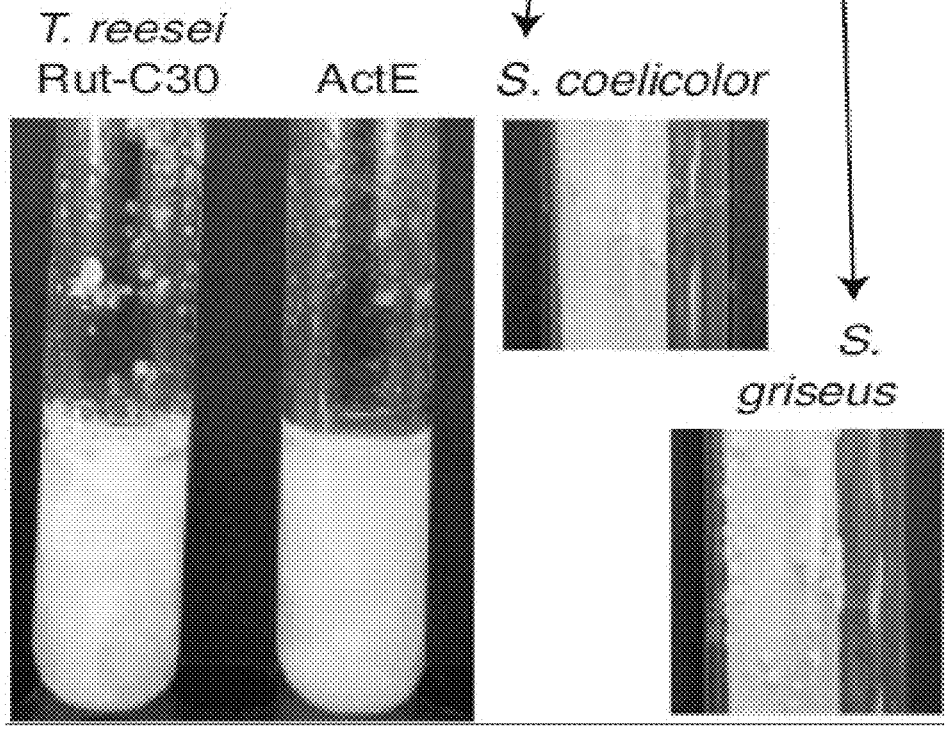

Figure 5 A-B

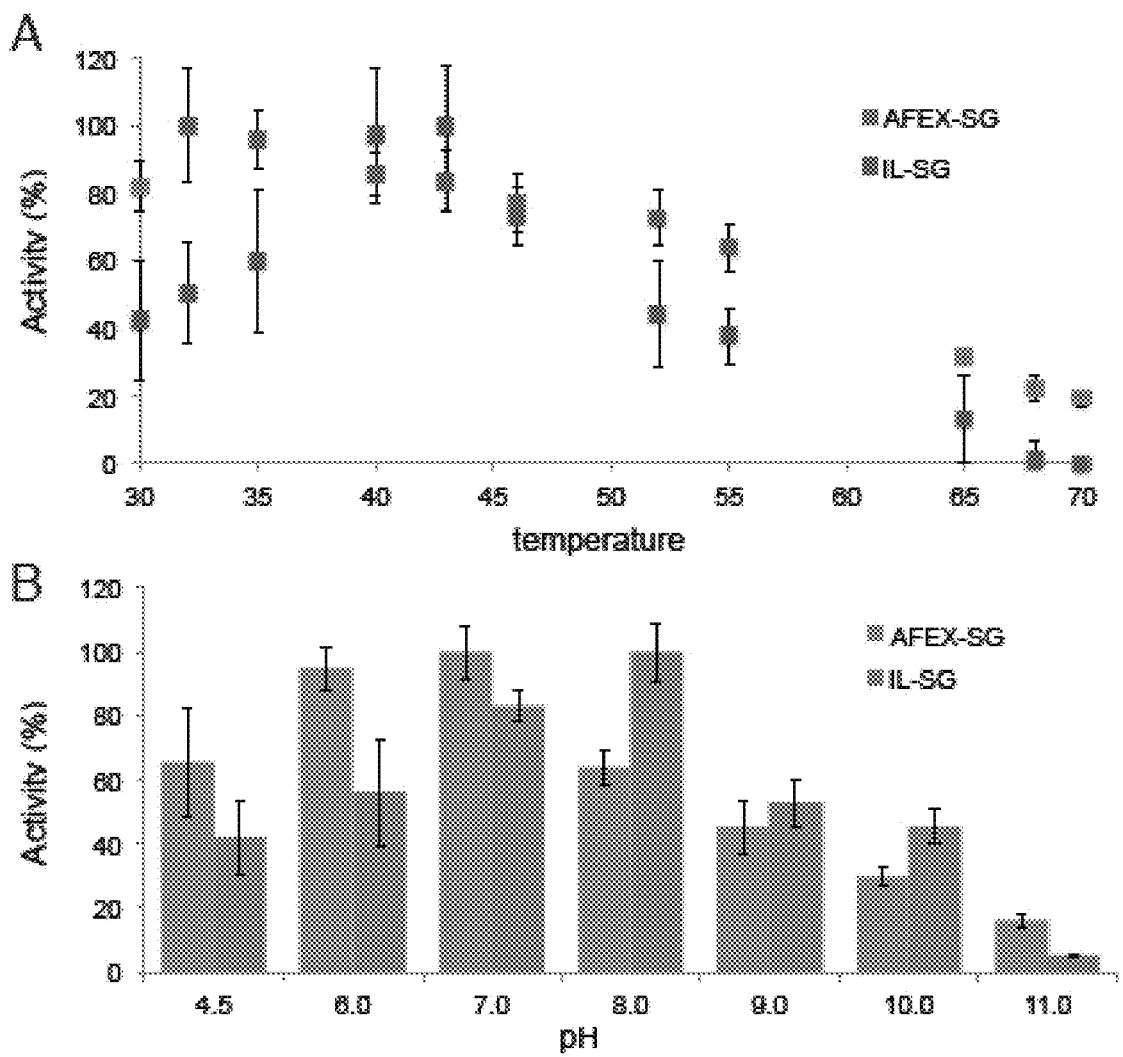
Figure 8 A-B

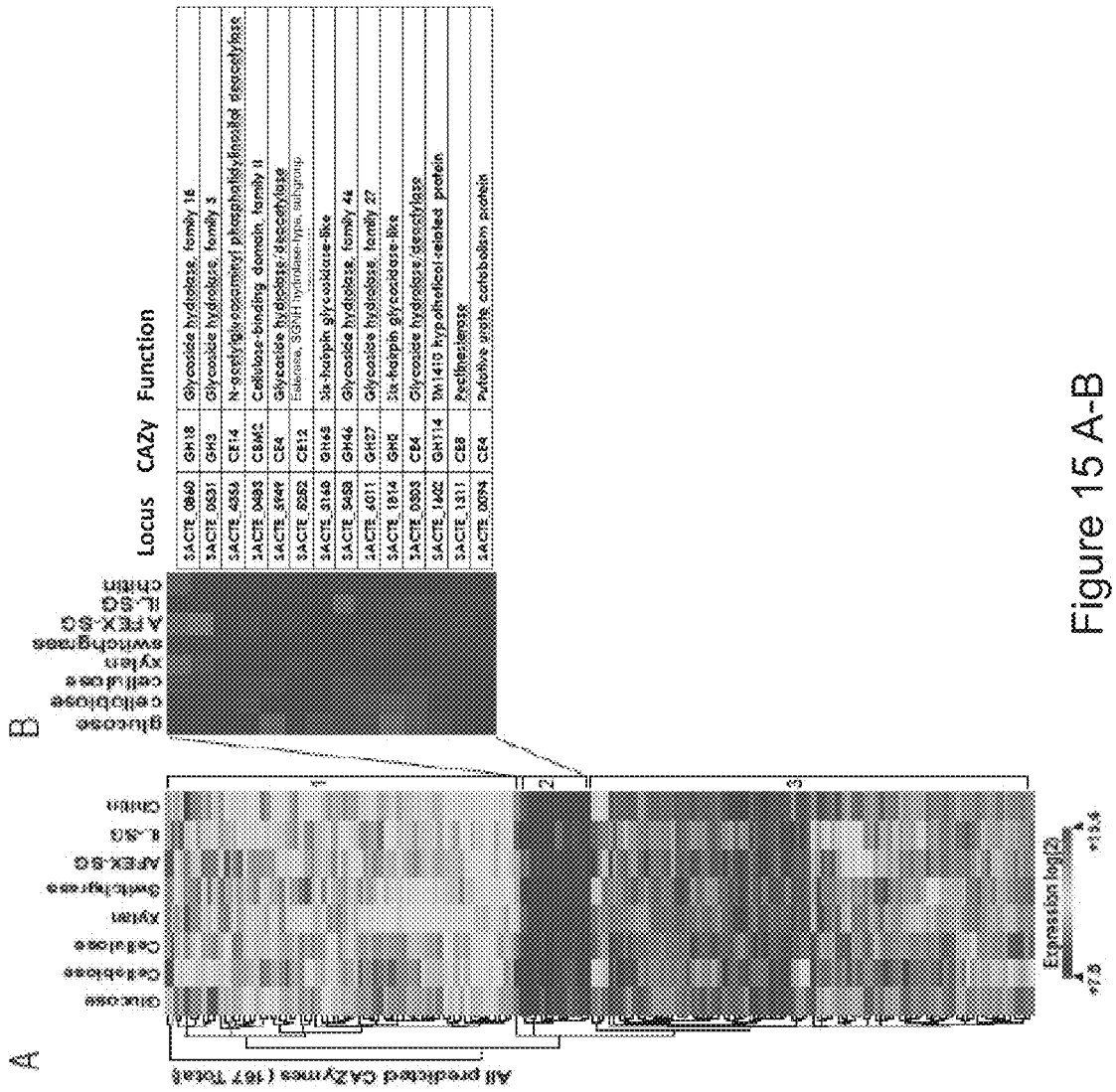
Figure 15 A-B

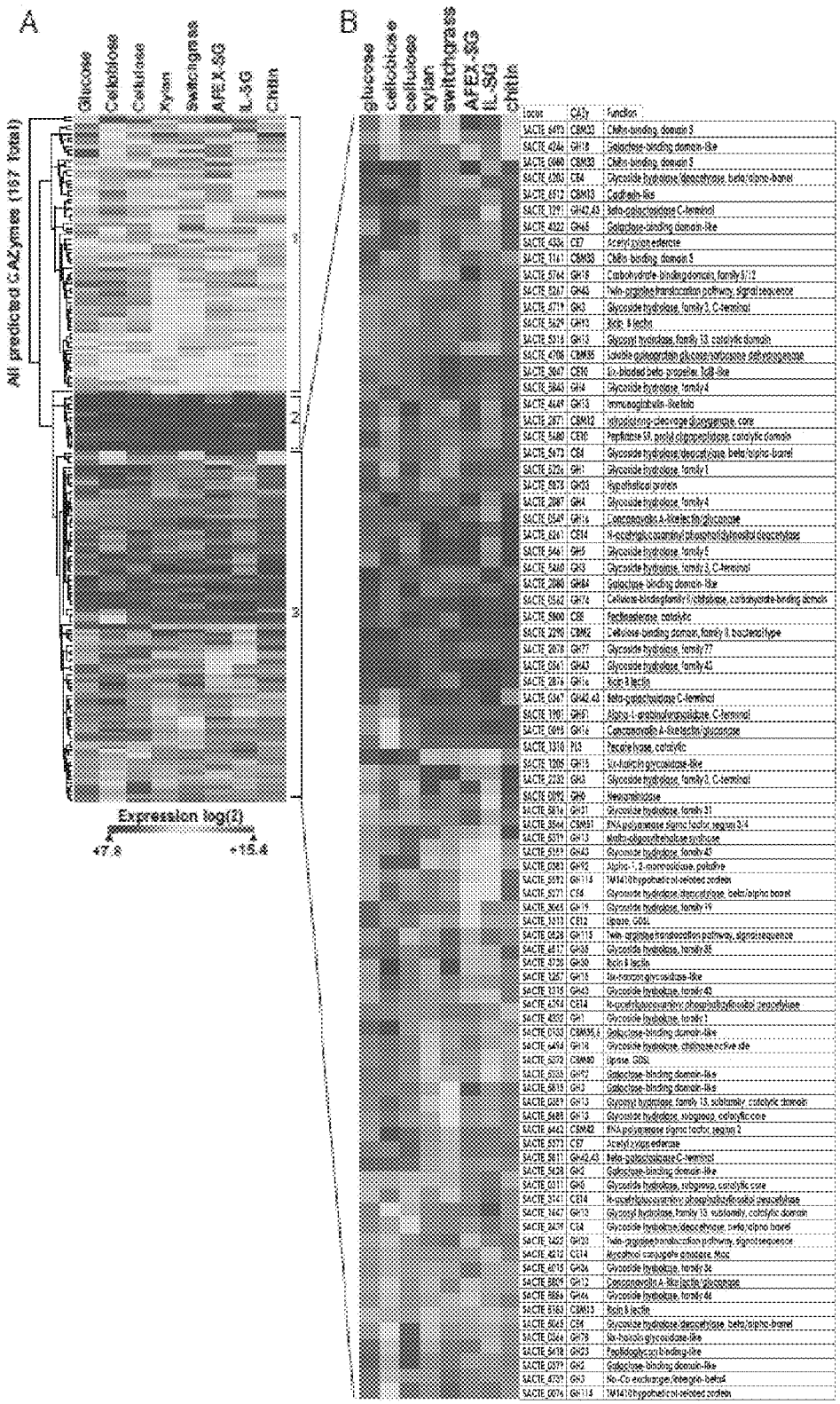
Figure 16 A-B

Figure 17

| Protein band[a] | Locus | Catalytic domain | CBM | Functional class[b] |
|---|---|---|---|---|
| a | SACTE_3159 | CBM33 | CBM2 | cellulase |
| b | SACTE_0265 | GH10 | CBM2 | xylanase |
| c | SACTE_4755 | GH64 | | beta-1,3-glucanase |
| d | SACTE_0482 | GH5 | CBM2 | cellulase |
| e | SACTE_0237 | GH6 | CBM2 | cellulase |
| f | SACTE_0236 | GH48 | CBM2 | cellulase |
| g | SACTE_3717 | GH9 | CBM2 | cellulase |
| h | SACTE_2347 | GH5 | CBM2 | mannanase |

[a] Protein bands labeled in Figure 3A were identified by MALDI-TOF mass spectrometry. [b] Function identified by assays of individual fractions from ion exchange chromatography.

Figure 18

Figure 18: Spectra count of proteins identified on each substrate, where top 95 % spectra covered were bolded on glucose, cellobiose, cellulose, xylan switchgrass, AFEX-SG, IL-SG and chitin, repsectively.

| Locus | CAZy | Identified Proteins (414) | glucose | cellobiose | cellulose | xylan | switchgrass | AFEX-SG | IL-SG | chitin |
|---|---|---|---|---|---|---|---|---|---|---|
| SACTE_0237 | GH6 | ACTE_1, 4-beta cellobiohydrolase | 0 | 462 | 3965 | 8 | 3330 | 3300 | 3520 | 0 |
| SACTE_0236 | GH48 | ACTE_Glycoside hydrolase, 48F | 0 | 44 | 1296 | 0 | 577 | 905 | 1045 | 0 |
| SACTE_2347 | GH5,CE3 | ACTE_Cellulose-binding family II/chitobiase, carbohydrate-binding domain | 0 | 28 | 624 | 0 | 185 | 240 | 205 | 0 |
| SACTE_3159 | CBM33,2 | ACTE_Cellulose-binding domain, family II, bacterial type | 0 | 4 | 564 | 29 | 493 | 646 | 847 | 8 |
| SACTE_0482 | GH5 | ACTE_Cellulose-binding family II/chitobiase, carbohydrate-binding domain | 0 | 11 | 156 | 0 | 92 | 113 | 153 | 0 |
| SACTE_0265 | GH10 | ACTE_Glycoside hydrolase, family 10 | 0 | 13 | 90 | 778 | 118 | 220 | 101 | 0 |
| SACTE_0357 | CE4 | ACTE_Glycoside hydrolase/deacetylase, beta/alpha-barrel | 0 | 12 | 87 | 938 | 94 | 195 | 190 | 3 |
| SACTE_4439 | | ACTE_Catalase, N-terminal | 0 | 65 | 83 | 30 | 50 | 20 | 30 | 271 |
| SACTE_0562 | GH74 | ACTE_Cellulose-binding family II/chitobiase, carbohydrate-binding domain | 0 | 0 | 83 | 0 | 29 | 48 | 30 | 0 |
| SACTE_0358 | GH11 | ACTE_Glycoside hydrolase, family 11, active site | 0 | 0 | 67 | 649 | 165 | 324 | 119 | 7 |
| SACTE_4343 | | ACTE_Bacterial extracellular solute-binding protein, family 5 | 67 | 298 | 53 | 60 | 55 | 43 | 30 | 19 |
| SACTE_1546 | | ACTE_Bacterioferritin | 0 | 117 | 32 | 42 | 32 | 22 | 24 | 35 |
| SACTE_1310 | PL3 | ACTE_Pectate lyase, catalytic | 0 | 57 | 26 | 14 | 226 | 96 | 48 | 25 |
| SACTE_4638 | | ACTE_Chondroitin AC/alginate lyase | 0 | 41 | 23 | 135 | 34 | 59 | 59 | 14 |
| SACTE_5668 | | ACTE_Alpha/beta hydrolase fold-1 | 29 | 30 | 21 | 23 | 0 | 0 | 9 | 39 |
| SACTE_3717 | GH9 | ACTE_Carbohydrate-binding, CenC-like | 0 | 49 | 21 | 0 | 342 | 432 | 143 | 0 |
| SACTE_3590 | | ACTE_Phospholipase C, phosphatidylinositol-specific, X domain | 0 | 5 | 21 | 0 | 0 | 4 | 7 | 0 |
| SACTE_4571 | GH18 | ACTE_EF-Hand 1, calcium-binding site | 0 | 9 | 20 | 5 | 18 | 14 | 10 | 1758 |
| SACTE_2172 | | ACTE_Citrate synthase-like, core | 19 | 95 | 20 | 51 | 47 | 12 | 15 | 46 |
| SACTE_5978 | PL1 | ACTE_Galactose-binding domain-like | 0 | 5 | 20 | 525 | 287 | 245 | 10 | 0 |
| SACTE_6428 | CBM33 | ACTE_Chitin-binding, domain 3 | 0 | 3 | 20 | 0 | 6 | 5 | 8 | 0 |
| SACTE_2313 | CBM33 | ACTE_Chitin-binding, domain 3 | 0 | 11 | 19 | 0 | 12 | 0 | 11 | 308 |
| SACTE_0366 | GH78 | ACTE_Six-hairpin glycosidase-like | 0 | 4 | 17 | 30 | 0 | 0 | 5 | 20 |
| SACTE_1604 | | ACTE_Pyridine nucleotide-disulphide oxidoreductase, class I, active site | 72 | 473 | 16 | 96 | 25 | 18 | 26 | 57 |
| SACTE_4702 | | ACTE_Protein of unknown function DUF756 | 0 | 26 | 16 | 18 | 0 | 2 | 26 | 26 |
| SACTE_2059 | | ACTE_Manganese/iron superoxide dismutase, C-terminal | 0 | 83 | 13 | 6 | 13 | 16 | 0 | 62 |
| SACTE_4755 | GH64 | ACTE_Twin-arginine translocation pathway, signal sequence | 2 | 92 | 12 | 23 | 33 | 30 | 30 | 24 |
| SACTE_4945 | | ACTE_Extracellular solute-binding protein, family 3 | 38 | 26 | 12 | 18 | 16 | 4 | 22 | 9 |
| SACTE_4730 | GH30 | ACTE_Ricin B lectin | 0 | 40 | 12 | 41 | 22 | 25 | 51 | 7 |
| SACTE_2556 | | ACTE_Enolase, N-terminal | 57 | 84 | 12 | 47 | 10 | 4 | 19 | 0 |
| SACTE_1041 | | ACTE_ABC-type glycine betaine transport system, substrate-binding domain | 25 | 71 | 11 | 8 | 6 | 6 | 10 | 17 |
| SACTE_4246 | GH18 | ACTE_Galactose-binding domain-like | 0 | 20 | 10 | 15 | 7 | 9 | 11 | 1115 |
| SACTE_0880 | | ACTE_S-adenosylmethionine synthetase, central domain | 0 | 15 | 10 | 25 | 6 | 3 | 12 | 33 |
| SACTE_5330 | | ACTE_Peptidase S1/S6, chymotrypsin/Hap | 0 | 13 | 10 | 6 | 9 | 11 | 11 | 14 |
| SACTE_0464 | GH16 | ACTE_Ricin B lectin | 0 | 7 | 10 | 14 | 6 | 4 | 8 | 9 |
| SACTE_5335 | | ACTE_ABC transporter, substrate-binding protein, aliphatic sulphonates | 4 | 58 | 9 | 24 | 4 | 11 | 9 | 35 |
| SACTE_2232 | GH3 | ACTE_Glycoside hydrolase, family 3, C-terminal | 8 | 32 | 9 | 31 | 0 | 0 | 0 | 9 |
| SACTE_0132 | | ACTE_hypothetical protein | 0 | 0 | 9 | 0 | 6 | 0 | 16 | 0 |
| SACTE_2289 | | ACTE_Bacterial extracellular solute-binding, family 1 | 0 | 13 | 9 | 8 | 6 | 0 | 7 | 0 |
| SACTE_1130 | | ACTE_Galactose-binding domain-like | 0 | 43 | 9 | 55 | 22 | 11 | 6 | 0 |
| SACTE_5457 | GH46 | ACTE_Glycoside hydrolase, family 46 | 0 | 461 | 8 | 148 | 21 | 23 | 12 | 57 |
| SACTE_3803 | | ACTE_Pyridoxal phosphate-dependent transferase, major domain | 6 | 165 | 8 | 14 | 11 | 0 | 13 | 23 |
| SACTE_1422 | GH23 | ACTE_Twin-arginine translocation pathway, signal sequence | 27 | 19 | 8 | 34 | 0 | 0 | 2 | 19 |
| SACTE_3306 | | ACTE_6-phosphogluconate dehydrogenase related protein | 11 | 86 | 8 | 18 | 8 | 0 | 9 | 18 |
| SACTE_5230 | | ACTE_Xylose isomerase-like, TIM barrel domain | 0 | 15 | 8 | 1019 | 150 | 183 | 245 | 6 |
| SACTE_0383 | GH92 | ACTE_Alpha-1,2-mannosidase, putative | 0 | 0 | 8 | 8 | 0 | 0 | 0 | 0 |
| SACTE_5647 | GH87 | ACTE_Galactose-binding domain-like | 0 | 46 | 8 | 96 | 75 | 63 | 36 | 0 |
| SACTE_4676 | | ACTE_Bacterial extracellular solute-binding protein, family 5 | 9 | 25 | 8 | 12 | 11 | 3 | 9 | 0 |
| SACTE_0642 | | ACTE_Peptidase S33, tripeptidyl-peptidase C-terminal | 2 | 74 | 8 | 0 | 15 | 0 | 0 | 0 |
| SACTE_3779 | GH31 | ACTE_Glycoside hydrolase, family 31 | 0 | 5 | 8 | 0 | 0 | 0 | 0 | 0 |

Figure 18 (Continued)

| ID | Family | Description | C1 | C2 | C3 | C4 | C5 | C6 |
|---|---|---|---|---|---|---|---|---|
| SACTE_0746 | | ACTE_Twin-arginine translocation pathway, signal sequence | 0 | 0 | 0 | 0 | 2 | 47 |
| SACTE_4468 | | ACTE_Bacterial extracellular solute-binding, family 1 | 0 | 4 | 7 | 0 | 0 | 43 |
| SACTE_4363 | GH55 | ACTE_hypothetical protein | 0 | 72 | 7 | 18 | 16 | 19 | 12 |
| SACTE_5166 | GH43 | ACTE_Twin-arginine translocation pathway, signal sequence | 0 | 62 | 7 | 37 | 23 | 24 | 4 |
| SACTE_1369 | | ACTE_Glyceraldehyde 3-phosphate dehydrogenase, NAD(P) binding domain | 10 | 176 | 7 | 10 | 30 | 29 | 36 | 20 |
| SACTE_1364 | | ACTE_Phosphoglucose isomerase, conserved site | 2 | 147 | 6 | 16 | 14 | 13 | 13 | 0 |
| SACTE_5519 | | ACTE_YD repeat | 9 | 0 | 6 | 0 | 0 | 0 | 20 |
| SACTE_0244 | | ACTE_N-acetylmuramoyl-L-alanine amidase, family 2 | 6 | 27 | 5 | 22 | 0 | 0 | 25 |
| SACTE_4612 | | ACTE_hypothetical protein | 0 | 8 | 5 | 200 | 67 | 30 | 31 |
| SACTE_3458 | | ACTE_Surface protein from Gram-positive cocci | 9 | 21 | 4 | 14 | 5 | 3 | 7 | 82 |
| SACTE_4198 | | ACTE_NAD(P)-binding domain | 6 | 66 | 4 | 19 | 14 | 5 | 8 | 24 |
| SACTE_2033 | | ACTE_Nucleoside diphosphate kinase, core | 0 | 7 | 4 | 8 | 12 | 4 | 4 | 16 |
| SACTE_1367 | | ACTE_Triosephosphate isomerase | 0 | 151 | 4 | 13 | 0 | 4 | 10 | 7 |
| SACTE_0379 | GH2 | ACTE_Galactose-binding domain-like | 0 | 72 | 4 | 10 | 6 | 3 | 10 | 3 |
| SACTE_5371 | | ACTE_Neuraminidase | 0 | 4 | 4 | 5 | 2 | 2 | 3 | 3 |
| SACTE_5629 | GH93 | ACTE_Ricin B lectin | 0 | 80 | 3 | 0 | 0 | 4 | 3 | 2 |
| SACTE_4858 | GH18 | ACTE_Galactose-binding domain-like | 0 | 17 | 3 | 18 | 5 | 5 | 4 | 384 |
| SACTE_0844 | GH18 | ACTE_Glycoside hydrolase, subgroup, catalytic core | 0 | 19 | 3 | 0 | 0 | 0 | 0 | 155 |
| SACTE_5589 | | ACTE_Gamma-glutamyltranspeptidase | 9 | 33 | 3 | 31 | 0 | 0 | 0 | 4 |
| SACTE_5240 | | ACTE_hypothetical protein | 0 | 30 | 3 | 3 | 0 | 0 | 3 | 0 |
| SACTE_0604 | GH109 | ACTE_NAD(P)-binding domain | 3 | 2 | 3 | 0 | 8 | 0 | 2 | 0 |
| SACTE_4231 | | ACTE_Serine/cysteine peptidase, trypsin-like | 0 | 4 | 3 | 9 | 0 | 0 | 0 | 0 |
| SACTE_5267 | GH43 | ACTE_Twin-arginine translocation pathway, signal sequence | 4 | 2 | 3 | 0 | 0 | 0 | 0 | 0 |
| SACTE_4727 | | ACTE_Isocitrate/isopropylmalate dehydrogenase | 0 | 17 | 2 | 5 | 0 | 0 | 3 | 36 |
| SACTE_1302 | PL1 | ACTE_Twin-arginine translocation pathway, signal sequence | 0 | 8 | 2 | 4 | 116 | 43 | 7 | 7 |
| SACTE_6439 | GH43 | ACTE_Glycoside hydrolase, family 43 | 0 | 66 | 2 | 9 | 4 | 7 | 3 | 4 |
| SACTE_6549 | | ACTE_Peptidase S11, D-alanyl-D-alanine carboxypeptidase A | 0 | 0 | 2 | 0 | 0 | 0 | 3 | 3 |
| SACTE_3711 | | ACTE_Glycosyl transferase, family 20 | 0 | 22 | 2 | 3 | 3 | 2 | 3 | 0 |
| SACTE_3064 | GH19 | ACTE_Glycoside hydrolase, family 19, catalytic | 0 | 21 | 0 | 37 | 19 | 12 | 0 | 1333 |
| SACTE_5764 | GH18 | ACTE_Carbohydrate-binding domain, family 5/12 | 0 | 3 | 0 | 0 | 0 | 0 | 0 | 365 |
| SACTE_0081 | GH19 | ACTE_Glycoside hydrolase, family 19 | 0 | 40 | 0 | 26 | 0 | 0 | 0 | 322 |
| SACTE_1701 | | ACTE_Htaa | 4 | 78 | 0 | 77 | 0 | 9 | 0 | 77 |
| SACTE_6494 | GH18 | ACTE_Glycoside hydrolase, chitinase active site | 0 | 0 | 0 | 0 | 0 | 0 | 0 | 69 |
| SACTE_2768 | | ACTE_Surface protein from Gram-positive cocci | 0 | 13 | 0 | 12 | 0 | 0 | 0 | 54 |
| SACTE_2062 | | ACTE_DSBA oxidoreductase | 0 | 22 | 0 | 6 | 5 | 0 | 0 | 51 |
| SACTE_0860 | GH18 | ACTE_Carbohydrate-binding domain, family 5/12 | 0 | 0 | 0 | 0 | 0 | 0 | 0 | 44 |
| SACTE_4908 | | ACTE_Exoribonuclease, phosphorolytic domain 2 | 9 | 13 | 0 | 43 | 26 | 21 | 24 | 33 |
| SACTE_0926 | | ACTE_Vitamin B6 biosynthesis protein | 15 | 13 | 0 | 19 | 3 | 2 | 0 | 25 |
| SACTE_3097 | | ACTE_Heat shock protein Hsp70 | 39 | 4 | 0 | 0 | 0 | 0 | 0 | 25 |
| SACTE_4178 | | ACTE_FAD-dependent pyridine nucleotide-disulphide oxidoreductase | 5 | 21 | 0 | 17 | 0 | 0 | 3 | 21 |
| SACTE_3666 | | ACTE_Histidine phosphatase superfamily, clade-1 | 30 | 0 | 0 | 17 | 0 | 0 | 0 | 21 |
| SACTE_1858 | | ACTE_Bacterial stress protein | 0 | 25 | 0 | 17 | 11 | 0 | 0 | 19 |
| SACTE_4083 | | ACTE_Malate dehydrogenase, active site | 90 | 19 | 0 | 2 | 0 | 0 | 0 | 19 |
| SACTE_2384 | | ACTE_Phosphotransferase system, EIIC component, type 1 | 0 | 0 | 0 | 12 | 0 | 0 | 0 | 19 |
| SACTE_0634 | | ACTE_Periplasmic binding protein | 0 | 3 | 0 | 6 | 5 | 0 | 0 | 17 |
| SACTE_3078 | | ACTE_Ketose-bisphosphate aldolase, class-II | 0 | 314 | 0 | 26 | 26 | 14 | 12 | 16 |
| SACTE_4669 | | ACTE_Pyridoxal phosphate-dependent transferase, major domain | 12 | 24 | 0 | 161 | 10 | 7 | 4 | 16 |
| SACTE_3685 | | ACTE_Molybdate/tungstate binding | 0 | 7 | 0 | 24 | 4 | 0 | 0 | 14 |
| SACTE_3452 | | ACTE_Cobaltochelatase, CobN subunit | 22 | 0 | 0 | 0 | 7 | 0 | 0 | 13 |
| SACTE_4039 | | ACTE_IMP dehydrogenase/GMP reductase | 9 | 3 | 0 | 15 | 0 | 0 | 0 | 12 |
| SACTE_1356 | | ACTE_Transaldolase, active site | 0 | 9 | 0 | 4 | 3 | 0 | 2 | 12 |
| SACTE_4472 | | ACTE_Glucosamine-6-phosphate isomerase, subgroup | 0 | 0 | 0 | 13 | 0 | 0 | 0 | 12 |
| SACTE_1702 | | ACTE_Htaa | 0 | 0 | 0 | 0 | 0 | 0 | 0 | 12 |
| SACTE_0450 | | ACTE_Dak kinase | 0 | 16 | 0 | 0 | 7 | 8 | 8 | 11 |

Figure 18 (Continued)

| | | | | | | | |
|---|---|---|---|---|---|---|---|
| SACTE_3389 | | ACTE_Peptidase M24B, X-Pro dipeptidase/aminopeptidase P, conserved sit | 6 | 38 | 0 | 7 | 6 | 2 | 3 | 11 |
| SACTE_4607 | | ACTE_Protein of unknown function DUF1557 | 0 | 10 | 0 | 18 | 5 | 3 | 0 | 11 |
| SACTE_6308 | | ACTE_Periplasmic binding protein | 5 | 25 | 0 | 23 | 0 | 0 | 0 | 11 |
| SACTE_5342 | | ACTE_Nitrite/sulphite reductase, hemoprotein beta-component, ferrodoxi | 0 | 6 | 0 | 0 | 3 | 0 | 4 | 9 |
| SACTE_5751 | | ACTE_Twin-arginine translocation pathway, signal sequence | 0 | 45 | 0 | 16 | 33 | 4 | 3 | 9 |
| SACTE_5260 | | ACTE_FAD-dependent pyridine nucleotide-disulphide oxidoreductase | 0 | 11 | 0 | 4 | 0 | 4 | 0 | 9 |
| SACTE_0264 | | ACTE_Protein of unknown function DUF541 | 0 | 7 | 0 | 0 | 0 | 0 | 0 | 9 |
| SACTE_4493 | | ACTE_Superoxide dismutase, Nickel-type | 17 | 10 | 0 | 30 | 20 | 11 | 23 | 8 |
| SACTE_4145 | | ACTE_Basic membrane lipoprotein | 4 | 13 | 0 | 4 | 2 | 0 | 4 | 8 |
| SACTE_4515 | GH25 | ACTE_Twin-arginine translocation pathway, signal sequence | 0 | 45 | 0 | 35 | 6 | 12 | 21 | 7 |
| SACTE_5263 | | ACTE_Dimeric alpha-beta barrel | 3 | 25 | 0 | 9 | 2 | 0 | 2 | 7 |
| SACTE_3058 | | ACTE_Bacterial stress protein | 174 | 253 | 0 | 140 | 31 | 12 | 0 | 7 |
| SACTE_3164 | | ACTE_hypothetical protein | 0 | 0 | 0 | 7 | 2 | 0 | 0 | 7 |
| SACTE_2049 | | ACTE_Ribose 5-phosphate isomerase, actinobacteria | 12 | 18 | 0 | 5 | 0 | 0 | 0 | 6 |
| SACTE_3319 | | ACTE_Pyridine nucleotide-disulphide oxidoreductase, class-II, active site | 0 | 0 | 0 | 0 | 0 | 0 | 4 | 6 |
| SACTE_3012 | | ACTE_AMP-binding, conserved site | 18 | 0 | 0 | 0 | 13 | 2 | 3 | 6 |
| SACTE_2323 | | ACTE_Fumarylacetoacetase, C-terminal-related | 0 | 0 | 0 | 0 | 0 | 0 | 0 | 6 |
| SACTE_2490 | | ACTE_S-adenosyl-L-homocysteine hydrolase, conserved site | 0 | 0 | 0 | 0 | 5 | 0 | 0 | 5 |
| SACTE_1949 | | ACTE_Peptidase M4, thermolysin | 0 | 604 | 0 | 86 | 0 | 0 | 0 | 5 |
| SACTE_0985 | | ACTE_N-acetyl-gamma-glutamyl-phosphate reductase | 0 | 0 | 0 | 0 | 0 | 0 | 0 | 5 |
| SACTE_3327 | | ACTE_NAD(P)-binding domain | 62 | 1 | 0 | 0 | 0 | 0 | 0 | 4 |
| SACTE_5418 | GH23 | ACTE_Peptidoglycan binding-like | 0 | 9 | 0 | 34 | 21 | 15 | 31 | 4 |
| SACTE_2585 | | ACTE_Phosphoribosyltransferase | 6 | 35 | 0 | 10 | 12 | 15 | 10 | 4 |
| SACTE_5220 | | ACTE_Aconitase/3-isopropylmalate dehydratase large subunit, alpha/beta | 45 | 26 | 0 | 46 | 9 | 0 | 7 | 4 |
| SACTE_4843 | | ACTE_Aminotransferase class-III | 0 | 9 | 0 | 0 | 12 | 4 | 3 | 4 |
| SACTE_0639 | | ACTE_Formyl transferase, N-terminal | 0 | 53 | 0 | 5 | 2 | 0 | 0 | 4 |
| SACTE_4243 | | ACTE_Erdoribonuclease L-PSP/chorismate mutase-like | 0 | 13 | 0 | 0 | 5 | 0 | 0 | 4 |
| SACTE_4738 | GH16 | ACTE_Galactose-binding domain-like | 0 | 208 | 0 | 10 | 11 | 14 | 0 | 4 |
| SACTE_2260 | | ACTE_Acyl-CoA dehydrogenase/oxidase, N-terminal | 0 | 0 | 0 | 0 | 5 | 0 | 0 | 3 |
| SACTE_4078 | | ACTE_MGS-like | 12 | 7 | 0 | 20 | 4 | 0 | 0 | 3 |
| SACTE_5657 | | ACTE_MaoC-like dehydratase | 0 | 14 | 0 | 3 | 4 | 0 | 0 | 3 |
| SACTE_4436 | | ACTE_Uncharacterised protein family UPF0182 | 0 | 9 | 0 | 3 | 0 | 0 | 0 | 3 |
| SACTE_4946 | | ACTE_ABC transporter, conserved site | 0 | 3 | 0 | 0 | 0 | 0 | 0 | 3 |
| SACTE_6131 | | ACTE_Purple acid phosphatase-like, N-terminal | 0 | 0 | 0 | 0 | 0 | 0 | 0 | 3 |
| SACTE_0324 | GH55 | ACTE_Galactose-binding domain-like | 0 | 3 | 0 | 5 | 0 | 0 | 8 | 2 |
| SACTE_1137 | | ACTE_Peptidase S45, penicillin amidase | 0 | 0 | 0 | 4 | 0 | 4 | 0 | 2 |
| SACTE_1074 | | ACTE_Proteasome, subunit alpha/beta | 0 | 0 | 0 | 9 | 0 | 9 | 0 | 2 |
| SACTE_6558 | | ACTE_Quinoprotein amine dehydrogenase, beta chain-like | 6 | 16 | 0 | 11 | 17 | 3 | 0 | 2 |
| SACTE_4718 | | ACTE_Delta-1-pyrroline-5-carboxylate dehydrogenase 1 | 3 | 0 | 0 | 3 | 14 | 24 | 0 | 2 |
| SACTE_0841 | | ACTE_Winged helix-turn-helix transcription repressor DNA-binding | 0 | 0 | 0 | 0 | 8 | 4 | 0 | 2 |
| SACTE_1897 | | ACTE_hypothetical protein | 0 | 3 | 0 | 0 | 4 | 0 | 0 | 2 |
| SACTE_4728 | | ACTE_Aminotransferase, class IV | 0 | 0 | 0 | 0 | 0 | 0 | 0 | 2 |
| SACTE_1619 | | ACTE_Glutamine synthetase, beta-Grasp | 0 | 0 | 0 | 2 | 0 | 3 | 5 | 0 |
| SACTE_5859 | | ACTE_hypothetical protein | 0 | 13 | 0 | 6 | 66 | 27 | 51 | 0 |
| SACTE_5231 | GH31 | ACTE_Glycoside hydrolase, family 31 | 0 | 2 | 0 | 41 | 2 | 4 | 21 | 0 |
| SACTE_1073 | | ACTE_Proteasome, alpha subunit | 0 | 0 | 0 | 0 | 2 | 2 | 11 | 0 |
| SACTE_1901 | GH51 | ACTE_Alpha-L-arabinofuranosidase, C-terminal | 0 | 0 | 0 | 0 | 8 | 9 | 7 | 0 |
| SACTE_1074 | | ACTE_Proteasome, subunit alpha/beta | 0 | 0 | 0 | 0 | 7 | 0 | 7 | 0 |
| SACTE_6558 | | ACTE_Quinoprotein amine dehydrogenase, beta chain-like | 6 | 16 | 0 | 11 | 17 | 24 | 5 | 0 |
| SACTE_4718 | | ACTE_Delta-1-pyrroline-5-carboxylate dehydrogenase 1 | 3 | 0 | 0 | 3 | 14 | 4 | 5 | 0 |
| SACTE_6303 | | ACTE_Serine/cysteine peptidase, trypsin-like | 0 | 0 | 0 | 0 | 8 | 0 | 5 | 0 |
| SACTE_5482 | | ACTE_Aldo/keto reductase, conserved site | 5 | 4 | 0 | 3 | 4 | 0 | 5 | 0 |
| SACTE_1650 | | ACTE_Bacterial extracellular solute-binding, family 1 | 6 | 2 | 0 | 0 | 0 | 0 | 4 | 0 |
| SACTE_0782 | | ACTE_Transcription regulator PadR N-terminal-like | 0 | 0 | 0 | 0 | 0 | 0 | 4 | 0 |
| SACTE_1895 | | ACTE_Mandelate racemase/muconate lactonizing enzyme, N-terminal | 0 | 0 | 0 | 2 | 9 | 6 | 3 | 0 |

Figure 18 (Continued)

| ID | Family | Description | | | | | | |
|---|---|---|---|---|---|---|---|---|
| SACTE_3219 | | ACTE_Methionyl-tRNA synthetase, class Ia, N-terminal | 14 | 7 | 0 | 0 | 2 | 0 |
| SACTE_6051 | | ACTE_Catalase | 0 | 8 | 0 | 0 | 0 | 0 |
| SACTE_1473 | | ACTE_Dienelactone hydrolase | 0 | 0 | 0 | 0 | 0 | 3 |
| SACTE_0534 | | ACTE_Bacterial extracellular solute-binding, family 1 | 0 | 0 | 0 | 0 | 0 | 3 |
| SACTE_1136 | | ACTE_Peptidoglycan recognition protein | 3 | 1 | 0 | 11 | 0 | 3 |
| SACTE_1344 | | ACTE_Pyridoxal phosphate-dependent transferase, major domain | 13 | 0 | 0 | 0 | 5 | 2 |
| SACTE_1859 | | ACTE_Bacterial stress protein | 9 | 395 | 0 | 298 | 77 | 2 |
| SACTE_2065 | | ACTE_Peptidase S8/S53, subtilisin/kexin/sedolisin | 31 | 1219 | 0 | 121 | 26 | 38 |
| SACTE_3700 | | ACTE_Bacterial stress protein | 162 | 207 | 0 | 198 | 68 | 37 |
| SACTE_4624 | GH16 | ACTE_Concanavalin A-like lectin/glucanase | 0 | 26 | 0 | 0 | 17 | 28 |
| SACTE_1250 | | ACTE_Peptidase S8/S53, subtilisin, active site | 7 | 8 | 0 | 50 | 13 | 11 |
| SACTE_5685 | GH13 | ACTE_Glycoside hydrolase, subgroup, catalytic core | 0 | 10 | 0 | 5 | 14 | 8 |
| SACTE_0364 | GH87 | ACTE_Galactose-binding domain-like | 0 | 0 | 0 | 5 | 9 | 5 |
| SACTE_1312 | PL1 | ACTE_Pectate lyase/Amb allergen | 0 | 0 | 0 | 5 | 4 | 4 |
| SACTE_5682 | | ACTE_Galactose-binding domain-like | 0 | 44 | 0 | 14 | 4 | 3 |
| SACTE_5606 | | ACTE_D-hydantoinase | 0 | 1 | 0 | 3 | 3 | 2 |
| SACTE_3777 | | ACTE_Aldo/keto reductase | 0 | 4 | 0 | 0 | 15 | 2 |
| SACTE_5880 | | ACTE_Twin-arginine translocation pathway, signal sequence | 0 | 19 | 0 | 7 | 12 | 0 |
| SACTE_5741 | | ACTE_NAD(P)-binding domain | 0 | 0 | 0 | 0 | 8 | 0 |
| SACTE_2762 | | ACTE_hypothetical protein | 0 | 0 | 0 | 0 | 8 | 0 |
| SACTE_1162 | | ACTE_Lipase, class 2 | 0 | 0 | 0 | 0 | 7 | 0 |
| SACTE_1640 | GH13 | ACTE_Glycoside hydrolase, carbohydrate-binding | 0 | 0 | 0 | 0 | 7 | 0 |
| SACTE_2544 | | ACTE_Thiolase, C-terminal | 0 | 5 | 0 | 0 | 6 | 0 |
| SACTE_2213 | | ACTE_NAD(P)-binding domain | 0 | 0 | 0 | 0 | 5 | 0 |
| SACTE_4459 | | ACTE_Peptidoglycan binding-like | 0 | 0 | 0 | 0 | 5 | 0 |
| SACTE_4102 | | ACTE_Fumarate reductase/succinate dehydrogenase, FAD-binding site | 20 | 12 | 0 | 15 | 4 | 0 |
| SACTE_5740 | | ACTE_Twin-arginine translocation pathway, signal sequence | 0 | 0 | 0 | 10 | 4 | 0 |
| SACTE_0133 | CBM35,6 | ACTE_Galactose-binding domain-like | 0 | 0 | 0 | 2 | 3 | 0 |
| SACTE_4566 | | ACTE_ATPase, F1 complex, alpha subunit, C-terminal | 72 | 0 | 0 | 2 | 3 | 0 |
| SACTE_4568 | | ACTE_ATPase, F1 complex, beta subunit | 32 | 0 | 0 | 0 | 3 | 0 |
| SACTE_6063 | | ACTE_Protein of unknown function DUF336 | 0 | 0 | 0 | 0 | 3 | 0 |
| SACTE_3962 | | ACTE_Peptidase S1A, chymotrypsin | 0 | 0 | 0 | 0 | 3 | 0 |
| SACTE_2518 | | ACTE_Acyl-CoA dehydrogenase/oxidase, N-terminal | 0 | 0 | 0 | 0 | 3 | 0 |
| SACTE_1738 | | ACTE_N-acetyl-gamma-glutamyl-phosphate reductase | 0 | 0 | 0 | 0 | 3 | 0 |
| SACTE_3227 | | ACTE_Peptidase M18, aminopeptidase I | 0 | 24 | 0 | 5 | 2 | 0 |
| SACTE_1995 | | ACTE_Gamma-glutamyl phosphate reductase GPR | 0 | 0 | 0 | 3 | 2 | 0 |
| SACTE_5109 | | ACTE_Luciferase-like | 0 | 29 | 0 | 0 | 2 | 0 |
| SACTE_5881 | | ACTE_Multicopper oxidase, type 2 | 0 | 0 | 0 | 0 | 2 | 0 |
| SACTE_3741 | | ACTE_Twin-arginine translocation pathway, signal sequence | 0 | 0 | 0 | 0 | 2 | 0 |
| SACTE_1638 | | ACTE_Tautomerase | 0 | 0 | 0 | 0 | 2 | 0 |
| SACTE_0528 | GH115 | ACTE_Twin-arginine translocation pathway, signal sequence | 0 | 0 | 0 | 50 | 0 | 0 |
| SACTE_3197 | | ACTE_Heat shock protein DnaJ-like protein djlA | 241 | 0 | 0 | 44 | 0 | 0 |
| SACTE_4483 | | ACTE_Cyclic nucleotide-binding-like | 0 | 0 | 0 | 24 | 0 | 0 |
| SACTE_5630 | | ACTE_Aldo/keto reductase | 0 | 0 | 0 | 17 | 0 | 0 |
| SACTE_1603 | | ACTE_Peptidase M17, leucyl aminopeptidase, C-terminal | 0 | 20 | 0 | 16 | 0 | 0 |
| SACTE_1239 | | ACTE_Enoyl-[acyl-carrier-protein] reductase (NADH) | 0 | 0 | 0 | 14 | 0 | 0 |
| SACTE_0169 | | ACTE_Glyceraldehyde 3-phosphate dehydrogenase, active site | 0 | 41 | 0 | 12 | 0 | 0 |
| SACTE_3335 | | ACTE_Single-strand DNA-binding | 7 | 35 | 0 | 12 | 0 | 0 |
| SACTE_0365 | | ACTE_Peptidase S8/S53, subtilisin/kexin/sedolisin | 0 | 15 | 0 | 11 | 0 | 0 |
| SACTE_1434 | | ACTE_5'-Nucleotidase/apyrase | 12 | 14 | 0 | 11 | 0 | 0 |
| SACTE_1680 | | ACTE_Cupredoxin | 0 | 3 | 0 | 10 | 0 | 0 |
| SACTE_1003 | | ACTE_NAD(P)-binding domain | 0 | 0 | 0 | 10 | 0 | 0 |
| SACTE_0549 | GH16 | ACTE_Concanavalin A-like lectin/glucanase | 0 | 14 | 0 | 9 | 0 | 0 |
| SACTE_1325 | | ACTE_Dihydrodipicolinate synthetase | 0 | 0 | 0 | 9 | 0 | 0 |

Figure 18 (Continued)

| ID | Category | Description | | | | |
|---|---|---|---|---|---|---|
| SACTE_1324 | | ACTE_hypothetical protein | 0 | 0 | 0 | 0 |
| SACTE_0222 | | ACTE_Peptidase M4, propeptide, PepSY | 0 | 21 | 0 | 9 |
| SACTE_2068 | | ACTE_Peptidase M1, aminopeptidase N actinomycete-type | 6 | 15 | 0 | 8 |
| SACTE_1281 | | ACTE_Surface protein from Gram-positive cocci | 0 | 3 | 0 | 8 |
| SACTE_4038 | | ACTE_Cystathionine beta-synthase, core | 6 | 0 | 0 | 8 |
| SACTE_4081 | | ACTE_NAD(P)-binding domain | 13 | 7 | 0 | 7 |
| SACTE_2819 | | ACTE_Chaperonin ClpA/B, conserved site | 5 | 0 | 0 | 7 |
| SACTE_3589 | | ACTE_5'-Nucleotidase/apyrase | 0 | 0 | 0 | 7 |
| SACTE_6144 | | ACTE_Twin-arginine translocation pathway, signal sequence | 0 | 2 | 0 | 6 |
| SACTE_4739 | GH3 | ACTE_Na-Ca exchanger/integrin-beta4 | 0 | 1 | 0 | 6 |
| SACTE_4768 | | ACTE_Glutamyl/glutaminyl-tRNA synthetase, class Ic, catalytic domain | 0 | 0 | 0 | 6 |
| SACTE_4860 | | ACTE_Aminotransferase class-III | 17 | 5 | 0 | 5 |
| SACTE_3765 | | ACTE_hypothetical protein | 0 | 4 | 0 | 5 |
| SACTE_0687 | | ACTE_Protein of unknown function DUF885, bacterial | 7 | 0 | 0 | 5 |
| SACTE_1715 | | ACTE_Intermediate filament, C-terminal | 0 | 45 | 0 | 4 |
| SACTE_0325 | | ACTE_Bacterial stress protein | 0 | 7 | 0 | 4 |
| SACTE_5146 | | ACTE_FMN-binding split barrel, related | 0 | 0 | 0 | 4 |
| SACTE_4910 | | ACTE_Dihydrodipicolinate reductase, N-terminal | 0 | 0 | 0 | 4 |
| SACTE_0213 | | ACTE_Luciferase-like | 0 | 0 | 0 | 4 |
| SACTE_1311 | CE8 | ACTE_Pectinesterase, catalytic | 0 | 0 | 0 | 4 |
| SACTE_1313 | CE12 | ACTE_Lipase, GDSL | 0 | 0 | 0 | 3 |
| SACTE_6512 | CBM13 | ACTE_Cadherin-like | 0 | 15 | 0 | 3 |
| SACTE_5114 | | ACTE_Ornithine carbamoyltransferase | 0 | 1 | 0 | 3 |
| SACTE_2698 | | ACTE_hypothetical protein | 0 | 1 | 0 | 3 |
| SACTE_4618 | | ACTE_Phosphofructokinase, pyrophosphate dependent | 5 | 0 | 0 | 3 |
| SACTE_1240 | | ACTE_NAD(P)-binding domain | 3 | 0 | 0 | 3 |
| SACTE_6206 | | ACTE_hypothetical protein | 0 | 0 | 0 | 3 |
| SACTE_4814 | | ACTE_Ribosomal protein L19 | 0 | 0 | 0 | 2 |
| SACTE_2318 | | ACTE_HAD-superfamily hydrolase, subfamily IIA | 2 | 0 | 0 | 2 |
| SACTE_1862 | | ACTE_Transketolase, C-terminal/Pyruvate-ferredoxin oxidoreductase, dom | 0 | 0 | 0 | 0 |
| SACTE_5493 | | ACTE_Periplasmic binding protein/Lacl transcriptional regulator | 0 | 12 | 0 | 0 |
| SACTE_1002 | | ACTE_Twin-arginine translocation pathway, signal sequence | 5 | 4 | 0 | 0 |
| SACTE_2381 | | ACTE_Exoribonuclease, phosphorolytic domain 2 | 0 | 1 | 0 | 0 |
| SACTE_1703 | | ACTE_Periplasmic binding protein | 2 | 81 | 0 | 0 |
| SACTE_5235 | GH92 | ACTE_Galactose-binding domain-like | 0 | 25 | 0 | 0 |
| SACTE_2966 | | ACTE_Pyridoxal phosphate-dependent transferase, major domain | 0 | 24 | 0 | 0 |
| SACTE_2238 | | ACTE_Putative agmatinase | 5 | 21 | 0 | 0 |
| SACTE_1694 | | ACTE_NAD(P)-binding domain | 0 | 21 | 0 | 0 |
| SACTE_0323 | CBM32 | ACTE_Galactose-binding domain-like | 5 | 16 | 0 | 0 |
| SACTE_4616 | | ACTE_Acetate/butyrate kinase | 5 | 15 | 0 | 0 |
| SACTE_5312 | | ACTE_Peptidase M24, structural domain | 0 | 15 | 0 | 0 |
| SACTE_4503 | | ACTE_NAD(P)-binding domain | 0 | 13 | 0 | 0 |
| SACTE_4366 | | ACTE_4Fe-4S ferredoxin, iron-sulpur binding domain | 0 | 13 | 0 | 0 |
| SACTE_0275 | | ACTE_Aldehyde/histidinol dehydrogenase | 0 | 13 | 0 | 0 |
| SACTE_0800 | | ACTE_Glycine cleavage system P-protein, N-terminal | 7 | 10 | 0 | 0 |
| SACTE_5452 | | ACTE_Transthyretin/hydroxyisourate hydrolase | 0 | 10 | 0 | 0 |
| SACTE_0378 | | ACTE_Twin-arginine translocation pathway, signal sequence | 0 | 10 | 0 | 0 |
| SACTE_1426 | | ACTE_Extracellular ligand-binding receptor | 6 | 9 | 0 | 0 |
| SACTE_2063 | | ACTE_Peptidase M1, aminopeptidase N actinomycete-type | 0 | 9 | 0 | 0 |
| SACTE_1081 | | ACTE_tRNA methyltransferase complex GCD14 subunit | 0 | 9 | 0 | 0 |
| SACTE_6392 | | ACTE_Peptidase S33, prolyl aminopeptidase | 0 | 8 | 0 | 0 |
| SACTE_5353 | | ACTE_NAD(P)-binding domain | 0 | 7 | 0 | 0 |
| SACTE_3611 | | ACTE_L-asparaginase II | 0 | 7 | 0 | 0 |
| SACTE_3235 | | ACTE_Peptidase S11, D-alanyl-D-alanine carboxypeptidase A | 0 | 7 | 0 | 0 |

Figure 18 (Continued)

| ID | CAZy | Description | C1 | C2 | C3 | C4 | C5 |
|---|---|---|---|---|---|---|---|
| SACTE_1582 | | ACTE_Cytochrome c oxidase subunit II C-terminal | 0 | 7 | 0 | 0 | 0 |
| SACTE_5319 | GH13 | ACTE_Malto-oligosyltrehalose synthase | 0 | 7 | 0 | 0 | 0 |
| SACTE_6361 | | ACTE_Molybdenum-pterin binding | 0 | 6 | 0 | 0 | 0 |
| SACTE_5555 | | ACTE_Beta-lactamase-like | 0 | 6 | 0 | 0 | 0 |
| SACTE_5395 | | ACTE_Barstar (barnase inhibitor) | 0 | 6 | 0 | 0 | 0 |
| SACTE_4606 | | ACTE_Cobalamin (vitamin B12)-dependent enzyme, catalytic subdomain | 0 | 6 | 0 | 0 | 0 |
| SACTE_4371 | | ACTE_Conserved hypothetical protein CHP00730 | 0 | 6 | 0 | 0 | 0 |
| SACTE_1827 | | ACTE_Protease inhibitor I4, serpin | 0 | 6 | 0 | 0 | 0 |
| SACTE_5743 | CBM6 | ACTE_PKD/Chitinase domain | 0 | 6 | 0 | 0 | 0 |
| SACTE_4399 | | ACTE_Protein of unknown function DUF3107 | 14 | 5 | 0 | 0 | 0 |
| SACTE_3023 | | ACTE_hypothetical protein | 0 | 5 | 0 | 0 | 0 |
| SACTE_1131 | | ACTE_N-acetylmuramoyl-L-alanine amidase, family 2 | 0 | 5 | 0 | 0 | 0 |
| SACTE_0847 | | ACTE_Twin-arginine translocation pathway, signal sequence | 0 | 5 | 0 | 0 | 0 |
| SACTE_4591 | | ACTE_Thiolase-like | 20 | 4 | 0 | 0 | 0 |
| SACTE_1151 | | ACTE_Cupin, RmlC-type | 2 | 4 | 0 | 0 | 0 |
| SACTE_6170 | | ACTE_Domain of unknown function DUF1996 | 0 | 4 | 0 | 0 | 0 |
| SACTE_5742 | | ACTE_Xylose isomerase-like, TIM barrel domain | 0 | 4 | 0 | 0 | 0 |
| SACTE_5113 | | ACTE_Arginine deiminase | 0 | 4 | 0 | 0 | 0 |
| SACTE_4590 | | ACTE_Glyoxalase/bleomycin resistance protein/dioxygenase | 0 | 4 | 0 | 0 | 0 |
| SACTE_4101 | | ACTE_Ferredoxin | 0 | 4 | 0 | 0 | 0 |
| SACTE_2614 | | ACTE_Deoxyribonuclease, TatD Mg-dependent, prokaryote | 0 | 4 | 0 | 0 | 0 |
| SACTE_2342 | | ACTE_hypothetical protein | 0 | 4 | 0 | 0 | 0 |
| SACTE_1575 | | ACTE_Rieske [2Fe-2S] iron-sulphur domain | 0 | 4 | 0 | 0 | 0 |
| SACTE_1224 | | ACTE_Band 7 protein | 0 | 4 | 0 | 0 | 0 |
| SACTE_0983 | | ACTE_Arginine biosynthesis protein ArgJ | 0 | 4 | 0 | 0 | 0 |
| SACTE_0872 | | ACTE_Cystathionine beta-synthase, core | 0 | 4 | 0 | 0 | 0 |
| SACTE_6011 | GH27 | ACTE_Glycoside hydrolase, family 27 | 0 | 4 | 0 | 0 | 0 |
| SACTE_6458 | GH25 | ACTE_Glycoside hydrolase, family 25 subgroup | 0 | 4 | 0 | 0 | 0 |
| SACTE_6165 | | ACTE_NAD(P)-binding domain | 0 | 3 | 0 | 0 | 0 |
| SACTE_5944 | | ACTE_FMN-binding split barrel, related | 0 | 3 | 0 | 0 | 0 |
| SACTE_5619 | | ACTE_Isocitrate dehydrogenase NADP-dependent, monomeric type | 0 | 3 | 0 | 0 | 0 |
| SACTE_5406 | | ACTE_Aldehyde oxidase/xanthine dehydrogenase, molybdopterin binding | 0 | 3 | 0 | 0 | 0 |
| SACTE_4968 | | ACTE_Bacterial stress protein | 0 | 3 | 0 | 0 | 0 |
| SACTE_3045 | | ACTE_Lipase, GDSL | 0 | 3 | 0 | 0 | 0 |
| SACTE_2702 | | ACTE_Luciferase-like | 0 | 3 | 0 | 0 | 0 |
| SACTE_2272 | | ACTE_Acyl-CoA dehydrogenase/oxidase, N-terminal | 0 | 3 | 0 | 0 | 0 |
| SACTE_1479 | | ACTE_Imidazoleglycerol-phosphate dehydratase, conserved site | 0 | 3 | 0 | 0 | 0 |
| SACTE_5320 | GH13 | ACTE_Immunoglobulin-like fold | 0 | 3 | 0 | 0 | 0 |
| SACTE_5226 | GH1 | ACTE_Glycoside hydrolase, family 1 | 0 | 3 | 0 | 0 | 0 |
| SACTE_1368 | | ACTE_Phosphoglycerate kinase | 13 | 2 | 0 | 0 | 0 |
| SACTE_4205 | | ACTE_Cys/Met metabolism, pyridoxal phosphate-dependent enzyme | 7 | 2 | 0 | 0 | 0 |
| SACTE_5135 | | ACTE_Concanavalin A-like lectin/glucanase | 0 | 2 | 0 | 0 | 0 |
| SACTE_4745 | | ACTE_Periplasmic binding protein | 0 | 2 | 0 | 0 | 0 |
| SACTE_4639 | | ACTE_Galactose-binding domain-like | 0 | 2 | 0 | 0 | 0 |
| SACTE_3833 | | ACTE_Ferredoxin | 0 | 2 | 0 | 0 | 0 |
| SACTE_2202 | | ACTE_Metallophosphoesterase | 0 | 2 | 0 | 0 | 0 |
| SACTE_0583 | | ACTE_Serine/threonine-protein kinase, active site | 0 | 2 | 0 | 0 | 0 |
| SACTE_0561 | GH43 | ACTE_Glycoside hydrolase, family 43 | 0 | 2 | 0 | 0 | 0 |
| SACTE_4106 | GH20 | ACTE_Glycoside hydrolase, family 20 | 0 | 2 | 0 | 0 | 0 |
| SACTE_5065 | CE4 | ACTE_Glycoside hydrolase/deacetylase, beta/alpha-barrel | 0 | 2 | 0 | 0 | 0 |
| SACTE_2290 | CBM2 | ACTE_Cellulose-binding domain, family II, bacterial type | 0 | 2 | 0 | 0 | 0 |
| SACTE_4042 | | ACTE_FAD-dependent glycerol-3-phosphate dehydrogenase | 0 | 1 | 0 | 0 | 0 |
| SACTE_3354 | | ACTE_Cys/Met metabolism, pyridoxal phosphate-dependent enzyme | 0 | 1 | 0 | 0 | 0 |
| SACTE_3102 | | ACTE_DeoxyUTP pyrophosphatase domain | 0 | 1 | 0 | 0 | 0 |

Figure 18 (Continued)

| ID | Category | Description | V1 | V2 | V3 | V4 | V5 | V6 |
|---|---|---|---|---|---|---|---|---|
| SACTE_2853 | | ACTE_Protein of unknown function DUF2342 | 0 | 0 | 0 | 0 | 0 | 0 |
| SACTE_2831 | | ACTE_Pyridoxal phosphate-dependent transferase, major domain | 0 | 0 | 1 | 0 | 0 | 0 |
| SACTE_2532 | | ACTE_Peptidase M20, dimerisation | 0 | 0 | 1 | 0 | 0 | 0 |
| SACTE_2215 | | ACTE_Peptidase M7, snapalysin | 0 | 0 | 1 | 0 | 0 | 0 |
| SACTE_1681 | | ACTE_Nitrilase/cyanide hydratase, conserved site | 0 | 0 | 1 | 0 | 0 | 0 |
| SACTE_1509 | | ACTE_Predicted pyridoxal phosphate-dependent enzyme, YBL036C type | 0 | 0 | 1 | 0 | 0 | 0 |
| SACTE_1424 | | ACTE_Aspartate decarboxylase-like fold | 0 | 0 | 1 | 0 | 0 | 0 |
| SACTE_1355 | | ACTE_Transketolase, C-terminal/Pyruvate-ferredoxin oxidoreductase, dom | 0 | 0 | 1 | 0 | 0 | 0 |
| SACTE_2877 | GH64 | ACTE_Twin-arginine translocation pathway, signal sequence | 0 | 0 | 1 | 0 | 0 | 0 |
| SACTE_4708 | CBM35 | ACTE_Soluble quinoprotein glucose/sorbosone dehydrogenase | 0 | 0 | 0 | 0 | 0 | 0 |
| SACTE_1419 | | ACTE_Ribosomal protein S1, RNA-binding domain | 126 | 0 | 0 | 0 | 0 | 0 |
| SACTE_1888 | | ACTE_Acyl carrier protein-like | 60 | 0 | 0 | 0 | 0 | 0 |
| SACTE_2468 | | ACTE_Bacterial NAD-glutamate dehydrogenase | 36 | 0 | 0 | 0 | 0 | 0 |
| STRACTE_3896 | | STRACTE_03857 | 35 | 0 | 0 | 0 | 0 | 0 |
| STRACTE_3716 | | STRACTE_03676 | 28 | 0 | 0 | 0 | 0 | 0 |
| SACTE_4281 | | STRACTE_04237 | 27 | 0 | 0 | 0 | 0 | 0 |
| SACTE_3955 | | STRACTE_03916 | 25 | 0 | 0 | 0 | 0 | 0 |
| SACTE_4565 | | STRACTE_04519 | 23 | 0 | 0 | 0 | 0 | 0 |
| SACTE_4031 | | ACTE_Chaperonin Cpn60 | 22 | 0 | 0 | 0 | 0 | 0 |
| SACTE_3086 | | ACTE_hypothetical protein | 22 | 0 | 0 | 0 | 0 | 0 |
| SACTE_4376 | | STRACTE_04332 | 19 | 0 | 0 | 0 | 0 | 0 |
| SACTE_4194 | | ACTE_Twin-arginine translocation pathway, signal sequence | 18 | 0 | 0 | 0 | 0 | 0 |
| SACTE_1934 | | ACTE_ATP-grasp fold, subdomain 2 | 18 | 0 | 0 | 0 | 0 | 0 |
| SACTE_4501 | | STRACTE_04456 | 17 | 0 | 0 | 0 | 0 | 0 |
| SACTE_4959 | | STRACTE_04913 | 16 | 0 | 0 | 0 | 0 | 0 |
| SACTE_2103 | | ACTE_Protein of unknown function DUF756 | 16 | 0 | 0 | 0 | 0 | 0 |
| SACTE_4795 | | ACTE_SCP-like extracellular | 15 | 0 | 0 | 0 | 0 | 0 |
| SACTE_4073 | | ACTE_NAD(P)-binding domain | 15 | 0 | 0 | 0 | 0 | 0 |
| SACTE_2558 | | STRACTE_02525 | 15 | 0 | 0 | 0 | 0 | 0 |
| SACTE_4224 | | STRACTE_04182 | 13 | 0 | 0 | 0 | 0 | 0 |
| SACTE_3067 | | STRACTE_03033 | 13 | 0 | 0 | 0 | 0 | 0 |
| SACTE_4462 | | STRACTE_04417 | 12 | 0 | 0 | 0 | 0 | 0 |
| SACTE_3361 | | STRACTE_03325 | 12 | 0 | 0 | 0 | 0 | 0 |
| SACTE_3995 | | ACTE_RNA polymerase, alpha subunit, C-terminal | 11 | 0 | 0 | 0 | 0 | 0 |
| SACTE_0514 | | STRACTE_00503 | 11 | 0 | 0 | 0 | 0 | 0 |
| SACTE_6342 | | ACTE_Biotin/lipoyl attachment | 10 | 0 | 0 | 0 | 0 | 0 |
| SACTE_4610 | | STRACTE_04564 | 10 | 0 | 0 | 0 | 0 | 0 |
| SACTE_1068 | | STRACTE_01051 | 10 | 0 | 0 | 0 | 0 | 0 |
| SACTE_4926 | | ACTE_Ferritin-related | 9 | 0 | 0 | 0 | 0 | 0 |
| SACTE_4830 | | STRACTE_04784 | 9 | 0 | 0 | 0 | 0 | 0 |
| SACTE_3392 | | STRACTE_03356 | 9 | 0 | 0 | 0 | 0 | 0 |
| SACTE_3037 | | ACTE_Tellurium resistance | 9 | 0 | 0 | 0 | 0 | 0 |
| SACTE_2403 | | STRACTE_02370 | 9 | 0 | 0 | 0 | 0 | 0 |
| SACTE_5983 | | STRACTE_05928 | 8 | 0 | 0 | 0 | 0 | 0 |
| SACTE_4283 | | STRACTE_04239 | 8 | 0 | 0 | 0 | 0 | 0 |
| SACTE_3385 | | STRACTE_03349 | 8 | 0 | 0 | 0 | 0 | 0 |
| SACTE_1328 | | STRACTE_01307 | 8 | 0 | 0 | 0 | 0 | 0 |
| SACTE_4415 | | STRACTE_04372 | 7 | 0 | 0 | 0 | 0 | 0 |
| SACTE_2431 | | STRACTE_02398 | 7 | 0 | 0 | 0 | 0 | 0 |
| SACTE_1586 | | STRACTE_01564 | 7 | 0 | 0 | 0 | 0 | 0 |
| SACTE_1201 | | STRACTE_01182 | 7 | 0 | 0 | 0 | 0 | 0 |
| SACTE_5081 | | ACTE_5-methyltetrahydropteroyltriglutamate--homocysteine S-methyltran | 6 | 0 | 0 | 0 | 0 | 0 |
| SACTE_4873 | | STRACTE_04827 | 6 | 0 | 0 | 0 | 0 | 0 |
| SACTE_3960 | | ACTE_Translation elongation factor EFG/EF2 | 6 | 0 | 0 | 0 | 0 | 0 |

Figure 18 (Continued)

| ID | Name | Count | | | | |
|---|---|---|---|---|---|---|
| SACTE_2756 | STRACTE_02721 | 6 | | | | |
| SACTE_3956 | ACTE_DNA-directed RNA polymerase, beta subunit, bacterial-type | 5 | | | 0 | 0 |
| SACTE_3948 | STRACTE_03909 | 5 | | | 0 | 0 |
| SACTE_2801 | STRACTE_02766 | 5 | | | 0 | 0 |
| SACTE_0810 | ACTE_Alpha-D-phosphohexomutase, alpha/beta/alpha domain II | 5 | | | 0 | 0 |
| SACTE_0669 | STRACTE_00659 | 5 | | | 0 | 0 |
| SACTE_5028 | STRACTE_04982 | 4 | | | 0 | 0 |
| SACTE_4567 | ACTE_ATPase, F1 complex, gamma subunit | 4 | | | 0 | 0 |
| SACTE_4397 | ACTE_Ferritin/ribonucleotide reductase-like | 4 | | | 0 | 0 |
| SACTE_4191 | ACTE_L-Aspartase-like | 4 | | | 0 | 0 |
| SACTE_4030 | ACTE_Chaperonin Cpn10, subgroup | 4 | | | 0 | 0 |
| SACTE_3961 | STRACTE_03922 | 4 | | | 0 | 0 |
| SACTE_3438 | ACTE_Uracil phosphoribosyl transferase | 4 | | | 0 | 0 |
| SACTE_3371 | STRACTE_03335 | 4 | | | 0 | 0 |
| SACTE_3088 | ACTE_Chaperonin ClpB | 4 | | | 0 | 0 |
| SACTE_2755 | STRACTE_02720 | 4 | | | 0 | 0 |
| SACTE_2729 | STRACTE_02694 | 4 | | | 0 | 0 |
| SACTE_2036 | ACTE_Aminoacyl-tRNA synthetase, class 1a, anticodon-binding | 4 | | | 0 | 0 |
| SACTE_1285 | STRACTE_01266 | 4 | | | 0 | 0 |
| SACTE_1006 | STRACTE_00988 | 4 | | | 0 | 0 |
| SACTE_0548 | ACTE_Aldo/keto reductase | 4 | | | 0 | 0 |
| SACTE_6004 | STRACTE_05949 | 3 | | | 0 | 0 |
| SACTE_5818 | STRACTE_05765 | 3 | | | 0 | 0 |
| SACTE_5021 | STRACTE_04975 | 3 | | | 0 | 0 |
| SACTE_5002 | ACTE_DNA topoisomerase, type IIA, subunit A/C-terminal | 3 | | | 0 | 0 |
| SACTE_4828 | ACTE_Translation elongation factor EFTs/EF1B, dimerisation | 3 | | | 0 | 0 |
| SACTE_4295 | STRACTE_04251 | 3 | | | 0 | 0 |
| SACTE_4186 | ACTE_Acetyl-coenzyme A carboxyltransferase, C-terminal | 3 | | | 0 | 0 |
| SACTE_3957 | ACTE_DNA-directed RNA polymerase, subunit beta-prime | 3 | | | 0 | 0 |
| SACTE_3895 | ACTE_Polyprenyl synthetase | 3 | | | 0 | 0 |
| SACTE_3892 | ACTE_Fumarylacetoacetase, N-terminal | 3 | | | 0 | 0 |
| SACTE_3284 | ACTE_Serine/threonine-protein kinase, active site | 3 | | | 0 | 0 |
| SACTE_2533 | STRACTE_02500 | 2 | | | 0 | 0 |
| SACTE_2035 | STRACTE_02006 | 2 | | | 0 | 0 |
| SACTE_1872 | ACTE_Beta-lactamase-related | 2 | | | 0 | 0 |
| SACTE_1045 | ACTE_Periplasmic binding protein | 2 | | | 0 | 0 |
| SACTE_5618 | STRACTE_05563 | 2 | | | 0 | 0 |
| SACTE_3950 | ACTE_Transcription antitermination protein, NusG | 2 | | | 0 | 0 |
| SACTE_3301 | STRACTE_03267 | 2 | | | 0 | |
| SACTE_0900 | ACTE_Chorismate synthase | 2 | | | 0 | |

Figure 19

>SACTE_0237|1, 4-beta cellobiohydrolase|GH6 (SEQ ID NO:17)
atgagccgcacgagccgcaccacctgcgccgatcccgaacagcactcatggcggcgggcgccctcgtcgccgcagccgcgggctcc
gccgcagccgcggcacccttcggtgccaccgccgccgcggcggccggctgcaccgtcgactacaagatccagaaccagtggaacggc
gggctcaccgcctcggtgagcgtcaccaacaacggggacgccatctccggctggcagctccagtggagcttcgccggcggcgagcag
gtcagccagggggtggaacgccaccgtctctcagagcggctccgccgtcaccgccaaggacgccggctacaacgccgccctggccacc
ggggcatcggcctccttcggtttcaacgcgacgggcaacggcaacagcgtcgtccccgcgacgttcaagctgaacggcgtcacctgcaa
cggcggcaccacgggcccgaccgatcccacggaccccacggacccgacggacccgaccgacccgccgcgggcaaccgtgtggac
aaccctaccagggagccaaggtctatgtgaaccggagtggtcggcgaacgccgcggccgagccgggcggcgacagaatcgccga
ccagcccaccggcgtctggctggaccgcatcgccgcgatcgagggcgcgaacggttcgatggtctgcgcgaccatctcgacgaggcc
ctgacgcagaaggctccggcgaactcgtcgtccaggtcgtcatctacaacctgcccggggcgagactgcgcggcgctggcctccaacgg
tgagctcggaccgaccgagatcggccgctacaagaccgagtacatcgaccgatcgcggagatcctcggcgaccgaagtacgcgggc
ctgcgcatcgtcaccacggtcgagatcgactcgctgccgaacctcgtcaccaacgccggcggccgccccacggccactccggcctgtga
cgtcatgaaggccaacggcaactacgtcaaggggcgtcggctacgcgctcaacaagctcggcgacgcgccaacgtctacaactacatcg
acgcgggccaccacggctggatcggctgggacgacaacttcggcgcctccgcggagatcttccacgaggccgcgaccgccgagggcg
cgaccgtcaacgacgtgcacggcttcatcaccaacaccgccaactacagcgcgctgaaggaggagaacttctccatcgacgacgccgtg
aacggcacgtcggtccggcagtcgaagtgggtcgactggaaccgctacacggacgagctgtccttcgcgcaggccttccgcaacgagct
ggtctccgtcggcttcaactccggcatcggcatgctcatcgacacctcccgcaacggctggggcggcgcgaaccggccgagcggaccg
ggcgcgaacaccagcgtcgacacctatgtggacggcggcgctacgaccgccgcatccacctgggcaactggtgcaaccaggcagga
gcgggtctcggcgaacgccgcaggccgccccgagccggggatcgacgcgtacgtctggatgaagcccccggggagtccgacgg
ttccagctcggagatcccgaacgacgagggcaagggattcgaccggatgtgcgacccgacctacacgggtaacgccgtaacaacaac
aacatgtcggggcgctggtggcgccccgtctccgggaagtggttctcggcccagttccaggagctcatgaagaacgcctacccggc
gctctag >SACTE_0236|glycoside hydrolase family 48|GH48 (SEQ ID NO:18)
gtggccgccctcgccctccccttgggaatgaccgcagcggccggcacggaggcccaggccgccgccgtcgcgtgcagcgtcgactac
acgaccagtgactggggatcggggttcaccaccgaactcaccctgaccaaccgggggctccgccgcgatcgacggctggaccctgacgt
acgactacgccgggaaccagcagctcacgagcggctggagcggcacctggtcccagtcaggcaagaccgtcagcgtgaagaacgcag
cctggaacggtgcgatcgccgccggtgccgccgtcacgaccggcgcgcagttcacctacagcggcgccaacaccgcaccgaccacctt
cgccgtcaacggcacggtctgcgcggggggccaccagccgccgatcgccgtcctcacctccccggcggcgggcgccgtcttctccgcc
ggggacccggttccgctggcggcgaccgccgcggccgcggacggggcgacgatcagcaaggtcgagttctacgacgacacgaccctc
ctcggcaccgacaccaccctcccgtacagctacgaggccgggcaactggcggccggcagccactccgtgtacgccagggcctacgaca
gcctcggcgcctccgcggattccccgcccgccggcatcaccgtcgtcaccggccccgcggtcgtcgtctccccgctcaactcggcgtcc
agcaggccaggtcgggaaccttcgacgtctcgctgtccaccgcgcccgcggcggacgtcaccgtcacggccgcccggtccgcgggtaa
caccgggctgagcgtcaccggcgggtcgaccctcaccttcaccccgcgaactggtccacaccccagaaggtgaccgtcacggccgac
ggctccggcaccggggccgcgaccttcaccgtcacggcccccggccaaggcgaggtcaccgtcacccagctggcggcggc
gaaggagtacgacgcccgttcctcgacctctacgggaagatcaccgatcccgcgaacggctacttctcgccggagggaatccctacca
ctccgtcgagacgctgatcgtcgaggcgcccgaccacgggcacgagaccacctcggaggcctacagctacctgatctggctgcaggcg
atgtacggcaagatcaccggcgactggaccaagttcaacggtgcgtgggacaccatggagacgtacatgatccccacccacgccgacca
gcccacgaactccttctacgacgcgtccaagcccgccacctacgcgcccgagcacgacacccgaacgagtacccgcggtgctcgac
ggctccgcctcctcggctccgaccgatcgcggcagagctgaagagcgcgtacggcaccgacgacatctacggcatgcactggatcca
ggacgtcgacaacgtctacggatacggcaacgcgcccggcacgtgcgcggccggccccacccaggccggtccgtcctacatcaacacc
ttccagcgcggctcgcaggagtcggtctgggagaccgtcacccacccgacctgcgacaacttcacgtacggcggcgccaacggctacct
cgacctgttcaccggggactcctcgtacgccaagcagtggaagttcaccaacgccccgacgccgacgccgcgccgtgcaggccgcc
tactgggccgacgtctgggcgaaggagcaggggaaggcggcgaagtcgccgacaccgtcggcaaggcggcgaagatgggtgacta Figure 19 (continued)

cctgcgctactccatgttcgacaagtacttcaagaagatcggcgactgcgtcggcccgaccacctgcccggccggctccggcaaggaca
gcgcgcactacctgatgtcctggtactacgcctggggcggcgccaccgacacctcggccggctggtcctggcggatcggctccagccac
gcccacggggggataccagaacccgatggcggcctacgcgctgagctccgtggccgacctcaagcccaagtcggccaccggagcgcag
gactgggccaagagcctggaccgccaactggacttctaccagtggctccagtccgacgagggtgccatcgcgggcggtgccgaccaaca
gctggaagggcagctacgcccagcccccggccggcacgccgaccttctacggcatgtactacgacgagaagcccgtgtaccacgaccc
gccgtccaaccagtggttcggcttccaggcgtggtccatggagcgcgtcgccgagtactaccacgagtcgggtgacgccaggcgaagg
ccgtgctcgacaagtgggtcgactgggccctgtccgagacgaccgtcaacccggacggcacctatctgatgccctccaccctccagtggt
cgggcgcgccggacacctggaacgcctcgaaccccggtgccaacgccagctccacgtcacggtcgccgactacaccgacgacgtcg
gcgtggccggcgcgtacgcccggacactgacctactacgcgccaagtccggtgacacggaggccgaggccaccgccgaggcgctg
ctcgacggcatgtggcagcaccaccaggacgacgccggcgtggcggtgcccgagacccgcgccgactacaaccggttcgacgacccg
gtctacgtccccggtggctggacgggcgccatgcccaacggtgacaccgtcgacgaggactcgacgttcctctccatccgctccttctaca
aggacgacccgaactggccccaggtgcaggcgtacctggacggcggtgccgccccggtcttcacctaccaccggttctgggcgcaggc
cgacatcgcactggccctggggggcgtacgccgacctcctggagtga >SACTE_3159|chitin-binding domain 3 protein|CBM33,2 (SEQ ID NO:19)
atggctagacgcagcagactcatctccctggcagcggtgctggccaccctgctcggggcgctcggcctcaccgcactctggccgggcaa
ggcggaggcgcacggtgtcgcgatgaccccggatcgcgtacctatctgtgccagctcgacgcctgtccggcaccggcgcgctgaac
cccacgaacccggcctgccgggacgcgctgagccagagcggcgcgaacgcgctgtacaactggttcgccgtgctcgactccaacgcg
ggcggccgcggcgcgggatatgtgccggacggcagcctgtgcagtgccggtgaccgctccccgtacgacttctccgcctacaacgcg
cccgcgccgactggccccggacacatctgacctccggtgcgacgctcaaggtgcagtacagcaactgggccgccaccccggtgacttc
cgggtctacctgaccaagccgggctgggcacccacgtccgaactcgcttgggacgaccttcagttggtacagaccgtaagcaacccgcc
gcagcagggcggggcgggcaccaacgcgggcactactactgggacctggcgctgccgtcgggccgttccggtgacgcgctgatgttc
atccagtgggtgcgttcggacagtcaggagaacttcttctcctgctcggacatcgtcttcgacggcggcaacggcgaggtgacgggaatcg
gcggcacgggcacccccaccccactccgaccccgactccgaccccgacggacccggagcactccggttcctgcatggccgt
ctacaacgtcgtcagctcctgggccggtggcttccaggcctccgtcgaggtgatgaaccacggtacggaaccgcgcaacggctgggccg
tgcagtggaagcccggttccgggacgcagatcaacagcgtgtggaacggctccctctccaccgggtccgacggcaccgtgacggtgcg
cgacgtggaccacaaccgtgtcatcgcccggacggcagtgtgaccttcgggttcaccgccacctccacgggcaacgactaccccgccg
ggacgatcgggtgtgtgacgtcctag >SACTE_0482|glycoside hydrolase family 5|GH5 (SEQ ID NO:20)
gtgaaacgcttctggccttactggccacctgcgcgacggtcctgggcctcacggcactgaccggccccaggcggtggccgccgcggg
ctgcacggccgactacacgatcaccagccagtggcagggcggcttccaggccgcggtgaaggtcaccaacctgggaaccccgtgacc
gggtggaagctcacgttcaccctgccggacgcgggacagaaggtcgtccagggctggaacgccgctggtcgcagtcgggttccgcgg
tcaccgccgccggcgccgactggaacggcacactggccaccggcgcgtcggccgaggcgggcttcgtgggctccttcacgggcgcca
acccgcctccacggcgttcgcgctcaacggtgtcgcctgtacgggctccaccggagaaccccggccggctccgacggcggcacccc
cgtggacgtcaacggcagctccacgtctgcggggtgaacctctgcaaccagtacgaccggcccgtgcagctgcggggtatgagcacg
cacggcatccagtggttcgacgcctgctacgacgccgcccctggacgcgctggcgaacgactggaagtcggacctgctgcgcatcgc
catgtacgtgcaggaggacggttacgagaccgacccggcgggcttcacccggcgcgtgaacgacctcgtcgacatggccgaggcccgc
ggcatgtacgcgttgatcgacttccacaccctgaccccggcgacccgaacgtcaacctcgaccgcgccaagacgttcttcgcgtccgtc
gccgcgcgcaacgccggcaagaagaacgtgatctacgagatcgccaacgagcccaacggcgtgacctggacggccgtcaagagctac
gccgagcaggtcatcccggtgatccgggccgccgaccccgacgccgtcgtcatcgtcggcacccgcggctggtcctcgctgggcgtctc
ggacggctccgacgagagcgaggtcgtcaacagccccgtcaatgccaccaacatcatgtacgcgttccactctacgcagcgagccaca
aggacgcctaccgctccacgctgagccggggcggcggcgcggcttccgctcttcgtcaccgagttcggcacggtgagcgccaccggcgg
cggggcgatggaccgggcgagcaccacggcctggctggacctgctcgaccagctgaagatcagctatgcgaactggacctattccgac Figure 19 (continued)

gcgcccgagagcagcgcggcgttccggccgggcacctgcggcggcggcgactacagcggcagcggcgtgctgaccgagtccgggg
cgctgctcaagaaccggatcagcaccccgattccttccccaccggctga >SACTE_0265|glycoside hydrolase family 10|GH10 (SEQ ID NO:21)
atggccaagaaaatccccgcccgtgccagacgggcactctccgtcctgacggcgggcgtgctcgccgccgccggcgtcgtctcgctcgc
cggcacggccgaggcagcaggcaccctgggtgacgcggcggcggcgaaggggccggtacttcggcaccgcggtcgcggcgaaccac
ctcggcgaggcaccgtacgcgtccacgctggacgcccagttcgactcggtcacccccgagaacgagatgaagtgggacgcggtcgag
ggcagccgcaactccttcaccttcacggccgccgaccagatcgtcagtcacgcccagagcaagggaatgaaggtgcgcgggcacaccc
tggtgtggcactcgcagctgccgggctgggtcgcggcctgggcgccaccgacctccgcggcggcgatgaacaaccacatcacccaggt
gatgacgcactacaagggcaagatccattcctgggacgtggtgaacgaggccttcaggacggcaacagcggtgcccggcgcagctctc
ccttccaggacaagctgggtgacggcttcatcgaggaggcgttccgcaccgcccgtacggtcgatcgaccgcgaagctctgttacaacg
actacaacaccgacggccggaacgcgaagagcgacgcggtctacgccatggcgaaggacttcaagcagcgcggtgtgccgatcgact
gcgtgggcttccagtcccacttcaacagcaactccccgtgccctccgactaccgggccaatctccagcgcttcgccgacctcggtctcga
cgtccagatcaccgaactggacatcgagggttccggctcggccaggccgcgaactacacgagcgtcgtgaacgcgtgcctggccgtga
cccgctgcaccggcctcaccgtctgggtgtcaccgacaagtactcctggcgcagcagcggcacgccgctgctcttcgacggcgactac
aacaagaagccggcgtacgacgcggtgctcgccgcgctcggcggcacccccgacggtggcggtgacgacggcggcggcgacaacg
gcggcgggaacaccggcagctgcacggcgacgtacacgcagaccgccacgtggaacggcggggtacaacggtgaggtgacggtcaag
gcaggctcctccggcatcaccacctggtcggtgccggtgaccgtgccctcgtcccagcaggtctccgccctctggaacggcgccccac
gtggaacgccggcaacaccgtgatgacggtgaagcccacctacaacgggaccctggcggccggtgcctcgacgagcttcgggttcacc
gtcatgacgaacggcaacacctcggcgcccgccgtcggcgcctgcaccgcctcctga >SACTE_2347|cellulose-binding family II|GH5,CE3 (SEQ ID NO:22)
gtgagaacagcgatacgcacagcacgacgaccacagccctggcccttctgctgagaggtctggccgccttcctggggctcgccctcgc
cggagccctcggcccggccaccgcgcgggccgcggacctgccccagcgggcggaggcgcgggccgccggcctccacatcagcgac
gggcgcctggtcgaaggcaacggcaacgacttcgtcatgcgcggcatcaaccacgcccacacctggtatccgggcgagacccagtccct
cgccgacatcaaggcgaccggcgcgaacacggtccgcgtggtgctgtccgacggctaccgctggagcgagaacagccccgaggacgt
cgcctcgatcatcgcccggtgcaaggccgagcggctcatctgcgtcctggaggtccacgacaccaccgggtacggggaggacgccgcc
gccggaacccctcgaccacgcggccgactactggatcggcctgaaggacgtactcgacggcgaggaggactacgtcgtcatcaacatcg
gcaacgagccctgggcaacgccgatccggcggctgaccgcccccacgacggccgcgatccagaagctgcgcgccgccggtttc
gcccacacgatcatggtggacgcgcccaactggggccaggactggagggcgtcatgcgggccgacgcccggagcgtgtacgacgc
cgacccgaccggcaatctgatctttctcgatccacatgtacagcgtctacgacaccgccgcgaaggtcaccgactacctcaacgccttcgtc
gacgccggacttcccctgctcatcggcgagttcgcggcccccgcggaccagtacggcgaccccggacgaggacacgatgatggccacc
gccgaggagttggggctcggttacctggccggtcctggagcggcaacacggatccggtcctcgacctggtcctcgacttcgaccccacc
cggctcagctcgtggggcgagcgcgtcctccacggccccgacggcatcaccgagacgtccgtgaggccacggtcttcggcggcggg
cagggcggggcgacaccgaggccccgaccgcacccggcaccccgacggcctccggggtgacggcgacctccgtcaccctcggctg
gagtgccgccaccgacgacgtcggcgtcaccgcgtacgacgtggtccgcgtgaccggcggctccgagacgaaggtcgcctcctccgcg
gccacctcggtcaccgtgaccggtctgagcgccggcaccgcgtacagcttcgccgtctacgcccgggacgcggccggcaaccgttcgg
cgcgctccggcacggtgtcggtcaccaccgacgagggcggcagcgtgcccggggcgcctgctccgtgggctaccgggtgatcggcg
agtggccgggcggcttccaggggagatcaccctccggaacaccggcgccgccgccgtcgacggctggacgctgggcttcgccttcgc
cgacgggcagaccgtcacgaacatgtggggcggcaccgcgacgcagagcggggcgcggtgagcgtcacccggcctcgtacacct
ccacgatcgccgccggcggctcggtcaccgtcggcttcaccggcaccctgactggcgcgaacgccgccccggcggccttcacgctcaa
cggcgccacctgcaccgcggcctga >SACTE_0357|polysaccharide deacetylase|CE4 (SEQ ID NO:23)

Figure 19 (continued)

atgagcatcacacccgtccctccctgcgcgccatggtcaccggtctcgccgtcgccgcgtccgccctggcgggcggcgccgtcaccgc
cgcaccggccgggccgccgcttgcaacggctacgtcgggctcaccttcgacgacggaccgtcggcggccagaccccggccctgct
gtccgcgctcaagcagaacggcctgcgggccaccatgttcaaccagggcaactacgccgcctccaaccccgccaggtcaaggccag
gtcgacgccggcatgtgggtcggcaaccacagctacagccaccgcacctgacccagcagagccaggcgcagatggactccgagatct
cccggacccagcaggccatcgccgccggaggcggcggcacaccgaaactgttccgcccgccgtacggcgagaccaacgccacgctg
cggtcggtcgaggcgaagtacggtctcaccgaggtcatctgggacgtcgactcgcaggactggaacggcgcgagcaccgacgcgatcg
tgcaggcggtctccggctcaccgccggtcaggtcatcctgatgcacgagtggcccgccaacaccctcgccgcgatcccgcgcatcgcc
cagaccctgtccgccaaggggttgtgttccggcatgatctccccgcagaccggccgcgccgtcgctcccgacggcggcggcaacggtg
gaggggggcggtggcggtggcgggtgcaccgcgacgttgtcggcggtgagaagtggggtgaccggtacaacctgaacgtggcggtga
gcggctccagcaactggacggtgacgatgaacgtgccgtcgggcgagagggtcatgacgacctggaacgtcagcgcgagttatccgag
cgcgcaggtcctggtcgccaagccgaacgggagcgggaacaactggggtgcgacgatccaggccaacggcaactggacctggccga
ccgtctcctgcaccacgagctga >SACTE_0358|Endo-1,4-beta-xylanase|GH11 (SEQ ID NO:24)
atgaacccactcgtgtacacggagcgccgcagacgcggccggctcacctcgctggccggcagcgtctgcgccctggtactggccgccg
cggccgcgatgctgctgcccggcacggccagtgccgacacggtcgtcacgacgaaccagaccggcaacaacaacggctactactactc
gttctggaccgacggcggcggccaggtctccatgaacctggcctccggcggcagctacagcacctcgtggacgaacaccggcaacttcg
tcgccggcaagggctggagcacgggcggccgtaagagcgtcacctactcgggcaccttcaacccgtccggcaacgcctacctgacgct
gtacggatggtcgacgaacccgctcgtcgagtactacatcgtggacaactggggcacctaccggccaccggtacgttcaaggggcacgg
tctccagcgacggcggcacgtacgacatctacgagaccacccgcaccaacgccccctccatcgagggtacgaagaccttcaagcagtct
ggagcgtccggcagtcgaagcggaccggcggcaccatcaccaccggcaaccacttcgacgcctggggcccgcaacggcatgaacctcg
gcaccatgaactacatgatcctcgccaccgagggctaccagagcagcggcagctccaacatcacggtgagcgagggcggatccggtgg
tggcggcgacaacggtggagggggcggtggcggtggcgggtgcaccgccacgttgtcggcggtgagaagtggggtgaccggtaca
acctgaacgtggcggtgagcggctccagcaactggacggtgacgatgaacgtgccgtcggcggagaaggtgctgtcgacctggaacat
cagcgcgagttatccgagctcccaggtcctggtcgccaagccgaacgggagcgggaacaactggggtgcgacgatccaggccaacgg
caactggacgtggccgaccgtctcctgcaccacgagctga >SACTE_1310|Pectate lyase|PL3 (SEQ ID NO:25)
atgagtgaaagagccgcatcccacgtacccaccggcgccgccccggccgccggcgcatcgccaccgcgctgacggcggcactgggg
cctcaccggcgccgcactggccaccggcgtgatgctccagccggccggcgcggccaccaccgcgatcccgcctggccctccgccac
gggcagccagtccgtctcgaagaccatcgaggtctccgggacgtacgacgcggtctgaagcgcttcaccggcagcggtgacctgggc
gacggtggccaggacgagggccaggacccgatcttcaagctgaaggacggggcgacgatcaagaacgtcatcctgggcactccggcc
gccgacggcatccactgctccggcagctgcacgatccagaacgtctggtgggaggacgtcggcgaggacgccgcgtccttcaagggca
cctccacgtcgtccgtgtacacggtgtacggcggcggcgcgaagaaggcctccgacaaggtcttccagttcaacggcgcgggcaagctg
gtcgtgacgaagttccaggtcgccgacttcggcaagctggtccgctcgtgcggcaactgctccaagcagtacaagcgcgagatcatcgtc
aacgacgtcgacgtcacggcgccgggcaagtccctggtcggcatcaacaccaactacggggacaccgcggcgctgcgctcggtgcgc
gtccacggcgacagcagcaagaagatcaagccctgcgtccgctacaccggcaacagcacgggcgcggaaccgaaggagacgggcag
cggtccggacggcacgtactgcaagtacaccgcctcggacctgagctacgactag >SACTE_3717|glycoside hydrolase family 9|GH9 (SEQ ID NO:26)
atgtggtgtcacccgtacctccgcctccgcacgtccggacgaaaggtttcctcggtgaacgccttccaccccccgcccggccgcaccc
gtccgaccacggtccggtacgggcggcgcgtgctcgggatgtcggccgccgccctgctgtcgcaggggccctggccgtgccggta
cggccatggccgacgacgccgaacccggacccggccccgagcagatcaccaacggcgacttcgccaccggtacctcagcccgtggt Figure 19 (continued)

ggtggacgccgaacgcctcggccgccgtgtccgagggccggctctgcgtggaggtgcccgccggcacggccaacgcctgggacgtca
tcgtcggccagaacgacgtaccgatcgtcgcgggcgagagctacgagctgtcctacacggcgcgttcgaccgtgcccctgaccgttcag
accgggtccaggaggcggtggagccctacacgacggtgctggcgacggcggatccggtgggcggaggacacgcgggtcgcc
gcacgttcacggcctcggtggaccagcccgccgcgtcggtgcagttgcagatcggtggcggggagcgggcgacgacgttctgcctgga
cgacgtgtcgctgcggggcggggccgagccgcccgtgtacgtaccggacaccggctcgccggtccgcgtcaaccaggtcgggtatctg
ccccgcggtcccaagagcggcaccgtggtcaccgacgccgaggcgccgctgacctggacggtcaaagccgaggacggttcgacggc
cgccaccggtacgaccgttccgcgaggtgaggaccccagctcgcgccgacggtccacaccttcgacttcggcgacctcaccacggcg
ggggacggctacaccgtggaggtcgacggtgaggtgagcgagccgttctcgatccgcggggacctgtacgactccctgcgctcggacg
cgctggcgtacttctaccacaaccgcagcggcatcgagatcgacgcggaccctcgtcggtgagcagtacgcgcgcccggccggtcacatc
ggcgtcgcgcccaacaagggcgacacggacgtgccgtgccgacctggggtctgcgactaccggctggacgtgtcgggcgctggtac
gacgcgggcgaccacggcaagtacgtggtcaacggcgggatctcggtggcccagctgatggccacgtacgagcggaccctcaccgcc
ccggacgcggagtcggccgagctcggcgacggcgcgctgcgggtgcccgagcgcgacaacggggtgccggacatcctggacgagg
cgcgctgggagatggacttcctcatcaagatgcaggtcccggcgggcgagcagctggcggggatggtccaccacaagatgcacgacgc
cgagtggaccgggctgccgatgaagccgcacctggacccgcagcagcgcgagctgcaccgccgtcgacggccgccacactcaacct
cgccgccacggccgcccagtgcgcccggctctacgcgcccttcgacgcggacttcgcggaccgctgcctgcgggccgccgagaccgc
gtgggacgcggcgaagcggcacccggacgtgctcgccgacccgaacgacggcatcggcggcggtgcgtacaacgacgacgacgtct
cggacgagttctactgggcggccgccgagctcttcaccacgacgggcaaggacatctaccggcaggcggtgctctcctccgcatggcac
ggtgacgcgggcgcggtcttcccggcgggcggcggaatctcctggggctccacggccggactcggcgtgctcaccctggccaccgtgc
ccaacgccctgacgtccgatcagctcgcccaggtgcgcacggtggtgaccgagggcgccgaccgctacgccgcgcagtcccgtgagc
aggcgtacgggctgccgtacgcgccccggggggaggactacgtctggggtccaacagtcaggtgctcaacaacatggtcgtcctggc
caccgccacgacctgaccggtgacgccgcctaccaggacgccgtgctgcggggcgccgactatctgctgggccgcaacccgctgaac
cagtcgtacgtcaccggctacggcgagcgggactcgcacaaccagcaccaccgcttctgggcgcaccagaacgacccccagcctgccga
acccggcgcccggttcgatcgcgggcggccccaacctcaccgcgatcgcctccggtgacccggtggcggcggagaagctcagcggct
gcgcgcccgccatgtgctacgtcgacgacatcggctcctgggcgaccaacgagatcaccatcaactggaacgcaccgctcgccttcatcg
cctcctacctggacgacgcgggcgagggcgggcagaccgccgcggcccgcacctgccaggtcacgtactcctcgcacccgtggaaca
gcgggtcgacggtgacggtacgggtcgagaacaccggctcggatcccgtctcgccctgggcgctgacctggctgctccccggcgagca
gcggctgagccacacgtggagcgcggagttcgaccagcacggccgtacggtcagcgcccggccgctgtcgtggaaccggaccctggc
acccggcgcggcggtcgacttcggcttcaacacctcggcggcgggctcctcgcccgagccgggcgcgttcaagctgaacggccgggc
ctgctcagcgggctga >SACTE_4638|conserved hypothetical protein| (SEQ ID NO:27)
atgcgtaccggatccatcgcgcgcgtcctgggcctcgccgccgccctggccgcactgctcaccacggccttcatggccccggccatggc
cggcaaacacgacgccaccgactcccgtccgccgcggccgccccggcgtcctcacccaccccggcgtcctggtcagccggccgca
gctcgacttcgtacgcggcaaggtccaggcgggggcccagccgtggaagggggcgtacgaccagatgctggccagtccctacgcctcg
ctctcgcggaccgccaagccccgcgccgtcgtggagtgcggcttcgtactccaaccccaacaacggctgcaccgacgagcgcgaggac
gcgctggccgcgtacaccctctcgctggcctggtacatcagccaggacggccgctacgcccagaaggcgatccagatcatggacgcctg
gtcgggcgtgatcaaggaccacaccaacagcaacgccccgctgcagacgggctgggccggctcctcctggccgcgggcggccgagat
catcaagtacacgtacggcaactggccggcgtccggccgcttcggcaccatgctgcgtgacgtctacctgccccaaggtcgccaacggctc
gaacagcaacggcaactggaactctccatgaccgaggccgcgatcggcatcgcggtcttcctggaggaccggggcgcctacgacagg
gccgtcgccaagttccgcggccgcgtccccgcgtacatatacgtgaccgccgacggatcgctgccgaaggccgcgcccggcagcggtc
tcgacacgcgggaaaagatcatcaactactggcagggccagtcgaccttcgtggacgggctcgcaggagacctgccgcgacctcacc
cacaccggctacgggctctccgcgatctcccacatcgccgagaccagccggatccagggccaggacctctaccggaggtcgccgacc
ggctccgtcacgcgctggggctgcacgccaagtaccagctgggggagaaggtccgtcctccctgtgcggcggctcgctcaaggacag
cctcggcccggtcaccgaggtcggcttcaacgccctgcacaaccgcatgggttacgccatgacgaacacccagaccctcaccgagcggc
agcggcccgccgcctcgaacaacctgttcgtggcctgggagaccctgacgcacgccgacaacccgaactga Figure 19 (continued)

>SACTE_4738|glycoside hydrolase family 16|GH16 (SEQ ID NO:28)
atgccctcccgtacgacgttgatcgccaccaccgcggccctggtcgccctcgccgcccccatggccttcgcggctcccgccccgccccc
gaccccgccgtcgaggccgccgccgcggccctgggacaccgaccgcgcggcgtccgcctacgcggcgaaccccgccgcgtcaccgc
gtccggcagcgagaaccccgcctccggaccgggcgccgccaccgacggcgacgccaccacccgctggtccagcgacttcgccgaca
acgcctggatacgcgtcgacctcggctccaccatccggatcaaccaggtgaagctggagtggggaggccgcctacggcaagaagtacgtc
ctggaagtctccaaggacggcaccaactggaccccttctacacggaggacgcgggcaccggcggcaccgtcacgccacacctacc
cgcaggaggtcaccggccgctacgtgcggatgcgcggcgtcgaacgcgccacggcctggggctactccctcttctccttccaggtctacg
ggggcgagccggccccgcctcgaccaccgcagcaacctcgccctcaaccacccgcctacggcgacctctaccagcacgccggca
actcgcccgcattcgtcaccgacggcggctggcccgccgacctgaaggcggaccgctccgctggtcctccgactggaacgcggaccg
ctgggtcgcgtcgacctcggcgcgacctccaccatcaacagcgtcgacctctactggaggcggctacgccgtcgactacgagatcc
aggtgtccgacgacaaccggacctggcggaccgtccaccgccctccgccgccgaggtcgccgccagacgcgccgacgtcaaggccc
cggccgaggccgtcggacgccacgacaccatcaacctgcccaccccggccaccggccgctacgtccggatgctgggcaaggagcgcc
gttccttctacaacccggcacctccaccgcccagttcggctactcgctctacgagttccaggtgtggggcaccggcggcagcgcggacg
ccgcctaccccgcctgcccaagaaccccggcggcgcctaccgcaccaccttcttcgacgacttcaccggctccggctggaccgctcc
aagtggcgcgtggtgcgcaccggtacggagatgggcccggtcaacggggagtcccaggcctacgtcgactcgccggacaacatccgta
ccgagaacggcgccctggtcctggagtccaagtactgcaagggctgcaccccacgcccaacggcaccttcgacttcacctcgggccgc
gtcgacaccaacaccaagttcgacttcacctacggcaaggtgagcgcccgtatgaagctcccggtcggcgacgttctggccggcgttct
ggctgctgggcagcgacgtcgacgacccggcggtcctggcccggctccggcgagacggacatcatggagaacatcggctacggcg
actggaccagctccggcctgcacggacccggctactccgcagacggcaacatcggcgcctcccagacctacccgaacggcggccggg
ccgacgagtggcacacctacgcgtcgaatggaccccgaaggcatgaccttcaccgtcgacgaccgcgtcgtgcagcagacctcccg
ccagaagctggagtccaccgcggcaagtgggtcttcgaccacaaccagtacgtgatcctcaacctggccctcggcggcgcctaccgg
gcggatacaaccaggtcacccagccctactggggccttccgcagtccagcgtcgaccgcatcgcacagggcggcatcaaggcggagat
cgactgggtacgggtcgagcagaagtaa >SACTE_4755|conserved hypothetical protein|GH64 (SEQ ID NO:29)
gtgatttcgcgcagaatgttcctgaccggcgccgccgcctccgcgaccgcgctcacctatccgctctggggcaccgccctgagcccgcgc
acgtcggcggcggccgccacgtgcgaactggccctcgagaaccgttcgttgcccggtacggtgcacgcctacgtcaccggtcacgagca
gggcaccgacagctgggtgctgctgcggggccgacggcagcgtgtaccgccccgagtcgccggccgctccgcagacccctctgccggt
ggactgcgccatcccgctgaacggcgccggcgccggcccggtcgtcctgacgctgccccagatgtacggcgcgcgggtctacttcgtcc
gtgacgacaagctggacttctacctgaacccgggccctcgctggtcgagccggcttcgcgacgcccaccgacccgaactacgggcgc
acctggtcgttctgcgagttcaccttcaacccgcagcagctgtacgcgaacatcagctacgtcgacctggtcaccgccctgccgatcggcct
gaccctggagggcgactccacccacaccgtcgcccctcccggacggcgccgtgcagcgcatcgccgacgacctgacggcccaggc
ggccgccgacgggcagccgtgggacaagctggtcacccgtggctcggacgccaggtgctgcgggtcgtctcgccagaacctgat
ggcgccgtacttcgaccggcccgacgagatgccgttccgggacctgttcgcggcccagatcgacgaggtctgggagaagtaccgctcca
ccgacctgcggatcgacctccaggcggccggggcacctggcgggccgggtcagcggggacacgctgaccttcgagggcgacac
accttctccaagcccacctcgaaggacatcttcacctgcaaccacggtccgttcacgaacaacccgagcgactcggacgacaagaaggc
gctgctggccaggatcgcggcgggcttcaaccggtcgatcatgctgagccaccccagccagccgaacggcacctcggtggcggactact
accaggacgcggtgaccaaccactggtcgcgggtcgtccacgcgaactcccccatcgggtacgcgttcccgtacgacgacgtacgcccc
gacggtgagccggacgtctcgggcgcggcgaacgacggcaaccccggcgcttcacggtgagcgtgggttcctga >SACTE_5457|Chitosanase|GH46 (SEQ ID NO:30)
gtgcttcaccccacaaccgcaccgcacgtcgcaccactcggctcacccgcaccggcggtctcgccgcgcggccctcgggctcgcgct
catggcgctccccgtcaccgctcacgccggcgcccccacgcagccggccgctcatcatctggaggccgccgcgaccggactggacgat
cccgcgaagaaggacatcgccatgcagttggtctccagcgcggagaactccacgctggactggaaggcgcagtacggctacatcgagg
acatcggcgacggacgcggctacaccgccggcatcatcggcttctgctccgggaccggagacatgctcgccctggtcgagcgctacacg Figure 19 (continued)

gaccgctcaccgggcaacgtactggcgtcgtacctgcccgccctgcgcgaggtcgacgggaccgactcgcacgacgggctcgacccc
ggcttccccgggactgggccgaggccgcgaaggacccggtgttccagcaggcgcagaacgacgagcgggaccgggtgtacttcgac
ccggcggtgcgccaggccaaggacgacgggctggggacgctcggccagttcgcgtactacgacgccatcgtcatgcacggaggcggc
ggggacagcacgagcttcgggtccatccggcagcgcgcgctcgcggaggcggaaccgccctcgcggggcggtgacgaggtcgccta
cctcgacgcgttcctggacgcgcgggtctgggcgatgcggcaggaggaggcccactcggacaccagccgggtcgacaccgcgcagc
gcgtcttcctgcgcgacgggaatctgaacctggatccgccgctggactggcaggtgtacggcgacagcttccacatcggctga >SACTE_5647|coagulation factor 5/8 type domain protein|GH87 (SEQ ID NO:31)
atgaccccaccgcacagacaccgccgttcaggcgctcggtgtccgcttccctctcgctggccctcaccgccgtcggcaccgccgcgcg
gtcgtcctggccggtgccccggcggcccaggccgccgcggtccccgcaccctccccggtcggcatatccggccggggcgccgccgtc
ccgttcacggagcaggaggccgagtacgccgcgaccaacggcacgctcatcggcccggaccggcgctacggctcactgccctcggag
gcgtccggccggcaggccgtcacgctcgacgcggccggtgagtacgtggagttcaccctcaccgcccccgccaacgcgatgaccttcc
gctattcgctgccggacaacgccgccgggacgggccgggacgcctctctcgacctgcgggtgaacggctcggtcctcaagagcgtgcc
ggtgacctcgaagtacggctggtactacggggggttaccccttcaacaacaaccccggggacaccaacccgcaccatttctacgacgagac
ccggaccatgttcggctcgaccctgcccgccggtacgaaggtccggctgcaggtggcgtccaccgccggctcgccctcgttcaccgtcg
acctggccgacttcgagcaggtggccgcgcccgtcggcaagccgtccggcgcactggacgtggtgagcgacttcggggccgacccga
ccggggcggccgactccaccgcgaagatccaggcggcggtcgacgcggggcgcacccagggcaaggtcgtctacatcccgcagggg
accttccaggtcgtgaccacatcgtcgtggaccaggtgacgctgcgcggcgccggccctggtacagcgtgctgacggggcgtcaccc
cacggaccggagcaaggcggtcggtgtctacgggaagtactcggcgcaggcggcagcaggaacgtcaccctcaaggacttcgccatc
atcggcgacatccaggagcgtgtggacaacgaccaggtcaacgccatcggcggggccatgtccgactcggtcgtcgacaacgtctggat
gcagcacaccaagtgcggcgcctggatggacggcccgatggacaatttcaccatcaagaacagtcgcatcctggaccagaccgcggac
ggcgtgaacttccactacggggtcacgaactcgaccgtcacgaacaccttcgtccgcaacaccggtgacgacggcctggccatgtgggc
ggagaacgtcccgaacgtgaagaacaagttcacgttcaacacggtgatcctgccgatcctggccaacaacatcgtgacgtacggcggcaa
ggacatcacgatctccgacaacgtcatggcggacaccatcaccaacgcggcgggctgcacatcgccaacgctacccgggcgtcaact
cggggcaggggacggccgtcgcggggacgcacacggccgcgcgcaacaccctgatccgtaccggcaacagcgacttcaactggaact
tcggcgtcggggcgatctggttcagcgggctcaacgaaccgatcagcaacgccaccatcaacatcaccgacagcgaggtcctggacagc
tcctacgcgcgatccacctgatcgaggtgcgagcaacgggctgcacttcaagaacgtcaagatcgacggggcgggtacctacgccct
gcagatccaggcaccgggcacggccaccttcgagaacgtcgtggccacccacatcgcccagtccaacccgatccacaactgtgtcggca
gcggcttccagatcaccccggggcagcggcaactccggctggtacgccgaccgccgctgcaccggggtctggcccgaccgggtgtg
gaccaacggcggcgtgcccggaggcggcggtccaccaacccgaccgaccccaccgaccccaccgaccgacggaccccaccgac
ccgcctgaggagacgggcaacctcgcccggggacgcaccgtcaccgagaccagccacacggacgtgtacggcgcggccaacaccgt
cgacggcaacgcggacacgtactgggagagccgcaacaacgccttcccgcagtccgtcaccgtcgacctcggcgctgccaaggcggtg
aagcgggtggtgctgaagctcccgccggccgccgcgtgggcgacccgcacgcagacgctctccgtgtccggcagcaccgacaacggg
acgtacaactcgctgaaggcgtcggcgggtacaccttcaacccgtcgagcggcaacaccgcgacggtctccctcccggggacgccggt
ccggtacctgcggctgaccttcacccagaacaccgggtggcccgccgcccagctgtccgaactggaggcctacaccagctga >SACTE_5978|Pectate lyase/Amb allergen|PL1 (SEQ ID NO:32)
atgaggagaccagtcgccctgcgactcagcgcggcgggggccacccctggccctggctgccgcgaccggcgcactgatggcgatgccc
gaggcggcgtcggcagcgaccgcggcgtcaccggatacgcgaccagaacggcggcaccaccggcggcgccggcgggcagacg
gtgcgggccaccaccgggaccgcgatccacgccgccctgtgcggcggggccagcagctccaccccgctcaccatccaggtcgagggg
accatcaaccacggcaacaccgacaaggtctcgggcagcagctgcaacaccgccgcgggagtcatcgagctgaagcagatcagcaac
gtcacgatcgtcggcgtggccggcggcgccgtcttcgaccaagtaggcatccacgtccgcgagtccagcaacatcatccagaacgtc
accgtcaagaacgtcaagaagtccggctcgcccacgtcaacggcggtgacgccatcggcatggagaaggacgtccgcaacgtctggg Figure 19 (continued)

tggaccacaccacccctggaggcctcgggcggcgagtcggagggcttcgacggcctcttcgacatgaaggccggcacccagtacgtgac
gctgtcctacagcatcctgcgcaactccggccggggaggcctcgtcggctccagcgagagcgacctctcgaacggcttcatcacctacca
ccacaacctgtacgagaacatcgactcccgcgcccctctgctgcggggcggcgtcgcccacatctacaacaaccactacgtgggactcag
caagtcgggcatcaactcccgggccggcgcccgcgccaaggtggacaacaactacttcgaggactccaaggacgtcctgggcaccttct
acaccgacgcggccggctactggcaggtcagcggcaacgtcttcgacaacgtgacgtggtccggccgcagcagcgacaacaaccccg
cgggcccggacccgcagtccaacacctcggtcagcatccctacgcctacaccctcgacggggcgaactgcgtaccgtccgtcgtgagc
cggacggcgggcgcgaacacggggctgaaggtgtcggacggcagctgctcgccgcagacgccggacccgaccgaccccaccccg
acccgacgccggacccgaccgaccccactccgccaccgggaccaacctcagcctcgggccggctcggacggctccagcaaggcg
agcgggaccagctacggcgacgtgcgggacggtgacatgagcacctactggtcaccgtccggctcgaccggttccgtctcgatcaagtg
gagctccgccaccaccgtccaagatcaacgtgcgcgaggcggcgggctccacgggctccatcacctcctggaaggtcggcaacgcc
gacaccggcgccgtcctggcctccggcagcggggcgggcgtcatcacgttcccgcagacctcgctgcgcaagatcacgttcgagatcac
gggctcgacgggcacgccgaaggtcgccgagttcgagacgtacgccggctga >SACTE_5230|xylose isomerase| (SEQ ID NO:48)
atgccggagcgtttcactccactcctgaggacaagttcacgttcggtctgtggaccgtgggctggcggggcaacgacccgttcggtgagc
cgacgcgtccggtgctggacccgtggagtcggtcgagcggctggcggagctcggtgcgcacgggtgacgttcatgacgacgacct
gattccgttcgggtcggacgaccgtgagcgggcgcggctggtcgggcggttcagggaggcgctggagcgtaccgggctcaaggtgcc
gatggcgacgacgaacctgtcacgcacccggtgttcaaggacggcgggttcacctccaacgaccgtgacgtgcgcggttcgcgctgc
gcaaggtgatccgcaacatcgatctcgcggtggagctcggcgcgcagacgtatgtggcctggggcgggcgtgagggcgccgagtccg
gtgcggccaaggacgtgcggtcggccctggaccggatgaaggaggccttcgacctgctgggcgactacgtcaccgagcagggctacga
cctgccggttcgcgatcgagcccaagcccaacgagccccgcggtgacatcctgctgcccacgatcgggcacgcgctggccttcatcgagc
gcctggagcgccccgagctggtcggggtgaacccggagaccgggcacgagcagatggcccgggctgaacttccccacggcatcgcgc
aggcccctgtgggcgggcaagctcttccacatcgacctcaacggccagtccgggatcaagtacgaccaggacttccgcttcggcgccggt
gacctgcgccaggcgttctggctcgtggacctcctggagacggccggctgggacggctcacgccacttcgacttcaagccggtacgcac
cgacggcatcgacggggtgtgggagtccgcgaagaactgcatgcgcaactacctcatcctcaaggagcgcgccgccgccttccgcgcc
gaccccgccgtccaggaggccctcaccgcctcccgcctcgacgaactcgcccgccccaccgccgacgacggcctcaaggcactcctcg
ccgaccgcaccgcctacgaggacttcgacgccaccgccgccgccgaacgctccatggccttcgaagccctcgaccagctcgccatgga
ccacctcctcaacgtccgctga >SACTE_4571|glycoside hydrolase family 18|GH18 (SEQ ID NO:49)
atgacaagcgcgctcagggcgacgcaggggtttgcagtccacgaaccaccccgttgtcggacctcacccgaggagcaccgttgagcac
tgaatccccccgaagaagttcccgtctcagatggagactcggcccggggcgggccacccgggccaaggcggtcgcgggcttcaccgca
ctgctgctgccgctcgccgcgatggtcggcctggcgtccccggccaggccgcgacctcggcgaccgccacctacctcaagaagtcgg
actggggcagcggcttcgagggccagtggacggtgaagaacaccggcaccaccgccctgtcctcctggacgatcgagtgggacttccc
ctccggcaccgcggtcggctccgcctggacgcctccgtgaccagctccggcacccactggaccgccaagaacctcggctggaacggt
acggtcgccccgggtgccagcatcagcttcggcttcaacggcaccggatccggctccccaccggctgcaagctgaacggtgcctcctgt
gacggcgcggcacggtccccggcgacagcgccccgtccaagcccggcaccccaccgcgagcggcatcaccgacacctcggtgaa
gctctcctggagcgcagccaccgacgacaagggcatcaagaactacgacgtcctgcgcgacggcgccaaggtcgcgacggtcaccac
gacgacgtacaccgacaccggcctcaccaagggcacggactactcctactccgtgcaggccgcgacaccgccgaccagaccggacc
ggtcagcggcgcggtggccgtgcgcaccacgggcgggaacgacaacccggggcccggcaccggcagcaaggtcaacctcggctact
tcaccaactggggcgtctacggcgcaactaccacgtcaagaacctggtgacctcgggctcggccgagaagatcacgcacatcaactac
gccttcggcaacgtccaggcggcaagtgcaccatcggcgactcctacgccgactacgacaaggcctacaccgccgaccagtcggtcg
acggcgtcgccgacacgtgggaccagccgctgcgcggcaacttcaaccagctgcgcaagctcaaggcgaagtacccgcacatcaaggt
gatctggtcgttcggcggcggctggacctggtccggcggcttcggtgccgcggcgcagaaccccggccgcgttcgcccagtcctgctacgacct Figure 19 (continued)

ggtggaggaccccgctgggccgatgtcttcgacggcatcgacatcgactgggagtaccccaacgcctgcggcctgacctgtgacacca
gcggccccgccgcgctgaagaacctgtcctccgcgctccgcgccaagttcggcgcgaagaacctggtcaccgccgcgatcaccgcgga
cggctcggacgcggcaagatcgacgccgccgactacgcgggcgccgcgcagtccttcgactggtacaacgtgatgacgtacgacttct
tcggcgcctgggaggcgaagggtccgacggccccgcactccccgctgaacgcgtacgccggcatcccgcaggacggcttcaactccg
ccgccgccatcgccaagctgaaggccaagggcgtcccggcctcgaagctgctgctcggcatcggcttctacgccgcggctggacggg
cgtgacccaggcggcaccgggcggcaccgccaccggcgcggccccgggcacgtacgaggcgggcatcgaggactacaaggtcctca
agaccagctgcccggccaccggcacgatcgccggcaccgcgtacgcgcactgcggcaccaactggtggagctacgacaccccggcga
ccatcacctccaagatggcctggcgaacagccagggcctcggcggtgcgttcttctgggagttcagcggcgacaccgccaacggcga
gctcgtgagcgccatggacagcggcctcaactag >SACTE_2313|chitin-binding domain 3 protein|CBM33 (SEQ ID NO:50)
atgcggaaaagggcaagcgcggccgtcataggcctggcgatcgccggcgtctcgatgttcgccaccagcagtgccagcagccacggct
acaccgattcccccatcagcagacagaagctgtgtgccaacgcaccgtcaccggctgcggcaacatccagtgggagccgcagagcgt
cgagggcccgaagggcttcccggcggcaggtccggcggacggcaagatctgcgccggcggaaacagctccttcgccgcgctcgacga
cccgcgcgggggcaactggcccgccacccaggtcaccggcggccagggctacaacttcgctggcagttcaccgccgccacgccac
gaccgacttccgtactacatcaccaaggacggctgggactccaccaagccgctcaccaggccgccctggagtcgcagcccttcatga
cggtgccgtacgggaaccagcagcccccggcgaccctgacccaccagggcaccatccccacccagaagtccggcaagcacatcatcct
ggccgtctggaacgtggctgacaccgccaacgcgttctacgcgtgctcggacgtgaagttctga >SACTE_4246|Carbohydrate-binding CenC domain protein|GH18 (SEQ ID NO:51)
gtggccgccctcgcggccggcgccctgaccgtgaccggtctggtcggcaccgcacaggcggccgacatcaacgtcgccaagaacgcc
gggttcgagagcggcctcagcggctggacctgtaccggcggcagcggcgccaccgtctcctcccccgtgcacggcggctccgccgccc
tcaaggccaccccgagcggccaggacaacgcgaagtgcacccagaccgtggccgtgaagcccaactccacctatgcgctcagttcctg
ggtgcagggcgggtacgcctacctcggggcgagcggcaccggcaccaccgacgtctccacctggaccccggcagcaccggctgga
cccagctgcgcacgagcttcaccaccggcccgtccaccacctcggtgcaggtctacacccacggctggtacggccaggcggcctactac
gcggacgacgtcgcggtcaccggacccgacggcggcggcgtacggaggagcccggcccggcgatccccggcgcccccgccggtc
tggccgtcggcaccaccacgtcctcctcggtggccctgtcgtggaacgcggtctccggcgccaccggctacaccgtctaccggacggc
accaaggcgaccaccaccaccggcacctccgcgacggtgagcggcctggccgccgacaccgcgtaccagttctcggtgagcgccacc
aacgccgccggtgagtccgtcaggtcggcgaccgtgagcggacgtacggccaagaaggacgagaccggcccgggcccctcgacctc
cgtgcccaagcacgccgtgaccggctactggcagaacttcaacaacgccgcggccgtccagaagctcagcgacgtgcccgcgaactac
gacatcatcgccgtcccttcgcggacgccgcggtaccccggggtgccgtcacctccaacctcgactcggcgggcctgaacggctacacc
gtcgcccagttcaaggccgacatcaaggccaagcaggccgcgggcaagaacgtcatcatctccgtcggcggcgagaagggcaccgtct
cggtcaacagcgacgcctcggcgaacgcgttcgcggactcgctgtacacgctgatccaggagtacggcttcaacgcgtcgacatcgac
ctggagaacggcctcaactccacctacatgacgaaggccctgcggtcgctgtcctcgaaggtgggctccggtctcgtcatcacgatggcg
ccgcagacgatcgacatgcagtcgacgtcgggtgagtactcaagacggcgctcaacatcaaggacatcctgaccgtcgtcaacatgcag
tactacaacagcggttcgatgctgggctgcgacggcaaggtctactcgcagggctcggtggacttcctcaccgcgctcgcctgcatccagt
tggagggcggcctcgccccgtcccaggtcggcctcggtgtgcccgcctccacccgcggcgcgggcagcggctacgtcgcccgtcggt
cgtgaacgcggccctggactgcctggccaagggcaccggctgcggttccttcaagccgtccaggacgtacccggacatccgtggtgcga
tgacctggtcgacgaactggacgccacggcgggcaacgcctggtccaacgcggtcggcccgcacgtccacggccttccgtaa >SACTE_3064|Chitinase|GH19 (SEQ ID NO:52)
gtgatcagacgcgtcatgggcctgctcaccgcgctggccgcggtcgtcgcgacgctcgtcttcctccccgccgccacggcctcggcggc
cacctgcgccccggcctggaacgcctcgtccgtgtacacgggcggcggctccgcctcgtacaacgggcacaactggtcggcgaagtgg
tggacgcagaacgagcgtccgggcacctcggacgtctgggccgaccaggcgcctgcggttcgggcgcggcggcaccgacccgaa
ccctcgggcttcgtcgtcagcgaggcgcagttcaaccagatgttcccgagccggaactccttctacacctacagcgggctcaccgcgc
gctgagcgcctaccccgccttcgccaacaccggcagcgacaccgtgaagaagcaggaggcggcggcgttcctcgccaacgtcagccat Figure 19 (continued)

gagaccggcggcctggtccacatcgtggagcagaacaccgccaactacccgcactactgcgacaccagccagtcctacggctgcccgg
ccggccaggccgcctactacggccgcggccccatccagctcagctggaacttcaactacaaggcggccggtgacgccctcggcatcga
cctgctgggcaaccctggcaggtggagcagaacgcctccgtggcctggaagaccggcctctggtactggaacacccagtccggcccc
ggcaccatgacgccccacaacgccatcgtcaacggctccggatcggtgagaccatccggtccatcaacggcagcatcgagtgcaacgg
cggcaaccccggccaggtccagagccgcgtcaacacctaccagtcgttcgtccagatcctcggtaccacgcccggctcgaacctgagct
gctga >SACTE_5764|Chitinase|GH18  (SEQ ID NO:53)
atgagacgctcacgatccgtccgcgcgctggtgacggcggccgtcaccacggtggccgcggcaggcatggccgtgctgggctccggca
ccgcccaggcggcgaccccgctgcccgaccacgtcttcgcccctacttcgagtcgtggaccggagagagcccggcggccatggcgg
ccgagtccggggcgaaacacctgaccatggcgttcctccagacgacggccaaggggctcctgcacgccgtactggaacggcgacaccgg
cctgccgatcgcccaggcgtccttcggcgccgacatcgacacgatccaggccggaggcggcgacgtcatcccgtcgttcggcggctaca
ccgcggacaccaccggcacggagatcgccgacagctgcaccgacgtcgaccagatcgccgcggcctaccagaaggtcgtcacgacgt
acgacgtctcgcggctcgacatggacatcgaggtcgactccctcgacgacaccgccgggatcgaccggcggaacaaggccatcaagaa
gctccaggactgggcggacgcgaacggccgtgacctggagatctcctacacgcttccgacgaccaccgcggactggcctccagcggc
ctcgccgtgctgcgcaacgccgtgaccaacggggcacgggtcgacgtcgtgaacctgatgacgttcgactactacgacaacgcgtccca
cgacatggccgccgacaccgagaccgccgccagggcctgtacgaccagctcgcgaagctgtacccgggcaggaccgccacccagct
gtggtccatggtcggcgtcaccgagatgcccggcgtcgacgacttcggccccggccgagaccttcacgctcgccaacgccgcccgggtgt
acgactgggcggtggccaagggcatcaacaccctgtccttctgggcgctccagcgcgacaacggcggctgccccggcggccggccg
ccgacgactgctccggcatccagcagaacacctgggacttcaccgcgtcttcgcgcccttcaccagcggcaccacgcgccggacgac
gacttctcggtgacggccacgcccgcctccgggacggtgaccgcgggcggttcggccaccaccacggtgaagaccgccgtgaccaag
ggcgcggcacagcaggtcggcctcacggtcagcggggtcccggccggtgtcaccgcctcccctcagccctcctcggtgaccgcgggc
ggccggtcaacgctcacctcgccacgacccaggccgccgtctcgggcacgtaccggatcagcgtcaccggtacgagcccgtcgggca
gccacgcgacggcctacacgctgaccgtcaccggcggcaccggcagccagtgcacggcggggccgtggcgggcgggacggtctac
accggcggccagcaggtctcgtacaaggccacacctggaaggccaagtggtggacgacgggcgaggagcccggcaccaccggtga
gtggggcgtctggcaggacctgggcgcctgctga >SACTE_4439|Catalase|  (SEQ ID NO:54)
gtgacgcagggaccgctcaccacggaggccggcgcgccggtagccgacaaccagaacagtgagaccgcaggccccggtggaccggt
tctcgttcaggaccaggcgcttctggagaagctggcccacttcaaccgggagcgcatcccggagcgcgtcgtgcatgcccggggagccg
gcgcgtacggcacgttcacgctgaccgtgacgtctcgcagtggacgcgtgcgaagttcctctcggaggtcggcaaggagaccgagacc
ttcctgcgcttctccaccgtcgcgggcaacctcggctcggccgacgcggcgcgtgacccgcgcggctgggcgctgaagttctacaccga
agagggcaactacgacctcgtcggcaacaacacccgtgttcttcatcaaggacgccatcaagttccccgacttcatccacacccagaag
cgcgaccgtacacgggctcccaggaggcggacaacgtctgggacttctggggcctgtcgccggaatccaccccaccaggtgacctggct
cttcggtgaccgcggcatcccggcctcgttccgtcacatgaacggctacggctcgcacacgttccagtggaacaacgaggccggcgagg
tcttctgggtcaagtaccacttcaagaccgaccagggcatcaagaacctcaccaccgaggaggccgtccgcctctccggcgtcgacccgg
acagccaccagcgcgatctgcgtgagtccatcgagcgcggtgacttcccgacctggacggtgcaggtccagatcatgccggcggccga
ggcggccacgtaccgcttcaaccgttcgacctgaccaaggtgtggccgcacgaggactacccgccgatcgagatcggcaagctggag
ctcaaccgcaacccggagaacatcttcgccgaggtcgagcagtcgatcttcagcccggcgcacttcgtaccccggcatcggcccgtcccg
gacaagatgctccagggccgcctgttcgcgtacggcgacgcccaccgctaccgcgtcggcatcaacgccgaccacctgccggtgaacc
gtccgcacgccaccgaggcgcgtaccaacagccgtgacggctacctgtacgacggccggcacaagggcacgaagaactacgagccga
acagcttcggcggcccggtccagaccgacaggccgctctggcagcccgtctccgtcaccggcggtacgggcaaccacgaggccgcg
tccacgcggaggacaacgacttcgtgcaggccggcaatctctaccggctgatgtcggaggacgagaagggccggctgatcgacaacct
ggccgggttcatcgcgaaggtgtcgcgcgacgacatcgccgatcgcgcgatcaacaacttccgtcaggccgacgcggacttcggcaagc
ggctggaggtcgcggtccaggccctgcgcggctga Figure 19 (continued)

>SACTE_0562|cellulose-binding family II|GH74 (SEQ ID NO:55)
gtgtatgccatgccctccaccgccctgcggcggtccagtccggagaggacgctcccgtgcgttcaagcccagaccttcgccgccctg
ctggcggcgctcgccctgaccgcagggttgtcactcatcggaacccctgccgtggcgcgcgctccgacgaggcacctgctgcgacagaagc
atcggatgtgtccatagccgcggacacctacacctggaagaacgcccggatcgacggcggcggcttcgtccccgggatcgtcttcaaccg
gtccgagaagaacctcgcctacgcccggaccgacatcggcggcgcctaccgctgggaccagtccggcaagcagtggaagcccctgctg
gactgggtggactgggaccgctggggctggacgggcgtggtgagcctcgcctccgacacggtcgaccccgacaacgtgtacgccgcc
gtggggacgtacaccaacagctgggacccgaccgacggcgcggtcctgcgctcctcggaccggggcgcctcctggaaggcggccacc
ctcccgttcaagctcggcggcaacatgccggacgcggcatgggggagcggctcgcggtcgaccgaacaagaactccgtgctctacct
gggcgcgcccagcggcaacggcctctggcggtccaccgacgcggggagtcagctggtccgaggtgacggccttccccaaccccgggaa
ctacgcgcaggacccgtcggacaccagcggctacggcaacgacaaccagggcatcgtctgggtgaccttcgacgagcgttccgcagc
gcggggcagcgccacccaggacatctacgtcggggtcgccgacaaggagaacaccgtctaccgctccacggacggcggcgccacctgg
tcgcggatcccggggccagccaccggctacctcgcgcacaagggcgtactcgactccgcgaccggccacctctatctgacgctgagcga
cacggggcggcccctacgacggcggcaagggccggatctggcggtacgacacggcgtccggcgcctggcaggacgtcagcccggtgg
cggaggccgacgcctactacggcttcagcgggctctccgtggaccggcagaagcccggcaccctgatggccaccgcctacagctcctg
gtggcccgacacccagatcttccgctccacggacagcggtgccacctggacccaggcctgggactacaccggctacccgaaccgctcca
accgctacacgctggacgtcctccgtgccgtggctcctggggcgcttccccgcaccgcccgagaccgccccgaagctgggctgg
atgacggaggcgctggagatcgacccgttcgactcggaccggatgatgtacggcaccggagcgacggtctacggcaccgaggacctca
cgtcctgggactccgcggcacgttcaggatcaccccatggtgaaggggatcgaggagacgccgtcaacgacctggccagcccgcc
ctccggggcaccgttgctgagcgcactcggtgacatcggggcttccggcacaccgacctcgacgccgtgccggacctgatgtacacct
ccccgaacctcgactcgaccaccagcctggacttcgcggagagctcgcccggcacggtcgtccgggtcggcaactccgacgccgcc
ccacatcggcttctccaccgacaacgggggccaactggttccaggggctcggagccttcggccgtcaccggcggcggcacggtcgcggcg
gcggcggacggcagcggcttcgtgtggagcccggagggcgcgggcgtccaccacaccaccggcttcggcacctcctggaccgcctcc
accggcatcccggccggtgccacggtcgagtccgaccggaagaaccccgagaagttctacggattcgaggcgggcacttctacgtctc
gaccgacggcggggcgaccttcaccgccgaggccaccgggctgcccgccgagggcaacgtccgcttccaggcactgcccgggacgg
agggcgacatctggctcgcgggcggctccgacaccggggcgtacggtctgtggcgctccaccgactccggggcgacgttcacgaagtc
cgccggcgtcgagcaggcggacagcgtgggcttcggcaaggccgccccggcgcctcgtaccggacggtgttcgtcagcgcgaagat
cggcgggggtgcgcggcatcttccggtccaccgacgccggggcgagctggaccaggatcaacgacgacgccaccagtggggctgga
ccggcgccgcgatcacgggcgaccccagggtctacgggcgcgtctacgtctccaccaacgggcgcgggatccaggtgggcgagacct
ccgacagcggcggcggaggcacggaccccggcaccgatcccggcaccgatcccggcaccgatcccggtccggagcagcccgcgga
cgccgcctgtgcggtgacgtacgcggtcaccaaccagtggccggcggcttccaggccgatgtgacggtcaccaacacgggtgacgcc
gcgtacaacggctggaagctcggctggtcgttccccggcggcagcagatcagccagatctggaacgcctcgcaccggcaggacggg
gtgaaggtcaccgtcacggacgccggctggaacggcacggtggcgcccggctcgtcggcgggcttcggcttcaccggcagttgggcgg
ggagcaacgccgaaccggccgccttcaccctggacggccaggcctgcaccgtgggctga >SACTE_4343|extracellular solute-binding protein family 5| (SEQ ID NO:56)
atgcgcggtgccaagagcgccaagtgggtcgcgggagcggcaatcatcgccctggccgcgaccgcctgtggtgcggcgacagcgac
agcgacaacggtgccaagggcgccgtcgacgcggacggcatattctccgtcgaggtcggtgagccgcagaaccccgctgcagccggcc
aacacgatggagtcgaacggcagcatcgtcaccgacgccatcttctcgcagctcgtcgactacgaccccgacggcaagctcgagatgatc
aacgccgagtccgtcgagacgaccgacagcaagctgtggacggtcaagctcaagaaggactggaagttccacgacggcaccccgtca
ccgccgactcctacgtcaaggcctggaactggccgcgaacatcgagaacgcgcagacgaacgcctcctggttcgccgacatcaaggg
ctacgccgacgtccaccccgacggcgagggcgccaagccgaagtccgacgccatgtccggcctgaagaaggtggacgactacaccttc
accatcgagctcaactcggccgtcccgtacttctcgtacaagctcggctacacggtcttctcgccgctgcccgagtccttctacgcggaccc Figure 19 (continued)

gaaggccgccggtgagaagccggtcggcaacggcgcgtacaagttcgtcagctgggaccacaagaagcagatcaaggtcgtccgcaa
cgacgactacaagggccccgacaaggcgaagaacggtggtgtgatcttcaagaactacaccaccctcgagaccgcctacgaggacctca
agtccggcaacgtcgacgtgctccgccagatcggccccgaaggacctcccggtctaccgtgccgacctcgaggaccgcgccgtggacaa
ggcctactccgcggttcagacgctcggtgtcgccatgtacaccgaccagtggaagaacacggacccgaaggtcctccaggccctgtcgat
ggccatcgaccgggacacgatcaccaagacggtgctccagggcacccgcgagccggccacgggctgggtcgccaagggcgtcctcg
gttaccaggagaacgtcgccggtgacgtcaccaagtacgaccggcgaaggccaaggccctcatcaaggagggtggcggtgttccggg
caacgagatcttcatccagttcaacgccgacggcggccacaaggagtggatcgaggcggtctgcaacagcatcacgcaggccaccggc
gtcaagtgcaccggcgactcgaaggccgacttccaggccgacctgaacgccgcgacgccaagcaggtgaagtcgttctaccgcagtg
gctgggtcctcgactaccgggtcaacgccaacttcatcagcgacctgttccgcaccggtgcggccggcaacaacggcttcttctccaacaa
ggacctcgacgcgaagatcaaggccgcggactccgccgcgagcctcgacgattcggtcaaggcctaccaggagatcgagaaggagct
ggtcaactacatgccagcatcccgctctggtactacaaggtcaacgccggctactcggagaacgtcaagaacgtggactacgcgcagga
cggcgacccgatcctgaccgaagtccaggtcatcaagtaa >SACTE_1546|bacterioferritin| (SEQ ID NO:57)
atgcagggcgaccccgaggtcctcgagttcctgaacgaacagctgaccgccgaattgactgccatcaatcagtacttcctgcacgcgaag
atgcaggatcaccgcggctggaccaagctcgccaaacacacccgggccgagtcgttcgacgagatgaagcacgcggagatcctgaccg
accggatcctgctgctggacggcctgcccaactatcagcggctgttccacgtgcgggtgggccagaccgtcacggagatgttccaggccg
accggcaggtcgaggtcgaggcgatcgaccgactgcggcgcggtgtcgatctgatgcgcgccaagagcgacatcacgtccgccaacat
cttcgaacggatcctggaggacgaggagcaccacatcgactatctcgacacccagctggagctgatcgagaagctcggggagccgctct
acctcgccaggtcatcgagcaggtcgagctctga >SACTE_3590|phosphatidylinositol-specific phospholipase C X region| (SEQ ID NO:58)
atgagcccgtacaccgccacgcgccggaccttcctcaccggcgccctggccgccgccaccggagtcgtcctcggtggtacgcccgccct
cgccgccccgcgagagtcctggggacccaggactggatgggggccctcgccgactccacccgctgcgacgcctcacgatccccgg
cacccacaacgcgggggcccgctacggcggaccctggaccgagtgccagaacaccacggtggccgagcagctcggcagcggcatcc
gcttcctggacgtgcgctgccggatcaccggcgacgcgttcgcgatccaccacgcgcctcgtaccagaacctgatgttcggggacgtcc
tcatcgcctgccgggacttcctggccgcgcacccgtccgagacggtgctgatgcgggtcaagcaggagtactcggaggagagcgacgc
cgcgttccggcagatcttcgacctgtacctcgacggcaagggctggcgccccgctcttccgcctcgaccccaccctgccggacctcggcgg
cgccccggggcaaggtcgtgctcctcgcggacaacggcggcctgcccggggtccggtacgccgacccggcggtcttcgacatccagga
cgactacatgccgagcccttcggcaagtaccccaagatcgaggcgcagttccgcaaggccgcccagcagccggcaagctcttcatga
actacgtgtccaccgctgccctgctgccgccgcgctcgaacgccgaccggctcaacccgcaggtccacacgttcctcgacggctccgag
gcggcgggctggaccggcctcggaatcgtcccgctggactatccggcgacccgccccggcctggtcgagtcgctgatcaggcacaacc
cggtggcctga >SACTE_2172|citrate synthase I| (SEQ ID NO:59)
gtgagcgagcacaccaacaacgctgtagtactgcgggtacggcgatgacgagtacacctaccccggtgatcgacagcaccgtcggcgacaa
gggcttcgacatcgggaagctccgggccaatacgggcctggtcacgctggacagcggatacggcaacaccgccgcctataaatccgcc
atcacctatctcgacggcgaacagggcatcctgcgctaccgcgggctacccgatcgagcagctcgcggagagctcgacgttcctcgaggtc
gcctacacgctgatcaacggcgaccttcccaaggtcgacgagctgtcggccttcaagaacgagatcacccagcacacgctgctgcacga
ggacgtcaagcgcttcttcgacggcttcccgcgcgacgccacccgatggccatgctgtcctcggtcgtcagcgcgctgtccacgttctac
caggacagccacaacccgttcgacgaggagcagcgtcacctctcgacgatccggctgctggccaagctcccgacgatcgccgcgtacg
cgtacaagaagtcgatcggtcacccgttcgtctacccgcgcaacgacctcggttacgtcgagaacttcctgcgcatgaccttctcggtcccg
gccaggagtacgtgccggacccgatcgtcgtctcggcgctcgagaagctgctcatcctgcacgcggaccacgagcagaactgttcgac
ctccaccgtgcgtctggtcggctcctcgcaggccaacatgttcgcctccatctccgccggcatctcggcgctgtggggcccgctgcacggt Figure 19 (continued)

ggcgccaaccagtcggtgctggagatgctggaaggcatccaggccaacggcggcgacgtcgactccttcatccagaaggtcaagaaca
aggaggacggcgtccgcctgatgggcttcggccaccgggtgtacaagtccttcgacccgcgcgccaagatcatcaaggccgcggccca
cgacgtcctctcctcgctcggcaagtccgacgagctgctggacatcgcgctcaagctggaggagcacgcgctctccgacgactacttcgtc
tcgcgcaacctctaccccaacgtggacttctacacgggcctgatctacgggccatgggcttcccgaccgagatgttcaccgtgctcttcgc
gctcggccgcctcccggctggatcgctcagtggcacgagatgatcaaggagccgggttcccgcatcggccgcccgcgccagatctaca
ccggcgaggtcctgcgcgacttcgtccccgtcgagagccgctga >SACTE_5668|Serine Protease| (SEQ ID NO:60)
atgacgaaacgtgcaggcattctggtcgcagtcggcgccacggtcgccggactggtcaccgcggttccgtccgccgcgtccaccgcgcc
cggggcccctggggccgccgcgccgctgaagtggaccgcttgcgggacgaaggcgtatccgacccagcagtgcgcaaccgttcgcgc
cccactggaccatgacaggccgtcaggacggcaggtcacgctcgccctcgcccgatcccgcacacggcgaagacctcgcagggtcc
gctgctggtcaaccccggcggccccggcggcagcgggctctcgatggccggcttcgtggcgtcctcgctgccggcgaagctcgccgcc
cagtacgacgtgatcggcttcgacccgcgcgggtcggcaggagcagcccggcgctggactgcgtaccgaagcacttcgacccggtac
gccccgacaccgtgcccggctcccgcgggacgagcggaccaacgggaacgcgccgcgtccttcgccgacgcgtgcggcgagaag
cacggggacctgctgccgttcatggacacggtcagcaccgcgaaggacctggacgtgatccgccgggccctcggcgcacggcagatca
actactccggctactcctacggcacctacctgggcgccgtctacgccaagctgttcccggagcgcgtgcggcgcctggtgctcgactcgat
cgtcgacccggacggcgtcggtacgaggacaacctcggccaggactacgccttcgacgcccgtcacaaggcgttcgccgcctgggtg
gcgaagaacgacgccacctaccggctcggcaccgacccggcgaaggtcgaagccgcctggtaccggatgcgggccgcggtgaagaa
gcaccccgcggcgggcaaggtcggccccgagcgagctggaggacaccttcctgcccggcggctactacaacggctactggccgcaact
ggccgaggcgttcgccgcgtacgtgaacgacaaggacgaggacgcgctggccacggcgtacgacgacttcgcggcggtcgacgcga
gcggggacaacggctactccgtctacacggccgtccagtgccgcgacacgggctggccgaagtcctggaccacctggcgcaacgacac
ctggcaggcgcaccgcaaggcgccgttcatgtcctggaacaacacctggtacaacgcgccctgccacctggcccgtcgcaccgctgc
ggccggtgcgggtcaccaaccgcgagatcccgccggcgctcctcttccaggccaccgacgacgcggcgacccctacgagggcggcc
tgagcatgcaccgcaagctcaaggctcgcgcctggtcgtcgaggagggcggcggcaaccacggcatcagcctgagcggcaacgact
gcctcgacgcgcacctgatcgcctacctcaccgacggcaccctgccccgctccggcggcagcggcgccgacgcggtctgcgacgcgct
ccccgagccggaggcggcggcgaccgcgaaggcgaaggccgctacgggccagaagggcagcaccctgcacagcctgctcggcttcc
ggggctga >SACTE_6428|chitin-binding domain 3 protein|CBM33 (SEQ ID NO:61)
atgaattgtcatgatcgcatcaacttacgcggctggacgacacgctgagcggtctgttcgtcgccgccgtgctctgtctgctcccgtggac
gggcacggccgaggccacggctcggtcgtcgaccccgcgtcccgcaactacggctgctggctccgctggggcagcgacttccagaac
cccgccatggcgcaggaagacccatgtgctggcaggcatggcaggccgacccgaacgccatgtggaactggaacgcctgtaccgc
aacgagtccgccggcaacttccggcagtgatccccgacgggcagctgtgcagcggcggccggaccgagggcgccggtacaacgc
gctggacaccgtggcgctggcaggccacggacatcacggacgacttcaccgtgaggctggaggaccaggccagccacggcgccg
actacttccgggtgtacgtcaccgagcagggcttcgaccccactgctcagccctgacctggggcgcactcgacctggtggcggagacc
ggacgttacggtcccagtacgagctacgagatccccgtgagtacgtcggggtacaccggccgccatgtcgtctacacgatctggcaggcc
tcgcacatggaccagacgtactcctgtgcagtgacgtgaacttcggctga >SACTE_0366|alpha-L-rhamnosidase|GH78 (SEQ ID NO:62)
gtgatcagcagaagacgactgctcagcaccaccgccgccaccgccgccctcgccgcggtctcctcgcccgccgccgcgccgccgcc
ccggccgacaccgcggccggtcggctccgcgtcaccgggccgaccgtggagtacgtacgccgccgctcggcctcgacgtctcccgc
ccccggctgagctggcccctcgcctcggaccacccggaccacggccagtccgcctaccaggtgcgggtcgccacctcgccggaccgc Figure 19 (continued)

ctggcccgccccgacgtctgggacagcggcaaggtcgtgtccccgacgtcggtgctggtcccgtacgcgggcccggcgctggtctccc
gtacgcgctaccactggtcggtgcgcgtgtgggaccaggacggacgcgtctcggcctggagcgagccgtcctggtgggagaccgggct
cctggacgaggccgactggtcggcggggtggatcggcgcgcccgccggcgctgacctcctcaccctccctggaggcggcctcctggatct
ggttcccggagggcgatccggccgtgggcgctccggcggccacccggtggttccgcggccgggtggagatccccgagggcgtcaccc
gcgcccgcctggtcatgaccgccgacgacggcttcaccgccctggtcgacggtgtccaggtggcccgtaccgagcccgacggcccgc
ggagaactggcgtcgtcccgtggtggtggacgtgacggcgcacctctcccccggctcccgggtcgtcgccgtgacggccaccaacgcg
gtggacggcccggccggtctgctcggggcgctggagctgaccaccgccgacggtgcggtcacactcgccacgggaaccggatggcgg
gccaccgaccgggagccggacggggactgggcgtccggcggctacgacgacaccggctggcccgccgcagcggtcctcgcccgtg
gggttccggcccctggggcgaggtacgggcggccctctccccgccacccagctgcgcacggaattccggctgggccgcaagcgcgt
cgcgcgggccggctgtactcgaccgcgctcggcctgtacgaggtgttcctgaacggcgcacgtgtcggcgaggaccggctcgcgccc
ggctggaccgactaccgcaagcgcgtccagtaccagacgtacgacgtgacggcactgcttcggtccggcggcaacgctctcggggtcac
cctcgcgccggggtggtacgccgggaacatcgctggttcggaccgcaccagtacggcgaacgtccggccgtactggcccagttggag
gtcaccttcaccgacgggtcgatcgagcgggtgctgtcgggcaccggctgggccgccgcgacccgggcccgtcaccgccaccgacctca
tggcaggcgaggagtacgacgcccggctggagaccgacggctggagccgcgccggattcgacgcgtcggggtggctcgcggcagaa
gcggtggaaggggtcacggccgtgccggtcgccgcggtggacggggcctgccgtgtcgagcgcgagctgacggcccgcgaggtgac
cgaacccgagcccggggtctacgtgttcgacctcggacagaacatggtgggcacggtacggctccttgtctcggggccggcggggcacg
acggtgcggctgcgccacgccgaggtgctgaacccggacggcaccctctacacggccaacctgcgcaccgcacgggccaccgacacc
tacacgctcaggggcggcggaccggagacgtacgagccccgcttcacccttccacggtttccgctacgtcgaggtgacgggctttccgggc
cgccccgggccggacgcggtggtgggccgggtcatccacacctcggcgccgttcaccatggccttctcgaccgacgtccccatgctcga
ccggctccacagcaacatcacctgggggcagcgcggcaacttcctctccgtcccgaccgacacgcccgcgcgcgacgaacgcctcggc
tggaccggcgacatcaacgtcttcgcgcccaccgccgcgtacacgatggagtcggcccgcttcctcggcaagtggctccaggacctgcg
cgacgaccagctggccgacggcgccttcccgaacgtcgccccggaccctccgggcgtcggcagcggggcggccggctggggcgacg
ccggggtgacggtcccgtgggccctgtaccaggcgtacggggacgtgcgggtgctggagcagtcctggtcgtcgatggtggcctggctg
gagtacctccaggcgcacagcgacggtcctgcgcgccggccgatgggtacggggactggctcaacatcgaggacgagacacccaag
gacgtcatcggcacggcgtacttcgcccacagcgccgacctcacggcccggaccgcgaggtgctgggcaaggaccccgggccctac
cgcacgctgtccggccgggtgcgcgacgcgttccgggcggcgtacgtgggcgacggcgggcgggtgaaggcgacacgcagaccg
cgtacgtcctggccctgtcgatggacctgctggagccgggcgaccgcgcaccggctgcggacaggctggtcgcgctgatcgaggcgaa
ggactggcacctgtcgacggggttcctcggcacaccgcgcctgctgccggtgctgaccgacaccgggcacacggacgtcgcctaccgg
ctgctgacgcggcggacgttcccgagctgggggtaccagatcgaccggggtgccaccacgatgtgggagcgctgggactccgtgcggc
cggacggcggttccaggacgccgggatgaactccttcaaccactacgcctacgggtcggtgggcgagtggatgtacgcgaacatcgcg
ggcatcgcccggcggcgcccggcttccgcgagatccgggtgcgtccgcgtccggggggcggggtgcaccgggccgaggcccggtt
cgactccctgtacgggccggtcaccaccgctggacctcggacggggcggcttcgcgcttcgggtggtcctgcccgccaacacgacg
gccgaggtgtgggtgccggcggtgacgggaggagctccgtccggggcaccgccgtgttcctgcggcgggaggacgggtgcgcggt
cttcgcggccggctcgggcatccaccgcttcacgcgccggcctga

Figure 20

>SACTE_0237|1, 4-beta cellobiohydrolase|GH6|GI:344313496 (SEQ ID NO:1)
MSRTSRTTLRRSRTALMAAGALVAAAAGSAAAAAPFGATAAAAAGCTVDYKIQNQW
NGGLTASVSVTNNGDAISGWQLQWSFAGGEQVSQGWNATVSQSGSAVTAKDAGYNA
ALATGASASFGFNATGNGNSVVPATFKLNGVTCNGGTTGPTDPTDPTDPTDPPAGN
RVDNPYQGAKVYVNPEWSANAAAEPGGDRIADQPTGVWLDRIAAIEGANGSMGLRDH
LDEALTQKGSGELVVQVVIYNLPGRDCAALASNGELGPTEIGRYKTEYIDPIAEILGDPK
YAGLRIVTTVEIDSLPNLVTNAGGRPTATPACDVMKANGNYVKGVGYALNKLGDAPN
VYNYIDAGHHGWIGWDDNFGASAEIFHEAATAEGATVNDVHGFITNTANYSALKEENF
SIDDAVNGTSVRQSKWVDWNRYTDELSFAQAFRNELVSVGFNSGIGMLIDTSRNGWGG
ANRPSPGPGANTSVDTYVDGGRYDRRIHLGNWCNQAGAGLGERPQAAPEPGIDAYVWM
KPPGESDGSSSEIPNDEGKGFDRMCDPTYTGNARNNNNMSGALGGAPVSGKWFSAQFQ
ELMKNAYPAL*

>SACTE_0236|glycoside hydrolase family 48|GH48|GI:344313495 (SEQ ID NO:2)
VAALALPLGMTAAAGTEAQAAAVACSVDYTTSDWGSGFTTELTLTNRGSAAIDGWTLT
YDYAGNQQLTSGWSGTWSQSGKTVSVKNAAWNGAIAAGAAVTTGAQFTYSGANTAP
TTFAVNGTVCAGAHQPPIAVLTSPAAGAVFSAGDPVPLAATAAAADGATISKVEFYDDT
TLLGTDTTSPYSYEAGQLAAGSHSVYARAYDSLGASADSPPAGITVVTGPAVVVSPAQL
GVQQGRSGTFDVSLSTAPAADVTVTAARSAGNTGLSVTGGSTLTFTPANWSTPQKVTV
TADGSGTGAATFTVTAPGHGKAEVTVTQLAAAKEYDARFLDLYGKITDPANGYFSPEGI
PYHSVETLIVEAPDHGHETTSEAYSYLIWLQAMYGKITGDWTKFNGAWDTMETYMIPT
HADQPTNSFYDASKPATYAPEHDTPNEYPAVLDGSASSGSDPIAAELKSAYGTDDIYGM
HWIQDVDNVYGYGNAPGTCAAGPTQAGPSYINTFQRGSQESVWETVTHPTCDNFTYGG
ANGYLDLFTGDSSYAKQWKFTNAPDADARAVQAAYWADVWAKEQGKAGEVADTVG
KAAKMGDYLRYSMFDKYFKKIGDCVGPTTCPAGSGKDSAHYLMSWYYAWGGATDTS
AGWSWRIGSSHAHGGYQNPMAAYALSSVADLKPKSATGAQDWAKSLDRQLDFYQWL
QSDEGAIAGGATNSWKGSYAQPPAGTPTFYGMYYDEKPVYHDPPSNQWFGFQAWSME
RVAEYYHESGDAQAKAVLDKWVDWALSETTVNPDGTYLMPSTLQWSGAPDTWNASN
PGANAQLHVTVADYTDDVGVAGAYARTLTYYAAKSGDTEAEATAEALLDGMWQHHQ
DDAGVAVPETRADYNRFDDPVYVPGGWTGAMPNGDTVDEDSTFLSIRSFYKDDPNWP
QVQAYLDGGAAPVFTYHRFWAQADIALALGAYADLLE*

>SACTE_3159|chitin-binding domain 3 protein|CBM33,2|GI:344316337 (SEQ ID NO:3)
MARRSRLISLAAVLATLLGALGLTALWPGKAEAHGVAMTPGSRTYLCQLDALSGTGAL
NPTNPACRDALSQSGANALYNWFAVLDSNAGGRGAGYVPDGSLCSAGDRSPYDFSAY
NAARADWPRTHLTSGATLKVQYSNWAAHPGDFRVYLTKPGWAPTSELAWDDLQLVQ
TVSNPPQQGGAGTNGGHYYWDLALPSGRSGDALMFIQWVRSDSQENFFSCSDIVFDGG
NGEVTGIGGTGTPTPTPTPTPTPTDPEHSGSCMAVYNVVSSWAGGFQASVEVMNHGT
EPRNGWAVQWKPGSGTQINSVWNGSLSTGSDGTVTVRDVDHNRVIAPDGSVTFGFTAT
STGNDYPAGTIGCVTS*

Figure 20 (continued)

VKRFLALLATCATVLGLTALTGPQAVAAAGCTADYTITSQWQGGFQAAVKVTNLGTPV
TGWKLTFTLPDAGQKVVQGWNAAWSQSGSAVTAAGADWNGTLATGASAEAGFVGSF
TGANPPPTAFALNGVACTGSTGEPPAGSDGGTPVDVNGQLHVCGVNLCNQYDRPVQLR
GMSTHGIQWFDACYDAASLDALANDWKSDLLRIAMYVQEDGYETDPAGFTRRVNDLV
DMAEARGMYALIDFHTLTPGDPNVNLDRAKTFFASVAARNAGKKNVIYEIANEPNGVT
WTAVKSYAEQVIPVIRAADPDAVVIVGTRGWSSLGVSDGSDESEVVNSPVNATNIMYAF
HFYAASHKDAYRSTLSRAAARLPLFVTEFGTVSATGGGAMDRASTTAWLDLLDQLKIS
YANWTYSDAPESSAAFRPGTCGGGDYSGSGVLTESGALLKNRISTPDSFPTG*

>SACTE_0265|glycoside hydrolase family 10|GH10|GI:344313522 (SEQ ID NO:5)
MAKKIPARARRALSVLTAGVLAAAGVVSLAGTAEAAGTLGDAAAAKGRYFGTAVAAN
HLGEAPYASTLDAQFDSVTPENEMKWDAVEGSRNSFTFTAADQIVSHAQSKGMKVRG
HTLVWHSQLPGWVGGLGATDLRAAMNNHITQVMTHYKGKIHSWDVVNEAFQDGNSG
ARRSSPFQDKLGDGFIEEAFRTARTVDPTAKLCYNDYNTDGRNAKSDAVYAMAKDFKQ
RGVPIDCVGFQSHFNSNSPVPSDYRANLQRFADLGLDVQITELDIEGSGSAQAANYTSVV
NACLAVTRCTGLTVWGVTDKYSWRSSGTPLLFDGDYNKKPAYDAVLAALGGTPDGGG
DDGGGDNGGGNTGSCTATYTQTATWNGGYNGEVTVKAGSSGITTWSVPVTVPSSQQV
SALWNGAPTWNAGNTVMTVKPTYNGTLAAGASTSFGFTVMTNGNTSAPAVGACTAS*

>SACTE_2347|cellulose-binding family II|GH5,CE3|GI:344315549 (SEQ ID NO:6)
VRTAIRTARRPQPLALLLRGLAAFLGLALAGALGPATARAADLPQRAEARAAGLHISDG
RLVEGNGNDFVMRGINHAHTWYPGETQSLADIKATGANTVRVVLSDGYRWSENSPED
VASHARCKAERLICVLEVHDTTGYGEDAAAGTLDHAADYWIGLKDVLDGEEDYVVINI
GNEPWGNADPAGWTAPTTAAIQKLRAAGFAHTIMVDAPNWGQDWEGVMRADARSVY
DADPTGNLIFSIHMYSVYDTAAKVTDYLNAFVDAGLPLLIGEFGGPADQYGDPDEDTM
MATAEELGLGYLAWSWSGNTDPVLDLVLDFDPTRLSSWGERVLHGPDGITETSREATV
FGGGQGGGDTEAPTAPGTPTASGVTATSVTLGWSAATDDVGVTAYDVVRVTGGSETK
VASSAATSVTVTGLSAGTAYSFAVYARDAAGNRSARSGTVSVTTDEGGSVPGGACSVG
YRVIGEWPGGFQGEITLRNTGAAAVDGWTLGFAFADGQTVTNMWGGTATQSGGAVSV
TPASYTSTIAAGGSVTVGFTGTLTGANAAPAAFTLNGATCTAA*

>SACTE_0357|polysaccharide deacetylase|CE4|GI:344313612 (SEQ ID NO:7)
MSITPRPSLRAMVTGLAVAASALAGGAVTAAPARAAACNGYVGLTFDDGPSAAQTPAL
LSALKQNGLRATMFNQGNYAASNPAQVKAQVDAGMWVGNHSYSHPHLTQQSQAQM
DSEISRTQQAIAAGGGGTPKLFRPPYGETNATLRSVEAKYGLTEVIWDVDSQDWNGAST
DAIVQAVSRLTAGQVILMHEWPANTLAAIPRIAQTLSAKGLCSGMISPQTGRAVAPDGG
GNGGGGGGGGGCTATLSAGEKWGDRYNLNVAVSGSSNWTVTMNVPSGERVMTTWN
VSASYPSAQVLVAKPNGSGNNWGATIQANGNWTWPTVSCTTS*

>SACTE_0358|Endo-1,4-beta-xylanase|GH11|GI:344313613 (SEQ ID NO:8)
MNPLVYTERRRRGRLTSLAGSVCALVLAAAAAMLLPGTASADTVVTTNQTGNNNGYY
YSFWTDGGGQVSMNLASGGSYSTSWTNTGNFVAGKGWSTGGRKSVTYSGTFNPSGNA
YLTLYGWSTNPLVEYYIVDNWGTYRPTGTFKGTVSSDGGTYDIYETTRTNAPSIEGTKTF Figure 20 (continued)

KQFWSVRQSKRTGGTITTGNHFDAWARNGMNLGTMNYMILATEGYQSSGSSNITVSEG
GSGGGGDNGGGGGGGGGCTATLSAGEKWGDRYNLNVAVSGSSNWTVTMNVPSAEKV
LSTWNISASYPSSQVLVAKPNGSGNNWGATIQANGNWTWPTVSCTTS*

>SACTE_1310|Pectate lyase|PL3|GI:344314542 (SEQ ID NO:9)
MSERAASPRTHRRRPGRRRIATALTAALGLTGAALATGVMLQPAGAATTAIPAWPSAT
GSQSVSKTIEVSGTYDGGLKRFTGSGDLGDGGQDEGQDPIFKLKDGATIKNVILGTPAAD
GIHCSGSCTIQNVWWEDVGEDAASFKGTSTSSVYTVYGGGAKKASDKVFQFNGAGKL
VVTKFQVADFGKLVRSCGNCSKQYKREIIVNDVDVTAPGKSLVGINTNYGDTAALRSV
RVHGDSSKKIKPCVRYTGNSTGAEPKETGSGPDGTYCKYTASDLSYD*

>SACTE_3717|glycoside hydrolase family 9|GH9|GI:344316877 (SEQ ID NO:10)
MWCHPYLRLRTSGRKVSSVNALPPPARPAPVRPRSRYGRRVLGMSAAALLCAGALAVP
GTAMADDAEPGPGPEQITNGDFATGTSAPWWWTPNASAAVSEGRLCVEVPAGTANAW
DVIVGQNDVPIVAGESYELSYTARSTVPLTVQTRVQEAVEPYTTVLATADPVGAEDTRV
ARTFTASVDQPAASVQLQIGGGERATTFCLDDVSLRGGAEPPVYVPDTGSPVRVNQVG
YLPRGPKSGTVVTDAEAPLTWTVKAEDGSTAATGTTVPRGEDPSSRRRVHTFDFGDLTT
AGDGYTVEVDGEVSEPFSIRGDLYDSLRSDALAYFYHNRSGIEIDADLVGEQYARPAGHI
GVAPNKGDTDVPCRPGVCDYRLDVSGGWYDAGDHGKYVVNGGISVAQLMATYERTL
TAPDAESAELGDGALRVPERDNGVPDILDEARWEMDFLIKMQVPAGEQLAGMVHHKM
HDAEWTGLPMKPHLDPQQRELHPPSTAATLNLAATAAQCARLYAPFDADFADRCLRA
AETAWDAAKRHPDVLADPNDGIGGGAYNDDDVSDEFYWAAAELFTTTGKDIYRQAVL
SSAWHGDAGAVFPAGGGISWGSTAGLGVLTLATVPNALTSDQLAQVRTVVTEGADRY
AAQSREQAYGLPYAPRGEDYVWGSNSQVLNNMVVLATAHDLTGDAAYQDAVLRGAD
YLLGRNPLNQSYVTGYGERDSHNQHHRFWAHQNDPSLPNPAPGSIAGGPNLTAIASGDP
VAAEKLSGCAPAMCYVDDIGSWATNEITINWNAPLAFIASYLDDAGEGGQTAAARTCQ
VTYSSHPWNSGSTVTVRVENTGSDPVSPWALTWLLPGEQRLSHTWSAEFDQHGRTVSA
RPLSWNRTLAPGAAVDFGFNTSAAGSSPEPGAFKLNGRACSAG*

>SACTE_4638|conserved hypothetical protein||GI:344317777 (SEQ ID NO:11)
MRTGSIARVLGLAAALAALLTTAFMAPAMAGKHDATDSPSAAAAPASFTHPGVLVSRP
QLDFVRGKVQAGAQPWKGAYDQMLASPYASLSRTAKPRAVVECGSYSNPNNGCTDER
EDALAAYTLSLAWYISQDGRYAQKAIQIMDAWSGVIKDHTNSNAPLQTGWAGSSWPR
AAEIIKYTYGNWPASGRFGTMLRDVYLPKVANGSNSNGNWELSMTEAAIGIAVFLEDR
GAYDRAVAKFRGRVPAYIYVTADGSLPKAAPGSGLDTREKIINYWQGQSTFVDGLSQET
CRDLTHTGYGLSAISHIAETSRIQGQDLYPEVADRLRHALGLHAKYQLGEKVPSSLCGGS
LKDSLGPVTEVGFNALHNRMGYAMTNTQTLTERQRPAASNNLFVAWETLTHADNPN*

>SACTE_4738|glycoside hydrolase family 16|GH16|GI:344317876 (SEQ ID NO:12)
MPSRTTLIATTAALVALAAPMAFAAPAPAPDPAVEAAAAAWDTDRAASAYAANPAAV
TASGSENPASGPGAATDGDATTRWSSDFADNAWIRVDLGSTIRINQVKLEWEAAYGKK
YVLEVSKDGTNWTPFYTEDAGTGGTVTAHTYPQEVTGRYVRMGVERATAWGYSLFS Figure 20 (continued)

FQVYGGEPAPASTTRSNLALNHPAYGDLYQHAGNSPAFVTDGGWPADLKADRSRWSS
DWNADRWVGVDLGATSTINSVDLYWEAAYAVDYEIQVSDDNRTWRTVHRPSAAEVA
ARRADVKAPAEAVGRHDTINLPTPATGRYVRMLGKERRSFYNPAPSTAQFGYSLYEFQ
VWGTGGSADAAYPALPKNPGGAYRTTFFDDFTGSGLDRSKWRVVRTGTEMGPVNGES
QAYVDSPDNIRTENGALVLESKYCKGCTPTPNGTFDFTSGRVDTNTKFDFTYGKVSARM
KLPVGDGFWPAFWLLGSDVDDPAVSWPGSGETDIMENIGYGDWTSSGLHGPGYSADG
NIGASQTYPNGGRADEWHTYGVEWTPEGMTFTVDDRVVQQTSRQKLESTRGKWVFDH
NQYVILNLALGGAYPGGYNQVTQPYWGLPQSSVDRIAQGGIKAEIDWVRVEQK*

>SACTE_4755|conserved hypothetical protein|GH64|GI:344317893 (SEQ ID NO:13)
VISRRMFLTGAAASATALTYPLWGTALSPRTSAAAATCELALENRSLPGTVHAYVTGHE
QGTDSWVLLRADGSVYRPESPGAPQTPLPVDCAIPLNGAGAGPVVLTLPQMYGARVYF
VRDDKLDFYLNPGPSLVEPAFATPDPNYGRTWSFCEFTFNPQQLYANISYVDLVTALPI
GLTLEGDSTHTVAPLPDGAVQRIADDLTAQAAADGQPWDKLVTRGSDGQVLRVVSPQ
NLMAPYFDRPDEMPFRDLFAAQIDEVWEKYRSTDLRIDLQGGRGTLAGRVSGDTLTFE
GGHTFSKPTSKDIFTCNHGPFTNNPSDSDDKKALLARIAAGFNRSIMLSHPSQPNGTSVA
DYYQDAVTNHWSRVVHANSPIGYAFPYDDVRPDGEPDVSGAANDGNPRRFTVSVGS*

>SACTE_5457|Chitosanase|GH46|GI:344318578 (SEQ ID NO:14)
VLHPHNRTARRTTRLTRTGGLAAAALGLALMALPVTAHAGAPTQPAAHHLEAAATGL
DDPAKKDIAMQLVSSAENSTLDWKAQYGYIEDIGDGRGYTAGIIGFCSGTGDMLALVER
YTDRSPGNVLASYLPALREVDGTDSHDGLDPGFPRDWAEAAKDPVFQQAQNDERDRV
YFDPAVRQAKDDGLGTLGQFAYYDAIVMHGGGDSTSFGSIRQRALAEAEPPSRGGDE
VAYLDAFLDARVWAMRQEEAHSDTSRVDTAQRVFLRDGNLNLDPPLDWQVYGDSFHI
G*

>SACTE_5647|coagulation factor 5/8 type domain protein|GH87|GI:344318749 (SEQ ID NO:15)
MTPPHRHRLFRRSVSASLSLALTAVGTAAAVVLAGAPAAQAAAVPAPSPVGISRGAA
VPFTEQEAEYAATNGTLIGPDRRYGSLPSEASGRQAVTLDAAGEYVEFTLTAPANAMTF
RYSLPDNAAGTGRDASLDLRVNGSVLKSVPVTSKYGWYYGGYPFNNNPGDTNPHHFY
DETRTMFGSTLPAGTKVRLQVASTAGSPSFTVDLADFEQVAAPVGKPSGALDVVSDFG
ADPTGAADSTAKIQAAVDAGRTQGKVVYIPQGTFQVRDHIVVDQVTLRGAGPWYSVLT
GRHPTDRSKAVGVYGKYSAQGGSRNVTLKDFAIIGDIQERVDNDQVNAIGGAMSDSVV
DNVWMQHTKCGAWMDGPMDNFTIKNSRILDQTADGVNFHYGVTNSTVTNTFVRNTG
DDGLAMWAENVPNVKNKFTFNTVILPILANNIVTYGGKDITISDNVMADTITNGGGLHI
ANRYPGVNSGQGTAVAGTHTAARNTLIRTGNSDFNWNFGVGAIWFSGLNEPISNATINI
TDSEVLDSSYAAIHLIEGASNGLHFKNVKIDGAGTYALQIQAPGTATFENVVATHIAQSN
PIHNCVGSGFQITRGSGNSGWYADPPACTGVWPDPVWTNGGVPGGGPTNPTDPDPT
DPTDPTDPPEETGNLARGRTVTETSHTDVYGAANTVDGNADTYWESRNNAFPQSVTVD
LGAAKAVKRVVLKLPPAAAWATRTQTLSVSGSTDNGTYNSLKASAGYTFNPSSGNTAT
VSLPGTPVRYLRLTFTQNTGWPAAQLSELEAYTS*

>SACTE_5978|Pectate lyase/Amb allergen|PL1|GI:344319072 (SEQ ID NO:16)

Figure 20 (continued)

MRRPVALRLSAAGATLALAAATGALMAMPEAASAATGGVTGYATQNGGTTGGAGGQ
TVRATTGTAIHAALCGRASSSTPLTIQVEGTINHGNTDKVSGSSCNTAAGVIELKQISNVT
IVGVGGGAVFDQVGIHVRESSNIIIQNVTVKNVKKSGSPTSNGGDAIGMEKDVRNVWVD
HTTLEASGGESEGFDGLFDMKAGTQYVTLSYSILRNSGRGGLVGSSESDLSNGFITYHHN
LYENIDSRAPLLRGGVAHIYNNHYVGLSKSGINSRAGARAKVDNNYFEDSKDVLGTFYT
DAAGYWQVSGNVFDNVTWSGRSSDNNPAGPDPQSNTSVSIPYAYTLDGANCVPSVVSR
TAGANTGLKVSDGSCSPQTPDPTDPTPDPTDPTPPTGTNLSLGAGSDGSSKASGTS
YGDVRDGDMSTYWSPSGSTGSVSIKWSSATTVSKINVREAAGSTGSITSWKVGNADTG
AVLASGSGAGVITFPQTSLRKITFEITGSTGTPKVAEFETYAG*

>SACTE_5230|xylose isomerase|GI:344318358 (SEQ ID NO:33)
MPERFTPTPEDKFTFGLWTVGWRGNDPFGEPTRPVLDPVESVERLAELGAHGVTFHDD
DLIPFGSDDRERARLVGRFREALERTGLKVPMATTNLFTHPVFKDGGFTSNDRDVRRFA
LRKVIRNIDLAVELGAQTYVAWGGREGAESGAAKDVRSALDRMKEAFDLLGDYVTEQ
GYDLRFAIEPKPNEPRGDILLPTIGHALAFIERLERPELVGVNPETGHEQMAGLNFPHGIA
QALWAGKLFHIDLNGQSGIKYDQDFRFGAGDLRQAFWLVDLLETAGWDGSRHFDFKP
VRTDGIDGVWESAKNCMRNYLILKERAAAFRADPAVQEALTASRLDELARPTADDGLK
ALLADRTAYEDFDATAAAERSMAFEALDQLAMDHLLNVR*

>SACTE_4571|glycoside hydrolase family 18|GH18|GI:344317711 (SEQ ID NO:34)
MTSALRATQGLQSTNHPRLSDLTRGAPLSTESPRRSSRLRWRLGPGRATRAKAVAGFTA
LLLPLAAMVGLASPAQAATSATATYLKKSDWGSGFEGQWTVKNTGTTALSSWTIEWDF
PSGTAVGSAWDASVTSSGTHWTAKNLGWNGTVAPGASISFGFNGTGSGSPTGCKLNGA
SCDGGGTVPGDSAPSKPGTPTASGITDTSVKLSWSAATDDKGIKNYDVLRDGAKVATV
TTTTYTDTGLTKGTDYSYSVQARDTADQTGPVSGAVAVRTTGGNDNPGPGTGSKVNLG
YFTNWGVYGRNYHVKNLVTSGSAEKITHINYAFGNVQGGKCTIGDSYADYDKAYTAD
QSVDGVADTWDQPLRGNFNQLRKLKAKYPHIKVIWSFGGWTWSGGFGAAAQNPAAFA
QSCYDLVEDPRWADVFDGIDIDWEYPNACGLTCDTSGPAALKNLSSALRAKFGAKNLV
TAAITADGSDGGKIDAADYAGAAQSFDWYNVMTYDFFGAWEAKGPTAPHSPLNAYAG
IPQDGFNSAAAIAKLKAKGVPASKLLLGIGFYGRGWTGVTQAAPGGTATGAAPGTYEA
GIEDYKVLKTSCPATGTIAGTAYAHCGTNWWSYDTPATITSKMAWANSQGLGGAFFWE
FSGDTANGELVSAMDSGLN*

>SACTE_2313|chitin-binding domain 3 protein|CBM33|GI:344315516 (SEQ ID NO:35)
MRKRASAAVIGLAIAGVSMFATSSASSHGYTDSPISRQKLCANGTVTGCGNIQWEPQSV
EGPKGFPAAGPADGKICAGGNSSFAALDDPRGGNWPATQVTGGQGYNFRWQFTARHA
TTDFRYYITKDGWDSTKPLTRAALESQPFMTVPYGNQQPPATLTHQGTIPTQKSGKHIIL
AVWNVADTANAFYACSDVKF*

>SACTE_4246|Carbohydrate-binding CenC domain protein|GH18|GI:344317395 (SEQ ID NO:36)
VAALAAGALTVTGLVGTAQAADINVAKNAGFESGLSGWTCTGGSGATVSSPVHGGSA
ALKATPSGQDNAKCTQTVAVKPNSTYALSSWVQGGYAYLGASGTGTTDVSTWTPGST
GWTQLRTSFTTGPSTTSVQVYTHGWYGQAAYYADDVAVTGPDGGGGTEEPGPAIPGAP
AGLAVGTTTSSSVALSWNAVSGATGYTVYRDGTKATTTTGTSATVSGLAADTAYQFSV
SATNAAGESVRSATVSGRTAKKDETGPGPSTSVPKHAVTGYWQNFNNGAAVQKLSDV Figure 20 (continued)

PANYDIIAVSFADAAGTPGAVTFNLDSAGLNGYTVAQFKADIKAKQAAGKNVIISVGGE
KGTVSVNSDASANAFADSLYTLIQEYGFNGVDIDLENGLNSTYMTKALRSLSSKVGSGL
VITMAPQTIDMQSTSGEYFKTALNIKDILTVVNMQYYNSGSMLGCDGKVYSQGSVDFLT
ALACIQLEGGLAPSQVGLVPASTRGAGSGYVAPSVVNAALDCLAKGTGCGSFKPSRT
YPDIRGAMTWSTNWDATAGNAWSNAVGPHVHGLP*

>SACTE_3064|Chitinase|GH19|GI:344316244 (SEQ ID NO:37)
VIRRVMGLLTALAAVVATLVFLPAATASAATCAPAWNASSVYTGGGSASYNGHNWSA
KWWTQNERPGTSDVWADQGACGSGGGGTDPNPSGFVVSEAQFNQMFPSRNSFYTYSG
LTAALSAYPAFANTGSDTVKKQEAAAFLANVSHETGGLVHIVEQNTANYPHYCDTSQS
YGCPAGQAAYYGRGPIQLSWNFNYKAAGDALGIDLLGNPWQVEQNASVAWKTGLWY
WNTQSGPGTMTPHNAIVNGSFGETIRSINGSIECNGGNPGQVQSRVNTYQSFVQILGTT
PGSNLSC*

>SACTE_5764|Chitinase|GH18|GI:344318865 (SEQ ID NO:38)
MRRSRSVRALVTAAVTTVAAAGMAVLGSGTAQAATPLPDHVFAPYFESWTGESPAAM
AAESGAKHLTMAFLQTTAKGSCTPYWNGDTGLPIAQASFGADIDTIQAGGGDVIPSFGG
YTADTTGTEIADSCTDVDQIAAAYQKVVTTYDVSRLDMDIEVDSLDDTAGIDRRNKAIK
KLQDWADANGRDLEISYTLPTTTRGLASSGLAVLRNAVTNGARVDVVNLMTFDYYDN
ASHDMAADTETAAQGLYDQLAKLYPGRTATQLWSMVGVTEMPGVDDFGPAETFTLAN
AARVYDWAVAKGINTLSFWALQRDNGGCPGGPAADDCSGIQQNTWDFTRVFAPFTSG
TTAPDDDFSVTATPASGTVTAGGSATTTVKTAVTKGAAQQVGLTVSGVPAGVTASLSPS
SVTAGGRSTLTLATTQAAVSGTYRISVTGTSPSGSHATAYTLTVTGGTGSQCTAGPWAG
GTVYTGGQQVSYKGHTWKAKWWTTGEEPGTTGEWGVWQDLGAC*

>SACTE_4439|Catalase||GI:344317584 (SEQ ID NO:39)
VTQGPLTTEAGAPVADNQNSETAGPGGPVLVQDQALLEKLAHFNRERIPERVVHARGA
GAYGTFTLTRDVSQWTRAKFLSEVGKETETFLRFSTVAGNLGSADAARDPRGWALKFY
TEEGNYDLVGNNTPVFFIKDAIKFPDFIHTQKRDPYTGSQEADNVWDFWGLSPESTHQV
TWLFGDRGIPASFRHMNGYGSHTFQWNNEAGEVFWVKYHFKTDQGIKNLTTEEAVRLS
GVDPDSHQRDLRESIERGDFPTWTVQVQIMPAAEAATYRFNPFDLTKVWPHEDYPPIEIG
KLELNRNPENIFAEVEQSIFSPAHFVPGIGPSPDKMLQGRLFAYGDAHRYRVGINADHLP
VNRPHATEARTNSRDGYLYDGRHKGTKNYEPNSFGGPVQTDRPLWQPVSVTGGTGNH
EAAVHAEDNDFVQAGNLYRLMSEDEKGRLIDNLAGFIAKVSRDDIADRAINNFRQADA
DFGKRLEVAVQALRG*

>SACTE_0562|cellulose-binding family II|GH74|GI:344313814 (SEQ ID NO:40)
VYAMPSTAPAAVQSGEDAPVRSSPRPFAALLAALALTAGLSLIGTPAVARSDEAPAATE
ASDVSIAADTYTWKNARIDGGGFVPGIVFNRSEKNLAYARTDIGGAYRWDQSGKQWKP
LLDWVDWDRWGWTGVVSLASDTVDPDNVYAAVGTYTNSWDPTDGAVLRSSDRGAS
WKAATLPFKLGGNMPGRGMGERLAVDPKNSVLYLGAPSGNGLWRSTDAGVSWSEV
TAFPNPGNYAQDPSDTSGYGNDQGIVWVTFDERSGSAGSATQDIYVGVADKENTVYR
STDGGATWSRIPGQPTGYLAHKGVLDSATGHLYLTLSDTGGPYDGGKGRIWRYDTASG
AWQDVSPVAEADAYYGFSGLSVDRQKPGTLMATAYSSWWPDTQIFRSTDSGATWTQA
WDYTGYPNRSNRYTLDVSSVPWLSWGASPAPPETAPKLGWMTEALEIDPFDSDRMMY Figure 20 (continued)

GTGATVYGTEDLTSWDSGGTFRITPMVKGIEETAVNDLASPPSGAPLLSALGDIGGFRHT
DLDAVPDLMYTSPNLDSTTSLDFAESSPGTVVRVGNSDAAPHIGFSTDNGANWFQGSEP
SGVTGGGTVAAAADGSGFVWSPEGAGVHHTTGFGTSWTASTGIPAGATVESDRKNPEK
FYGFEAGTFYVSTDGGATFTAEATGLPAEGNVRFQALPGTEGDIWLAGGSDTGAYGLW
RSTDSGATFTKSAGVEQADSVGFGKAAPGASYRTVFVSAKIGGVRGIFRSTDAGASWTR
INDDAHQWGWTGAAITGDPRVYGRVYVSTNGRGIQVGETSDSGGGGTDPGTDPGTDPG
TDPGPEQPADAACAVTYAVTNQWPGGFQADVTVTNTGDAAYNGWKLGWSFPGGQQIS
QIWNASHRQDGVKVTVTDAGWNGTVAPGSSAGFGFTGSWAGSNAEPAAFTLDGQACT
VG*

>SACTE_4343|extracellular solute-binding protein family 5||GI:344317489 (SEQ ID NO:41)
MRGAKSAKWVAGAAIIALAATACGGGDSDSDNGAKGAVDADGIFSVEVGEPQNPLQP
ANTMESNGSIVTDAIFSQLVDYDPDGKLEMINAESVETTDSKLWTVKLKKDWKFHDGT
PVTADSYVKAWNWAANIENAQTNASWFADIKGYADVHPDGEGAKPKSDAMSGLKKV
DDYTFTIELNSAVPYFSYKLGYTVFSPLPESFYADPKAAGEKPVGNGAYKFVSWDHKKQ
IKVVRNDDYKGPDKAKNGGVIFKNYTTLETAYEDLKSGNVDVLRQIGPKDLPVYRADL
EDRAVDKAYSAVQTLGVAMYTDQWKNTDPKVLQGLSMAIDRDTITKTVLQGTREPAT
GWVAKGVLGYQENVAGDVTKYDPAKAKALIKEGGGVPGNEIFIQFNADGGHKEWIEA
VCNSITQATGVKCTGDSKADFQADLNARDAKQVKSFYRSGWVLDYPVNANFISDLFRT
GAAGNNGFFSNKDLDAKIKAADSAASLDDSVKAYQEIEKELVNYMPSIPLWYYKVNAG
YSENVKNVDYAQDGDPILTEVQVIK*

>SACTE_1546|bacterioferritin||GI:344314774 (SEQ ID NO:42)
MQGDPEVLEFLNEQLTAELTAINQYFLHAKMQDHRGWTKLAKHTRAESFDEMKHAEIL
TDRILLLDGLPNYQRLFHVRVGQTVTEMFQADRQVEVEAIDRLRRGVDLMRAKSDITSA
NIFERILEDEEHHIDYLDTQLELIEKLGEPLYLAQVIEQVEL*

>SACTE_3590|phosphatidylinositol-specific phospholipase C X region||GI:344316754 (SEQ ID NO:43)
MSPYTATRRTFLTGALAAATGVVLGGTPALAAPARVLGTQDWMGALADSTPLRRLTIP
GTHNAGARYGGPWTECQNTTVAEQLGSGIRFLDVRCRITGDAFAIHHGASYQNLMFGD
VLIACRDFLAAHPSETVLMRVKQEYSEESDAAFRQIFDLYLDGKGWRPLFRLDPTLPDL
GGARGKVVLLADNGGLPGVRYADPAVFDIQDDYMAEPFGKYPKIEAQFRKAAQQPGK
LFMNYVSTAALLPPRSNADRLNPQVHTFLDGSEAAGWTGLGIVPLDYPATRPGLVESLI
RHNPVA*

>SACTE_2172|citrate synthase I||GI:344315379 (SEQ ID NO:44)
VSEHTNNAVVLRYGDDEYTYPVIDSTVGDKGFDIGKLRANTGLVTLDSGYGNTAAYKS
AITYLDGEQGILRYRGYPIEQLAESSTFLEVAYTLINGDLPKVDELSAFKNEITQHTLLHE
DVKRFFDGFPRDAHPMAMLSSVVSALSTFYQDSHNPFDEEQRHLSTIRLLAKLPTIAAYA
YKKSIGHPFVYPRNDLGYVENFLRMTFSVPAQEYVPDPIVVSALEKLLILHADHEQNCST
STVRLVGSSQANMFASISAGISALWGPLHGGANQSVLEMLEGIQANGGDVDSFIQKVKN
KEDGVRLMGFGHRVYKSFDPRAKIIKAAAHDVLSSLGKSDELLDIALKLEEHALSDDYF Figure 20 (continued)

VSRNLYPNVDFYTGLIYRAMGFPTEMFTVLFALGRLPGWIAQWHEMIKEPGSRIGRPRQI
YTGEVLRDFVPVESR*

>SACTE_5668|TAP domain protein||GI:344318769 (SEQ ID NO:45)
MTKRAGILVAVGATVAGLVTAVPSAASTAPGAPGAAAPLKWTACGTKAYPTQQCATV
RAPLDHDRPSGRQVTLALARIPHTAKTSQGPLLVNPGGPGGSGLSMAGFVASSLPAKLA
AQYDVIGFDPRGVGRSSPALDCVPKHFDPVRPDTVPGSPRDERTNRERAASFADACGEK
HGDLLPFMDTVSTAKDLDVIRRALGARQINYFGYSYGTYLGAVYAKLFPERVRRLVLD
SIVDPDGVWYEDNLGQDYAFDARHKAFAAWVAKNDATYRLGTDPAKVEAAWYRMR
AAVKKHPAAGKVGPSELEDTFLPGGYYNGYWPQLAEAFAAYVNDKDEDALATAYDDF
AAVDASGDNGYSVYTAVQCRDTGWPKSWTTWRNDTWQAHRKAPFMSWNNTWYNAP
CATWPVAPLRPVRVTNREIPPALLFQATDDAATPYEGGLSMHRKLKGSRLVVEEGGGN
HGISLSGNDCLDAHLIAYLTDGTLPRSGGSGADAVCDALPEPEAAATAKAKAATGQKGS
TLHSLLGFRG*

>SACTE_6428|chitin-binding domain 3 protein|CBM33|GI:344319509 (SEQ ID NO:46)
MNCHDRINLRGWTTRLSGLFVAAVLCLLPWTGTAEAHGSVVDPASRNYGCWLRWGSD
FQNPAMAQEDPMCWQAWQADPNAMWNWNGLYRNESAGNFPAVIPDGQLCSGGRTE
GGRYNALDTVGAWQATDITDDFTVRLEDQASHGADYFRVYVTEQGFDPTAQPLTWGA
LDLVAETGRYGPSTSYEIPVSTSGYTGRHVVYTIWQASHMDQTYFLCSDVNFG*

>SACTE_0366|alpha-L-rhamnosidase|GH78|GI:344313621 (SEQ ID NO:47)
VISRRRLLSTTAATAALAAVSSPAARAAAPADTAAGRLRVTGPTVEYVRRPLGLDVSRP
RLSWPLASDHPDHGQSAYQVRVATSPDRLARPDVWDSGKVVSPTSVLVPYAGPALVSR
TRYHWSVRVWDQDGRVSAWSEPSWWETGLLDEADWSAGWIGAPAALTSSPSLEAAS
WIWFPEGDPAVGAPAATRWFRGRVEIPEGVTRARLVMTADDGFTALVDGVQVARTEP
DGPAENWRRPVVVDVTAHLSPGSRVVAVTATNAVDGPAGLLGALELTTADGAVTLAT
GTGWRATDREPDGDWASGGYDDTGWPAAAVLAPWGSGPWGEVRAALSPATQLRTEF
RLGRKRVARARLYSTALGLYEVFLNGARVGEDRLAPGWTDYRKRVQYQTYDVTALLR
SGGNALGVTLAPGWYAGNIAWFGPHQYGERPAVLAQLEVTFTDGSIERVLSGTGWAAA
TGPVTATDLMAGEEYDARLETDGWSRAGFDASGWLAAEAVEGVTAVPVAAVDGACR
VERELTAREVTEPEPGVYVFDLGQNMVGTVRLLVSGPAGTTVRLRHAEVLNPDGTLYT
ANLRTARATDTYTLRGGGPETYEPRFTHGFRYVEVTGFPGRPGPDAVVGRVIHTSAPF
TMAFSTDVPMLDRLHSNITWGQRGNFLSVPTDTPARDERLGWTGDINVFAPTAAYTME
SARFLGKWLQDLRDDQLADGAFPNVAPDLPGVGSGAAGWGDAGVTVPWALYQAYGD
VRVLEQSWSSMVAWLEYLQAHSDGLLRPADGYGDWLNIEDETPKDVIGTAYFAHSAD
LTARTAEVLGKDPGPYRTLSGRVRDAFRAAYVGDGGRVKGDTQTAYVLALSMDLLEP
GDRAPAADRLVALIEAKDWHLSTGFLGTPRLLPVLTDTGHTDVAYRLLTRRTFPSWGY
QIDRGATTMWERWDSVRPDGGFQDAGMNSFNHYAYGSVGEWMYANIAGIAPAAPGF
REIRVRPRPGGGVHRAEARFDSLYGPVTTRWTSDGGGFALRVVLPANTTAEVWVPGGD
GRSSVRGTAVFLRREDGCAVFAAGSGIHRFTAPA*

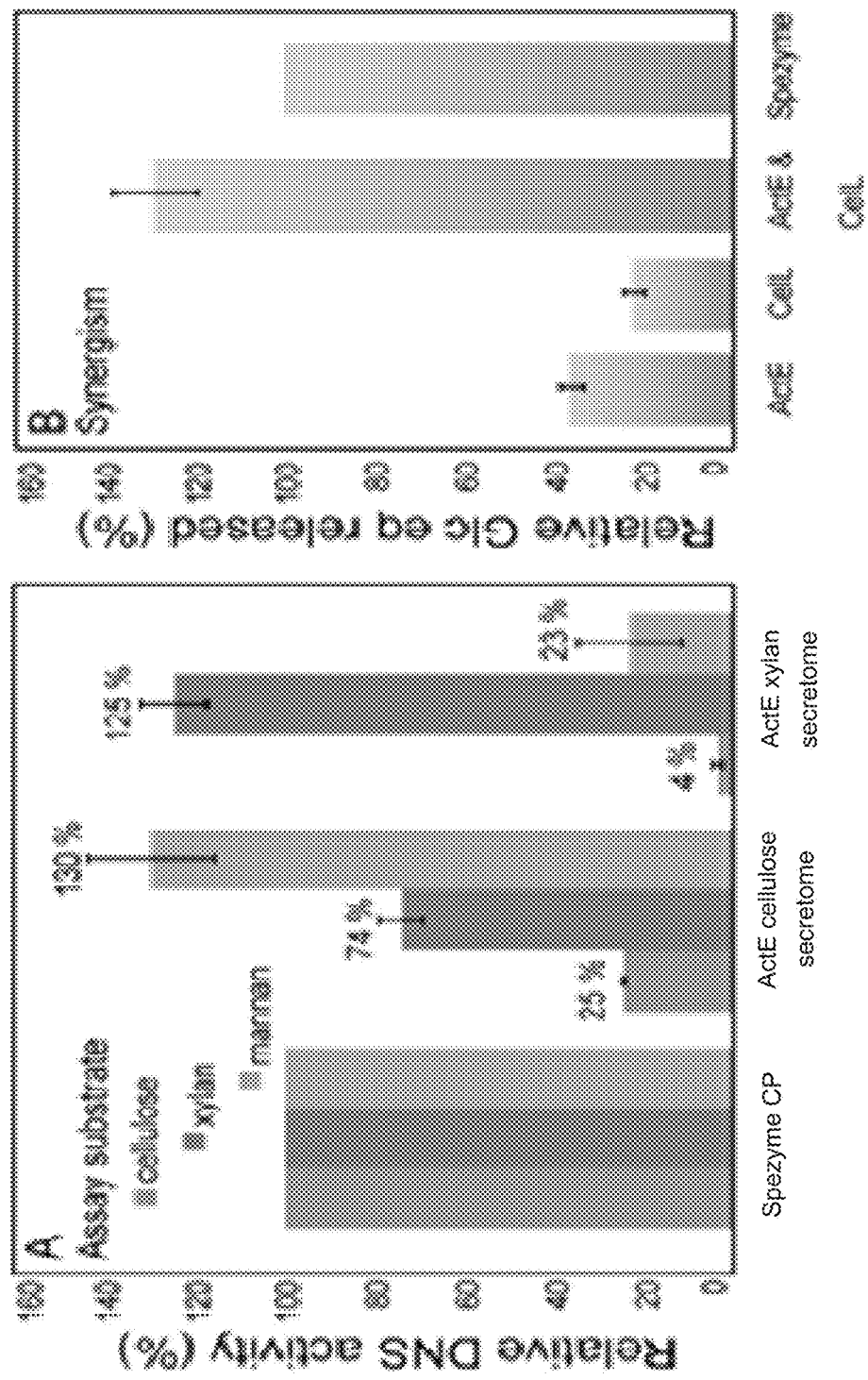
Figure 21 A-B

```
5'  ATGGGACATCACCATCATCACCATCACCATGCATCCGAAAACCTGTACTTCCAGGCGATC
                                                                    60
                          N-terminal tag
1   M  G  H  H  H  H  H  H  H  A  S  E  N  L  Y  F  Q  A  I 5'  GCCATGgatccgaacaatgacgactggctgcatgttgaaggtaacaaaatagtggacatg
                                                                    120
    N-te..tag                      cell.cc
1   A  M  D  P  N  N  D  D  W  L  H  V  E  G  N  K  I  V  D  M 5'  tacggtaatcaggtctggctgaccggctgcaactggtttggattcaataccggtaccaat
                                                                    180
                              cell.cc
1   Y  G  N  Q  V  W  L  T  G  C  N  W  F  G  F  N  T  G  T  N 5'  gtgtttgacggagtatggagctgcaatatgagagaagccctcaagggtatggcggacaga
                                                                    240
                              cell.cc
1   V  F  D  G  V  W  S  C  N  M  R  E  A  L  K  G  M  A  D  R 5'  ggaataaattttttgagaatacctatttcaacagaattgctgtatcaatggtctcaagga
                                                                    300
                              cell.cc
1   G  I  N  F  L  R  I  P  I  S  T  E  L  L  Y  Q  W  S  Q  G 5'  atatatcccaaagcaaatgttaatgattttgtaaatccggagctgaaaggaaagaacagc
                                                                    360
                              cell.cc
1   I  Y  P  K  A  N  V  N  D  F  V  N  P  E  L  K  G  K  N  S 5'  cttgagcttttgactttgccgttcagtgctgcaaagaattcggaataaagataatggtg
                                                                    420
                              cell.cc
1   L  E  L  F  D  F  A  V  Q  C  C  K  E  F  G  I  K  I  M  V 5'  gatatacacagtccggcaacagatgccatggggcatatgtatcctttatggtatgacggt
                                                                    480
                              cell.cc
1   D  I  H  S  P  A  T  D  A  M  G  H  M  Y  P  L  W  Y  D  G
```

Figure 22 (SEQ ID NOs: 63 & 64)

```
5'  caatttacaacagagatatggatttcaactttggagtggttgacggaaagatataaaaat
                                                                      540
            Q  F  T  T  E  I  W  I  S  T  L  E  W  L  T  E  R  Y  K  N 5'  gatgacacaattcttgcactggaccttaaaaatgagcctcacggcaccccgggcagcgaa
                                                                      600
            D  D  T  I  L  A  L  D  L  K  N  E  P  H  G  T  P  G  S  E 5'  ttaatggccaaatgggatggttccacggatttgaacaactggaagcatgctgctgaaaca
                                                                      660
            L  M  A  K  W  D  G  S  T  D  L  N  N  W  K  H  A  A  E  T 5'  tgcgcaaagagaatccttgcaataaatccgaatattcttattgtggtagaaggagtggaa
                                                                      720
            C  A  K  R  I  L  A  I  N  P  N  I  L  I  V  V  E  G  V  E 5'  gtttatccaaagcctggctatgattataccgcagtggacgaatggggaaaagagagtaaa
                                                                      780
            V  Y  P  K  P  G  Y  D  Y  T  A  V  D  E  W  G  K  E  S  K 5'  tatttctataactggtggggaggaaatttaagaggagtcagggattatcccattgacctt
                                                                      840
            Y  F  Y  N  W  W  G  G  N  L  R  G  V  R  D  Y  P  I  D  L 5'  ggcaagcatcagaagcagcttgtatactcacctcacgattacggtcccctcgtacataaa
                                                                      900
            G  K  H  Q  K  Q  L  V  Y  S  P  H  D  Y  G  P  L  V  H  K 5'  caaccttggttctatgaaggctttaacaaagaaactttgtataatgattgctggagagat
                                                                      960
            Q  P  W  F  Y  E  G  F  N  K  E  T  L  Y  N  D  C  W  R  D
```

Figure 22 cont'd (SEQ ID NOs: 63 & 64)

```
5'  aactgggcatacatacacgaggaaaacatcgctcctctgatagtgggtgaatggggaggt
                                                                              1020
                              cellcc
1   N  W  A  Y  I  H  E  N  I  A  P  L  I  V  G  E  W  G  G 5'  ttcatggaccgcggagacaacgagaaatggatgaaagcgctgagagattatatgattgag
                                                                              1080
                              cellcc
1   F  M  D  R  G  D  N  E  K  W  M  K  A  L  R  D  Y  M  I  E 5'  aataaaatatcccacacttttggtgctataatgcaaattccggtgataccggaggactt
                                                                              1140
                              cellcc
1   N  K  I  S  H  T  F  W  C  Y  N  A  N  S  G  D  T  G  G  L 5'  gtatactatgatttattacctgggacgaagaaaatgctcttctgaagcctgcatta
                                                                              1200
                              cellcc
1   V  Y  Y  D  F  I  T  W  D  E  E  K  Y  A  L  L  K  P  A  L 5'  tggcagacagaggacggaaagtttataggccttgaccatcagatacctcttggttcaaat
                                                                              1260
                              cellcc
1   W  Q  T  E  D  G  K  F  I  G  L  D  H  Q  I  P  L  G  S  N 5'  ggaGGTTTAAACGCGACTCCCACTAAAGGTGCCACTCCTACCAATACGGCGACTCCGACT
                                                                              1320
        Pmel bsite          40aa Linker + CBM3 from CipA
1   G  G  L  N  A  T  P  T  K  G  A  T  P  T  N  T  A  T  P  T 5'  AAGTCGGCAACGGCAACGCCCACTCGCCCCAGCGTACCGACCAATACTCCGACTAATACC
                                                                              1380
                       40aa Linker + CBM3 from CipA
1   K  S  A  T  A  T  P  T  R  P  S  V  P  T  N  T  P  T  N  T 5'  CCGGCGAACACCCCAGTAAGCGGTAACCTGAAGGTTGAATTTTATAACTCCAACCCAAGC
                                                                              1440
                       40aa Linker + CBM3 from CipA
1   P  A  N  T  P  V  S  G  N  L  K  V  E  F  Y  N  S  N  P  S
```

Figure 22 cont'd (SEQ ID NOs: 63 & 64)

```
5'  GACACAACGAATAGCATCAATCCGCAGTTCAAAGTCACGAACACTGGCAGTTCAGCTATC
    ++++|++++|++++|++++|++++|++++|++++|++++|++++|++++|++++|++++|  1500
                    40aa Linker + CBM3 from CipA
1    D  T  T  N  S  I  N  P  Q  F  K  V  T  N  T  G  S  S  A  I 5'  GATCTGTCGAAACTGACCCTTCGTTACTACTATACGGTTGATGGCCAAAAAGATCAGACC
    ++++|++++|++++|++++|++++|++++|++++|++++|++++|++++|++++|++++|  1560
                    40aa Linker + CBM3 from CipA
1    D  L  S  K  L  T  L  R  Y  Y  Y  T  V  D  G  Q  K  D  Q  T 5'  TTTTGGTGCGACCATGCAGCAATCATCGGTAGCAATGGTTCTTATAACGGCATTACTTCT
    ++++|++++|++++|++++|++++|++++|++++|++++|++++|++++|++++|++++|  1620
                    40aa Linker + CBM3 from CipA
1    F  W  C  D  H  A  A  I  I  G  S  N  G  S  Y  N  G  I  T  S 5'  AATGTAAAAGGCACCTTTGTGAAGATGTCAAGTAGCACCAACAATGCTGATACCTACCTG
    ++++|++++|++++|++++|++++|++++|++++|++++|++++|++++|++++|++++|  1680
                    40aa Linker + CBM3 from CipA
1    N  V  K  G  T  F  V  K  M  S  S  S  T  N  N  A  D  T  Y  L 5'  GAAATTAGCTTCACGGGTGGCACACTTGAACCAGGAGCCCACGTCCAGATCCAGGGCCGT
    ++++|++++|++++|++++|++++|++++|++++|++++|++++|++++|++++|++++|  1740
                    40aa Linker + CBM3 from CipA
1    E  I  S  F  T  G  G  T  L  E  P  G  A  H  V  Q  I  Q  G  R 5'  TTTGCGAAAAACGATTGGAGCAACTATACGCAATCAAACGATTATAGTTTCAAAAGCGCG
    ++++|++++|++++|++++|++++|++++|++++|++++|++++|++++|++++|++++|  1800
                    40aa Linker + CBM3 from CipA
1    F  A  K  N  D  W  S  N  Y  T  Q  S  N  D  Y  S  F  K  S  A 5'  TCTCAATTCGTAGAATGGGATCAGGTGACCGCATATTTGAACGGAGTGCTGGTTTGGGGG
    ++++|++++|++++|++++|++++|++++|++++|++++|++++|++++|++++|++++|  1860
                    40aa Linker + CBM3 from CipA
1    S  Q  F  V  E  W  D  Q  V  T  A  Y  L  N  G  V  L  V  W  G 5'  AAAGAACCAGGA
    ++++|++++|++                                                   1872
    40aa Lin...om CipA
1    K  E  P  G
```

Figure 22 cont'd (SEQ ID NOs: 63 & 64)

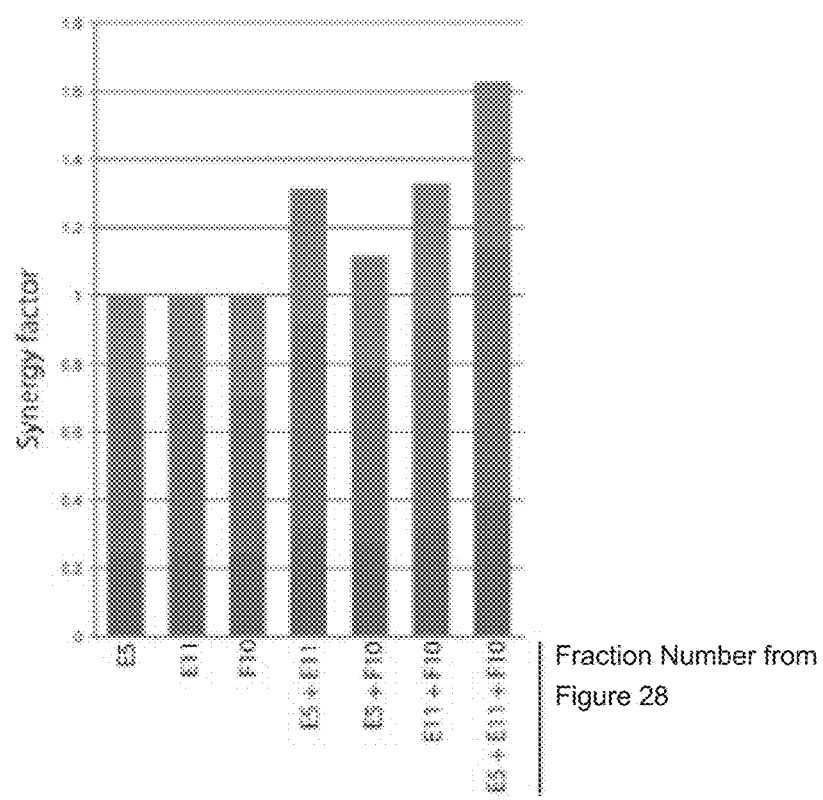
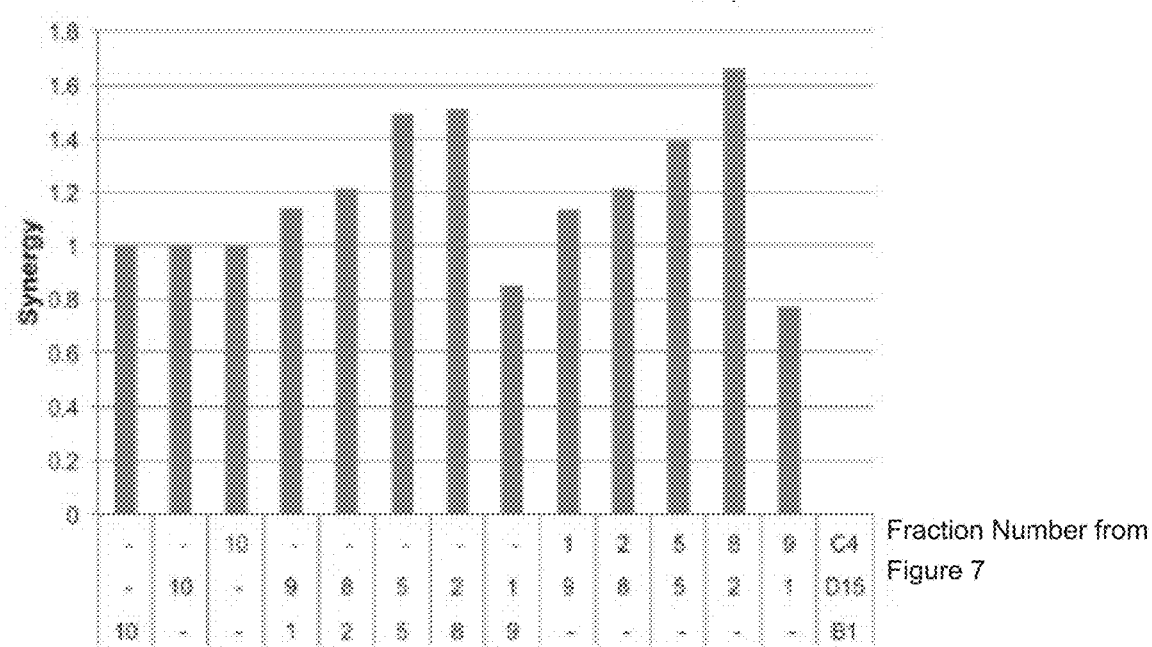
Figure 25 A-B

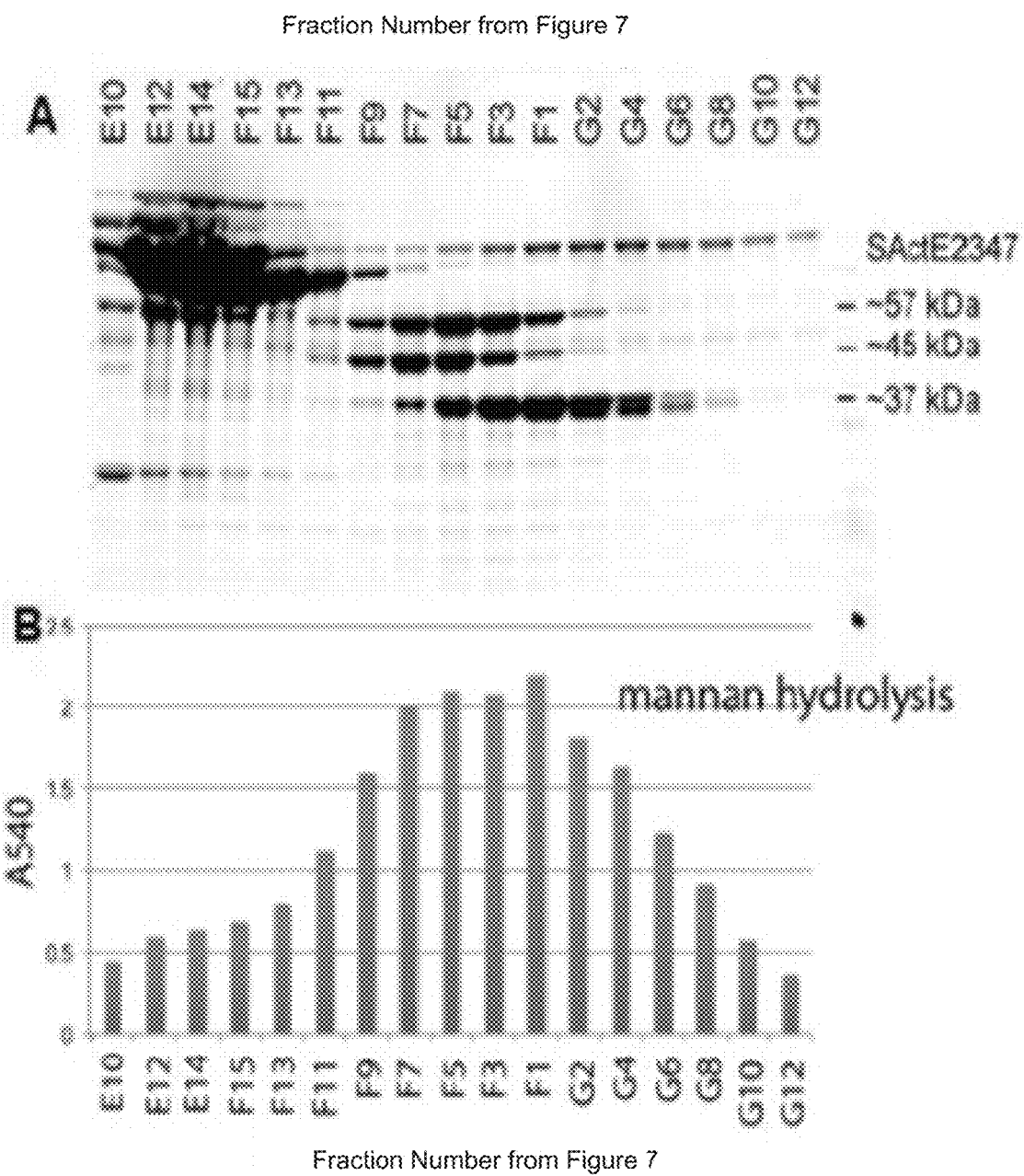
Figure 26 A-B

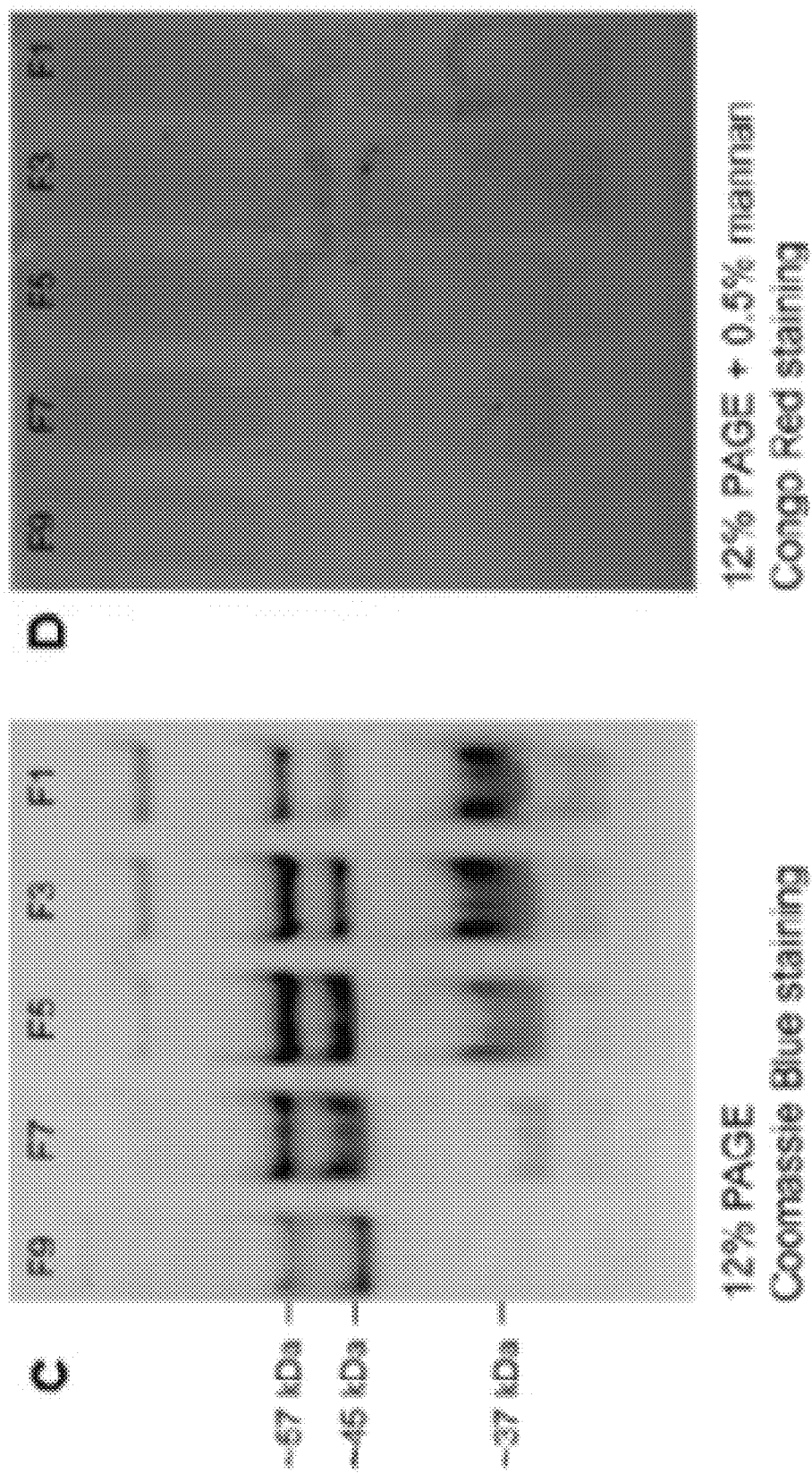
Figure 26 C-D

Figure 28B

| MS # | ID | Function | CAZY | CBM | AA | Best BLAST |
|---|---|---|---|---|---|---|
| 3 | SACTE_4738 | glycoside hydrolase family 16 | GH16 | CBM32 | 627 | beta-1,3-glucanase |
| 4 | SACTE_3159 | chitin-binding domain 3 protein | CBM33,2 | CBM33,2 | 363 | cellulose oxygenase |
| 5 | SACTE_3159 | chitin-binding domain 3 protein | CBM33,2 | CBM33,2 | 363 | |
| 6 | SACTE_3159 | chitin-binding domain 3 protein | CBM33,2 | CBM33,2 | 363 | |
| 7 | SACTE_3159 | chitin-binding domain 3 protein | CBM33,2 | CBM33,2 | 363 | |
| 8 | SACTE_0265 | glycoside hydrolase family 10 | GH10 | CBM2 | 439 | xylanase |
| 9 | SACTE_5083 | putative RNA polymerase | #N/A | #N/A | 418 | |
| 10 | SACTE_0237 | 1,4-beta cellobiohydrolase | GH6 | CBM2 | 587 | 1,4-beta cellobiohydrolase |
| 11 | SACTE_0482 | glycoside hydrolase family 5 | GH5 | CBM2 | 457 | endo-1,4-beta-glucanase |
| 12 | SACTE_4755 | beta-1,3-glucanase | GH64 | | 409 | beta-1,3-glucanase |
| 13 | SACTE_0482 | glycoside hydrolase family 5 | GH5 | CBM2 | 457 | |
| 14 | SACTE_0237 | 1,4-beta cellobiohydrolase | GH6 | CBM2 | 587 | 1,4-beta cellobiohydrolase |
| 15 | SACTE_0949 | glucan endo-1,3-beta-D-glucosidase | GH16 | CBM54 | 307 | beta-1,3-glucanase |
| 16 | SACTE_0236 | glycoside hydrolase family 48 | GH48 | CBM2,37 | 955 | cellulose 1,4-beta-cellobiosidase |
| 17 | SACTE_0236 | glycoside hydrolase family 48 | GH48 | CBM2,37 | 955 | |
| 18 | SACTE_5457 | chitosanase | GH46 | | 298 | chitosanase |
| 19 | SACTE_0236 | glycoside hydrolase family 48 | GH48 | CBM2,37 | 955 | cellulose 1,4-beta-cellobiosidase |
| 20 | SACTE_3717 | carbohydrate-binding, CenC-like | GH9 | CBM2,4 | 909 | endo-1,4-beta-glucanase |
| 21 | SACTE_2347 | cellulose-binding family II | GH5,CE3 | CBM2,37 | 563 | secreted beta-mannosidase |
| 22 | SACTE_2347 | cellulose-binding family II | GH5,CE3 | CBM2,37 | 563 | secreted beta-mannosidase |
| 23 | SACTE_2347 | cellulose-binding family II | GH5,CE3 | CBM2,37 | 563 | secreted beta-mannosidase |
| 24 | SACTE_5629 | Ricin B lectin | GH93 | CBM42,13 | 993 | exo-a-L-1,5-arabinanase |
| 25 | SACTE_4363 | putative secreted protein | GH55 | CBM56,54,57 | 606 | endo-beta-1,3-glucanase |

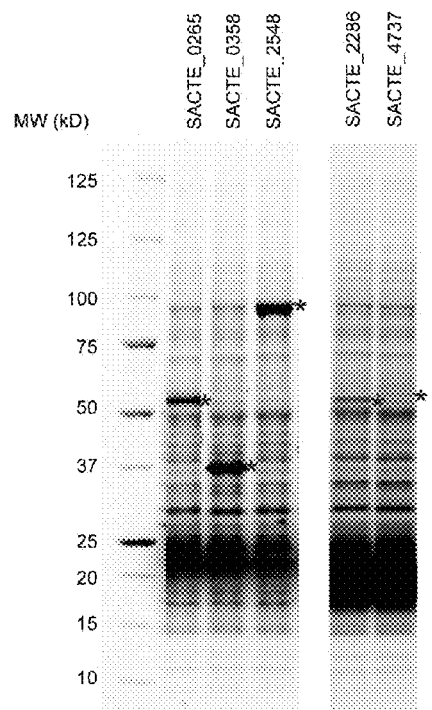
Figure 29 A-B

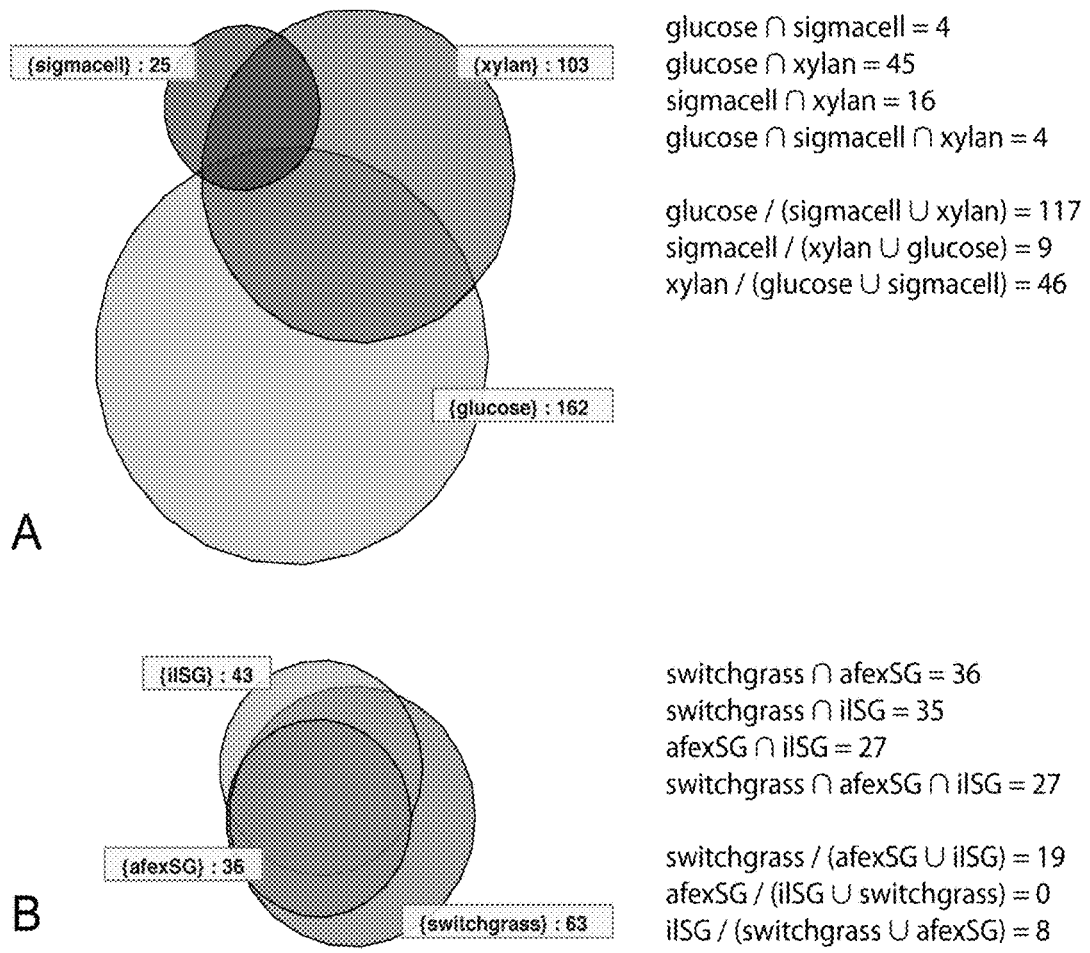
Figure 34A-B

SEQUENCE LISTING

<160> NUMBER OF SEQ ID NOS: 64

<210> SEQ ID NO 1
<211> LENGTH: 586
<212> TYPE: PRT
<213> ORGANISM: Streptomyces sp. ACTE

<400> SEQUENCE: 1

```
Met Ser Arg Thr Ser Arg Thr Thr Leu Arg Arg Ser Arg Thr Ala Leu
1               5                   10                  15

Met Ala Ala Gly Ala Leu Val Ala Ala Ala Ala Gly Ser Ala Ala Ala
            20                  25                  30

Ala Ala Pro Phe Gly Ala Thr Ala Ala Ala Ala Gly Cys Thr Val
        35                  40                  45

Asp Tyr Lys Ile Gln Asn Gln Trp Asn Gly Leu Thr Ala Ser Val
    50                  55                  60

Ser Val Thr Asn Asn Gly Asp Ala Ile Ser Gly Trp Gln Leu Gln Trp
65                  70                  75                  80

Ser Phe Ala Gly Gly Glu Gln Val Ser Gln Gly Trp Asn Ala Thr Val
                85                  90                  95

Ser Gln Ser Gly Ser Ala Val Thr Ala Lys Asp Ala Gly Tyr Asn Ala
            100                 105                 110

Ala Leu Ala Thr Gly Ala Ser Ala Ser Phe Gly Phe Asn Ala Thr Gly
        115                 120                 125

Asn Gly Asn Ser Val Val Pro Ala Thr Phe Lys Leu Asn Gly Val Thr
    130                 135                 140

Cys Asn Gly Gly Thr Thr Gly Pro Thr Asp Pro Thr Asp Pro Thr Asp
145                 150                 155                 160

Pro Thr Asp Pro Thr Asp Pro Ala Gly Asn Arg Val Asp Asn Pro
                165                 170                 175

Tyr Gln Gly Ala Lys Val Tyr Val Asn Pro Glu Trp Ser Ala Asn Ala
            180                 185                 190

Ala Ala Glu Pro Gly Gly Asp Arg Ile Ala Asp Gln Pro Thr Gly Val
        195                 200                 205

Trp Leu Asp Arg Ile Ala Ala Ile Glu Gly Ala Asn Gly Ser Met Gly
    210                 215                 220

Leu Arg Asp His Leu Asp Glu Ala Leu Thr Gln Lys Gly Ser Gly Glu
225                 230                 235                 240

Leu Val Val Gln Val Val Ile Tyr Asn Leu Pro Gly Arg Asp Cys Ala
```

```
            245                 250                 255
Ala Leu Ala Ser Asn Gly Glu Leu Gly Pro Thr Glu Ile Gly Arg Tyr
        260                 265                 270

Lys Thr Glu Tyr Ile Asp Pro Ile Ala Glu Ile Leu Gly Asp Pro Lys
    275                 280                 285

Tyr Ala Gly Leu Arg Ile Val Thr Thr Val Glu Ile Asp Ser Leu Pro
290                 295                 300

Asn Leu Val Thr Asn Ala Gly Arg Pro Thr Ala Thr Pro Ala Cys
305                 310                 315                 320

Asp Val Met Lys Ala Asn Gly Asn Tyr Val Lys Gly Val Gly Tyr Ala
                325                 330                 335

Leu Asn Lys Leu Gly Asp Ala Pro Asn Val Tyr Asn Tyr Ile Asp Ala
            340                 345                 350

Gly His His Gly Trp Ile Gly Trp Asp Asp Asn Phe Gly Ala Ser Ala
        355                 360                 365

Glu Ile Phe His Glu Ala Ala Thr Ala Glu Gly Ala Thr Val Asn Asp
    370                 375                 380

Val His Gly Phe Ile Thr Asn Thr Ala Asn Tyr Ser Ala Leu Lys Glu
385                 390                 395                 400

Glu Asn Phe Ser Ile Asp Asp Ala Val Asn Gly Thr Ser Val Arg Gln
                405                 410                 415

Ser Lys Trp Val Asp Trp Asn Arg Tyr Thr Asp Glu Leu Ser Phe Ala
            420                 425                 430

Gln Ala Phe Arg Asn Glu Leu Val Ser Val Gly Phe Asn Ser Gly Ile
        435                 440                 445

Gly Met Leu Ile Asp Thr Ser Arg Asn Gly Trp Gly Gly Ala Asn Arg
    450                 455                 460

Pro Ser Gly Pro Gly Ala Asn Thr Ser Val Asp Thr Tyr Val Asp Gly
465                 470                 475                 480

Gly Arg Tyr Asp Arg Arg Ile His Leu Gly Asn Trp Cys Asn Gln Ala
                485                 490                 495

Gly Ala Gly Leu Gly Glu Arg Pro Gln Ala Ala Pro Glu Pro Gly Ile
            500                 505                 510

Asp Ala Tyr Val Trp Met Lys Pro Pro Gly Glu Ser Asp Gly Ser Ser
        515                 520                 525

Ser Glu Ile Pro Asn Asp Glu Gly Lys Gly Phe Asp Arg Met Cys Asp
    530                 535                 540

Pro Thr Tyr Thr Gly Asn Ala Arg Asn Asn Asn Met Ser Gly Ala
545                 550                 555                 560

Leu Gly Gly Ala Pro Val Ser Gly Lys Trp Phe Ser Ala Gln Phe Gln
                565                 570                 575

Glu Leu Met Lys Asn Ala Tyr Pro Ala Leu
            580                 585

<210> SEQ ID NO 2
<211> LENGTH: 954
<212> TYPE: PRT
<213> ORGANISM: Streptomyces sp. ACTE

<400> SEQUENCE: 2

Val Ala Ala Leu Ala Leu Pro Leu Gly Met Thr Ala Ala Gly Thr
1               5                   10                  15

Glu Ala Gln Ala Ala Ala Val Ala Cys Ser Val Asp Tyr Thr Thr Ser
            20                  25                  30
```

-continued

Asp Trp Gly Ser Gly Phe Thr Thr Glu Leu Thr Leu Thr Asn Arg Gly
                35                  40                  45

Ser Ala Ala Ile Asp Gly Trp Thr Leu Thr Tyr Asp Tyr Ala Gly Asn
 50                  55                  60

Gln Gln Leu Thr Ser Gly Trp Ser Gly Thr Trp Ser Gln Ser Gly Lys
 65                  70                  75                  80

Thr Val Ser Val Lys Asn Ala Ala Trp Asn Gly Ala Ile Ala Ala Gly
                 85                  90                  95

Ala Ala Val Thr Thr Gly Ala Gln Phe Thr Tyr Ser Gly Ala Asn Thr
                100                 105                 110

Ala Pro Thr Thr Phe Ala Val Asn Gly Thr Val Cys Ala Gly Ala His
                115                 120                 125

Gln Pro Pro Ile Ala Val Leu Thr Ser Pro Ala Ala Gly Ala Val Phe
130                 135                 140

Ser Ala Gly Asp Pro Val Pro Leu Ala Ala Thr Ala Ala Ala Ala Asp
145                 150                 155                 160

Gly Ala Thr Ile Ser Lys Val Glu Phe Tyr Asp Asp Thr Thr Leu Leu
                165                 170                 175

Gly Thr Asp Thr Thr Ser Pro Tyr Ser Tyr Glu Ala Gly Gln Leu Ala
                180                 185                 190

Ala Gly Ser His Ser Val Tyr Ala Arg Ala Tyr Asp Ser Leu Gly Ala
                195                 200                 205

Ser Ala Asp Ser Pro Pro Ala Gly Ile Thr Val Val Thr Gly Pro Ala
210                 215                 220

Val Val Val Ser Pro Ala Gln Leu Gly Val Gln Gln Gly Arg Ser Gly
225                 230                 235                 240

Thr Phe Asp Val Ser Leu Ser Thr Ala Pro Ala Ala Asp Val Thr Val
                245                 250                 255

Thr Ala Ala Arg Ser Ala Gly Asn Thr Gly Leu Ser Val Thr Gly Gly
                260                 265                 270

Ser Thr Leu Thr Phe Thr Pro Ala Asn Trp Ser Thr Pro Gln Lys Val
                275                 280                 285

Thr Val Thr Ala Asp Gly Ser Gly Thr Gly Ala Ala Thr Phe Thr Val
                290                 295                 300

Thr Ala Pro Gly His Gly Lys Ala Glu Val Thr Val Thr Gln Leu Ala
305                 310                 315                 320

Ala Ala Lys Glu Tyr Asp Ala Arg Phe Leu Asp Leu Tyr Gly Lys Ile
                325                 330                 335

Thr Asp Pro Ala Asn Gly Tyr Phe Ser Pro Glu Gly Ile Pro Tyr His
                340                 345                 350

Ser Val Glu Thr Leu Ile Val Glu Ala Pro Asp His Gly His Glu Thr
                355                 360                 365

Thr Ser Glu Ala Tyr Ser Tyr Leu Ile Trp Leu Gln Ala Met Tyr Gly
370                 375                 380

Lys Ile Thr Gly Asp Trp Thr Lys Phe Asn Gly Ala Trp Asp Thr Met
385                 390                 395                 400

Glu Thr Tyr Met Ile Pro Thr His Ala Asp Gln Pro Thr Asn Ser Phe
                405                 410                 415

Tyr Asp Ala Ser Lys Pro Ala Thr Tyr Ala Pro Glu His Asp Thr Pro
                420                 425                 430

Asn Glu Tyr Pro Ala Val Leu Asp Gly Ser Ala Ser Gly Ser Asp
                435                 440                 445

Pro Ile Ala Ala Glu Leu Lys Ser Ala Tyr Gly Thr Asp Asp Ile Tyr

```
            450                 455                 460
Gly Met His Trp Ile Gln Asp Val Asp Asn Val Tyr Gly Tyr Gly Asn
465                 470                 475                 480

Ala Pro Gly Thr Cys Ala Ala Gly Pro Thr Gln Ala Gly Pro Ser Tyr
                485                 490                 495

Ile Asn Thr Phe Gln Arg Gly Ser Gln Glu Ser Val Trp Glu Thr Val
                    500                 505                 510

Thr His Pro Thr Cys Asp Asn Phe Thr Tyr Gly Gly Ala Asn Gly Tyr
            515                 520                 525

Leu Asp Leu Phe Thr Gly Asp Ser Ser Tyr Ala Lys Gln Trp Lys Phe
            530                 535                 540

Thr Asn Ala Pro Asp Ala Asp Ala Arg Ala Val Gln Ala Ala Tyr Trp
545                 550                 555                 560

Ala Asp Val Trp Ala Lys Glu Gln Gly Lys Ala Gly Glu Val Ala Asp
                565                 570                 575

Thr Val Gly Lys Ala Ala Lys Met Gly Asp Tyr Leu Arg Tyr Ser Met
                580                 585                 590

Phe Asp Lys Tyr Phe Lys Lys Ile Gly Asp Cys Val Gly Pro Thr Thr
            595                 600                 605

Cys Pro Ala Gly Ser Gly Lys Asp Ser Ala His Tyr Leu Met Ser Trp
610                 615                 620

Tyr Tyr Ala Trp Gly Gly Ala Thr Asp Thr Ser Ala Gly Trp Ser Trp
625                 630                 635                 640

Arg Ile Gly Ser Ser His Ala His Gly Gly Tyr Gln Asn Pro Met Ala
                645                 650                 655

Ala Tyr Ala Leu Ser Ser Val Ala Asp Leu Lys Pro Lys Ser Ala Thr
                660                 665                 670

Gly Ala Gln Asp Trp Ala Lys Ser Leu Asp Arg Gln Leu Asp Phe Tyr
            675                 680                 685

Gln Trp Leu Gln Ser Asp Glu Gly Ala Ile Ala Gly Gly Ala Thr Asn
            690                 695                 700

Ser Trp Lys Gly Ser Tyr Ala Gln Pro Pro Ala Gly Thr Pro Thr Phe
705                 710                 715                 720

Tyr Gly Met Tyr Tyr Asp Glu Lys Pro Val Tyr His Asp Pro Pro Ser
                725                 730                 735

Asn Gln Trp Phe Gly Phe Gln Ala Trp Ser Met Glu Arg Val Ala Glu
                740                 745                 750

Tyr Tyr His Glu Ser Gly Asp Ala Gln Ala Lys Ala Val Leu Asp Lys
            755                 760                 765

Trp Val Asp Trp Ala Leu Ser Glu Thr Thr Val Asn Pro Asp Gly Thr
            770                 775                 780

Tyr Leu Met Pro Ser Thr Leu Gln Trp Ser Gly Ala Pro Asp Thr Trp
785                 790                 795                 800

Asn Ala Ser Asn Pro Gly Ala Asn Ala Gln Leu His Val Thr Val Ala
                805                 810                 815

Asp Tyr Thr Asp Asp Val Gly Val Ala Gly Ala Tyr Ala Arg Thr Leu
                820                 825                 830

Thr Tyr Tyr Ala Ala Lys Ser Gly Asp Thr Glu Ala Glu Ala Thr Ala
            835                 840                 845

Glu Ala Leu Leu Asp Gly Met Trp Gln His His Gln Asp Asp Ala Gly
            850                 855                 860

Val Ala Val Pro Glu Thr Arg Ala Asp Tyr Asn Arg Phe Asp Asp Pro
865                 870                 875                 880
```

```
Val Tyr Val Pro Gly Gly Trp Thr Gly Ala Met Pro Asn Gly Asp Thr
                885                 890                 895

Val Asp Glu Asp Ser Thr Phe Leu Ser Ile Arg Ser Phe Tyr Lys Asp
            900                 905                 910

Asp Pro Asn Trp Pro Gln Val Gln Ala Tyr Leu Asp Gly Gly Ala Ala
        915                 920                 925

Pro Val Phe Thr Tyr His Arg Phe Trp Ala Gln Ala Asp Ile Ala Leu
    930                 935                 940

Ala Leu Gly Ala Tyr Ala Asp Leu Leu Glu
945                 950

<210> SEQ ID NO 3
<211> LENGTH: 362
<212> TYPE: PRT
<213> ORGANISM: Streptomyces sp. ACTE

<400> SEQUENCE: 3

Met Ala Arg Arg Ser Arg Leu Ile Ser Leu Ala Val Leu Ala Thr
1               5                   10                  15

Leu Leu Gly Ala Leu Gly Leu Thr Ala Leu Trp Pro Gly Lys Ala Glu
                20                  25                  30

Ala His Gly Val Ala Met Thr Pro Gly Ser Arg Thr Tyr Leu Cys Gln
            35                  40                  45

Leu Asp Ala Leu Ser Gly Thr Gly Ala Leu Asn Pro Thr Asn Pro Ala
        50                  55                  60

Cys Arg Asp Ala Leu Ser Gln Ser Gly Ala Asn Ala Leu Tyr Asn Trp
65                  70                  75                  80

Phe Ala Val Leu Asp Ser Asn Ala Gly Gly Arg Gly Ala Gly Tyr Val
                85                  90                  95

Pro Asp Gly Ser Leu Cys Ser Ala Gly Asp Arg Ser Pro Tyr Asp Phe
            100                 105                 110

Ser Ala Tyr Asn Ala Ala Arg Ala Asp Trp Pro Arg Thr His Leu Thr
        115                 120                 125

Ser Gly Ala Thr Leu Lys Val Gln Tyr Ser Asn Trp Ala Ala His Pro
130                 135                 140

Gly Asp Phe Arg Val Tyr Leu Thr Lys Pro Gly Trp Ala Pro Thr Ser
145                 150                 155                 160

Glu Leu Ala Trp Asp Asp Leu Gln Leu Val Gln Thr Val Ser Asn Pro
                165                 170                 175

Pro Gln Gln Gly Gly Ala Gly Thr Asn Gly Gly His Tyr Tyr Trp Asp
            180                 185                 190

Leu Ala Leu Pro Ser Gly Arg Ser Gly Asp Ala Leu Met Phe Ile Gln
        195                 200                 205

Trp Val Arg Ser Asp Ser Gln Glu Asn Phe Phe Ser Cys Ser Asp Ile
210                 215                 220

Val Phe Asp Gly Gly Asn Gly Glu Val Thr Gly Ile Gly Gly Thr Gly
225                 230                 235                 240

Thr Pro Thr Pro Thr Pro Thr Pro Thr Pro Thr Pro Thr Pro Thr Asp
                245                 250                 255

Pro Glu His Ser Gly Ser Cys Met Ala Val Tyr Asn Val Val Ser Ser
            260                 265                 270

Trp Ala Gly Gly Phe Gln Ala Ser Val Glu Val Met Asn His Gly Thr
        275                 280                 285

Glu Pro Arg Asn Gly Trp Ala Val Gln Trp Lys Pro Gly Ser Gly Thr
```

```
            290             295             300
Gln Ile Asn Ser Val Trp Asn Gly Ser Leu Ser Thr Gly Ser Asp Gly
305                 310                 315                 320

Thr Val Thr Val Arg Asp Val Asp His Asn Arg Val Ile Ala Pro Asp
                325                 330                 335

Gly Ser Val Thr Phe Gly Phe Thr Ala Thr Ser Thr Gly Asn Asp Tyr
            340                 345                 350

Pro Ala Gly Thr Ile Gly Cys Val Thr Ser
            355                 360

<210> SEQ ID NO 4
<211> LENGTH: 456
<212> TYPE: PRT
<213> ORGANISM: Streptomyces sp. ACTE

<400> SEQUENCE: 4

Val Lys Arg Phe Leu Ala Leu Leu Ala Thr Cys Ala Thr Val Leu Gly
1               5                   10                  15

Leu Thr Ala Leu Thr Gly Pro Gln Ala Val Ala Ala Gly Cys Thr
            20                  25                  30

Ala Asp Tyr Thr Ile Thr Ser Gln Trp Gln Gly Gly Phe Gln Ala Ala
            35                  40                  45

Val Lys Val Thr Asn Leu Gly Thr Pro Val Thr Gly Trp Lys Leu Thr
50                  55                  60

Phe Thr Leu Pro Asp Ala Gly Gln Lys Val Val Gln Gly Trp Asn Ala
65                  70                  75                  80

Ala Trp Ser Gln Ser Gly Ser Ala Val Thr Ala Ala Gly Ala Asp Trp
                85                  90                  95

Asn Gly Thr Leu Ala Thr Gly Ala Ser Ala Glu Ala Gly Phe Val Gly
            100                 105                 110

Ser Phe Thr Gly Ala Asn Pro Pro Thr Ala Phe Ala Leu Asn Gly
            115                 120                 125

Val Ala Cys Thr Gly Ser Thr Gly Glu Pro Ala Gly Ser Asp Gly
            130                 135                 140

Gly Thr Pro Val Asp Val Asn Gly Gln Leu His Val Cys Gly Val Asn
145                 150                 155                 160

Leu Cys Asn Gln Tyr Asp Arg Pro Val Gln Leu Arg Gly Met Ser Thr
                165                 170                 175

His Gly Ile Gln Trp Phe Asp Ala Cys Tyr Asp Ala Ala Ser Leu Asp
            180                 185                 190

Ala Leu Ala Asn Asp Trp Lys Ser Asp Leu Leu Arg Ile Ala Met Tyr
            195                 200                 205

Val Gln Glu Asp Gly Tyr Glu Thr Asp Pro Ala Gly Phe Thr Arg Arg
210                 215                 220

Val Asn Asp Leu Val Asp Met Ala Glu Ala Arg Gly Met Tyr Ala Leu
225                 230                 235                 240

Ile Asp Phe His Thr Leu Thr Pro Gly Asp Pro Asn Val Asn Leu Asp
                245                 250                 255

Arg Ala Lys Thr Phe Phe Ala Ser Val Ala Ala Arg Asn Ala Gly Lys
            260                 265                 270

Lys Asn Val Ile Tyr Glu Ile Ala Asn Glu Pro Asn Gly Val Thr Trp
            275                 280                 285

Thr Ala Val Lys Ser Tyr Ala Glu Gln Val Ile Pro Val Ile Arg Ala
            290                 295                 300
```

Ala Asp Pro Asp Ala Val Ile Val Gly Thr Arg Gly Trp Ser Ser
305                 310                 315                 320

Leu Gly Val Ser Asp Gly Ser Asp Glu Ser Glu Val Val Asn Ser Pro
            325                 330                 335

Val Asn Ala Thr Asn Ile Met Tyr Ala Phe His Phe Tyr Ala Ala Ser
            340                 345                 350

His Lys Asp Ala Tyr Arg Ser Thr Leu Ser Arg Ala Ala Arg Leu
            355                 360                 365

Pro Leu Phe Val Thr Glu Phe Gly Thr Val Ser Ala Thr Gly Gly Gly
            370                 375                 380

Ala Met Asp Arg Ala Ser Thr Thr Ala Trp Leu Asp Leu Leu Asp Gln
385                 390                 395                 400

Leu Lys Ile Ser Tyr Ala Asn Trp Thr Tyr Ser Asp Ala Pro Glu Ser
            405                 410                 415

Ser Ala Ala Phe Arg Pro Gly Thr Cys Gly Gly Asp Tyr Ser Gly
            420                 425                 430

Ser Gly Val Leu Thr Glu Ser Gly Ala Leu Leu Lys Asn Arg Ile Ser
            435                 440                 445

Thr Pro Asp Ser Phe Pro Thr Gly
    450                 455

<210> SEQ ID NO 5
<211> LENGTH: 458
<212> TYPE: PRT
<213> ORGANISM: Streptomyces sp. ACTE

<400> SEQUENCE: 5

Met Ala Lys Lys Ile Pro Ala Arg Ala Arg Arg Ala Leu Ser Val Leu
1               5                   10                  15

Thr Ala Gly Val Leu Ala Ala Ala Gly Val Val Ser Leu Ala Gly Thr
            20                  25                  30

Ala Glu Ala Ala Gly Thr Leu Gly Asp Ala Ala Ala Lys Gly Arg
        35                  40                  45

Tyr Phe Gly Thr Ala Val Ala Ala Asn His Leu Gly Glu Ala Pro Tyr
50                  55                  60

Ala Ser Thr Leu Asp Ala Gln Phe Asp Ser Val Thr Pro Glu Asn Glu
65                  70                  75                  80

Met Lys Trp Asp Ala Val Glu Gly Ser Arg Asn Ser Phe Thr Phe Thr
                85                  90                  95

Ala Ala Asp Gln Ile Val Ser His Ala Gln Ser Lys Gly Met Lys Val
            100                 105                 110

Arg Gly His Thr Leu Val Trp His Ser Gln Leu Pro Gly Trp Val Gly
        115                 120                 125

Gly Leu Gly Ala Thr Asp Leu Arg Ala Ala Met Asn Asn His Ile Thr
    130                 135                 140

Gln Val Met Thr His Tyr Lys Gly Lys Ile His Ser Trp Asp Val Val
145                 150                 155                 160

Asn Glu Ala Phe Gln Asp Gly Asn Ser Gly Ala Arg Arg Ser Ser Pro
                165                 170                 175

Phe Gln Asp Lys Leu Gly Asp Gly Phe Ile Glu Glu Ala Phe Arg Thr
            180                 185                 190

Ala Arg Thr Val Asp Pro Thr Ala Lys Leu Cys Tyr Asn Asp Tyr Asn
        195                 200                 205

Thr Asp Gly Arg Asn Ala Lys Ser Asp Ala Val Tyr Ala Met Ala Lys
    210                 215                 220

```
Asp Phe Lys Gln Arg Gly Val Pro Ile Asp Cys Val Gly Phe Gln Ser
225                 230                 235                 240

His Phe Asn Ser Asn Ser Pro Val Pro Ser Asp Tyr Arg Ala Asn Leu
            245                 250                 255

Gln Arg Phe Ala Asp Leu Gly Leu Asp Val Gln Ile Thr Glu Leu Asp
        260                 265                 270

Ile Glu Gly Ser Gly Ser Ala Gln Ala Ala Asn Tyr Thr Ser Val Val
    275                 280                 285

Asn Ala Cys Leu Ala Val Thr Arg Cys Thr Gly Leu Thr Val Trp Gly
290                 295                 300

Val Thr Asp Lys Tyr Ser Trp Arg Ser Ser Gly Thr Pro Leu Leu Phe
305                 310                 315                 320

Asp Gly Asp Tyr Asn Lys Lys Pro Ala Tyr Asp Ala Val Leu Ala Ala
                325                 330                 335

Leu Gly Gly Thr Pro Asp Gly Gly Asp Gly Gly Gly Asp Asn
            340                 345                 350

Gly Gly Gly Asn Thr Gly Ser Cys Thr Ala Thr Tyr Thr Gln Thr Ala
        355                 360                 365

Thr Trp Asn Gly Gly Tyr Asn Gly Glu Val Thr Val Lys Ala Gly Ser
370                 375                 380

Ser Gly Ile Thr Thr Trp Ser Val Pro Val Thr Val Pro Ser Ser Gln
385                 390                 395                 400

Gln Val Ser Ala Leu Trp Asn Gly Ala Pro Thr Trp Asn Ala Gly Asn
                405                 410                 415

Thr Val Met Thr Val Lys Pro Thr Tyr Asn Gly Thr Leu Ala Ala Gly
            420                 425                 430

Ala Ser Thr Ser Phe Gly Phe Thr Val Met Thr Asn Gly Asn Thr Ser
        435                 440                 445

Ala Pro Ala Val Gly Ala Cys Thr Ala Ser
    450                 455

<210> SEQ ID NO 6
<211> LENGTH: 562
<212> TYPE: PRT
<213> ORGANISM: Streptomyces sp. ACTE

<400> SEQUENCE: 6

Val Arg Thr Ala Ile Arg Thr Ala Arg Arg Pro Gln Pro Leu Ala Leu
1               5                   10                  15

Leu Leu Arg Gly Leu Ala Ala Phe Leu Gly Leu Ala Leu Ala Gly Ala
            20                  25                  30

Leu Gly Pro Ala Thr Ala Arg Ala Ala Asp Leu Pro Gln Arg Ala Glu
        35                  40                  45

Ala Arg Ala Ala Gly Leu His Ile Ser Asp Gly Arg Leu Val Glu Gly
    50                  55                  60

Asn Gly Asn Asp Phe Val Met Arg Gly Ile Asn His Ala His Thr Trp
65                  70                  75                  80

Tyr Pro Gly Glu Thr Gln Ser Leu Ala Asp Ile Lys Ala Thr Gly Ala
                85                  90                  95

Asn Thr Val Arg Val Val Leu Ser Asp Gly Tyr Arg Trp Ser Glu Asn
            100                 105                 110

Ser Pro Glu Asp Val Ala Ser Ile Ile Ala Arg Cys Lys Ala Glu Arg
        115                 120                 125

Leu Ile Cys Val Leu Glu Val His Asp Thr Thr Gly Tyr Gly Glu Asp
```

-continued

```
                130                 135                 140
Ala Ala Ala Gly Thr Leu Asp His Ala Ala Asp Tyr Trp Ile Gly Leu
145                 150                 155                 160

Lys Asp Val Leu Asp Gly Glu Glu Asp Tyr Val Val Ile Asn Ile Gly
                165                 170                 175

Asn Glu Pro Trp Gly Asn Ala Asp Pro Ala Gly Trp Thr Ala Pro Thr
                180                 185                 190

Thr Ala Ala Ile Gln Lys Leu Arg Ala Ala Gly Phe Ala His Thr Ile
                195                 200                 205

Met Val Asp Ala Pro Asn Trp Gly Gln Asp Trp Glu Gly Val Met Arg
210                 215                 220

Ala Asp Ala Arg Ser Val Tyr Asp Ala Asp Pro Thr Gly Asn Leu Ile
225                 230                 235                 240

Phe Ser Ile His Met Tyr Ser Val Tyr Asp Thr Ala Ala Lys Val Thr
                245                 250                 255

Asp Tyr Leu Asn Ala Phe Val Asp Ala Gly Leu Pro Leu Leu Ile Gly
                260                 265                 270

Glu Phe Gly Gly Pro Ala Asp Gln Tyr Gly Asp Pro Asp Glu Asp Thr
                275                 280                 285

Met Met Ala Thr Ala Glu Glu Leu Gly Leu Gly Tyr Leu Ala Trp Ser
290                 295                 300

Trp Ser Gly Asn Thr Asp Pro Val Leu Asp Leu Val Leu Asp Phe Asp
305                 310                 315                 320

Pro Thr Arg Leu Ser Ser Trp Gly Glu Arg Val Leu His Gly Pro Asp
                325                 330                 335

Gly Ile Thr Glu Thr Ser Arg Glu Ala Thr Val Phe Gly Gly Gly Gln
                340                 345                 350

Gly Gly Gly Asp Thr Glu Ala Pro Thr Ala Pro Gly Thr Pro Thr Ala
                355                 360                 365

Ser Gly Val Thr Ala Thr Ser Val Thr Leu Gly Trp Ser Ala Ala Thr
                370                 375                 380

Asp Asp Val Gly Val Thr Ala Tyr Asp Val Val Arg Val Thr Gly Gly
385                 390                 395                 400

Ser Glu Thr Lys Val Ala Ser Ser Ala Ala Thr Ser Val Thr Val Thr
                405                 410                 415

Gly Leu Ser Ala Gly Thr Ala Tyr Ser Phe Ala Val Tyr Ala Arg Asp
                420                 425                 430

Ala Ala Gly Asn Arg Ser Ala Arg Ser Gly Thr Val Ser Val Thr Thr
                435                 440                 445

Asp Glu Gly Gly Ser Val Pro Gly Gly Ala Cys Ser Val Gly Tyr Arg
                450                 455                 460

Val Ile Gly Glu Trp Pro Gly Gly Phe Gln Gly Glu Ile Thr Leu Arg
465                 470                 475                 480

Asn Thr Gly Ala Ala Val Asp Gly Trp Thr Leu Gly Phe Ala Phe
                485                 490                 495

Ala Asp Gly Gln Thr Val Thr Asn Met Trp Gly Gly Thr Ala Thr Gln
                500                 505                 510

Ser Gly Gly Ala Val Ser Val Thr Pro Ala Ser Tyr Thr Ser Thr Ile
                515                 520                 525

Ala Ala Gly Gly Ser Val Thr Val Gly Phe Thr Gly Thr Leu Thr Gly
                530                 535                 540

Ala Asn Ala Ala Pro Ala Ala Phe Thr Leu Asn Gly Ala Thr Cys Thr
545                 550                 555                 560
```

Ala Ala

<210> SEQ ID NO 7
<211> LENGTH: 328
<212> TYPE: PRT
<213> ORGANISM: Streptomyces sp. ACTE

<400> SEQUENCE: 7

```
Met Ser Ile Thr Pro Arg Pro Ser Leu Arg Ala Met Val Thr Gly Leu
 1               5                  10                  15

Ala Val Ala Ala Ser Ala Leu Ala Gly Gly Ala Val Thr Ala Ala Pro
            20                  25                  30

Ala Arg Ala Ala Ala Cys Asn Gly Tyr Val Gly Leu Thr Phe Asp Asp
        35                  40                  45

Gly Pro Ser Ala Ala Gln Thr Pro Ala Leu Leu Ser Ala Leu Lys Gln
    50                  55                  60

Asn Gly Leu Arg Ala Thr Met Phe Asn Gln Gly Asn Tyr Ala Ala Ser
65                  70                  75                  80

Asn Pro Ala Gln Val Lys Ala Gln Val Asp Ala Gly Met Trp Val Gly
                85                  90                  95

Asn His Ser Tyr Ser His Pro His Leu Thr Gln Gln Ser Gln Ala Gln
            100                 105                 110

Met Asp Ser Glu Ile Ser Arg Thr Gln Gln Ala Ile Ala Ala Gly Gly
        115                 120                 125

Gly Gly Thr Pro Lys Leu Phe Arg Pro Pro Tyr Gly Glu Thr Asn Ala
    130                 135                 140

Thr Leu Arg Ser Val Glu Ala Lys Tyr Gly Leu Thr Glu Val Ile Trp
145                 150                 155                 160

Asp Val Asp Ser Gln Asp Trp Asn Gly Ala Ser Thr Asp Ala Ile Val
                165                 170                 175

Gln Ala Val Ser Arg Leu Thr Ala Gly Gln Val Ile Leu Met His Glu
            180                 185                 190

Trp Pro Ala Asn Thr Leu Ala Ala Ile Pro Arg Ile Ala Gln Thr Leu
        195                 200                 205

Ser Ala Lys Gly Leu Cys Ser Gly Met Ile Ser Pro Gln Thr Gly Arg
    210                 215                 220

Ala Val Ala Pro Asp Gly Gly Asn Gly Gly Gly Gly Gly
225                 230                 235                 240

Gly Gly Cys Thr Ala Thr Leu Ser Ala Gly Glu Lys Trp Gly Asp Arg
                245                 250                 255

Tyr Asn Leu Asn Val Ala Val Ser Gly Ser Ser Asn Trp Thr Val Thr
            260                 265                 270

Met Asn Val Pro Ser Gly Glu Arg Val Met Thr Thr Trp Asn Val Ser
        275                 280                 285

Ala Ser Tyr Pro Ser Ala Gln Val Leu Val Ala Lys Pro Asn Gly Ser
    290                 295                 300

Gly Asn Asn Trp Gly Ala Thr Ile Gln Ala Asn Gly Asn Trp Thr Trp
305                 310                 315                 320

Pro Thr Val Ser Cys Thr Thr Ser
                325
```

<210> SEQ ID NO 8
<211> LENGTH: 335
<212> TYPE: PRT
<213> ORGANISM: Streptomyces sp. ACTE

<400> SEQUENCE: 8

```
Met Asn Pro Leu Val Tyr Thr Glu Arg Arg Arg Gly Arg Leu Thr
1               5                   10                  15

Ser Leu Ala Gly Ser Val Cys Ala Leu Val Leu Ala Ala Ala Ala
            20                  25                  30

Met Leu Leu Pro Gly Thr Ala Ser Ala Asp Thr Val Thr Thr Asn
        35                  40                  45

Gln Thr Gly Asn Asn Gly Tyr Tyr Tyr Ser Phe Trp Thr Asp Gly
    50                  55                  60

Gly Gly Gln Val Ser Met Asn Leu Ala Ser Gly Gly Ser Tyr Ser Thr
65                  70                  75                  80

Ser Trp Thr Asn Thr Gly Asn Phe Val Ala Gly Lys Gly Trp Ser Thr
                85                  90                  95

Gly Gly Arg Lys Ser Val Thr Tyr Ser Gly Thr Phe Asn Pro Ser Gly
            100                 105                 110

Asn Ala Tyr Leu Thr Leu Tyr Gly Trp Ser Thr Asn Pro Leu Val Glu
            115                 120                 125

Tyr Tyr Ile Val Asp Asn Trp Gly Thr Tyr Arg Pro Thr Gly Thr Phe
130                 135                 140

Lys Gly Thr Val Ser Ser Asp Gly Gly Thr Tyr Asp Ile Tyr Glu Thr
145                 150                 155                 160

Thr Arg Thr Asn Ala Pro Ser Ile Glu Gly Thr Lys Thr Phe Lys Gln
                165                 170                 175

Phe Trp Ser Val Arg Gln Ser Lys Arg Thr Gly Gly Thr Ile Thr Thr
            180                 185                 190

Gly Asn His Phe Asp Ala Trp Ala Arg Asn Gly Met Asn Leu Gly Thr
        195                 200                 205

Met Asn Tyr Met Ile Leu Ala Thr Glu Gly Tyr Gln Ser Ser Gly Ser
210                 215                 220

Ser Asn Ile Thr Val Ser Glu Gly Gly Ser Gly Gly Gly Gly Asp Asn
225                 230                 235                 240

Gly Gly Gly Gly Gly Gly Gly Gly Cys Thr Ala Thr Leu Ser Ala
                245                 250                 255

Gly Glu Lys Trp Gly Asp Arg Tyr Asn Leu Asn Val Ala Val Ser Gly
            260                 265                 270

Ser Ser Asn Trp Thr Val Thr Met Asn Val Pro Ser Ala Glu Lys Val
        275                 280                 285

Leu Ser Thr Trp Asn Ile Ser Ala Ser Tyr Pro Ser Ser Gln Val Leu
        290                 295                 300

Val Ala Lys Pro Asn Gly Ser Gly Asn Asn Trp Gly Ala Thr Ile Gln
305                 310                 315                 320

Ala Asn Gly Asn Trp Thr Trp Pro Thr Val Ser Cys Thr Thr Ser
                325                 330                 335
```

<210> SEQ ID NO 9
<211> LENGTH: 280
<212> TYPE: PRT
<213> ORGANISM: Streptomyces sp. ACTE

<400> SEQUENCE: 9

```
Met Ser Glu Arg Ala Ala Ser Pro Arg Thr His Arg Arg Pro Gly
1               5                   10                  15

Arg Arg Arg Ile Ala Thr Ala Leu Thr Ala Ala Leu Gly Leu Thr Gly
            20                  25                  30
```

```
Ala Ala Leu Ala Thr Gly Val Met Leu Gln Pro Ala Gly Ala Ala Thr
            35                  40                  45

Thr Ala Ile Pro Ala Trp Pro Ser Ala Thr Gly Ser Gln Ser Val Ser
 50                  55                  60

Lys Thr Ile Glu Val Ser Gly Thr Tyr Asp Gly Gly Leu Lys Arg Phe
 65                  70                  75                  80

Thr Gly Ser Gly Asp Leu Gly Asp Gly Gly Gln Asp Glu Gly Gln Asp
                 85                  90                  95

Pro Ile Phe Lys Leu Lys Asp Gly Ala Thr Ile Lys Asn Val Ile Leu
            100                 105                 110

Gly Thr Pro Ala Ala Asp Gly Ile His Cys Ser Gly Ser Cys Thr Ile
            115                 120                 125

Gln Asn Val Trp Trp Glu Asp Val Gly Glu Asp Ala Ala Ser Phe Lys
130                 135                 140

Gly Thr Ser Thr Ser Ser Val Tyr Thr Val Tyr Gly Gly Ala Lys
145                 150                 155                 160

Lys Ala Ser Asp Lys Val Phe Gln Phe Asn Gly Ala Gly Lys Leu Val
                165                 170                 175

Val Thr Lys Phe Gln Val Ala Asp Phe Gly Lys Leu Val Arg Ser Cys
            180                 185                 190

Gly Asn Cys Ser Lys Gln Tyr Lys Arg Glu Ile Ile Val Asn Asp Val
            195                 200                 205

Asp Val Thr Ala Pro Gly Lys Ser Leu Val Gly Ile Asn Thr Asn Tyr
210                 215                 220

Gly Asp Thr Ala Ala Leu Arg Ser Val Arg Val His Gly Asp Ser Ser
225                 230                 235                 240

Lys Lys Ile Lys Pro Cys Val Arg Tyr Thr Gly Asn Ser Thr Gly Ala
                245                 250                 255

Glu Pro Lys Glu Thr Gly Ser Gly Pro Asp Gly Thr Tyr Cys Lys Tyr
            260                 265                 270

Thr Ala Ser Asp Leu Ser Tyr Asp
            275                 280

<210> SEQ ID NO 10
<211> LENGTH: 909
<212> TYPE: PRT
<213> ORGANISM: Streptomyces sp. ACTE

<400> SEQUENCE: 10

Met Trp Cys His Pro Tyr Leu Arg Leu Arg Thr Ser Gly Arg Lys Val
 1               5                  10                  15

Ser Ser Val Asn Ala Leu Pro Pro Ala Arg Pro Ala Pro Val Arg
                 20                  25                  30

Pro Arg Ser Arg Tyr Gly Arg Arg Val Leu Gly Met Ser Ala Ala Ala
            35                  40                  45

Leu Leu Cys Ala Gly Ala Leu Ala Val Pro Gly Thr Ala Met Ala Asp
 50                  55                  60

Asp Ala Glu Pro Gly Pro Gly Pro Gln Ile Thr Asn Gly Asp Phe
 65                  70                  75                  80

Ala Thr Gly Thr Ser Ala Pro Trp Trp Trp Thr Pro Asn Ala Ser Ala
                 85                  90                  95

Ala Val Ser Glu Gly Arg Leu Cys Val Glu Val Pro Gly Thr Ala
            100                 105                 110

Asn Ala Trp Asp Val Ile Val Gly Gln Asn Asp Val Pro Ile Val Ala
```

```
            115                 120                 125
Gly Glu Ser Tyr Glu Leu Ser Tyr Thr Ala Arg Ser Thr Val Pro Leu
            130                 135                 140

Thr Val Gln Thr Arg Val Gln Glu Ala Val Glu Pro Tyr Thr Thr Val
145                 150                 155                 160

Leu Ala Thr Ala Asp Pro Val Gly Ala Glu Asp Thr Arg Val Ala Arg
                165                 170                 175

Thr Phe Thr Ala Ser Val Asp Gln Pro Ala Ala Ser Val Gln Leu Gln
                180                 185                 190

Ile Gly Gly Gly Glu Arg Ala Thr Thr Phe Cys Leu Asp Asp Val Ser
                195                 200                 205

Leu Arg Gly Gly Ala Glu Pro Pro Val Tyr Val Pro Asp Thr Gly Ser
    210                 215                 220

Pro Val Arg Val Asn Gln Val Gly Tyr Leu Pro Arg Gly Pro Lys Ser
225                 230                 235                 240

Gly Thr Val Val Thr Asp Ala Glu Ala Pro Leu Thr Trp Thr Val Lys
                245                 250                 255

Ala Glu Asp Gly Ser Thr Ala Ala Thr Gly Thr Thr Val Pro Arg Gly
                260                 265                 270

Glu Asp Pro Ser Ser Arg Arg Val His Thr Phe Asp Phe Gly Asp
                275                 280                 285

Leu Thr Thr Ala Gly Asp Gly Tyr Thr Val Glu Val Asp Gly Glu Val
    290                 295                 300

Ser Glu Pro Phe Ser Ile Arg Gly Asp Leu Tyr Asp Ser Leu Arg Ser
305                 310                 315                 320

Asp Ala Leu Ala Tyr Phe Tyr His Asn Arg Ser Gly Ile Glu Ile Asp
                325                 330                 335

Ala Asp Leu Val Gly Glu Gln Tyr Ala Arg Pro Ala Gly His Ile Gly
                340                 345                 350

Val Ala Pro Asn Lys Gly Asp Thr Asp Val Pro Cys Arg Pro Gly Val
                355                 360                 365

Cys Asp Tyr Arg Leu Asp Val Ser Gly Gly Trp Tyr Asp Ala Gly Asp
    370                 375                 380

His Gly Lys Tyr Val Val Asn Gly Gly Ile Ser Val Ala Gln Leu Met
385                 390                 395                 400

Ala Thr Tyr Glu Arg Thr Leu Thr Ala Pro Asp Ala Glu Ser Ala Glu
                405                 410                 415

Leu Gly Asp Gly Ala Leu Arg Val Pro Glu Arg Asp Asn Gly Val Pro
                420                 425                 430

Asp Ile Leu Asp Glu Ala Arg Trp Glu Met Asp Phe Leu Ile Lys Met
                435                 440                 445

Gln Val Pro Ala Gly Glu Gln Leu Ala Gly Met Val His His Lys Met
    450                 455                 460

His Asp Ala Glu Trp Thr Gly Leu Pro Met Lys Pro His Leu Asp Pro
465                 470                 475                 480

Gln Gln Arg Glu Leu His Pro Pro Ser Thr Ala Ala Thr Leu Asn Leu
                485                 490                 495

Ala Ala Thr Ala Ala Gln Cys Ala Arg Leu Tyr Ala Pro Phe Asp Ala
                500                 505                 510

Asp Phe Ala Asp Arg Cys Leu Arg Ala Glu Thr Ala Trp Asp Ala
                515                 520                 525

Ala Lys Arg His Pro Asp Val Leu Ala Asp Pro Asn Asp Gly Ile Gly
    530                 535                 540
```

Gly Gly Ala Tyr Asn Asp Asp Val Ser Asp Glu Phe Tyr Trp Ala
545                 550                 555                 560

Ala Ala Glu Leu Phe Thr Thr Thr Gly Lys Asp Ile Tyr Arg Gln Ala
                565                 570                 575

Val Leu Ser Ser Ala Trp His Gly Asp Ala Gly Ala Val Phe Pro Ala
            580                 585                 590

Gly Gly Gly Ile Ser Trp Gly Ser Thr Ala Gly Leu Gly Val Leu Thr
        595                 600                 605

Leu Ala Thr Val Pro Asn Ala Leu Thr Ser Asp Gln Leu Ala Gln Val
610                 615                 620

Arg Thr Val Val Thr Glu Gly Ala Asp Arg Tyr Ala Ala Gln Ser Arg
625                 630                 635                 640

Glu Gln Ala Tyr Gly Leu Pro Tyr Ala Pro Arg Gly Glu Asp Tyr Val
                645                 650                 655

Trp Gly Ser Asn Ser Gln Val Leu Asn Asn Met Val Val Leu Ala Thr
            660                 665                 670

Ala His Asp Leu Thr Gly Asp Ala Ala Tyr Gln Asp Ala Val Leu Arg
        675                 680                 685

Gly Ala Asp Tyr Leu Leu Gly Arg Asn Pro Leu Asn Gln Ser Tyr Val
690                 695                 700

Thr Gly Tyr Gly Glu Arg Asp Ser His Asn Gln His His Arg Phe Trp
705                 710                 715                 720

Ala His Gln Asn Asp Pro Ser Leu Pro Asn Pro Ala Pro Gly Ser Ile
                725                 730                 735

Ala Gly Gly Pro Asn Leu Thr Ala Ile Ala Ser Gly Asp Pro Val Ala
            740                 745                 750

Ala Glu Lys Leu Ser Gly Cys Ala Pro Ala Met Cys Tyr Val Asp Asp
        755                 760                 765

Ile Gly Ser Trp Ala Thr Asn Glu Ile Thr Ile Asn Trp Asn Ala Pro
770                 775                 780

Leu Ala Phe Ile Ala Ser Tyr Leu Asp Asp Ala Gly Glu Gly Gly Gln
785                 790                 795                 800

Thr Ala Ala Ala Arg Thr Cys Gln Val Thr Tyr Ser Ser His Pro Trp
                805                 810                 815

Asn Ser Gly Ser Thr Val Thr Val Arg Val Glu Asn Thr Gly Ser Asp
            820                 825                 830

Pro Val Ser Pro Trp Ala Leu Thr Trp Leu Pro Gly Glu Gln Arg
        835                 840                 845

Leu Ser His Thr Trp Ser Ala Glu Phe Asp Gln His Gly Arg Thr Val
850                 855                 860

Ser Ala Arg Pro Leu Ser Trp Asn Arg Thr Leu Ala Pro Gly Ala Ala
865                 870                 875                 880

Val Asp Phe Gly Phe Asn Thr Ser Ala Ala Gly Ser Ser Pro Glu Pro
                885                 890                 895

Gly Ala Phe Lys Leu Asn Gly Arg Ala Cys Ser Ala Gly
            900                 905

<210> SEQ ID NO 11
<211> LENGTH: 405
<212> TYPE: PRT
<213> ORGANISM: Streptomyces sp. ACTE

<400> SEQUENCE: 11

Met Arg Thr Gly Ser Ile Ala Arg Val Leu Gly Leu Ala Ala Ala Leu

```
1               5                   10                  15
Ala Ala Leu Leu Thr Thr Ala Phe Met Ala Pro Ala Met Ala Gly Lys
                20                  25                  30

His Asp Ala Thr Asp Ser Pro Ser Ala Ala Ala Pro Ala Ser Phe
            35                  40                  45

Thr His Pro Gly Val Leu Val Ser Arg Pro Gln Leu Asp Phe Val Arg
        50                  55                  60

Gly Lys Val Gln Ala Gly Ala Gln Pro Trp Lys Gly Ala Tyr Asp Gln
65                  70                  75                  80

Met Leu Ala Ser Pro Tyr Ala Ser Leu Ser Arg Thr Ala Lys Pro Arg
                85                  90                  95

Ala Val Val Glu Cys Gly Ser Tyr Ser Asn Pro Asn Asn Gly Cys Thr
            100                 105                 110

Asp Glu Arg Glu Asp Ala Leu Ala Ala Tyr Thr Leu Ser Leu Ala Trp
        115                 120                 125

Tyr Ile Ser Gln Asp Gly Arg Tyr Ala Gln Lys Ala Ile Gln Ile Met
        130                 135                 140

Asp Ala Trp Ser Gly Val Ile Lys Asp His Thr Asn Ser Asn Ala Pro
145                 150                 155                 160

Leu Gln Thr Gly Trp Ala Gly Ser Ser Trp Pro Arg Ala Ala Glu Ile
                165                 170                 175

Ile Lys Tyr Thr Tyr Gly Asn Trp Pro Ala Ser Gly Arg Phe Gly Thr
            180                 185                 190

Met Leu Arg Asp Val Tyr Leu Pro Lys Val Ala Asn Gly Ser Asn Ser
        195                 200                 205

Asn Gly Asn Trp Glu Leu Ser Met Thr Glu Ala Ala Ile Gly Ile Ala
        210                 215                 220

Val Phe Leu Glu Asp Arg Gly Ala Tyr Asp Arg Ala Val Ala Lys Phe
225                 230                 235                 240

Arg Gly Arg Val Pro Ala Tyr Ile Tyr Val Thr Ala Asp Gly Ser Leu
                245                 250                 255

Pro Lys Ala Ala Pro Gly Ser Gly Leu Asp Thr Arg Glu Lys Ile Ile
            260                 265                 270

Asn Tyr Trp Gln Gly Gln Ser Thr Phe Val Asp Gly Leu Ser Gln Glu
        275                 280                 285

Thr Cys Arg Asp Leu Thr His Thr Gly Tyr Gly Leu Ser Ala Ile Ser
        290                 295                 300

His Ile Ala Glu Thr Ser Arg Ile Gln Gly Gln Asp Leu Tyr Pro Glu
305                 310                 315                 320

Val Ala Asp Arg Leu Arg His Ala Leu Gly Leu His Ala Lys Tyr Gln
                325                 330                 335

Leu Gly Glu Lys Val Pro Ser Ser Leu Cys Gly Gly Ser Leu Lys Asp
            340                 345                 350

Ser Leu Gly Pro Val Thr Glu Val Gly Phe Asn Ala Leu His Asn Arg
        355                 360                 365

Met Gly Tyr Ala Met Thr Asn Thr Gln Thr Leu Thr Glu Arg Gln Arg
        370                 375                 380

Pro Ala Ala Ser Asn Asn Leu Phe Val Ala Trp Glu Thr Leu Thr His
385                 390                 395                 400

Ala Asp Asn Pro Asn
                405

<210> SEQ ID NO 12
```

```
<211> LENGTH: 626
<212> TYPE: PRT
<213> ORGANISM: Streptomyces sp. ACTE

<400> SEQUENCE: 12

Met Pro Ser Arg Thr Thr Leu Ile Ala Thr Ala Ala Leu Val Ala
1               5                   10                  15

Leu Ala Ala Pro Met Ala Phe Ala Ala Pro Ala Pro Ala Asp Pro
                20                  25                  30

Ala Val Glu Ala Ala Ala Ala Trp Asp Thr Asp Arg Ala Ala Ser
            35                  40                  45

Ala Tyr Ala Ala Asn Pro Ala Ala Val Thr Ala Ser Gly Ser Glu Asn
        50                  55                  60

Pro Ala Ser Gly Pro Gly Ala Ala Thr Asp Gly Asp Ala Thr Thr Arg
65                  70                  75                  80

Trp Ser Ser Asp Phe Ala Asp Asn Ala Trp Ile Arg Val Asp Leu Gly
                85                  90                  95

Ser Thr Ile Arg Ile Asn Gln Val Lys Leu Glu Trp Glu Ala Ala Tyr
                100                 105                 110

Gly Lys Lys Tyr Val Leu Glu Val Ser Lys Asp Gly Thr Asn Trp Thr
        115                 120                 125

Pro Phe Tyr Thr Glu Asp Ala Gly Thr Gly Gly Thr Val Thr Ala His
    130                 135                 140

Thr Tyr Pro Gln Glu Val Thr Gly Arg Tyr Val Arg Met Arg Gly Val
145                 150                 155                 160

Glu Arg Ala Thr Ala Trp Gly Tyr Ser Leu Phe Ser Phe Gln Val Tyr
                165                 170                 175

Gly Gly Glu Pro Ala Pro Ala Ser Thr Thr Arg Ser Asn Leu Ala Leu
            180                 185                 190

Asn His Pro Ala Tyr Gly Asp Leu Tyr Gln His Ala Gly Asn Ser Pro
        195                 200                 205

Ala Phe Val Thr Asp Gly Gly Trp Pro Ala Asp Leu Lys Ala Asp Arg
    210                 215                 220

Ser Arg Trp Ser Ser Asp Trp Asn Ala Asp Arg Trp Val Gly Val Asp
225                 230                 235                 240

Leu Gly Ala Thr Ser Thr Ile Asn Ser Val Asp Leu Tyr Trp Glu Ala
                245                 250                 255

Ala Tyr Ala Val Asp Tyr Glu Ile Gln Val Ser Asp Asp Asn Arg Thr
            260                 265                 270

Trp Arg Thr Val His Arg Pro Ser Ala Ala Glu Val Ala Ala Arg Arg
        275                 280                 285

Ala Asp Val Lys Ala Pro Ala Glu Ala Val Gly Arg His Asp Thr Ile
    290                 295                 300

Asn Leu Pro Thr Pro Ala Thr Gly Arg Tyr Val Arg Met Leu Gly Lys
305                 310                 315                 320

Glu Arg Arg Ser Phe Tyr Asn Pro Ala Pro Ser Thr Ala Gln Phe Gly
                325                 330                 335

Tyr Ser Leu Tyr Glu Phe Gln Val Trp Gly Thr Gly Ser Ala Asp
            340                 345                 350

Ala Ala Tyr Pro Ala Leu Pro Lys Asn Pro Gly Gly Ala Tyr Arg Thr
        355                 360                 365

Thr Phe Phe Asp Asp Phe Thr Gly Ser Gly Leu Asp Arg Ser Lys Trp
    370                 375                 380

Arg Val Val Arg Thr Gly Thr Glu Met Gly Pro Val Asn Gly Glu Ser
```

```
                385                 390                 395                 400
        Gln Ala Tyr Val Asp Ser Pro Asp Asn Ile Arg Thr Glu Asn Gly Ala
                        405                 410                 415

Leu Val Leu Glu Ser Lys Tyr Cys Lys Gly Cys Thr Pro Thr Pro Asn
                        420                 425                 430

Gly Thr Phe Asp Phe Thr Ser Gly Arg Val Asp Thr Asn Thr Lys Phe
                        435                 440                 445

Asp Phe Thr Tyr Gly Lys Val Ser Ala Arg Met Lys Leu Pro Val Gly
                450                 455                 460

Asp Gly Phe Trp Pro Ala Phe Trp Leu Leu Gly Ser Asp Val Asp Asp
        465                 470                 475                 480

Pro Ala Val Ser Trp Pro Gly Ser Gly Glu Thr Asp Ile Met Glu Asn
                        485                 490                 495

Ile Gly Tyr Gly Asp Trp Thr Ser Ser Gly Leu His Gly Pro Gly Tyr
                        500                 505                 510

Ser Ala Asp Gly Asn Ile Gly Ala Ser Gln Thr Tyr Pro Asn Gly Gly
                        515                 520                 525

Arg Ala Asp Glu Trp His Thr Tyr Gly Val Glu Trp Thr Pro Glu Gly
                        530                 535                 540

Met Thr Phe Thr Val Asp Asp Arg Val Val Gln Gln Thr Ser Arg Gln
        545                 550                 555                 560

Lys Leu Glu Ser Thr Arg Gly Lys Trp Val Phe Asp His Asn Gln Tyr
                        565                 570                 575

Val Ile Leu Asn Leu Ala Leu Gly Gly Ala Tyr Pro Gly Gly Tyr Asn
                        580                 585                 590

Gln Val Thr Gln Pro Tyr Trp Gly Leu Pro Gln Ser Ser Val Asp Arg
                        595                 600                 605

Ile Ala Gln Gly Gly Ile Lys Ala Glu Ile Asp Trp Val Arg Val Glu
                        610                 615                 620

Gln Lys
        625

<210> SEQ ID NO 13
<211> LENGTH: 408
<212> TYPE: PRT
<213> ORGANISM: Streptomyces sp. ACTE

<400> SEQUENCE: 13

Val Ile Ser Arg Arg Met Phe Leu Thr Gly Ala Ala Ala Ser Ala Thr
        1               5                   10                  15

Ala Leu Thr Tyr Pro Leu Trp Gly Thr Ala Leu Ser Pro Arg Thr Ser
                        20                  25                  30

Ala Ala Ala Ala Thr Cys Glu Leu Ala Leu Glu Asn Arg Ser Leu Pro
                        35                  40                  45

Gly Thr Val His Ala Tyr Val Thr Gly His Glu Gln Gly Thr Asp Ser
                        50                  55                  60

Trp Val Leu Leu Arg Ala Asp Gly Ser Val Tyr Arg Pro Glu Ser Pro
        65                  70                  75                  80

Gly Ala Pro Gln Thr Pro Leu Pro Val Asp Cys Ala Ile Pro Leu Asn
                        85                  90                  95

Gly Ala Gly Ala Gly Pro Val Val Leu Thr Leu Pro Gln Met Tyr Gly
                        100                 105                 110

Ala Arg Val Tyr Phe Val Arg Asp Asp Lys Leu Asp Phe Tyr Leu Asn
                        115                 120                 125
```

```
Pro Gly Pro Ser Leu Val Glu Pro Ala Phe Ala Thr Pro Thr Asp Pro
        130                 135                 140
Asn Tyr Gly Arg Thr Trp Ser Phe Cys Glu Phe Thr Phe Asn Pro Gln
145                 150                 155                 160
Gln Leu Tyr Ala Asn Ile Ser Tyr Val Asp Leu Val Thr Ala Leu Pro
                165                 170                 175
Ile Gly Leu Thr Leu Glu Gly Asp Ser Thr His Thr Val Ala Pro Leu
            180                 185                 190
Pro Asp Gly Ala Val Gln Arg Ile Ala Asp Asp Leu Thr Ala Gln Ala
        195                 200                 205
Ala Ala Asp Gly Gln Pro Trp Asp Lys Leu Val Thr Arg Gly Ser Asp
210                 215                 220
Gly Gln Val Leu Arg Val Val Ser Pro Gln Asn Leu Met Ala Pro Tyr
225                 230                 235                 240
Phe Asp Arg Pro Asp Glu Met Pro Phe Arg Asp Leu Phe Ala Ala Gln
                245                 250                 255
Ile Asp Glu Val Trp Glu Lys Tyr Arg Ser Thr Asp Leu Arg Ile Asp
            260                 265                 270
Leu Gln Gly Gly Arg Gly Thr Leu Ala Gly Arg Val Ser Gly Asp Thr
        275                 280                 285
Leu Thr Phe Glu Gly Gly His Thr Phe Ser Lys Pro Thr Ser Lys Asp
290                 295                 300
Ile Phe Thr Cys Asn His Gly Pro Phe Thr Asn Asn Pro Ser Asp Ser
305                 310                 315                 320
Asp Asp Lys Lys Ala Leu Leu Ala Arg Ile Ala Ala Gly Phe Asn Arg
                325                 330                 335
Ser Ile Met Leu Ser His Pro Ser Gln Pro Asn Gly Thr Ser Val Ala
            340                 345                 350
Asp Tyr Tyr Gln Asp Ala Val Thr Asn His Trp Ser Arg Val Val His
        355                 360                 365
Ala Asn Ser Pro Ile Gly Tyr Ala Phe Pro Tyr Asp Asp Val Arg Pro
370                 375                 380
Asp Gly Glu Pro Asp Val Ser Gly Ala Ala Asn Asp Gly Asn Pro Arg
385                 390                 395                 400
Arg Phe Thr Val Ser Val Gly Ser
                405

<210> SEQ ID NO 14
<211> LENGTH: 289
<212> TYPE: PRT
<213> ORGANISM: Streptomyces sp. ACTE

<400> SEQUENCE: 14

Val Leu His Pro His Asn Arg Thr Ala Arg Arg Thr Thr Arg Leu Thr
1               5                   10                  15
Arg Thr Gly Gly Leu Ala Ala Ala Ala Leu Gly Leu Ala Leu Met Ala
            20                  25                  30
Leu Pro Val Thr Ala His Ala Gly Ala Pro Thr Gln Pro Ala Ala His
        35                  40                  45
His Leu Glu Ala Ala Ala Thr Gly Leu Asp Asp Pro Ala Lys Lys Asp
    50                  55                  60
Ile Ala Met Gln Leu Val Ser Ser Ala Glu Asn Ser Thr Leu Asp Trp
65                  70                  75                  80
Lys Ala Gln Tyr Gly Tyr Ile Glu Asp Ile Gly Asp Gly Arg Gly Tyr
                85                  90                  95
```

```
Thr Ala Gly Ile Ile Gly Phe Cys Ser Gly Thr Gly Asp Met Leu Ala
            100                 105                 110

Leu Val Glu Arg Tyr Thr Asp Arg Ser Pro Gly Asn Val Leu Ala Ser
        115                 120                 125

Tyr Leu Pro Ala Leu Arg Glu Val Asp Gly Thr Asp Ser His Asp Gly
    130                 135                 140

Leu Asp Pro Gly Phe Pro Arg Asp Trp Ala Glu Ala Lys Asp Pro
145                 150                 155                 160

Val Phe Gln Gln Ala Gln Asn Asp Glu Arg Asp Arg Val Tyr Phe Asp
                165                 170                 175

Pro Ala Val Arg Gln Ala Lys Asp Asp Gly Leu Gly Thr Leu Gly Gln
            180                 185                 190

Phe Ala Tyr Tyr Asp Ala Ile Val Met His Gly Gly Gly Gly Asp Ser
            195                 200                 205

Thr Ser Phe Gly Ser Ile Arg Gln Arg Ala Leu Ala Glu Ala Glu Pro
    210                 215                 220

Pro Ser Arg Gly Gly Asp Glu Val Ala Tyr Leu Asp Ala Phe Leu Asp
225                 230                 235                 240

Ala Arg Val Trp Ala Met Arg Gln Glu Glu Ala His Ser Asp Thr Ser
                245                 250                 255

Arg Val Asp Thr Ala Gln Arg Val Phe Leu Arg Asp Gly Asn Leu Asn
            260                 265                 270

Leu Asp Pro Pro Leu Asp Trp Gln Val Tyr Gly Asp Ser Phe His Ile
        275                 280                 285

Gly

<210> SEQ ID NO 15
<211> LENGTH: 790
<212> TYPE: PRT
<213> ORGANISM: Streptomyces sp. ACTE

<400> SEQUENCE: 15

Met Thr Pro Pro His Arg His Arg Leu Phe Arg Arg Ser Val Ser Ala
1               5                   10                  15

Ser Leu Ser Leu Ala Leu Thr Ala Val Gly Thr Ala Ala Val Val
            20                  25                  30

Leu Ala Gly Ala Pro Ala Ala Gln Ala Ala Val Pro Ala Pro Ser
        35                  40                  45

Pro Val Gly Ile Ser Gly Arg Gly Ala Ala Val Pro Phe Thr Glu Gln
    50                  55                  60

Glu Ala Glu Tyr Ala Ala Thr Asn Gly Thr Leu Ile Gly Pro Asp Arg
65                  70                  75                  80

Arg Tyr Gly Ser Leu Pro Ser Glu Ala Ser Gly Arg Gln Ala Val Thr
                85                  90                  95

Leu Asp Ala Ala Gly Glu Tyr Val Glu Phe Thr Leu Thr Ala Pro Ala
            100                 105                 110

Asn Ala Met Thr Phe Arg Tyr Ser Leu Pro Asp Asn Ala Ala Gly Thr
        115                 120                 125

Gly Arg Asp Ala Ser Leu Asp Leu Arg Val Asn Gly Ser Val Leu Lys
    130                 135                 140

Ser Val Pro Val Thr Ser Lys Tyr Gly Trp Tyr Tyr Gly Gly Tyr Pro
145                 150                 155                 160

Phe Asn Asn Asn Pro Gly Asp Thr Asn Pro His His Phe Tyr Asp Glu
                165                 170                 175
```

```
Thr Arg Thr Met Phe Gly Ser Thr Leu Pro Ala Gly Thr Lys Val Arg
            180                 185                 190

Leu Gln Val Ala Ser Thr Ala Gly Ser Pro Ser Phe Thr Val Asp Leu
            195                 200                 205

Ala Asp Phe Glu Gln Val Ala Ala Pro Val Gly Lys Pro Ser Gly Ala
            210                 215                 220

Leu Asp Val Val Ser Asp Phe Gly Ala Asp Pro Thr Gly Ala Ala Asp
225                 230                 235                 240

Ser Thr Ala Lys Ile Gln Ala Ala Val Asp Ala Gly Arg Thr Gln Gly
                245                 250                 255

Lys Val Val Tyr Ile Pro Gln Gly Thr Phe Gln Val Arg Asp His Ile
                260                 265                 270

Val Val Asp Gln Val Thr Leu Arg Gly Ala Gly Pro Trp Tyr Ser Val
                275                 280                 285

Leu Thr Gly Arg His Pro Thr Asp Arg Ser Lys Ala Val Gly Val Tyr
            290                 295                 300

Gly Lys Tyr Ser Ala Gln Gly Gly Ser Arg Asn Val Thr Leu Lys Asp
305                 310                 315                 320

Phe Ala Ile Ile Gly Asp Ile Gln Glu Arg Val Asp Asn Asp Gln Val
                325                 330                 335

Asn Ala Ile Gly Gly Ala Met Ser Asp Ser Val Val Asp Asn Val Trp
                340                 345                 350

Met Gln His Thr Lys Cys Gly Ala Trp Met Asp Gly Pro Met Asp Asn
            355                 360                 365

Phe Thr Ile Lys Asn Ser Arg Ile Leu Asp Gln Thr Ala Asp Gly Val
            370                 375                 380

Asn Phe His Tyr Gly Val Thr Asn Ser Thr Val Thr Asn Thr Phe Val
385                 390                 395                 400

Arg Asn Thr Gly Asp Asp Gly Leu Ala Met Trp Ala Glu Asn Val Pro
            405                 410                 415

Asn Val Lys Asn Lys Phe Thr Phe Asn Thr Val Ile Leu Pro Ile Leu
                420                 425                 430

Ala Asn Asn Ile Val Thr Tyr Gly Gly Lys Asp Ile Thr Ile Ser Asp
                435                 440                 445

Asn Val Met Ala Asp Thr Ile Thr Asn Gly Gly Leu His Ile Ala
            450                 455                 460

Asn Arg Tyr Pro Gly Val Asn Ser Gly Gln Gly Thr Ala Val Ala Gly
465                 470                 475                 480

Thr His Thr Ala Ala Arg Asn Thr Leu Ile Arg Thr Gly Asn Ser Asp
                485                 490                 495

Phe Asn Trp Asn Phe Gly Val Gly Ala Ile Trp Phe Ser Gly Leu Asn
            500                 505                 510

Glu Pro Ile Ser Asn Ala Thr Ile Asn Ile Thr Asp Ser Glu Val Leu
            515                 520                 525

Asp Ser Ser Tyr Ala Ala Ile His Leu Ile Glu Gly Ala Ser Asn Gly
            530                 535                 540

Leu His Phe Lys Asn Val Lys Ile Asp Gly Ala Gly Thr Tyr Ala Leu
545                 550                 555                 560

Gln Ile Gln Ala Pro Gly Thr Ala Thr Phe Glu Asn Val Val Ala Thr
                565                 570                 575

His Ile Ala Gln Ser Asn Pro Ile His Asn Cys Val Gly Ser Gly Phe
            580                 585                 590
```

-continued

```
Gln Ile Thr Arg Gly Ser Gly Asn Ser Gly Trp Tyr Ala Asp Pro Pro
            595                 600                 605

Ala Cys Thr Gly Val Trp Pro Asp Pro Val Trp Thr Asn Gly Gly Val
610                 615                 620

Pro Gly Gly Gly Pro Thr Asn Pro Thr Asp Pro Thr Asp Pro Thr
625                 630                 635                 640

Asp Pro Thr Asp Pro Thr Asp Pro Pro Glu Glu Thr Gly Asn Leu Ala
                645                 650                 655

Arg Gly Arg Thr Val Thr Glu Thr Ser His Thr Asp Val Tyr Gly Ala
                660                 665                 670

Ala Asn Thr Val Asp Gly Asn Ala Asp Thr Tyr Trp Glu Ser Arg Asn
            675                 680                 685

Asn Ala Phe Pro Gln Ser Val Thr Val Asp Leu Gly Ala Ala Lys Ala
        690                 695                 700

Val Lys Arg Val Val Leu Lys Leu Pro Pro Ala Ala Ala Trp Ala Thr
705                 710                 715                 720

Arg Thr Gln Thr Leu Ser Val Ser Gly Ser Thr Asp Asn Gly Thr Tyr
                725                 730                 735

Asn Ser Leu Lys Ala Ser Ala Gly Tyr Thr Phe Asn Pro Ser Ser Gly
            740                 745                 750

Asn Thr Ala Thr Val Ser Leu Pro Gly Thr Pro Val Arg Tyr Leu Arg
        755                 760                 765

Leu Thr Phe Thr Gln Asn Thr Gly Trp Pro Ala Ala Gln Leu Ser Glu
770                 775                 780

Leu Glu Ala Tyr Thr Ser
785                 790

<210> SEQ ID NO 16
<211> LENGTH: 514
<212> TYPE: PRT
<213> ORGANISM: Streptomyces sp. ACTE

<400> SEQUENCE: 16

Met Arg Arg Pro Val Ala Leu Arg Leu Ser Ala Ala Gly Ala Thr Leu
1               5                   10                  15

Ala Leu Ala Ala Ala Thr Gly Ala Leu Met Ala Met Pro Glu Ala Ala
                20                  25                  30

Ser Ala Ala Thr Gly Gly Val Thr Gly Tyr Ala Thr Gln Asn Gly Gly
            35                  40                  45

Thr Thr Gly Gly Ala Gly Gly Gln Thr Val Arg Ala Thr Thr Gly Thr
        50                  55                  60

Ala Ile His Ala Ala Leu Cys Gly Arg Ala Ser Ser Thr Pro Leu
65                  70                  75                  80

Thr Ile Gln Val Glu Gly Thr Ile Asn His Gly Asn Thr Asp Lys Val
                85                  90                  95

Ser Gly Ser Ser Cys Asn Thr Ala Gly Val Ile Glu Leu Lys Gln
            100                 105                 110

Ile Ser Asn Val Thr Ile Val Gly Val Gly Gly Ala Val Phe Asp
        115                 120                 125

Gln Val Gly Ile His Val Arg Glu Ser Ser Asn Ile Ile Gln Asn
    130                 135                 140

Val Thr Val Lys Asn Val Lys Lys Ser Gly Ser Pro Thr Ser Asn Gly
145                 150                 155                 160

Gly Asp Ala Ile Gly Met Glu Lys Asp Val Arg Asn Val Trp Val Asp
                165                 170                 175
```

His Thr Thr Leu Glu Ala Ser Gly Gly Glu Ser Gly Phe Asp Gly
            180                 185                 190

Leu Phe Asp Met Lys Ala Gly Thr Gln Tyr Val Thr Leu Ser Tyr Ser
        195                 200                 205

Ile Leu Arg Asn Ser Gly Arg Gly Gly Leu Val Gly Ser Ser Glu Ser
    210                 215                 220

Asp Leu Ser Asn Gly Phe Ile Thr Tyr His His Asn Leu Tyr Glu Asn
225                 230                 235                 240

Ile Asp Ser Arg Ala Pro Leu Leu Arg Gly Val Ala His Ile Tyr
            245                 250                 255

Asn Asn His Tyr Val Gly Leu Ser Lys Ser Gly Ile Asn Ser Arg Ala
            260                 265                 270

Gly Ala Arg Ala Lys Val Asp Asn Asn Tyr Phe Glu Asp Ser Lys Asp
            275                 280                 285

Val Leu Gly Thr Phe Tyr Thr Asp Ala Ala Gly Tyr Trp Gln Val Ser
            290                 295                 300

Gly Asn Val Phe Asp Asn Val Thr Trp Ser Gly Arg Ser Ser Asp Asn
305                 310                 315                 320

Asn Pro Ala Gly Pro Asp Pro Gln Ser Asn Thr Ser Val Ser Ile Pro
            325                 330                 335

Tyr Ala Tyr Thr Leu Asp Gly Ala Asn Cys Val Pro Ser Val Val Ser
            340                 345                 350

Arg Thr Ala Gly Ala Asn Thr Gly Leu Lys Val Ser Asp Gly Ser Cys
            355                 360                 365

Ser Pro Gln Thr Pro Asp Pro Thr Asp Pro Thr Pro Asp Pro Thr Pro
            370                 375                 380

Asp Pro Thr Asp Pro Thr Pro Pro Thr Gly Thr Asn Leu Ser Leu Gly
385                 390                 395                 400

Ala Gly Ser Asp Gly Ser Ser Lys Ala Ser Gly Thr Ser Tyr Gly Asp
            405                 410                 415

Val Arg Asp Gly Asp Met Ser Thr Tyr Trp Ser Pro Ser Gly Ser Thr
            420                 425                 430

Gly Ser Val Ser Ile Lys Trp Ser Ser Ala Thr Thr Val Ser Lys Ile
            435                 440                 445

Asn Val Arg Glu Ala Ala Gly Ser Thr Gly Ser Ile Thr Ser Trp Lys
    450                 455                 460

Val Gly Asn Ala Asp Thr Gly Ala Val Leu Ala Ser Gly Ser Gly Ala
465                 470                 475                 480

Gly Val Ile Thr Phe Pro Gln Thr Ser Leu Arg Lys Ile Thr Phe Glu
            485                 490                 495

Ile Thr Gly Ser Thr Gly Thr Pro Lys Val Ala Glu Phe Glu Thr Tyr
            500                 505                 510

Ala Gly

<210> SEQ ID NO 17
<211> LENGTH: 1761
<212> TYPE: DNA
<213> ORGANISM: Streptomyces sp. ACTE

<400> SEQUENCE: 17
atgagccgca cgagccgcac caccctgcgc cgatcccgaa cagcactcat ggcggcgggc      60
gccctcgtcg ccgcagccgc gggctccgcc gcagccgcgg cacccttcgg tgccaccgcc     120
gccgcggcgg ccggctgcac cgtcgactac aagatccaga accagtggaa cggcgggctc     180

```
accgcctcgg tgagcgtcac caacaacggg gacgccatct ccggctggca gctccagtgg      240
agcttcgccg gcggcgagca ggtcagccag gggtggaacg ccaccgtctc tcagagcggc      300
tccgccgtca ccgccaagga cgccggctac aacgccgccc tggccaccgg ggcatcggcc      360
tccttcggtt tcaacgcgac gggcaacggc aacagcgtcg tccccgcgac gttcaagctg      420
aacggcgtca cctgcaacgg cggcaccacg ggcccgaccg atcccacgga ccccacggac      480
ccgacggacc cgaccgaccc gcccgcgggc aaccgtgtgg acaaccccta ccagggagcc      540
aaggtctatg tgaacccgga gtggtcggcg aacgccgcgg ccgagccggg cggcgacaga      600
atcgccgacc agcccaccgg cgtctggctg gaccgcatcg ccgcgatcga gggcgcgaac      660
ggttcgatgg gtctgcgcga ccatctcgac gaggccctga cgcagaaggg ctccggcgaa      720
ctcgtcgtcc aggtcgtcat ctacaacctg cccgggcgag actgcgcggc gctgcctcc       780 aacggtgagc tcggaccgac cgagatcggc cgctacaaga ccgagtacat cgacccgatc      840
gcggagatcc tcgcgaccc gaagtacgcg ggcctgcgca tcgtcaccac ggtcgagatc       900
gactcgctgc cgaacctcgt caccaacgcc ggcggccgcc ccacggccac tccggcctgt      960
gacgtcatga aggccaacgg caactacgtc aagggcgtcg gctacgcgct caacaagctc     1020
ggcgacgcgc ccaacgtcta caactacatc gacgcgggcc accacggctg gatcggctgg     1080
gacgacaact tcgcgcctc cgcggagatc ttccacgagg ccgcgaccgc cgagggcgcg      1140
accgtcaacg acgtgcacgg cttcatcacc aacaccgcca actacagcgc gctgaaggag     1200
gagaacttct ccatcgacga cgccgtgaac ggcacgtcgg tccggcagtc gaagtgggtc     1260
gactggaacc gctacacgga cgagctgtcc ttcgcgcagg ccttccgcaa cgagctggtc     1320
tccgtcggct tcaactccgg catcggcatg ctcatcgaca cctcccgcaa cggctggggc     1380
ggcgcgaacc ggccgagcgg accgggcgcg aacaccagcg tcgacaccta tgtggacggc     1440
gggcgctacg accgccgcat ccacctgggc aactggtgca accaggcagg agcgggtctc     1500
ggcgaacggc cgcaggccgc ccccgagccg gggatcgacg cgtacgtctg gatgaagccc     1560 ccggggggagt ccgacggttc cagctcggag atcccgaacg acgagggcaa gggattcgac     1620
cggatgtgcg acccgaccta cacgggtaac gcccgtaaca acaacaacat gtcgggggcg     1680
ctgggtggcg ccccccgtctc cgggaagtgg ttctcggccc agttccagga gctcatgaag     1740
aacgcctacc cggcgctcta g                                              1761
```

<210> SEQ ID NO 18
<211> LENGTH: 2865
<212> TYPE: DNA
<213> ORGANISM: Streptomyces sp. ACTE

<400> SEQUENCE: 18

```
gtggccgccc tcgccctccc cttgggaatg accgcagcgg ccggcacgga ggcccaggcc       60
gccgccgtcg cgtgcagcgt cgactacacg accagtgact gggggatcggg gttcaccacc     120 gaactcaccc tgaccaaccg gggctccgcc gcgatcgacg gctggaccct gacgtacgac      180
tacgccggga accagcagct cacgagcggc tggagcggca cctggtccca gtcaggcaag     240
accgtcagcg tgaagaacgc agcctggaac ggtgcgatcg ccgccggtgc cgccgtcacg      300
accggcgcgc agttcaccta cagcggcgcc aacaccgcac cgaccacctt cgccgtcaac      360
ggcacggtct gcgcggggc ccaccagccg ccgatcgccg tcctcacctc cccggcggcg      420
ggcgccgtct tctccgccgg ggacccggtt ccgctggcgg cgaccgccgc ggccgcggac      480
```

```
ggggcgacga tcagcaaggt cgagttctac gacgacacga ccctcctcgg caccgacacc    540
acctccccgt acagctacga ggccgggcaa ctggcggccg gcagccactc cgtgtacgcc    600
agggcctacg acagcctcgg cgcctccgcg gattccccgc ccgccggcat caccgtcgtc    660
accgccccg cggtcgtcgt ctcccccgct caactcggcg tccagcaggg caggtcggga    720
accttcgacg tctcgctgtc caccgcgccc gcggcggacg tcaccgtcac ggccgcccgg    780
tccgcgggta acaccgggct gagcgtcacc ggcgggtcga ccctcacctt caccccgcg    840
aactggtcca caccccagaa ggtgaccgtc acggccgacg gctccggcac cggggccgcg    900
accttcaccg tcacggcccc cggccacggc aaggccgagg tcaccgtcac ccagctggcg    960
gcggcgaagg agtacgacgc ccgtttcctc gacctctacg ggaagatcac cgatcccgcg   1020
aacggctact tctcgccgga gggaatcccc taccactccg tcgagacgct gatcgtcgag   1080
gcgcccgacc acgggcacga gaccacctcg gaggcctaca gctacctgat ctggctgcag   1140
gcgatgtacg gcaagatcac cggcgactgg accaagttca cggtgcgtg ggacaccatg   1200
gagacgtaca tgatccccac ccacgccgac cagcccacga actccttcta cgacgcgtcc   1260
aagcccgcca cctacgcgcc cgagcacgac accccgaacg agtaccccgc ggtgctcgac   1320
ggctccgcct cctccggctc cgacccgatc gcggcagagc tgaagagcgc gtacggcacc   1380
gacgacatct acggcatgca ctggatccag gacgtcgaca cgtctacgg atacggcaac   1440
gcgcccggca cgtgcgcggc cggccccacc caggccggtc cgtcctacat caacaccttc   1500
cagcgcggct cgcaggagtc ggtctgggag accgtcaccc acccgacctg cgacaacttc   1560
acgtacggcg cgccaacgg ctacctcgac ctgttcaccg gggactcctc gtacgccaag   1620
cagtggaagt tcaccaacgc ccccgacgcc gacgcccgcg ccgtgcaggc cgcctactgg   1680
gccgacgtct gggcgaagga gcaggggaag gcgggcgaag tcgccgacac cgtcggcaag   1740
gcggcgaaga tgggtgacta cctgcgctac tccatgttcg acaagtactt caagaagatc   1800
ggcgactgcg tcgccccgac cacctgcccg gccggctccg gcaaggacag cgcgcactac   1860
ctgatgtcct ggtactacgc ctggggcggc gccaccgaca cctcggccgg ctggtcctgg   1920
cggatcggct ccagccacgc ccacggggga taccagaacc cgatggcggc ctacgcgctg   1980
agctccgtgg ccgacctcaa gcccaagtcg gccaccggag cgcaggactg gccaagagc   2040
ctggaccgcc aactggactt ctaccagtgg ctccagtccg acgagggtgc catcgcgggc   2100
ggtgcgacca acagctggaa gggcagctac gcccagcccc cggccggcac gccgaccttc   2160
tacggcatgt actacgacga gaagcccgtg taccacgacc cgccgtccaa ccagtggttc   2220
ggcttccagg cgtggtccat ggagcgcgtc gccgagtact accacgagtc gggtgacgcc   2280
caggcgaagg ccgtgctcga caagtgggtc gactgggccc tgtccgagac gaccgtcaac   2340
ccggacggca cctatctgat gccctccacc ctccagtggt cggcgcgcc ggacacctgg   2400
aacgcctcga ccccggtgc caacgcccag ctccacgtca cggtcgccga ctacaccgac   2460
gacgtcggcg tggccggcgc gtacgcccgg acactgacct actacgccgc caagtccggt   2520
gacacggagg ccgaggccac cgccgaggcg ctgctcgacg gcatgtggca gcaccaccag   2580
gacgacgccg gcgtggcggt gcccgagacc cgcgccgact acaaccggtt cgacgacccg   2640
gtctacgtcc ccggtggctg gacgggcgcc atgcccaacg gtgacaccgt cgacgaggac   2700
tcgacgttcc tctccatccg ctccttctac aaggacgacc cgaactgcc ccaggtgcag   2760
gcgtacctgg acgcggtgc cgccccgtc ttcacctacc accggttctg ggcgcaggcc   2820
gacatcgcac tggccctggg ggcgtacgcc gacctcctgg agtga             2865
```

<210> SEQ ID NO 19
<211> LENGTH: 1089
<212> TYPE: DNA
<213> ORGANISM: Streptomyces sp. ACTE

<400> SEQUENCE: 19

```
atggctagac gcagcagact catctccctg gcagcggtgc tggccaccct gctcggggcg      60
ctcggcctca ccgcactctg gccgggcaag gcggaggcgc acggtgtcgc gatgaccccc     120
ggatcgcgta cctatctgtg ccagctcgac gccctgtccg caccggcgc gctgaacccc      180
acgaacccgg cctgccggga cgcgctgagc cagagcggcg cgaacgcgct gtacaactgg     240
ttcgccgtgc tcgactccaa cgcgggcggc cgcggcgcgg atatgtgcc ggacggcagc      300
ctgtgcagtg ccggtgaccg ctccccgtac gacttctccg cctacaacgc cgcccgcgcc     360
gactggcccc ggacacatct gacctccggt gcgacgctca aggtgcagta cagcaactgg     420
gccgcccacc ccgtgacttc cgggtctac ctgaccaagc cggctgggc acccacgtcc       480
gaactcgctt gggacgacct tcagttggta cagaccgtaa gcaacccgcc gcagcagggc     540
ggggcgggca ccaacggcgg gcactactac tgggacctgg cgctgccgtc gggccgttcc     600
ggtgacgcgc tgatgttcat ccagtgggtg cgttcggaca gtcaggagaa cttcttctcc     660
tgctcggaca tcgtcttcga cggcggcaac ggcgaggtga cgggaatcgg cggcacgggc     720
accccccacc ccactccgac cccgactccg accccgaccc cgacggaccc ggagcactcc     780
ggttcctgca tggccgtcta caacgtcgtc agctcctggg ccggtggctt ccaggcctcc     840
gtcgaggtga tgaaccacgg tacggaaccg cgcaacggct gggccgtgca gtggaagccc     900
ggttccggga cgcagatcaa cagcgtgtgg aacggctccc tctccaccgg gtccgacggc     960
accgtgacgg tgcgcgacgt ggaccacaac cgtgtcatcg ccccggacgg cagtgtgacc    1020
ttcgggttca ccgccacctc cacgggcaac gactacccg ccgggacgat cgggtgtgtg     1080
acgtcctag                                                            1089
```

<210> SEQ ID NO 20
<211> LENGTH: 1371
<212> TYPE: DNA
<213> ORGANISM: Streptomyces sp. ACTE

<400> SEQUENCE: 20

```
gtgaaacgct ttctggcctt actggccacc tgcgcgacgg tcctgggcct cacggcactg      60
accgccccc aggcggtggc cgccgcgggc tgcacggccg actacacgat caccagccag     120
tggcagggcg gcttccaggc cgcggtgaag gtcaccaacc tgggaacccc cgtgaccggg     180
tggaagctca cgttcaccct gccggacgcg ggacagaagg tcgtccaggg ctggaacgcc     240
gcctggtcgc agtcgggttc cgcggtcacc gccgccggcg ccgactggaa cggcacactg     300
gccaccggcg cgtcggccga ggcgggcttc gtgggctcct tcacgggcgc caacccgcct     360
cccacggcgt tcgcgctcaa cggtgtcgcc tgtacgggct ccaccggaga accccggcc      420
ggctccgacg gcggcacccc cgtggacgtc aacgggcagc tccacgtctg cggggtgaac     480
ctctgcaacc agtacgaccg gcccgtgcag ctgcggggta tgagcacgca cggcatccag     540
tggttcgacg cctgctacga cgccgcctcc ctggacgcgc tggcgaacga ctggaagtcg     600
gacctgctgc gcatcgccat gtacgtgcag gaggacggtt acgagaccga cccggcgggc     660
ttcacccggc gcgtgaacga cctcgtcgac atggccgagg cccgcggcat gtacgcgttg     720
```

| | |
|---|---|
| atcgacttcc acaccctgac cccgggcgac ccgaacgtca acctcgaccg cgccaagacg | 780 |
| ttcttcgcgt ccgtcgccgc gcgcaacgcc ggcaagaaga acgtgatcta cgagatcgcc | 840 |
| aacgagccca acgcgtgac ctggacggcc gtcaagagct acgccgagca ggtcatcccg | 900 |
| gtgatccggg ccgccgaccc ggacgccgtc gtcatcgtcg gcacccgcgg ctggtcctcg | 960 |
| ctgggcgtct cggacggctc cgacgagagc gaggtcgtca acagcccgt caatgccacc | 1020 |
| aacatcatgt acgcgttcca cttctacgca gcgagccaca aggacgccta ccgctccacg | 1080 |
| ctgagccggg cggcggcgcg gcttccgctc ttcgtcaccg agttcggcac ggtgagcgcc | 1140 |
| accggcggcg gggcgatgga ccgggcgagc accacggcct ggctggacct gctcgaccag | 1200 |
| ctgaagatca gctatgcgaa ctggacctat tccgacgcgc ccgagagcag cgcggcgttc | 1260 |
| cggccgggca cctgcggcgg cggcgactac agcggcagcg gcgtgctgac cgagtccggg | 1320 |
| gcgctgctca agaaccggat cagcacccc gattccttcc ccaccggctg a | 1371 |

<210> SEQ ID NO 21
<211> LENGTH: 1377
<212> TYPE: DNA
<213> ORGANISM: Streptomyces sp. ACTE

<400> SEQUENCE: 21

| | |
|---|---|
| atggccaaga aaatccccgc ccgtgccaga cgggcactct ccgtcctgac ggcgggcgtg | 60 |
| ctcgccgccg ccggcgtcgt ctcgctcgcc ggcacggccg aggcagcagg caccctgggt | 120 |
| gacgcggcgg cggcgaaggg ccggtacttc ggcaccgcgg tcgcggcgaa ccacctcggc | 180 |
| gaggcaccgt acgcgtccac gctggacgcc cagttcgact cggtcacccc ggagaacgag | 240 |
| atgaagtggg acgcggtcga gggcagccgc aactccttca ccttcacggc cgccgaccag | 300 |
| atcgtcagtc acgcccagag caagggaatg aaggtgcgcg gcacaccct ggtgtggcac | 360 |
| tcgcagctgc cgggctgggt cggcggcctg gcgccaccg acctccgcgc ggcgatgaac | 420 |
| aaccacatca cccaggtgat gacgcactac aagggcaaga tccattcctg ggacgtggtg | 480 |
| aacgaggcct tccaggacgg caacagcggt gcccggcgca gctctccctt ccaggacaag | 540 |
| ctgggtgacg gcttcatcga ggaggcgttc cgcaccgccc gtacggtcga tccgaccgcg | 600 |
| aagctctgtt acaacgacta caacaccgac ggccggaacg cgaagagcga cgcggtctac | 660 |
| gccatggcga aggacttcaa gcagcgcggt gtgccgatcg actgcgtggg cttccagtcc | 720 |
| cacttcaaca gcaactcccc cgtgccctcc gactaccggg ccaatctcca gcgcttcgcc | 780 |
| gacctcggtc tcgacgtcca gatcaccgaa ctggacatcg agggttccgg ctcggcccag | 840 |
| gccgcgaact acacgagcgt cgtgaacgcg tgcctggccg tgacccgctg caccggcctc | 900 |
| accgtctggg gtgtcaccga caagtactcc tggcgcagca gcggcacgcc gctgctcttc | 960 |
| gacggcgact acaacaagaa gccggcgtac gacgcggtgc tcgccgcgct cggcggcacc | 1020 |
| cccgacggtg gcgtgacga cggcggcggc gacaacggcg gcgggaacac cggcagctgc | 1080 |
| acggcgacgt acacgcagac cgccacgtgg aacggcgggt acaacggtga ggtgacggtc | 1140 |
| aaggcaggct cctccggcat caccacctgg tcggtgccgg tgaccgtgcc ctcgtcccag | 1200 |
| caggtctccg ccctctggaa cggcgccccc acgtggaacg ccggcaacac cgtgatgacg | 1260 |
| gtgaagccca cctacaacgg gaccctggcg gccggtgcct cgacgagctt cgggttcacc | 1320 |
| gtcatgacga acggcaacac ctcggcgccc gccgtcggcg cctgcaccgc ctcctga | 1377 |

<210> SEQ ID NO 22
<211> LENGTH: 1689

<212> TYPE: DNA
<213> ORGANISM: Streptomyces sp. ACTE

<400> SEQUENCE: 22

```
gtgagaacag cgatacgcac agcacgacga ccacagcccc tggcccttct gctgagaggt      60
ctggccgcct tcctggggct cgccctcgcc ggagccctcg gcccgccac cgcgcgggcc      120
gcggacctgc cccagcgggc ggaggcgcgg ccgccggcc tccacatcag cgacgggcgc      180
ctggtcgaag caacggcaa cgacttcgtc atgcgcggca tcaaccacgc ccacacctgg      240
tatccgggcg agacccagtc cctcgccgac atcaaggcga ccggcgcgaa cacggtccgc      300
gtggtgctgt ccgacggcta ccgctggagc gagaacagcc ccgaggacgt cgcctcgatc      360
atcgcccggt gcaaggccga gcggctcatc tgcgtcctgg aggtccacga caccaccggg      420
tacggggagg acgccgccgc cggaaccctc gaccacgcgg ccgactactg gatcggcctg      480
aaggacgtac tcgacggcga ggaggactac gtcgtcatca acatcggcaa cgagccctgg      540
ggcaacgccg atccgcgggg ctggaccgcc cccacgacgg ccgcgatcca gaagctgcgc      600
gccgccggtt cgcccacac gatcatggtg gacgcgccca ctggggcca ggactgggag      660
ggcgtcatgc gggccgacgc ccggagcgtg tacgacgccg acccgaccgg caatctgatc      720
ttctcgatcc acatgtacag cgtctacgac accgccgcga aggtcaccga ctacctcaac      780
gccttcgtcg acgccggact ccccctgctc atcggcgagt cggcggccc cgcggaccag      840
tacggcgacc cggacgagga cacgatgatg ccaccgccg aggagttggg gctcggttac      900
ctggcctggt cctggagcgg caacacggat ccggtcctcg acctggtcct cgacttcgac      960
cccacccggc tcagctcgtg gggcgagcgc gtcctccacg gccccgacgg catcaccgag      1020
acgtcccgtg aggccacggt cttcggcggc gggcagggcg ggggcgacac cgaggccccg      1080
accgcacccg gcacccgac ggcctccggg gtgacggcga cctccgtcac cctcggctgg      1140
agtgccgcca ccgacgacgt cggcgtcacc gcgtacgacg tggtccgcgt gaccggcggc      1200
tccgagacga aggtcgcctc ctccgcgcc acctcggtca ccgtgaccgg tctgagcgcc      1260
ggcaccgcgt acagcttcgc cgtctacgcc cgggacgcgg ccggcaaccg ttcggcgcgc      1320
tccggcacgg tgtcggtcac caccgacgag ggcggcagcg tgcccggggg cgcctgctcc      1380
gtgggctacc gggtgatcgg cgagtggccg ggcggcttcc aggggagat caccctccgg      1440
aacaccggcg ccgccgccgt cgacggctgg acgctgggct cgccttcgc cgacgggcag      1500
accgtcacga acatgtgggg cggcaccgcg acgcagagcg ggggcgcggt gagcgtcacc      1560
ccggcctcgt cacctccac gatcgccgcc ggcggctcgg tcaccgtcgg cttcaccggc      1620
accctgactg gcgcgaacgc cgccccggcg gccttcacgc tcaacggcgc cacctgcacc      1680
gcggcctga                                                             1689
```

<210> SEQ ID NO 23
<211> LENGTH: 987
<212> TYPE: DNA
<213> ORGANISM: Streptomyces sp. ACTE

<400> SEQUENCE: 23

```
atgagcatca caccccgtcc ctcccctgcgc gccatggtca ccggtctcgc cgtcgccgcg      60
tccgccctgg cggcggcgc cgtcaccgcc gcaccggccc gggccgccgc ttgcaacggc      120
tacgtcgggc tcaccttcga cgacggaccg tcggcggccc agaccccggc cctgctgtcc      180
gcgctcaagc agaacggcct gcgggccacc atgttcaacc agggcaacta cgccgcctcc      240
```

| | |
|---|---|
| aaccccgccc aggtcaaggc ccaggtcgac gccggcatgt gggtcggcaa ccacagctac | 300 |
| agccacccgc acctgaccca gcagagccag gcgcagatgg actccgagat ctcccggacc | 360 |
| cagcaggcca tcgccgccgg aggcggcggc acaccgaaac tgttccgccc gccgtacggc | 420 |
| gagaccaacg ccacgctgcg gtcggtcgag gcgaagtacg gtctcaccga ggtcatctgg | 480 |
| gacgtcgact cgcaggactg gaacggcgcg agcaccgacg cgatcgtgca ggcggtctcc | 540 |
| cggctcaccg ccggtcaggt catcctgatg cacgagtggc cgccaacac cctgccgcg | 600 |
| atcccgcgca tcgcccagac cctgtccgcc aagggggttgt gttccggcat gatctccccg | 660 |
| cagaccggcc gcgccgtcgc tcccgacggc ggcggcaacg gtggaggggg cggtggcggt | 720 |
| ggcgggtgca ccgcgacgtt gtcggcgggt gagaagtggg gtgaccggta caacctgaac | 780 |
| gtggcggtga gcggctccag caactggacg gtgacgatga acgtgccgtc gggcgagagg | 840 |
| gtcatgacga cctggaacgt cagcgcgagt tatccgagcg cgcaggtcct ggtcgccaag | 900 |
| ccgaacggga gcgggaacaa ctggggtgcg acgatccagg ccaacggcaa ctggacctgg | 960 |
| ccgaccgtct cctgcaccac gagctga | 987 |

<210> SEQ ID NO 24
<211> LENGTH: 1008
<212> TYPE: DNA
<213> ORGANISM: Streptomyces sp. ACTE

<400> SEQUENCE: 24

| | |
|---|---|
| atgaacccac tcgtgtacac ggagcgccgc agacgcggcc ggctcacctc gctggccggc | 60 |
| agcgtctgcg ccctggtact ggccgccgcg gccgcgatgc tgctgcccgg cacggccagt | 120 |
| gccgacacgg tcgtcacgac gaaccagacc ggcaacaaca acggctacta ctactcgttc | 180 |
| tggaccgacg gcggcggcca ggtctccatg aacctggcct ccggcggcag ctacagcacc | 240 |
| tcgtggacga acaccggcaa cttcgtcgcc ggcaagggct ggagcacggg cggccgtaag | 300 |
| agcgtcacct actcgggcac cttcaacccg tccggcaacg cctacctgac gctgtacgga | 360 |
| tggtcgacga acccgctcgt cgagtactac atcgtggaca actggggcac ctaccggccc | 420 |
| accggtacgt tcaagggcac ggtctccagc gacggcggca cgtacgacat ctacgagacc | 480 |
| acccgcacca acgcccctc catcgagggt acgaagacct tcaagcagtt ctggagcgtc | 540 |
| cggcagtcga agcggaccgg cggcaccatc accaccggca accacttcga cgcctgggcc | 600 |
| cgcaacggca tgaacctcgg caccatgaac tacatgatcc tcgccaccga gggctaccag | 660 |
| agcagcggca gctccaacat cacggtgagc gagggcggat ccggtggtgg cggcgacaac | 720 |
| ggtggagggg gcggtggcgg tggcgggtgc accgccacgt tgtcggcggg tgagaagtgg | 780 |
| ggtgaccggt acaacctgaa cgtggcggtg agcggctcca gcaactggac ggtgacgatg | 840 |
| aacgtgccgt cgggcgagaa ggtgctgtcg acctggaaca tcagcgcgag ttatccgagc | 900 |
| tcccaggtcc tggtcgccaa gccgaacggg agcgggaaca ctggggtgc gacgatccag | 960 |
| gccaacggca actggacgtg gccgaccgtc tcctgcacca cgagctga | 1008 |

<210> SEQ ID NO 25
<211> LENGTH: 843
<212> TYPE: DNA
<213> ORGANISM: Streptomyces sp. ACTE

<400> SEQUENCE: 25

| | |
|---|---|
| atgagtgaaa gagccgcatc cccacgtacc caccggcgcc gccccggccg ccggcgcatc | 60 |
| gccaccgcgc tgacggcggc actgggcctc accggcgccg cactggccac cggcgtgatg | 120 |

```
ctccagccgg ccggcgcggc caccaccgcg atccccgcct ggccctccgc cacgggcagc      180
cagtccgtct cgaagaccat cgaggtctcc gggacgtacg acggcggtct gaagcgcttc      240
accggcagcg gtgacctggg cgacggtggc caggacgagg gccaggaccc gatcttcaag      300
ctgaaggacg gggcgacgat caagaacgtc atcctgggca ctccggccgc cgacggcatc      360
cactgctccg gcagctgcac gatccagaac gtctggtggg aggacgtcgg cgaggacgcc      420
gcgtccttca agggcacctc cacgtcgtcc gtgtacacgg tgtacggcgg cggcgcgaag      480
aaggcctccg acaaggtctt ccagttcaac ggcgcgggca agctggtcgt gacgaagttc      540
caggtcgccg acttcggcaa gctggtccgc tcgtgcggca actgctccaa gcagtacaag      600
cgcgagatca tcgtcaacga cgtcgacgtc acggcgccgg gcaagtccct ggtcggcatc      660
aacaccaact acggggacac cgcggcgctg cgctcggtgc gcgtccacgg cgacagcagc      720
aagaagatca agccctgcgt ccgctacacc ggcaacagca cgggcgcgga accgaaggag      780
acgggcagcg gtccggacgg cacgtactgc aagtacaccg cctcggacct gagctacgac      840
tag                                                                   843

<210> SEQ ID NO 26
<211> LENGTH: 2730
<212> TYPE: DNA
<213> ORGANISM: Streptomyces sp. ACTE

<400> SEQUENCE: 26
atgtggtgtc acccgtacct ccgcctccgc acgtccggac gaaaggtttc ctcggtgaac       60
gcccttccac ccccgcccg gcccgcaccc gtccgaccac ggtccgggta cgggcggcgc      120
gtgctcggga tgtcgccgc cgccctgctg tgcgcagggg ccctggccgt gcccggtacg      180
gccatggccg acgacgccga accggaccc ggccccgagc agatcaccaa cggcgacttc      240
gccaccggta cctcagcccc gtggtggtgg acgccgaacg cctcggccgc cgtgtccgag      300
ggccggctct gcgtggaggt gccgccggc acggccaacg cctgggacgt catcgtcggc      360
cagaacgacg taccgatcgt cgcgggcgag agctacgagc tgtcctacac ggcgcgttcg      420
accgtgcccc tgaccgttca gacccgggtc caggaggcg tggagcccta cacgacggtg      480
ctggcgacgg cggatccggt gggcgcggag gacacgcggg tcgcccgcac gttcacggcc      540
tcggtggacc agcccgccgc gtcggtgcag ttgcagatcg tggcggggga gcgggcgacg      600
acgttctgcc tggacgacgt gtcgctgcgg ggcggggccg agccgcccgt gtacgtaccg      660
gacaccggct cgccggtccg cgtcaaccag gtcgggtatc tgccccgcgg tcccaagagc      720
ggcaccgtgg tcaccgacgc cgaggcgccg ctgacctgga cggtcaaagc cgaggacggt      780
tcgacggccc ccaccggtac gaccgttccg cgaggtgagg accccagctc cgccgacgg      840 gtccacacct tcgacttcgg cgacctcacc acggcggggg acggctacac cgtggaggtc      900
gacggtgagg tgagcgagcc gttctcgatc cgcggggacc tgtacgactc cctgcgctcg      960
gacgcgctgg cgtacttcta ccacaaccgc agcggcatcg agatcgacgc ggacctcgtc     1020
ggtgagcagt acgcgcgccc ggccggtcac atcggcgtcg cgcccaacaa gggcgacacg     1080
gacgtgccgt gccgacctgg ggtctgcgac taccggctgg acgtgtcggg cggctggtac     1140
gacgcgggcg accacggcaa gtacgtggtc aacggcggga tctcggtggc ccagctgatg     1200
gccacgtacg agcggaccct caccgccccg gacgcggagt cggccgagct cggcgacggc     1260
gcgctgcggg tgcccgagcg cgacaacggg gtgccggaca tcctggacga ggcgcgctgg     1320
```

-continued

```
gagatggact tcctcatcaa gatgcaggtc ccggcgggcg agcagctggc ggggatggtc    1380
caccacaaga tgcacgacgc cgagtggacc gggctgccga tgaagccgca cctggacccg    1440
cagcagcgcg agctgcaccc gccgtcgacg gccgccacac tcaacctcgc cgccacggcc    1500
gcccagtgcg cccggctcta cgcgcccttc gacgcggact cgcggaccg ctgcctgcgg     1560 gccgccgaga ccgcgtggga cgcggcgaag cggcacccgg acgtgctcgc cgacccgaac    1620
gacggcatcg gcggcggtgc gtacaacgac gacgacgtct cggacgagtt ctactgggcg    1680
gccgccgagc tcttcaccac gacgggcaag gacatctacc ggcaggcggt gctctcctcc    1740
gcatggcacg tgacgcgggg cgcggtcttc ccggcgggcg gcggaatctc ctggggctcc    1800
acggccggac tcggcgtgct caccctggcc accgtgccca cgccctgac gtccgatcag     1860 ctcgcccagg tgcgcacggt ggtgaccgag ggcgccgacc gctacgccgc gcagtcccgt    1920
gagcaggcgt acgggctgcc gtacgcgccc cgggggagg actacgtctg ggggtccaac     1980
agtcaggtgc tcaacaacat ggtcgtcctg gccaccgccc acgacctgac cggtgacgcc    2040
gcctaccagg acgccgtgct gcggggcgcc gactatctgc tgggccgcaa cccgctgaac    2100
cagtcgtacg tcaccggcta cggcgagcgg gactcgcaca accagcacca ccgcttctgg    2160
gcgcaccaga acgaccccag cctgccgaac ccggcgcccg gttcgatcgc gggcggcccc    2220
aacctcaccg cgatcgcctc cggtgacccg gtggcggcgg agaagctcag cggctgcgcg    2280
cccgccatgt gctacgtcga cgacatcggc tcctgggcga ccaacgagat caccatcaac    2340
tggaacgcac cgctcgcctt catcgcctcc tacctggacg acgcgggcga gggcgggcag    2400
accgccgcgg cccgcacctg ccaggtcacg tactcctcgc acccgtggaa cagcgggtcg    2460
acggtgacgg tacgggtcga gaacaccggc tcggatcccg tctcgccctg ggcgctgacc    2520
tggctgctcc ccggcgagca gcggctgagc cacacgtgga gcgcggagtt cgaccagcac    2580
ggccgtacgg tcagcgcccg gccgctgtcg tggaaccgga ccctggcacc cggcgcggcg    2640
gtcgacttcg gcttcaacac ctcggcgcg ggctcctcgc ccgagccggg cgcgttcaag     2700
ctgaacggcc gggcctgctc agcgggctga                                    2730
```

<210> SEQ ID NO 27
<211> LENGTH: 1218
<212> TYPE: DNA
<213> ORGANISM: Streptomyces sp. ACTE

<400> SEQUENCE: 27

```
atgcgtaccg gatccatcgc gcgcgtcctg ggcctcgccg ccgccctggc cgcactgctc      60
accacggcct tcatggcccc ggccatggcc ggcaaacacg acgccaccga ctccccgtcc    120
gccgcggccg ccccggcgtc cttcacccac cccggcgtcc tggtcagccg gccgcagctc    180
gacttcgtac gcggcaaggt ccaggcgggg gcccagccgt ggaagggggc gtacgaccag    240
atgctggcca gtccctacgc ctcgctctcg cggaccgcca agcccgcgc cgtcgtggag     300 tgcggctcgt actccaaccc caacaacggc tgcaccgacg agcgcgagga cgcgctggcc    360
gcgtacaccc tctcgctggc ctggtacatc agccaggacg gccgctacgc ccagaaggcg    420
atccagatca tggacgcctg gtcgggcgtg atcaaggacc acaccaacag caacgccccg    480
ctgcagacgg gctgggccgg ctcctcctgg ccgcgggcgg ccgagatcat caagtacacg    540
tacggcaact ggccggcgtc cggccgcttc ggcaccatgc tgcgtgacgt ctacctgccc    600
aaggtcgcca acgctcgaa cagcaacggc aactgggaac tctccatgac cgaggccgcg     660
atcggcatcg cggtcttcct ggaggaccgg ggcgcctacg acagggccgt cgccaagttc    720
```

```
cgcggccgcg tccccgcgta catatacgtg accgccgacg gatcgctgcc gaaggccgcg    780
cccggcagcg gtctcgacac gcgggaaaag atcatcaact actggcaggg ccagtcgacc    840
ttcgtggacg ggctctcgca ggagacctgc cgcgacctca cccacaccgg ctacgggctc    900
tccgcgatct cccacatcgc cgagaccagc cggatccagg gccaggacct ctacccggag    960
gtcgccgacc ggctccgtca cgcgctgggg ctgcacgcca agtaccagct ggggagaag    1020 gtcccgtcct ccctgtgcgg cggctcgctc aaggacagcc tcggcccggt caccgaggtc    1080
ggcttcaacg ccctgcacaa ccgcatgggt tacgccatga cgaacaccca gaccctcacc    1140
gagcggcagc ggccccgccg ctcgaacaac ctgttcgtgg cctgggagac cctgacgcac    1200
gccgacaacc cgaactga                                                   1218

<210> SEQ ID NO 28
<211> LENGTH: 1881
<212> TYPE: DNA
<213> ORGANISM: Streptomyces sp. ACTE

<400> SEQUENCE: 28
atgccctccc gtacgacgtt gatcgccacc accgcgggcc cggtcgccct cgccgccccc    60
atggccttcg cggctcccgc ccccgccccc gaccccgccg tcgaggccgc cgccgcggcc    120
tgggacaccg accgcgcggc gtcgcctac gcggcgaacc ccgccgccgt caccgcgtcc    180
ggcagcgaga ccccgcctc cggaccgggc gccgccaccg acggcgacgc caccacccgc    240
tggtccagcg acttcgccga caacgcctgg atacgcgtcg acctcggctc caccatccgg    300
atcaaccagg tgaagctgga gtgggaggcc gcctacggca agaagtacgt cctggaagtc    360
tccaaggacg gcaccaactg gacccccttc tacacggagg acgcgggcac cggcggcacc    420
gtcaccgccc acacctaccc gcaggaggtc accggccgct acgtgcggat gcgcggcgtc    480
gaacgcgcca cggcctgggg ctactccctc ttctccttcc aggtctacgg gggcgagccg    540
gcccccgcct cgaccacccg cagcaacctc gccctcaacc accgccta cggcgaccctc    600 taccagcacg ccggcaactc gcccgcattc gtcaccgacg gcggctggcc cgccgacctg    660
aaggcggacc gctcccgctg gtcctccgac tggaacgcgg accgctgggt cggcgtcgac    720
ctcggcgcga cctccaccat caacagcgtc gacctctact gggaggcgg ctacgccgtc    780 gactacgaga tccaggtgtc cgacgacaac cggacctggc ggaccgtcca ccgcccctcc    840
gccgccgagg tcgccgccag acgcgccgac gtcaaggccc cggccgaggc cgtcggacgc    900
cacgacacca tcaacctgcc caccccggcc accggccgct acgtccggat gctgggcaag    960
gagcgccgtt ccttctacaa cccggcaccc tccaccgccc agttcggcta ctcgctctac    1020
gagttccagg tgtggggcac cggcggcagc cggacgccc ctaccccgc cctgcccaag    1080 aaccccggcg gcgcctaccg caccaccttc ttcgacgact tcaccggctc cggcctggac    1140
cgctccaagt ggcgcgtggt gcgcaccggt acggagatgg gccggtcaa cggggagtcc    1200 caggcctacg tcgactcgcc ggacaacatc cgtaccgaga acgcgccct ggtcctggag    1260 tccaagtact gcaagggctg caccccacg cccaacggca ccttcgactt cacctcgggc    1320
cgcgtcgaca ccaacaccaa gttcgacttc acctacggca aggtgagcgc ccgtatgaag    1380
ctcccggtcg gcgacggttt ctggccggcg ttctggctgc tgggcagcga cgtcgacgac    1440
ccggcggtct cctggcccgg ctcggcgag acggacatca tggagaacat cggctacggc    1500
gactggacca gctccggcct gcacggaccc ggctactccg cagacggcaa catcggcgcc    1560
```

| | |
|---|---|
| tcccagacct acccgaacgg cggccgggcc gacgagtggc acacctacgg cgtcgaatgg | 1620 |
| acccccgaag gcatgacctt caccgtcgac gaccgcgtcg tgcagcagac ctcccgccag | 1680 |
| aagctggagt ccacccgcgg caagtgggtc ttcgaccaca accagtacgt gatcctcaac | 1740 |
| ctggccctcg gcggcgccta cccggggcgga tacaaccagg tcacccagcc ctactggggc | 1800 |
| cttccgcagt ccagcgtcga ccgcatcgca cagggcggca tcaaggcgga gatcgactgg | 1860 |
| gtacgggtcg agcagaagta a | 1881 |

<210> SEQ ID NO 29
<211> LENGTH: 1227
<212> TYPE: DNA
<213> ORGANISM: Streptomyces sp. ACTE

<400> SEQUENCE: 29

| | |
|---|---|
| gtgatttcgc gcagaatgtt cctgaccggc gccgccgcct ccgcgaccgc gctcacctat | 60 |
| ccgctctggg gcaccgccct gagcccgcgc acgtcggcgg cggccgccac gtgcgaactg | 120 |
| gccctcgaga accgttcgtt gcccggtacg gtgcacgcct acgtcaccgg tcacgagcag | 180 |
| ggcaccgaca gctgggtgct gctgcgggcc gacggcagcg tgtaccgccc cgagtcgccg | 240 |
| ggcgctccgc agacccctct gccggtggac tgcgccatcc cgctgaacgg cgccggcgcc | 300 |
| ggcccggtcg tcctgacgct gccccagatg tacggcgcgc gggtctactt cgtccgtgac | 360 |
| gacaagctgg acttctacct gaacccgggc ccctcgctgg tcgagccggc cttcgcgacg | 420 |
| cccaccgacc cgaactacgg gcgcacctgg tcgttctgcg agttcacctt caacccgcag | 480 |
| cagctgtacg cgaacatcag ctacgtcgac ctggtcaccg ccctgccgat cggcctgacc | 540 |
| ctggagggcg actccaccca caccgtcgcc ccgctcccgg acggcgccgt gcagcgcatc | 600 |
| gccgacgacc tgacggccca ggcggccgcc gacgggcagc cgtgggacaa gctggtcacc | 660 |
| cgtggctcgg acggccaggt gctgcgggtc gtctcgccgc agaacctgat ggcgccgtac | 720 |
| ttcgaccggc ccgacgagat gccgttccgg gacctgttcg cggcccagat cgacgaggtc | 780 |
| tgggagaagt accgctccac cgacctgcgg atcgacctcc agggcggccg gggcaccctg | 840 |
| gcgggccggg tcagcgggga cacgctgacc ttcgagggcg gacacacctt ctccaagccc | 900 |
| acctcgaagg acatcttcac ctgcaaccac ggtccgttca cgaacaaccc gagcgactcg | 960 |
| gacgacaaga aggcgctgct ggccaggatc gcggcgggct tcaaccggtc gatcatgctg | 1020 |
| agccaccca gccagccgaa cggcaccctcg gtggcggact actaccagga cgcggtgacc | 1080 |
| aaccactggt cgcgggtcgt ccacgcgaac tcccccatcg ggtacgcgtt cccgtacgac | 1140 |
| gacgtacgcc ccgacggtga gccggacgtc tcgggcgcgg cgaacgacgg caaccccggg | 1200 |
| cgcttcacgg tgagcgtggg ttcctga | 1227 |

<210> SEQ ID NO 30
<211> LENGTH: 870
<212> TYPE: DNA
<213> ORGANISM: Streptomyces sp. ACTE

<400> SEQUENCE: 30

| | |
|---|---|
| gtgcttcacc cccacaaccg caccgcacgt cgcaccactc ggctcacccg caccggcggt | 60 |
| ctcgccgccg cggccctcgg gctcgcgctc atggcgctcc ccgtcaccgc tcacgccggc | 120 |
| gccccacgc agccggccgc tcatcatctg gaggccgccg cgaccggact ggacgatccc | 180 |
| gcgaagaagg acatcgccat gcagttggtc tccagcgcgg agaactccac gctggactgg | 240 |
| aaggcgcagt acggctacat cgaggacatc ggcgacggac gcggctacac cgccggcatc | 300 |

```
atcggcttct gctccgggac cggagacatg ctcgccctgg tcgagcgcta cacggaccgc    360
tcaccgggca acgtactggc gtcgtacctg cccgccctgc gcgaggtcga cgggaccgac    420
tcgcacgacg ggctcgaccc cggcttcccc cgggactggg ccgaggccgc gaaggacccg    480
gtgttccagc aggcgcagaa cgacgagcgg gaccgggtgt acttcgaccc ggcggtgcgc    540
caggccaagg acgacgggct ggggacgctc ggccagttcg cgtactacga cgccatcgtc    600
atgcacggag gcgcgggga cagcacgagc ttcgggtcca tccggcagcg cgcgctcgcg    660
gaggcggaac cgccctcgcg gggcggtgac gaggtcgcct acctcgacgc gttcctggac    720
gcgcgggtct gggcgatgcg gcaggaggag gcccactcgg acaccagccg ggtcgacacc    780
gcgcagcgcg tcttcctgcg cgacgggaat ctgaacctgg atccgccgct ggactggcag    840
gtgtacggcg acagcttcca catcggctga                                     870

<210> SEQ ID NO 31
<211> LENGTH: 2373
<212> TYPE: DNA
<213> ORGANISM: Streptomyces sp. ACTE

<400> SEQUENCE: 31
atgaccccac cgcacagaca ccgcctgttc aggcgctcgg tgtccgcttc cctctcgctg     60
gccctcaccg ccgtcggcac cgccgccgcg gtcgtcctgg ccggtgcccc ggcggcccag    120
gccgccgcgg tccccgcacc ctccccggtc ggcatatccg gccggggcgc cgccgtcccg    180
ttcacggagc aggaggccga gtacgccgcg accaacggca cgctcatcgg cccggaccgg    240
cgctacggct cactgccctc ggaggcgtcc ggccggcagg ccgtcacgct cgacgcggcc    300
ggtgagtacg tggagttcac cctcaccgcc ccgccaacg cgatgacctt ccgctattcg    360
ctgccggaca acgccgccgg acgggccgg gacgcctctc tcgacctgcg ggtgaacggc    420
tcggtcctca agagcgtgcc ggtgacctcg aagtacggct ggtactacgg gggttacccc    480
ttcaacaaca accccgggga caccaacccg caccatttct acgacgagac ccggaccatg    540
ttcggctcga ccctgccgc cggtacgaag gtccggctgc aggtggcgtc caccgccggc    600
tcgccctcgt tcaccgtcga cctggccgac ttcgagcagg tggccgcgcc cgtcggcaag    660
ccgtccggcg cactggacgt ggtgagcgac ttcggggccg acccgaccgg ggcggccgac    720
tccaccgcga agatccaggc ggcggtcgac gcggggcgca cccagggcaa ggtcgtctac    780
atcccgcagg ggaccttcca ggtgcgtgac acatcgtcg tggaccaggt gacgctgcgc    840
ggcgccggcc cctggtacag cgtgctgacg gggcgtcacc ccacgaccg gagcaaggcg    900 gtcggtgtct acgggaagta ctcggcgcag ggcggcagca ggaacgtcac cctcaaggac    960
ttcgccatca tcggcgacat ccaggagcgt gtggacaacg accaggtcaa cgccatcggc   1020
ggggccatgt ccgactcggt cgtcgacaac gtctggatgc agcacaccaa gtgcggcgcc   1080
tggatggacg gccgatgga caatttcacc atcaagaaca gtcgcatcct ggaccagacc   1140
gcggacggcg tgaacttcca ctacggggtc acgaactcga ccgtcacgaa caccttcgtc   1200
cgcaacaccg gtgacgacgg cctggccatg tgggcggaga acgtcccgaa cgtgaagaac   1260
aagttcacgt tcaacacggt gatcctgccg atcctggcca caacatcgt gacgtacggc   1320 ggcaaggaca tcacgatctc cgacaacgtc atggcggaca ccatcaccaa cggcggcggg   1380
ctgcacatcg ccaaccgcta cccgggcgtc aactcggggc aggggacggc cgtcgcgggg   1440
acgcacacgg ccgcgcgcaa caccctgatc cgtaccggca cagcgactt caactggaac   1500
```

```
ttcggcgtcg gggcgatctg gttcagcggg ctcaacgaac cgatcagcaa cgccaccatc    1560
aacatcaccg acagcgaggt cctggacagc tcctacgccg cgatccacct gatcgagggt    1620
gcgagcaacg ggctgcactt caagaacgtc aagatcgacg gggcgggtac ctacgccctg    1680
cagatccagg caccgggcac ggccaccttc gagaacgtcg tggccaccca catcgcccag    1740
tccaacccga tccacaactg tgtcggcagc ggcttccaga tcacccgggg cagcggcaac    1800
tccggctggt acgccgaccc gccgcctgc accggggtct ggcccgaccc ggtgtggacc     1860
aacggcggcg tgcccggagg cggcggtccc accaacccga ccgacccacc cgaccccacc    1920
gacccgacgg accccaccga cccgcctgag gagacgggca acctcgcccg gggacgcacc    1980
gtcaccgaga ccagccacac ggacgtgtac ggcgcggcca acaccgtcga cggcaacgcg    2040
gacacgtact gggagagccg caacaacgcc ttcccgcagt ccgtcaccgt cgacctcggc    2100
gctgccaagg cggtgaagcg ggtggtgctg aagctcccgc cggccgccgc gtgggcgacc    2160
cgcacgcaga cgctctccgt gtccggcagc accgacaacg ggacgtacaa ctcgctgaag    2220
gcgtcggcgg gttacacctt caacccgtcg agcggcaaca ccgcgacggt ctccctcccg    2280
gggacgccgg tccggtacct gcggctgacc ttcacccaga acaccggtg gcccgccgcc    2340 cagctgtccg aactggaggc ctacaccagc tga                                 2373

<210> SEQ ID NO 32
<211> LENGTH: 1545
<212> TYPE: DNA
<213> ORGANISM: Streptomyces sp. ACTE

<400> SEQUENCE: 32
atgaggagac cagtcgccct gcgactcagc gcggcggggg ccaccctggc cctggctgcc     60
gcgaccggcg cactgatggc gatgcccgag gcggcgtcgg cagcgaccgg cggcgtcacc    120
ggatacgcga cccagaacgg cggcaccacc ggcggcgccg cgggcagac ggtgcgggcc     180 accaccggga ccgcgatcca cgccgccctg tgcgggcggg ccagcagctc caccccgctc    240
accatccagg tcgaggggac catcaaccac ggcaacaccg acaaggtctc gggcagcagc    300
tgcaacaccg ccgccggagt catcgagctg aagcagatca gcaacgtcac gatcgtcggc    360
gtgggcggcg gcgccgtctt cgaccaagta ggcatccacg tccgcgagtc cagcaacatc    420
atcatccaga acgtcaccgt caagaacgtc aagaagtccg gctcgcccac gtccaacggc    480
ggtgacgcca tcggcatgga aaggacgtc cgcaacgtct gggtggacca caccaccctg     540
gaggcctcgg gcggcgagtc ggagggcttc gacggcctct tcgacatgaa ggccggcacc    600
cagtacgtga cgctgtccta cagcatcctg cgcaactccg gcggggagg cctcgtcggc     660 tccagcgaga gcgacctctc gaacggcttc atcacctacc accacaacct gtacgagaac    720
atcgactccc gcgcccctct gctgcgggc ggcgtcgccc acatctacaa caaccactac     780
gtgggactca gcaagtcggg catcaactcc cgggccggcg cccgcgccaa ggtgacaac     840 aactacttcg aggactccaa ggacgtcctg ggcaccttct acaccgacgc ggccggctac    900
tggcaggtca gcggcaacgt cttcgacaac gtgacgtggt ccggccgcag cagcgacaac    960
aaccccgcgg gccggaccc gcagtccaac acctcggtca gcatccccta cgcctacacc    1020
ctcgacgggg cgaactgcgt accgtccgtc gtgagccgga cggcgggcgc gaacacgggg    1080
ctgaaggtgt cggacggcag ctgctcgccg cagacgccgg accgaccga ccccaccccc     1140 gacccgacgc cggaccccgac cgaccccact ccgcccaccg gaccaacct cagcctcggg    1200 gccggctcgg acggctccag caaggcgagc gggaccagct acgcgacgt gcgggacggt    1260
```

```
gacatgagca cctactggtc accgtccggc tcgaccggtt ccgtctcgat caagtggagc   1320
tccgccacca ccgtctccaa gatcaacgtg cgcgaggcgg cgggctccac gggctccatc   1380
acctcctgga aggtcggcaa cgccgacacc ggcgccgtcc tggcctccgg cagcggggcg   1440
ggcgtcatca cgttcccgca gacctcgctg cgcaagatca cgttcgagat cacgggctcg   1500
acgggcacgc cgaaggtcgc cgagttcgag acgtacgccg gctga                  1545
```

<210> SEQ ID NO 33
<211> LENGTH: 389
<212> TYPE: PRT
<213> ORGANISM: Streptomyces sp. ACTE

<400> SEQUENCE: 33

```
Met Pro Glu Arg Phe Thr Pro Thr Pro Glu Asp Lys Phe Thr Phe Gly
1               5                   10                  15

Leu Trp Thr Val Gly Trp Arg Gly Asn Asp Pro Phe Gly Glu Pro Thr
            20                  25                  30

Arg Pro Val Leu Asp Pro Val Glu Ser Val Glu Arg Leu Ala Glu Leu
        35                  40                  45

Gly Ala His Gly Val Thr Phe His Asp Asp Leu Ile Pro Phe Gly
    50                  55                  60

Ser Asp Asp Arg Glu Arg Ala Arg Leu Val Gly Arg Phe Arg Glu Ala
65                  70                  75                  80

Leu Glu Arg Thr Gly Leu Lys Val Pro Met Ala Thr Thr Asn Leu Phe
                85                  90                  95

Thr His Pro Val Phe Lys Asp Gly Gly Phe Thr Ser Asn Asp Arg Asp
            100                 105                 110

Val Arg Arg Phe Ala Leu Arg Lys Val Ile Arg Asn Ile Asp Leu Ala
        115                 120                 125

Val Glu Leu Gly Ala Gln Thr Tyr Val Ala Trp Gly Gly Arg Glu Gly
    130                 135                 140

Ala Glu Ser Gly Ala Ala Lys Asp Val Arg Ser Ala Leu Asp Arg Met
145                 150                 155                 160

Lys Glu Ala Phe Asp Leu Leu Gly Asp Tyr Val Thr Glu Gln Gly Tyr
                165                 170                 175

Asp Leu Arg Phe Ala Ile Glu Pro Lys Pro Asn Glu Pro Arg Gly Asp
            180                 185                 190

Ile Leu Leu Pro Thr Ile Gly His Ala Leu Ala Phe Ile Glu Arg Leu
        195                 200                 205

Glu Arg Pro Glu Leu Val Gly Val Asn Pro Glu Thr Gly His Glu Gln
    210                 215                 220

Met Ala Gly Leu Asn Phe Pro His Gly Ile Ala Gln Ala Leu Trp Ala
225                 230                 235                 240

Gly Lys Leu Phe His Ile Asp Leu Asn Gly Gln Ser Gly Ile Lys Tyr
                245                 250                 255

Asp Gln Asp Phe Arg Phe Gly Ala Gly Asp Leu Arg Gln Ala Phe Trp
            260                 265                 270

Leu Val Asp Leu Leu Glu Thr Ala Gly Trp Asp Gly Ser Arg His Phe
        275                 280                 285

Asp Phe Lys Pro Val Arg Thr Asp Gly Ile Asp Gly Val Trp Glu Ser
    290                 295                 300

Ala Lys Asn Cys Met Arg Asn Tyr Leu Ile Leu Lys Glu Arg Ala Ala
305                 310                 315                 320
```

```
Ala Phe Arg Ala Asp Pro Ala Val Gln Glu Ala Leu Thr Ala Ser Arg
                325                 330                 335

Leu Asp Glu Leu Ala Arg Pro Thr Ala Asp Asp Gly Leu Lys Ala Leu
            340                 345                 350

Leu Ala Asp Arg Thr Ala Tyr Glu Asp Phe Asp Ala Thr Ala Ala Ala
            355                 360                 365

Glu Arg Ser Met Ala Phe Glu Ala Leu Asp Gln Leu Ala Met Asp His
        370                 375                 380

Leu Leu Asn Val Arg
385

<210> SEQ ID NO 34
<211> LENGTH: 655
<212> TYPE: PRT
<213> ORGANISM: Streptomyces sp. ACTE

<400> SEQUENCE: 34

Met Thr Ser Ala Leu Arg Ala Thr Gln Gly Leu Gln Ser Thr Asn His
1               5                   10                  15

Pro Arg Leu Ser Asp Leu Thr Arg Gly Ala Pro Leu Ser Thr Glu Ser
            20                  25                  30

Pro Arg Arg Ser Ser Arg Leu Arg Trp Arg Leu Gly Pro Gly Arg Ala
        35                  40                  45

Thr Arg Ala Lys Ala Val Ala Gly Phe Thr Ala Leu Leu Leu Pro Leu
    50                  55                  60

Ala Ala Met Val Gly Leu Ala Ser Pro Ala Gln Ala Ala Thr Ser Ala
65                  70                  75                  80

Thr Ala Thr Tyr Leu Lys Lys Ser Asp Trp Gly Ser Gly Phe Glu Gly
                85                  90                  95

Gln Trp Thr Val Lys Asn Thr Gly Thr Thr Ala Leu Ser Ser Trp Thr
            100                 105                 110

Ile Glu Trp Asp Phe Pro Ser Gly Thr Ala Val Gly Ser Ala Trp Asp
        115                 120                 125

Ala Ser Val Thr Ser Ser Gly Thr His Trp Thr Ala Lys Asn Leu Gly
    130                 135                 140

Trp Asn Gly Thr Val Ala Pro Gly Ala Ser Ile Ser Phe Gly Phe Asn
145                 150                 155                 160

Gly Thr Gly Ser Gly Ser Pro Thr Gly Cys Lys Leu Asn Gly Ala Ser
                165                 170                 175

Cys Asp Gly Gly Gly Thr Val Pro Gly Asp Ser Ala Pro Ser Lys Pro
            180                 185                 190

Gly Thr Pro Thr Ala Ser Gly Ile Thr Asp Thr Ser Val Lys Leu Ser
        195                 200                 205

Trp Ser Ala Ala Thr Asp Asp Lys Gly Ile Lys Asn Tyr Asp Val Leu
    210                 215                 220

Arg Asp Gly Ala Lys Val Ala Thr Val Thr Thr Thr Tyr Thr Asp
225                 230                 235                 240

Thr Gly Leu Thr Lys Gly Thr Asp Tyr Ser Tyr Ser Val Gln Ala Arg
                245                 250                 255

Asp Thr Ala Asp Gln Thr Gly Pro Val Ser Gly Ala Val Ala Val Arg
            260                 265                 270

Thr Thr Gly Gly Asn Asp Asn Pro Gly Pro Thr Gly Ser Lys Val
        275                 280                 285

Asn Leu Gly Tyr Phe Thr Asn Trp Gly Val Tyr Gly Arg Asn Tyr His
    290                 295                 300
```

```
Val Lys Asn Leu Val Thr Ser Gly Ser Ala Glu Lys Ile Thr His Ile
305                 310                 315                 320

Asn Tyr Ala Phe Gly Asn Val Gln Gly Gly Lys Cys Thr Ile Gly Asp
            325                 330                 335

Ser Tyr Ala Asp Tyr Asp Lys Ala Tyr Thr Ala Asp Gln Ser Val Asp
        340                 345                 350

Gly Val Ala Asp Thr Trp Asp Gln Pro Leu Arg Gly Asn Phe Asn Gln
    355                 360                 365

Leu Arg Lys Leu Lys Ala Lys Tyr Pro His Ile Lys Val Ile Trp Ser
370                 375                 380

Phe Gly Gly Trp Thr Trp Ser Gly Gly Phe Gly Ala Ala Ala Gln Asn
385                 390                 395                 400

Pro Ala Ala Phe Ala Gln Ser Cys Tyr Asp Leu Val Glu Asp Pro Arg
            405                 410                 415

Trp Ala Asp Val Phe Asp Gly Ile Asp Ile Asp Trp Glu Tyr Pro Asn
        420                 425                 430

Ala Cys Gly Leu Thr Cys Asp Thr Ser Gly Pro Ala Ala Leu Lys Asn
    435                 440                 445

Leu Ser Ser Ala Leu Arg Ala Lys Phe Gly Ala Lys Asn Leu Val Thr
450                 455                 460

Ala Ala Ile Thr Ala Asp Gly Ser Asp Gly Lys Ile Asp Ala Ala
465                 470                 475                 480

Asp Tyr Ala Gly Ala Ala Gln Ser Phe Asp Trp Tyr Asn Val Met Thr
            485                 490                 495

Tyr Asp Phe Phe Gly Ala Trp Glu Ala Lys Gly Pro Thr Ala Pro His
        500                 505                 510

Ser Pro Leu Asn Ala Tyr Ala Gly Ile Pro Gln Asp Gly Phe Asn Ser
    515                 520                 525

Ala Ala Ala Ile Ala Lys Leu Lys Ala Lys Gly Val Pro Ala Ser Lys
530                 535                 540

Leu Leu Leu Gly Ile Gly Phe Tyr Gly Arg Gly Trp Thr Gly Val Thr
545                 550                 555                 560

Gln Ala Ala Pro Gly Gly Thr Ala Thr Gly Ala Ala Pro Gly Thr Tyr
            565                 570                 575

Glu Ala Gly Ile Glu Asp Tyr Lys Val Leu Lys Thr Ser Cys Pro Ala
        580                 585                 590

Thr Gly Thr Ile Ala Gly Thr Ala Tyr Ala His Cys Gly Thr Asn Trp
    595                 600                 605

Trp Ser Tyr Asp Thr Pro Ala Thr Ile Thr Ser Lys Met Ala Trp Ala
610                 615                 620

Asn Ser Gln Gly Leu Gly Gly Ala Phe Phe Trp Glu Phe Ser Gly Asp
625                 630                 635                 640

Thr Ala Asn Gly Glu Leu Val Ser Ala Met Asp Ser Gly Leu Asn
            645                 650                 655

<210> SEQ ID NO 35
<211> LENGTH: 196
<212> TYPE: PRT
<213> ORGANISM: Streptomyces sp. ACTE

<400> SEQUENCE: 35

Met Arg Lys Arg Ala Ser Ala Val Ile Gly Leu Ala Ile Ala Gly
1               5                   10                  15

Val Ser Met Phe Ala Thr Ser Ser Ala Ser Ser His Gly Tyr Thr Asp
```

```
            20                  25                  30
Ser Pro Ile Ser Arg Gln Lys Leu Cys Ala Asn Gly Thr Val Thr Gly
            35                  40                  45

Cys Gly Asn Ile Gln Trp Glu Pro Gln Ser Val Glu Gly Pro Lys Gly
        50                  55                  60

Phe Pro Ala Ala Gly Pro Ala Asp Gly Lys Ile Cys Ala Gly Gly Asn
 65                  70                  75                  80

Ser Ser Phe Ala Ala Leu Asp Asp Pro Arg Gly Gly Asn Trp Pro Ala
                85                  90                  95

Thr Gln Val Thr Gly Gly Gln Gly Tyr Asn Phe Arg Trp Gln Phe Thr
            100                 105                 110

Ala Arg His Ala Thr Thr Asp Phe Arg Tyr Tyr Ile Thr Lys Asp Gly
        115                 120                 125

Trp Asp Ser Thr Lys Pro Leu Thr Arg Ala Ala Leu Glu Ser Gln Pro
    130                 135                 140

Phe Met Thr Val Pro Tyr Gly Asn Gln Gln Pro Ala Thr Leu Thr
145                 150                 155                 160

His Gln Gly Thr Ile Pro Thr Gln Lys Ser Gly Lys His Ile Ile Leu
                165                 170                 175

Ala Val Trp Asn Val Ala Asp Thr Ala Asn Ala Phe Tyr Ala Cys Ser
            180                 185                 190

Asp Val Lys Phe
        195

<210> SEQ ID NO 36
<211> LENGTH: 556
<212> TYPE: PRT
<213> ORGANISM: Streptomyces sp. ACTE

<400> SEQUENCE: 36

Val Ala Ala Leu Ala Ala Gly Ala Leu Thr Val Thr Gly Leu Val Gly
 1               5                  10                  15

Thr Ala Gln Ala Ala Asp Ile Asn Val Ala Lys Asn Ala Gly Phe Glu
            20                  25                  30

Ser Gly Leu Ser Gly Trp Thr Cys Thr Gly Gly Ser Gly Ala Thr Val
        35                  40                  45

Ser Ser Pro Val His Gly Gly Ser Ala Ala Leu Lys Ala Thr Pro Ser
    50                  55                  60

Gly Gln Asp Asn Ala Lys Cys Thr Gln Thr Val Ala Val Lys Pro Asn
 65                  70                  75                  80

Ser Thr Tyr Ala Leu Ser Ser Trp Val Gln Gly Gly Tyr Ala Tyr Leu
                85                  90                  95

Gly Ala Ser Gly Thr Gly Thr Thr Asp Val Ser Thr Trp Thr Pro Gly
            100                 105                 110

Ser Thr Gly Trp Thr Gln Leu Arg Thr Ser Phe Thr Thr Gly Pro Ser
        115                 120                 125

Thr Thr Ser Val Gln Val Tyr Thr His Gly Trp Tyr Gly Gln Ala Ala
    130                 135                 140

Tyr Tyr Ala Asp Asp Val Ala Val Thr Gly Pro Asp Gly Gly Gly Gly
145                 150                 155                 160

Thr Glu Glu Pro Gly Pro Ala Ile Pro Gly Ala Pro Ala Gly Leu Ala
                165                 170                 175

Val Gly Thr Thr Thr Ser Ser Ser Val Ala Leu Ser Trp Asn Ala Val
            180                 185                 190
```

```
Ser Gly Ala Thr Gly Tyr Thr Val Tyr Arg Asp Gly Thr Lys Ala Thr
            195                 200                 205

Thr Thr Thr Gly Thr Ser Ala Thr Val Ser Gly Leu Ala Ala Asp Thr
    210                 215                 220

Ala Tyr Gln Phe Ser Val Ser Ala Thr Asn Ala Ala Gly Glu Ser Val
225                 230                 235                 240

Arg Ser Ala Thr Val Ser Gly Arg Thr Ala Lys Lys Asp Glu Thr Gly
                245                 250                 255

Pro Gly Pro Ser Thr Ser Val Pro Lys His Ala Val Thr Gly Tyr Trp
            260                 265                 270

Gln Asn Phe Asn Asn Gly Ala Ala Val Gln Lys Leu Ser Asp Val Pro
    275                 280                 285

Ala Asn Tyr Asp Ile Ile Ala Val Ser Phe Ala Asp Ala Ala Gly Thr
290                 295                 300

Pro Gly Ala Val Thr Phe Asn Leu Asp Ser Ala Gly Leu Asn Gly Tyr
305                 310                 315                 320

Thr Val Ala Gln Phe Lys Ala Asp Ile Lys Ala Lys Gln Ala Ala Gly
                325                 330                 335

Lys Asn Val Ile Ile Ser Val Gly Gly Glu Lys Gly Thr Val Ser Val
            340                 345                 350

Asn Ser Asp Ala Ser Ala Asn Ala Phe Ala Asp Ser Leu Tyr Thr Leu
    355                 360                 365

Ile Gln Glu Tyr Gly Phe Asn Gly Val Asp Ile Asp Leu Glu Asn Gly
370                 375                 380

Leu Asn Ser Thr Tyr Met Thr Lys Ala Leu Arg Ser Leu Ser Ser Lys
385                 390                 395                 400

Val Gly Ser Gly Leu Val Ile Thr Met Ala Pro Gln Thr Ile Asp Met
                405                 410                 415

Gln Ser Thr Ser Gly Glu Tyr Phe Lys Thr Ala Leu Asn Ile Lys Asp
            420                 425                 430

Ile Leu Thr Val Val Asn Met Gln Tyr Tyr Asn Ser Gly Ser Met Leu
    435                 440                 445

Gly Cys Asp Gly Lys Val Tyr Ser Gln Gly Ser Val Asp Phe Leu Thr
450                 455                 460

Ala Leu Ala Cys Ile Gln Leu Glu Gly Gly Leu Ala Pro Ser Gln Val
465                 470                 475                 480

Gly Leu Gly Val Pro Ala Ser Thr Arg Gly Ala Gly Ser Gly Tyr Val
                485                 490                 495

Ala Pro Ser Val Val Asn Ala Ala Leu Asp Cys Leu Ala Lys Gly Thr
            500                 505                 510

Gly Cys Gly Ser Phe Lys Pro Ser Arg Thr Tyr Pro Asp Ile Arg Gly
    515                 520                 525

Ala Met Thr Trp Ser Thr Asn Trp Asp Ala Thr Ala Gly Asn Ala Trp
530                 535                 540

Ser Asn Ala Val Gly Pro His Val His Gly Leu Pro
545                 550                 555

<210> SEQ ID NO 37
<211> LENGTH: 295
<212> TYPE: PRT
<213> ORGANISM: Streptomyces sp. ACTE

<400> SEQUENCE: 37

Val Ile Arg Arg Val Met Gly Leu Leu Thr Ala Leu Ala Ala Val Val
1               5                   10                  15
```

```
Ala Thr Leu Val Phe Leu Pro Ala Ala Thr Ser Ala Ala Thr Cys
            20                  25                  30

Ala Pro Ala Trp Asn Ala Ser Ser Val Tyr Thr Gly Gly Ser Ala
            35                  40                  45

Ser Tyr Asn Gly His Asn Trp Ser Ala Lys Trp Trp Thr Gln Asn Glu
 50                  55                  60

Arg Pro Gly Thr Ser Asp Val Trp Ala Asp Gln Gly Ala Cys Gly Ser
 65                  70                  75                  80

Gly Gly Gly Gly Thr Asp Pro Asn Pro Ser Gly Phe Val Val Ser Glu
                85                  90                  95

Ala Gln Phe Asn Gln Met Phe Pro Ser Arg Asn Ser Phe Tyr Thr Tyr
                100                 105                 110

Ser Gly Leu Thr Ala Ala Leu Ser Ala Tyr Pro Ala Phe Ala Asn Thr
                115                 120                 125

Gly Ser Asp Thr Val Lys Lys Gln Glu Ala Ala Phe Leu Ala Asn
130                 135                 140

Val Ser His Glu Thr Gly Gly Leu Val His Ile Val Glu Gln Asn Thr
145                 150                 155                 160

Ala Asn Tyr Pro His Tyr Cys Asp Thr Ser Gln Ser Tyr Gly Cys Pro
                165                 170                 175

Ala Gly Gln Ala Ala Tyr Tyr Gly Arg Gly Pro Ile Gln Leu Ser Trp
                180                 185                 190

Asn Phe Asn Tyr Lys Ala Ala Gly Asp Ala Leu Gly Ile Asp Leu Leu
                195                 200                 205

Gly Asn Pro Trp Gln Val Glu Gln Asn Ala Ser Val Ala Trp Lys Thr
                210                 215                 220

Gly Leu Trp Tyr Trp Asn Thr Gln Ser Gly Pro Gly Thr Met Thr Pro
225                 230                 235                 240

His Asn Ala Ile Val Asn Gly Ser Gly Phe Gly Glu Thr Ile Arg Ser
                245                 250                 255

Ile Asn Gly Ser Ile Glu Cys Asn Gly Gly Asn Pro Gly Gln Val Gln
                260                 265                 270

Ser Arg Val Asn Thr Tyr Gln Ser Phe Val Gln Ile Leu Gly Thr Thr
                275                 280                 285

Pro Gly Ser Asn Leu Ser Cys
290                 295

<210> SEQ ID NO 38
<211> LENGTH: 507
<212> TYPE: PRT
<213> ORGANISM: Streptomyces sp. ACTE

<400> SEQUENCE: 38

Met Arg Arg Ser Arg Ser Val Arg Ala Leu Val Thr Ala Ala Val Thr
 1               5                   10                  15

Thr Val Ala Ala Ala Gly Met Ala Val Leu Gly Ser Gly Thr Ala Gln
                20                  25                  30

Ala Ala Thr Pro Leu Pro Asp His Val Phe Ala Pro Tyr Phe Glu Ser
                35                  40                  45

Trp Thr Gly Glu Ser Pro Ala Ala Met Ala Ala Glu Ser Gly Ala Lys
            50                  55                  60

His Leu Thr Met Ala Phe Leu Gln Thr Ala Lys Gly Ser Cys Thr
 65                  70                  75                  80

Pro Tyr Trp Asn Gly Asp Thr Gly Leu Pro Ile Ala Gln Ala Ser Phe
```

```
                    85                  90                  95
Gly Ala Asp Ile Asp Thr Ile Gln Ala Gly Gly Asp Val Ile Pro
                100                 105                 110
Ser Phe Gly Gly Tyr Thr Ala Asp Thr Thr Gly Thr Glu Ile Ala Asp
                115                 120                 125
Ser Cys Thr Asp Val Asp Gln Ile Ala Ala Ala Tyr Gln Lys Val Val
            130                 135                 140
Thr Thr Tyr Asp Val Ser Arg Leu Asp Met Asp Ile Glu Val Asp Ser
145                 150                 155                 160
Leu Asp Asp Thr Ala Gly Ile Asp Arg Arg Asn Lys Ala Ile Lys Lys
                165                 170                 175
Leu Gln Asp Trp Ala Asp Ala Asn Gly Arg Asp Leu Glu Ile Ser Tyr
                180                 185                 190
Thr Leu Pro Thr Thr Thr Arg Gly Leu Ala Ser Ser Gly Leu Ala Val
                195                 200                 205
Leu Arg Asn Ala Val Thr Asn Gly Ala Arg Val Asp Val Val Asn Leu
            210                 215                 220
Met Thr Phe Asp Tyr Tyr Asp Asn Ala Ser His Asp Met Ala Ala Asp
225                 230                 235                 240
Thr Glu Thr Ala Ala Gln Gly Leu Tyr Asp Gln Leu Ala Lys Leu Tyr
                245                 250                 255
Pro Gly Arg Thr Ala Thr Gln Leu Trp Ser Met Val Gly Val Thr Glu
                260                 265                 270
Met Pro Gly Val Asp Asp Phe Gly Pro Ala Glu Thr Phe Thr Leu Ala
            275                 280                 285
Asn Ala Ala Arg Val Tyr Asp Trp Ala Val Ala Lys Gly Ile Asn Thr
            290                 295                 300
Leu Ser Phe Trp Ala Leu Gln Arg Asp Asn Gly Gly Cys Pro Gly Gly
305                 310                 315                 320
Pro Ala Ala Asp Asp Cys Ser Gly Ile Gln Gln Asn Thr Trp Asp Phe
                325                 330                 335
Thr Arg Val Phe Ala Pro Phe Thr Ser Gly Thr Thr Ala Pro Asp Asp
                340                 345                 350
Asp Phe Ser Val Thr Ala Thr Pro Ala Ser Gly Thr Val Thr Ala Gly
            355                 360                 365
Gly Ser Ala Thr Thr Val Lys Thr Ala Val Thr Lys Gly Ala Ala
            370                 375                 380
Gln Gln Val Gly Leu Thr Val Ser Gly Val Pro Ala Gly Val Thr Ala
385                 390                 395                 400
Ser Leu Ser Pro Ser Ser Val Thr Ala Gly Gly Arg Ser Thr Leu Thr
                405                 410                 415
Leu Ala Thr Thr Gln Ala Ala Val Ser Gly Thr Tyr Arg Ile Ser Val
            420                 425                 430
Thr Gly Thr Ser Pro Ser Gly Ser His Ala Thr Ala Tyr Thr Leu Thr
            435                 440                 445
Val Thr Gly Gly Thr Gly Ser Gln Cys Thr Ala Gly Pro Trp Ala Gly
        450                 455                 460
Gly Thr Val Tyr Thr Gly Gly Gln Gln Val Ser Tyr Lys Gly His Thr
465                 470                 475                 480
Trp Lys Ala Lys Trp Trp Thr Thr Gly Glu Glu Pro Gly Thr Thr Gly
                485                 490                 495
Glu Trp Gly Val Trp Gln Asp Leu Gly Ala Cys
            500                 505
```

```
<210> SEQ ID NO 39
<211> LENGTH: 483
<212> TYPE: PRT
<213> ORGANISM: Streptomyces sp. ACTE

<400> SEQUENCE: 39

Val Thr Gln Gly Pro Leu Thr Thr Glu Ala Gly Ala Pro Val Ala Asp
1               5                   10                  15

Asn Gln Asn Ser Glu Thr Ala Gly Pro Gly Gly Pro Val Leu Val Gln
            20                  25                  30

Asp Gln Ala Leu Leu Glu Lys Leu Ala His Phe Asn Arg Glu Arg Ile
        35                  40                  45

Pro Glu Arg Val Val His Ala Arg Gly Ala Gly Ala Tyr Gly Thr Phe
    50                  55                  60

Thr Leu Thr Arg Asp Val Ser Gln Trp Thr Arg Ala Lys Phe Leu Ser
65                  70                  75                  80

Glu Val Gly Lys Glu Thr Glu Thr Phe Leu Arg Phe Ser Thr Val Ala
                85                  90                  95

Gly Asn Leu Gly Ser Ala Asp Ala Ala Arg Asp Pro Arg Gly Trp Ala
            100                 105                 110

Leu Lys Phe Tyr Thr Glu Glu Gly Asn Tyr Asp Leu Val Gly Asn Asn
        115                 120                 125

Thr Pro Val Phe Phe Ile Lys Asp Ala Ile Lys Phe Pro Asp Phe Ile
    130                 135                 140

His Thr Gln Lys Arg Asp Pro Tyr Thr Gly Ser Gln Glu Ala Asp Asn
145                 150                 155                 160

Val Trp Asp Phe Trp Gly Leu Ser Pro Glu Ser Thr His Gln Val Thr
                165                 170                 175

Trp Leu Phe Gly Asp Arg Gly Ile Pro Ala Ser Phe Arg His Met Asn
            180                 185                 190

Gly Tyr Gly Ser His Thr Phe Gln Trp Asn Asn Glu Ala Gly Glu Val
        195                 200                 205

Phe Trp Val Lys Tyr His Phe Lys Thr Asp Gln Gly Ile Lys Asn Leu
    210                 215                 220

Thr Thr Glu Glu Ala Val Arg Leu Ser Gly Val Asp Pro Asp Ser His
225                 230                 235                 240

Gln Arg Asp Leu Arg Glu Ser Ile Glu Arg Gly Asp Phe Pro Thr Trp
                245                 250                 255

Thr Val Gln Val Gln Ile Met Pro Ala Ala Glu Ala Ala Thr Tyr Arg
            260                 265                 270

Phe Asn Pro Phe Asp Leu Thr Lys Val Trp Pro His Glu Asp Tyr Pro
        275                 280                 285

Pro Ile Glu Ile Gly Lys Leu Glu Leu Asn Arg Asn Pro Glu Asn Ile
    290                 295                 300

Phe Ala Glu Val Glu Gln Ser Ile Phe Ser Pro Ala His Phe Val Pro
305                 310                 315                 320

Gly Ile Gly Pro Ser Pro Asp Lys Met Leu Gln Gly Arg Leu Phe Ala
                325                 330                 335

Tyr Gly Asp Ala His Arg Tyr Arg Val Gly Ile Asn Ala Asp His Leu
            340                 345                 350

Pro Val Asn Arg Pro His Ala Thr Glu Ala Arg Thr Asn Ser Arg Asp
        355                 360                 365

Gly Tyr Leu Tyr Asp Gly Arg His Lys Gly Thr Lys Asn Tyr Glu Pro
```

```
                370                 375                 380
Asn Ser Phe Gly Gly Pro Val Gln Thr Asp Arg Pro Leu Trp Gln Pro
385                 390                 395                 400

Val Ser Val Thr Gly Thr Gly Asn His Glu Ala Ala Val His Ala
                405                 410                 415

Glu Asp Asn Asp Phe Val Gln Ala Gly Asn Leu Tyr Arg Leu Met Ser
                420                 425                 430

Glu Asp Glu Lys Gly Arg Leu Ile Asp Asn Leu Ala Gly Phe Ile Ala
            435                 440                 445

Lys Val Ser Arg Asp Asp Ile Ala Asp Arg Ala Ile Asn Asn Phe Arg
450                 455                 460

Gln Ala Asp Ala Asp Phe Gly Lys Arg Leu Glu Val Ala Val Gln Ala
465                 470                 475                 480

Leu Arg Gly
```

<210> SEQ ID NO 40
<211> LENGTH: 926
<212> TYPE: PRT
<213> ORGANISM: Streptomyces sp. ACTE

<400> SEQUENCE: 40

```
Val Tyr Ala Met Pro Ser Thr Ala Pro Ala Val Gln Ser Gly Glu
1               5                   10                  15

Asp Ala Pro Val Arg Ser Pro Arg Pro Phe Ala Ala Leu Leu Ala
                20                  25                  30

Ala Leu Ala Leu Thr Ala Gly Leu Ser Leu Ile Gly Thr Pro Ala Val
            35                  40                  45

Ala Arg Ser Asp Glu Ala Pro Ala Ala Thr Glu Ala Ser Asp Val Ser
50                  55                  60

Ile Ala Ala Asp Thr Tyr Thr Trp Lys Asn Ala Arg Ile Asp Gly Gly
65                  70                  75                  80

Gly Phe Val Pro Gly Ile Val Phe Asn Arg Ser Glu Lys Asn Leu Ala
                85                  90                  95

Tyr Ala Arg Thr Asp Ile Gly Gly Ala Tyr Arg Trp Asp Gln Ser Gly
                100                 105                 110

Lys Gln Trp Lys Pro Leu Leu Asp Trp Val Asp Trp Asp Arg Trp Gly
            115                 120                 125

Trp Thr Gly Val Val Ser Leu Ala Ser Asp Thr Val Asp Pro Asp Asn
130                 135                 140

Val Tyr Ala Ala Val Gly Thr Tyr Thr Asn Ser Trp Asp Pro Thr Asp
145                 150                 155                 160

Gly Ala Val Leu Arg Ser Ser Asp Arg Gly Ala Ser Trp Lys Ala Ala
                165                 170                 175

Thr Leu Pro Phe Lys Leu Gly Gly Asn Met Pro Gly Arg Gly Met Gly
                180                 185                 190

Glu Arg Leu Ala Val Asp Pro Asn Lys Asn Ser Val Leu Tyr Leu Gly
            195                 200                 205

Ala Pro Ser Gly Asn Gly Leu Trp Arg Ser Thr Asp Ala Gly Val Ser
210                 215                 220

Trp Ser Glu Val Thr Ala Phe Pro Asn Pro Gly Asn Tyr Ala Gln Asp
225                 230                 235                 240

Pro Ser Asp Thr Ser Gly Tyr Gly Asn Asp Asn Gln Gly Ile Val Trp
                245                 250                 255

Val Thr Phe Asp Glu Arg Ser Gly Ser Ala Gly Ser Ala Thr Gln Asp
```

-continued

```
            260             265             270
Ile Tyr Val Gly Val Ala Asp Lys Glu Asn Thr Val Tyr Arg Ser Thr
            275             280             285
Asp Gly Gly Ala Thr Trp Ser Arg Ile Pro Gly Gln Pro Thr Gly Tyr
            290             295             300
Leu Ala His Lys Gly Val Leu Asp Ser Ala Thr Gly His Leu Tyr Leu
305             310             315             320
Thr Leu Ser Asp Thr Gly Gly Pro Tyr Asp Gly Gly Lys Gly Arg Ile
                325             330             335
Trp Arg Tyr Asp Thr Ala Ser Gly Ala Trp Gln Asp Val Ser Pro Val
            340             345             350
Ala Glu Ala Asp Ala Tyr Tyr Gly Phe Ser Gly Leu Ser Val Asp Arg
            355             360             365
Gln Lys Pro Gly Thr Leu Met Ala Thr Ala Tyr Ser Ser Trp Trp Pro
            370             375             380
Asp Thr Gln Ile Phe Arg Ser Thr Asp Ser Gly Ala Thr Trp Thr Gln
385             390             395             400
Ala Trp Asp Tyr Thr Gly Tyr Pro Asn Arg Ser Asn Arg Tyr Thr Leu
                405             410             415
Asp Val Ser Ser Val Pro Trp Leu Ser Trp Gly Ala Ser Pro Ala Pro
            420             425             430
Pro Glu Thr Ala Pro Lys Leu Gly Trp Met Thr Glu Ala Leu Glu Ile
            435             440             445
Asp Pro Phe Asp Ser Asp Arg Met Met Tyr Gly Thr Gly Ala Thr Val
            450             455             460
Tyr Gly Thr Glu Asp Leu Thr Ser Trp Asp Ser Gly Gly Thr Phe Arg
465             470             475             480
Ile Thr Pro Met Val Lys Gly Ile Glu Glu Thr Ala Val Asn Asp Leu
                485             490             495
Ala Ser Pro Pro Ser Gly Ala Pro Leu Leu Ser Ala Leu Gly Asp Ile
            500             505             510
Gly Gly Phe Arg His Thr Asp Leu Asp Ala Val Pro Asp Leu Met Tyr
            515             520             525
Thr Ser Pro Asn Leu Asp Ser Thr Thr Ser Leu Asp Phe Ala Glu Ser
530             535             540
Ser Pro Gly Thr Val Val Arg Val Gly Asn Ser Asp Ala Ala Pro His
545             550             555             560
Ile Gly Phe Ser Thr Asp Asn Gly Ala Asn Trp Phe Gln Gly Ser Glu
                565             570             575
Pro Ser Gly Val Thr Gly Gly Thr Val Ala Ala Ala Asp Gly
            580             585             590
Ser Gly Phe Val Trp Ser Pro Glu Gly Ala Gly Val His His Thr Thr
            595             600             605
Gly Phe Gly Thr Ser Trp Thr Ala Ser Thr Gly Ile Pro Ala Gly Ala
            610             615             620
Thr Val Glu Ser Asp Arg Lys Asn Pro Glu Lys Phe Tyr Gly Phe Glu
625             630             635             640
Ala Gly Thr Phe Tyr Val Ser Thr Asp Gly Ala Thr Phe Thr Ala
                645             650             655
Glu Ala Thr Gly Leu Pro Ala Glu Gly Asn Val Arg Phe Gln Ala Leu
            660             665             670
Pro Gly Thr Glu Gly Asp Ile Trp Leu Ala Gly Gly Ser Asp Thr Gly
            675             680             685
```

```
Ala Tyr Gly Leu Trp Arg Ser Thr Asp Ser Gly Ala Thr Phe Thr Lys
            690                 695                 700

Ser Ala Gly Val Glu Gln Ala Asp Ser Val Gly Phe Gly Lys Ala Ala
705                 710                 715                 720

Pro Gly Ala Ser Tyr Arg Thr Val Phe Val Ser Ala Lys Ile Gly Gly
                725                 730                 735

Val Arg Gly Ile Phe Arg Ser Thr Asp Ala Gly Ala Ser Trp Thr Arg
            740                 745                 750

Ile Asn Asp Asp Ala His Gln Trp Gly Trp Thr Gly Ala Ala Ile Thr
        755                 760                 765

Gly Asp Pro Arg Val Tyr Gly Arg Val Tyr Val Ser Thr Asn Gly Arg
770                 775                 780

Gly Ile Gln Val Gly Glu Thr Ser Asp Ser Gly Gly Gly Thr Asp
785                 790                 795                 800

Pro Gly Thr Asp Pro Gly Thr Asp Pro Gly Thr Asp Pro Gly Pro Glu
                805                 810                 815

Gln Pro Ala Asp Ala Ala Cys Ala Val Thr Tyr Ala Val Thr Asn Gln
            820                 825                 830

Trp Pro Gly Gly Phe Gln Ala Asp Val Thr Val Thr Asn Thr Gly Asp
        835                 840                 845

Ala Ala Tyr Asn Gly Trp Lys Leu Gly Trp Ser Phe Pro Gly Gly Gln
850                 855                 860

Gln Ile Ser Gln Ile Trp Asn Ala Ser His Arg Gln Asp Gly Val Lys
865                 870                 875                 880

Val Thr Val Thr Asp Ala Gly Trp Asn Gly Thr Val Ala Pro Gly Ser
                885                 890                 895

Ser Ala Gly Phe Gly Phe Thr Gly Ser Trp Ala Gly Ser Asn Ala Glu
            900                 905                 910

Pro Ala Ala Phe Thr Leu Asp Gly Gln Ala Cys Thr Val Gly
        915                 920                 925

<210> SEQ ID NO 41
<211> LENGTH: 543
<212> TYPE: PRT
<213> ORGANISM: Streptomyces sp. ACTE

<400> SEQUENCE: 41

Met Arg Gly Ala Lys Ser Ala Lys Trp Val Ala Gly Ala Ala Ile Ile
1               5                   10                  15

Ala Leu Ala Ala Thr Ala Cys Gly Gly Gly Asp Ser Asp Ser Asp Asn
            20                  25                  30

Gly Ala Lys Gly Ala Val Asp Ala Asp Gly Ile Phe Ser Val Glu Val
        35                  40                  45

Gly Glu Pro Gln Asn Pro Leu Gln Pro Ala Asn Thr Met Glu Ser Asn
    50                  55                  60

Gly Ser Ile Val Thr Asp Ala Ile Phe Ser Gln Leu Val Asp Tyr Asp
65                  70                  75                  80

Pro Asp Gly Lys Leu Glu Met Ile Asn Ala Glu Ser Val Glu Thr Thr
                85                  90                  95

Asp Ser Lys Leu Trp Thr Val Lys Leu Lys Asp Trp Lys Phe His
            100                 105                 110

Asp Gly Thr Pro Val Thr Ala Asp Ser Tyr Val Lys Ala Trp Asn Trp
        115                 120                 125

Ala Ala Asn Ile Glu Asn Ala Gln Thr Asn Ala Ser Trp Phe Ala Asp
```

```
            130                 135                 140
Ile Lys Gly Tyr Ala Asp Val His Pro Asp Gly Glu Gly Ala Lys Pro
145                 150                 155                 160

Lys Ser Asp Ala Met Ser Gly Leu Lys Lys Val Asp Asp Tyr Thr Phe
                165                 170                 175

Thr Ile Glu Leu Asn Ser Ala Val Pro Tyr Phe Ser Tyr Lys Leu Gly
                180                 185                 190

Tyr Thr Val Phe Ser Pro Leu Pro Glu Ser Phe Tyr Ala Asp Pro Lys
            195                 200                 205

Ala Ala Gly Glu Lys Pro Val Gly Asn Gly Ala Tyr Lys Phe Val Ser
210                 215                 220

Trp Asp His Lys Lys Gln Ile Lys Val Val Arg Asn Asp Asp Tyr Lys
225                 230                 235                 240

Gly Pro Asp Lys Ala Lys Asn Gly Gly Val Ile Phe Lys Asn Tyr Thr
                245                 250                 255

Thr Leu Glu Thr Ala Tyr Glu Asp Leu Lys Ser Gly Asn Val Asp Val
                260                 265                 270

Leu Arg Gln Ile Gly Pro Lys Asp Leu Pro Val Tyr Arg Ala Asp Leu
            275                 280                 285

Glu Asp Arg Ala Val Asp Lys Ala Tyr Ser Ala Val Gln Thr Leu Gly
290                 295                 300

Val Ala Met Tyr Thr Asp Gln Trp Lys Asn Thr Asp Pro Lys Val Leu
305                 310                 315                 320

Gln Gly Leu Ser Met Ala Ile Asp Arg Asp Thr Ile Thr Lys Thr Val
                325                 330                 335

Leu Gln Gly Thr Arg Glu Pro Ala Thr Gly Trp Val Ala Lys Gly Val
                340                 345                 350

Leu Gly Tyr Gln Glu Asn Val Ala Gly Asp Val Thr Lys Tyr Asp Pro
            355                 360                 365

Ala Lys Ala Lys Ala Leu Ile Lys Glu Gly Gly Val Pro Gly Asn
370                 375                 380

Glu Ile Phe Ile Gln Phe Asn Ala Asp Gly Gly His Lys Glu Trp Ile
385                 390                 395                 400

Glu Ala Val Cys Asn Ser Ile Thr Gln Ala Thr Gly Val Lys Cys Thr
                405                 410                 415

Gly Asp Ser Lys Ala Asp Phe Gln Ala Asp Leu Asn Ala Arg Asp Ala
                420                 425                 430

Lys Gln Val Lys Ser Phe Tyr Arg Ser Gly Trp Val Leu Asp Tyr Pro
            435                 440                 445

Val Asn Ala Asn Phe Ile Ser Asp Leu Phe Arg Thr Gly Ala Ala Gly
450                 455                 460

Asn Asn Gly Phe Phe Ser Asn Lys Asp Leu Asp Ala Lys Ile Lys Ala
465                 470                 475                 480

Ala Asp Ser Ala Ala Ser Leu Asp Asp Ser Val Lys Ala Tyr Gln Glu
                485                 490                 495

Ile Glu Lys Glu Leu Val Asn Tyr Met Pro Ser Ile Pro Leu Trp Tyr
                500                 505                 510

Tyr Lys Val Asn Ala Gly Tyr Ser Glu Asn Val Lys Asn Val Asp Tyr
            515                 520                 525

Ala Gln Asp Gly Asp Pro Ile Leu Thr Glu Val Gln Val Ile Lys
530                 535                 540

<210> SEQ ID NO 42
```

```
<211> LENGTH: 159
<212> TYPE: PRT
<213> ORGANISM: Streptomyces sp. ACTE

<400> SEQUENCE: 42

Met Gln Gly Asp Pro Glu Val Leu Glu Phe Leu Asn Glu Gln Leu Thr
1               5                   10                  15

Ala Glu Leu Thr Ala Ile Asn Gln Tyr Phe Leu His Ala Lys Met Gln
            20                  25                  30

Asp His Arg Gly Trp Thr Lys Leu Ala Lys His Thr Arg Ala Glu Ser
        35                  40                  45

Phe Asp Glu Met Lys His Ala Glu Ile Leu Thr Asp Arg Ile Leu Leu
50                  55                  60

Leu Asp Gly Leu Pro Asn Tyr Gln Arg Leu Phe His Val Arg Val Gly
65                  70                  75                  80

Gln Thr Val Thr Glu Met Phe Gln Ala Asp Arg Gln Val Glu Val Glu
                85                  90                  95

Ala Ile Asp Arg Leu Arg Arg Gly Val Asp Leu Met Arg Ala Lys Ser
            100                 105                 110

Asp Ile Thr Ser Ala Asn Ile Phe Glu Arg Ile Leu Glu Asp Glu Glu
        115                 120                 125

His His Ile Asp Tyr Leu Asp Thr Gln Leu Glu Leu Ile Glu Lys Leu
    130                 135                 140

Gly Glu Pro Leu Tyr Leu Ala Gln Val Ile Glu Gln Val Glu Leu
145                 150                 155

<210> SEQ ID NO 43
<211> LENGTH: 297
<212> TYPE: PRT
<213> ORGANISM: Streptomyces sp. ACTE

<400> SEQUENCE: 43

Met Ser Pro Tyr Thr Ala Thr Arg Arg Thr Phe Leu Thr Gly Ala Leu
1               5                   10                  15

Ala Ala Ala Thr Gly Val Val Leu Gly Gly Thr Pro Ala Leu Ala Ala
            20                  25                  30

Pro Ala Arg Val Leu Gly Thr Gln Asp Trp Met Gly Ala Leu Ala Asp
        35                  40                  45

Ser Thr Pro Leu Arg Arg Leu Thr Ile Pro Gly Thr His Asn Ala Gly
50                  55                  60

Ala Arg Tyr Gly Gly Pro Trp Thr Glu Cys Gln Asn Thr Thr Val Ala
65                  70                  75                  80

Glu Gln Leu Gly Ser Gly Ile Arg Phe Leu Asp Val Arg Cys Arg Ile
                85                  90                  95

Thr Gly Asp Ala Phe Ala Ile His His Gly Ala Ser Tyr Gln Asn Leu
            100                 105                 110

Met Phe Gly Asp Val Leu Ile Ala Cys Arg Asp Phe Leu Ala Ala His
        115                 120                 125

Pro Ser Glu Thr Val Leu Met Arg Val Lys Gln Glu Tyr Ser Glu Glu
    130                 135                 140

Ser Asp Ala Ala Phe Arg Gln Ile Phe Asp Leu Tyr Leu Asp Gly Lys
145                 150                 155                 160

Gly Trp Arg Pro Leu Phe Arg Leu Asp Pro Thr Leu Pro Asp Leu Gly
                165                 170                 175

Gly Ala Arg Gly Lys Val Val Leu Leu Ala Asp Asn Gly Gly Leu Pro
            180                 185                 190
```

```
Gly Val Arg Tyr Ala Asp Pro Ala Val Phe Asp Ile Gln Asp Asp Tyr
            195                 200                 205

Met Ala Glu Pro Phe Gly Lys Tyr Pro Lys Ile Glu Ala Gln Phe Arg
    210                 215                 220

Lys Ala Ala Gln Gln Pro Gly Lys Leu Phe Met Asn Tyr Val Ser Thr
225                 230                 235                 240

Ala Ala Leu Leu Pro Pro Arg Ser Asn Ala Asp Arg Leu Asn Pro Gln
                245                 250                 255

Val His Thr Phe Leu Asp Gly Ser Glu Ala Ala Gly Trp Thr Gly Leu
                260                 265                 270

Gly Ile Val Pro Leu Asp Tyr Pro Ala Thr Arg Pro Gly Leu Val Glu
            275                 280                 285

Ser Leu Ile Arg His Asn Pro Val Ala
        290                 295

<210> SEQ ID NO 44
<211> LENGTH: 432
<212> TYPE: PRT
<213> ORGANISM: Streptomyces sp. ACTE

<400> SEQUENCE: 44

Val Ser Glu His Thr Asn Asn Ala Val Val Leu Arg Tyr Gly Asp Asp
1               5                   10                  15

Glu Tyr Thr Tyr Pro Val Ile Asp Ser Thr Val Gly Asp Lys Gly Phe
                20                  25                  30

Asp Ile Gly Lys Leu Arg Ala Asn Thr Gly Leu Val Thr Leu Asp Ser
            35                  40                  45

Gly Tyr Gly Asn Thr Ala Ala Tyr Lys Ser Ala Ile Thr Tyr Leu Asp
        50                  55                  60

Gly Glu Gln Gly Ile Leu Arg Tyr Arg Gly Tyr Pro Ile Glu Gln Leu
65                  70                  75                  80

Ala Glu Ser Ser Thr Phe Leu Glu Val Ala Tyr Thr Leu Ile Asn Gly
                85                  90                  95

Asp Leu Pro Lys Val Asp Glu Leu Ser Ala Phe Lys Asn Glu Ile Thr
                100                 105                 110

Gln His Thr Leu Leu His Glu Asp Val Lys Arg Phe Phe Asp Gly Phe
            115                 120                 125

Pro Arg Asp Ala His Pro Met Ala Met Leu Ser Ser Val Val Ser Ala
    130                 135                 140

Leu Ser Thr Phe Tyr Gln Asp Ser His Asn Pro Phe Asp Glu Glu Gln
145                 150                 155                 160

Arg His Leu Ser Thr Ile Arg Leu Leu Ala Lys Leu Pro Thr Ile Ala
                165                 170                 175

Ala Tyr Ala Tyr Lys Lys Ser Ile Gly His Pro Phe Val Tyr Pro Arg
                180                 185                 190

Asn Asp Leu Gly Tyr Val Glu Asn Phe Leu Arg Met Thr Phe Ser Val
            195                 200                 205

Pro Ala Gln Glu Tyr Val Pro Asp Pro Ile Val Val Ser Ala Leu Glu
    210                 215                 220

Lys Leu Leu Ile Leu His Ala Asp His Glu Gln Asn Cys Ser Thr Ser
225                 230                 235                 240

Thr Val Arg Leu Val Gly Ser Ser Gln Ala Asn Met Phe Ala Ser Ile
                245                 250                 255

Ser Ala Gly Ile Ser Ala Leu Trp Gly Pro Leu His Gly Gly Ala Asn
```

```
                        260                 265                 270
        Gln Ser Val Leu Glu Met Leu Glu Gly Ile Gln Ala Asn Gly Gly Asp
                275                 280                 285

Val Asp Ser Phe Ile Gln Lys Val Lys Asn Lys Glu Asp Gly Val Arg
        290                 295                 300

Leu Met Gly Phe Gly His Arg Val Tyr Lys Ser Phe Asp Pro Arg Ala
        305                 310                 315                 320

Lys Ile Ile Lys Ala Ala His Asp Val Leu Ser Ser Leu Gly Lys
                        325                 330                 335

Ser Asp Glu Leu Leu Asp Ile Ala Leu Lys Leu Glu Glu His Ala Leu
                        340                 345                 350

Ser Asp Asp Tyr Phe Val Ser Arg Asn Leu Tyr Pro Asn Val Asp Phe
                    355                 360                 365

Tyr Thr Gly Leu Ile Tyr Arg Ala Met Gly Phe Pro Thr Glu Met Phe
                370                 375                 380

Thr Val Leu Phe Ala Leu Gly Arg Leu Pro Gly Trp Ile Ala Gln Trp
        385                 390                 395                 400

His Glu Met Ile Lys Glu Pro Gly Ser Arg Ile Gly Arg Pro Arg Gln
                        405                 410                 415

Ile Tyr Thr Gly Glu Val Leu Arg Asp Phe Val Pro Val Glu Ser Arg
                        420                 425                 430

<210> SEQ ID NO 45
<211> LENGTH: 527
<212> TYPE: PRT
<213> ORGANISM: Streptomyces sp. ACTE

<400> SEQUENCE: 45

Met Thr Lys Arg Ala Gly Ile Leu Val Ala Val Gly Ala Thr Val Ala
        1               5                   10                  15

Gly Leu Val Thr Ala Val Pro Ser Ala Ala Ser Thr Ala Pro Gly Ala
                        20                  25                  30

Pro Gly Ala Ala Ala Pro Leu Lys Trp Thr Ala Cys Gly Thr Lys Ala
                    35                  40                  45

Tyr Pro Thr Gln Gln Cys Ala Thr Val Arg Ala Pro Leu Asp His Asp
        50                  55                  60

Arg Pro Ser Gly Arg Gln Val Thr Leu Ala Leu Ala Arg Ile Pro His
        65                  70                  75                  80

Thr Ala Lys Thr Ser Gln Gly Pro Leu Leu Val Asn Pro Gly Gly Pro
                        85                  90                  95

Gly Gly Ser Gly Leu Ser Met Ala Gly Phe Val Ala Ser Ser Leu Pro
                    100                 105                 110

Ala Lys Leu Ala Ala Gln Tyr Asp Val Ile Gly Phe Asp Pro Arg Gly
                    115                 120                 125

Val Gly Arg Ser Ser Pro Ala Leu Asp Cys Val Pro Lys His Phe Asp
        130                 135                 140

Pro Val Arg Pro Asp Thr Val Pro Gly Ser Pro Arg Asp Glu Arg Thr
        145                 150                 155                 160

Asn Arg Glu Arg Ala Ala Ser Phe Ala Asp Ala Cys Gly Glu Lys His
                        165                 170                 175

Gly Asp Leu Leu Pro Phe Met Asp Thr Val Ser Thr Ala Lys Asp Leu
                    180                 185                 190

Asp Val Ile Arg Arg Ala Leu Gly Ala Arg Gln Ile Asn Tyr Phe Gly
                    195                 200                 205
```

```
Tyr Ser Tyr Gly Thr Tyr Leu Gly Ala Val Tyr Ala Lys Leu Phe Pro
    210                 215                 220

Glu Arg Val Arg Arg Leu Val Leu Asp Ser Ile Val Asp Pro Asp Gly
225                 230                 235                 240

Val Trp Tyr Glu Asp Asn Leu Gly Gln Asp Tyr Ala Phe Asp Ala Arg
                245                 250                 255

His Lys Ala Phe Ala Ala Trp Val Ala Lys Asn Asp Ala Thr Tyr Arg
                260                 265                 270

Leu Gly Thr Asp Pro Ala Lys Val Glu Ala Ala Trp Tyr Arg Met Arg
                275                 280                 285

Ala Ala Val Lys Lys His Pro Ala Ala Gly Lys Val Gly Pro Ser Glu
    290                 295                 300

Leu Glu Asp Thr Phe Leu Pro Gly Gly Tyr Tyr Asn Gly Tyr Trp Pro
305                 310                 315                 320

Gln Leu Ala Glu Ala Phe Ala Ala Tyr Val Asn Asp Lys Asp Glu Asp
                325                 330                 335

Ala Leu Ala Thr Ala Tyr Asp Asp Phe Ala Ala Val Asp Ala Ser Gly
                340                 345                 350

Asp Asn Gly Tyr Ser Val Tyr Thr Ala Val Gln Cys Arg Asp Thr Gly
                355                 360                 365

Trp Pro Lys Ser Trp Thr Thr Trp Arg Asn Asp Thr Trp Gln Ala His
    370                 375                 380

Arg Lys Ala Pro Phe Met Ser Trp Asn Asn Thr Trp Tyr Asn Ala Pro
385                 390                 395                 400

Cys Ala Thr Trp Pro Val Ala Pro Leu Arg Pro Val Arg Val Thr Asn
                405                 410                 415

Arg Glu Ile Pro Pro Ala Leu Leu Phe Gln Ala Thr Asp Asp Ala Ala
                420                 425                 430

Thr Pro Tyr Glu Gly Gly Leu Ser Met His Arg Lys Leu Lys Gly Ser
                435                 440                 445

Arg Leu Val Val Glu Glu Gly Gly Asn His Gly Ile Ser Leu Ser
    450                 455                 460

Gly Asn Asp Cys Leu Asp Ala His Leu Ile Ala Tyr Leu Thr Asp Gly
465                 470                 475                 480

Thr Leu Pro Arg Ser Gly Ser Gly Ala Asp Ala Val Cys Asp Ala
                485                 490                 495

Leu Pro Glu Pro Glu Ala Ala Thr Ala Lys Ala Lys Ala Ala Thr
                500                 505                 510

Gly Gln Lys Gly Ser Thr Leu His Ser Leu Leu Gly Phe Arg Gly
    515                 520                 525

<210> SEQ ID NO 46
<211> LENGTH: 222
<212> TYPE: PRT
<213> ORGANISM: Streptomyces sp. ACTE

<400> SEQUENCE: 46

Met Asn Cys His Asp Arg Ile Asn Leu Arg Gly Trp Thr Thr Arg Leu
1               5                   10                  15

Ser Gly Leu Phe Val Ala Ala Val Leu Cys Leu Leu Pro Trp Thr Gly
                20                  25                  30

Thr Ala Glu Ala His Gly Ser Val Val Asp Pro Ala Ser Arg Asn Tyr
                35                  40                  45

Gly Cys Trp Leu Arg Trp Gly Ser Asp Phe Gln Asn Pro Ala Met Ala
    50                  55                  60
```

-continued

```
Gln Glu Asp Pro Met Cys Trp Gln Ala Trp Gln Ala Asp Pro Asn Ala
 65                  70                  75                  80

Met Trp Asn Trp Asn Gly Leu Tyr Arg Asn Glu Ser Ala Gly Asn Phe
             85                  90                  95

Pro Ala Val Ile Pro Asp Gly Gln Leu Cys Ser Gly Gly Arg Thr Glu
            100                 105                 110

Gly Gly Arg Tyr Asn Ala Leu Asp Thr Val Gly Ala Trp Gln Ala Thr
        115                 120                 125

Asp Ile Thr Asp Asp Phe Thr Val Arg Leu Glu Asp Gln Ala Ser His
    130                 135                 140

Gly Ala Asp Tyr Phe Arg Val Tyr Val Thr Glu Gln Gly Phe Asp Pro
145                 150                 155                 160

Thr Ala Gln Pro Leu Thr Trp Gly Ala Leu Asp Leu Val Ala Glu Thr
                165                 170                 175

Gly Arg Tyr Gly Pro Ser Thr Ser Tyr Glu Ile Pro Val Ser Thr Ser
            180                 185                 190

Gly Tyr Thr Gly Arg His Val Val Tyr Thr Ile Trp Gln Ala Ser His
        195                 200                 205

Met Asp Gln Thr Tyr Phe Leu Cys Ser Asp Val Asn Phe Gly
    210                 215                 220
```

<210> SEQ ID NO 47
<211> LENGTH: 1065
<212> TYPE: PRT
<213> ORGANISM: Streptomyces sp. ACTE

<400> SEQUENCE: 47

```
Val Ile Ser Arg Arg Leu Leu Ser Thr Thr Ala Ala Thr Ala Ala
  1               5                  10                  15

Leu Ala Ala Val Ser Ser Pro Ala Ala Arg Ala Ala Pro Ala Asp
             20                  25                  30

Thr Ala Ala Gly Arg Leu Arg Val Thr Gly Pro Thr Val Glu Tyr Val
         35                  40                  45

Arg Arg Pro Leu Gly Leu Asp Val Ser Arg Pro Arg Leu Ser Trp Pro
 50                  55                  60

Leu Ala Ser Asp His Pro Asp His Gly Gln Ser Ala Tyr Gln Val Arg
 65                  70                  75                  80

Val Ala Thr Ser Pro Asp Arg Leu Ala Arg Pro Asp Val Trp Asp Ser
             85                  90                  95

Gly Lys Val Val Ser Pro Thr Ser Val Leu Val Pro Tyr Ala Gly Pro
            100                 105                 110

Ala Leu Val Ser Arg Thr Arg Tyr His Trp Ser Val Arg Val Trp Asp
        115                 120                 125

Gln Asp Gly Arg Val Ser Ala Trp Ser Glu Pro Ser Trp Trp Glu Thr
    130                 135                 140

Gly Leu Leu Asp Glu Ala Asp Trp Ser Ala Gly Trp Ile Gly Ala Pro
145                 150                 155                 160

Ala Ala Leu Thr Ser Ser Pro Ser Leu Glu Ala Ala Ser Trp Ile Trp
                165                 170                 175

Phe Pro Glu Gly Asp Pro Ala Val Gly Ala Pro Ala Thr Arg Trp
            180                 185                 190

Phe Arg Gly Arg Val Glu Ile Pro Glu Gly Val Thr Arg Ala Arg Leu
        195                 200                 205

Val Met Thr Ala Asp Asp Gly Phe Thr Ala Leu Val Asp Gly Val Gln
```

-continued

```
                210                 215                 220
Val Ala Arg Thr Glu Pro Asp Gly Pro Ala Glu Asn Trp Arg Pro
225                 230                 235                 240

Val Val Val Asp Val Thr Ala His Leu Ser Pro Gly Ser Arg Val Val
                245                 250                 255

Ala Val Thr Ala Thr Asn Ala Val Asp Gly Pro Ala Gly Leu Leu Gly
                260                 265                 270

Ala Leu Glu Leu Thr Thr Ala Asp Gly Ala Val Thr Leu Ala Thr Gly
                275                 280                 285

Thr Gly Trp Arg Ala Thr Asp Arg Glu Pro Asp Gly Asp Trp Ala Ser
                290                 295                 300

Gly Gly Tyr Asp Asp Thr Gly Trp Pro Ala Ala Ala Val Leu Ala Pro
305                 310                 315                 320

Trp Gly Ser Gly Pro Trp Gly Glu Val Arg Ala Ala Leu Ser Pro Ala
                325                 330                 335

Thr Gln Leu Arg Thr Glu Phe Arg Leu Gly Arg Lys Arg Val Ala Arg
                340                 345                 350

Ala Arg Leu Tyr Ser Thr Ala Leu Gly Leu Tyr Glu Val Phe Leu Asn
                355                 360                 365

Gly Ala Arg Val Gly Glu Asp Arg Leu Ala Pro Gly Trp Thr Asp Tyr
370                 375                 380

Arg Lys Arg Val Gln Tyr Gln Thr Tyr Asp Val Thr Ala Leu Leu Arg
385                 390                 395                 400

Ser Gly Gly Asn Ala Leu Gly Val Thr Leu Ala Pro Gly Trp Tyr Ala
                405                 410                 415

Gly Asn Ile Ala Trp Phe Gly Pro His Gln Tyr Gly Glu Arg Pro Ala
                420                 425                 430

Val Leu Ala Gln Leu Glu Val Thr Phe Thr Asp Gly Ser Ile Glu Arg
                435                 440                 445

Val Leu Ser Gly Thr Gly Trp Ala Ala Ala Thr Gly Pro Val Thr Ala
                450                 455                 460

Thr Asp Leu Met Ala Gly Glu Glu Tyr Asp Ala Arg Leu Glu Thr Asp
465                 470                 475                 480

Gly Trp Ser Arg Ala Gly Phe Asp Ala Ser Gly Trp Leu Ala Ala Glu
                485                 490                 495

Ala Val Glu Gly Val Thr Ala Val Pro Val Ala Ala Val Asp Gly Ala
                500                 505                 510

Cys Arg Val Glu Arg Glu Leu Thr Ala Arg Glu Val Thr Glu Pro Glu
                515                 520                 525

Pro Gly Val Tyr Val Phe Asp Leu Gly Gln Asn Met Val Gly Thr Val
                530                 535                 540

Arg Leu Leu Val Ser Gly Pro Ala Gly Thr Thr Val Arg Leu Arg His
545                 550                 555                 560

Ala Glu Val Leu Asn Pro Asp Gly Thr Leu Tyr Thr Ala Asn Leu Arg
                565                 570                 575

Thr Ala Arg Ala Thr Asp Thr Tyr Thr Leu Arg Gly Gly Pro Glu
                580                 585                 590

Thr Tyr Glu Pro Arg Phe Thr Phe His Gly Phe Arg Tyr Val Glu Val
                595                 600                 605

Thr Gly Phe Pro Gly Arg Pro Gly Pro Asp Ala Val Val Gly Arg Val
                610                 615                 620

Ile His Thr Ser Ala Pro Phe Thr Met Ala Phe Ser Thr Asp Val Pro
625                 630                 635                 640
```

```
Met Leu Asp Arg Leu His Ser Asn Ile Thr Trp Gly Gln Arg Gly Asn
                645                 650                 655

Phe Leu Ser Val Pro Thr Asp Thr Pro Ala Arg Asp Glu Arg Leu Gly
            660                 665                 670

Trp Thr Gly Asp Ile Asn Val Phe Ala Pro Thr Ala Tyr Thr Met
        675                 680                 685

Glu Ser Ala Arg Phe Leu Gly Lys Trp Leu Gln Asp Leu Arg Asp Asp
    690                 695                 700

Gln Leu Ala Asp Gly Ala Phe Pro Asn Val Ala Pro Asp Leu Pro Gly
705                 710                 715                 720

Val Gly Ser Gly Ala Ala Gly Trp Gly Asp Ala Gly Val Thr Val Pro
                725                 730                 735

Trp Ala Leu Tyr Gln Ala Tyr Gly Asp Val Arg Val Leu Glu Gln Ser
            740                 745                 750

Trp Ser Ser Met Val Ala Trp Leu Glu Tyr Leu Gln Ala His Ser Asp
        755                 760                 765

Gly Leu Leu Arg Pro Ala Asp Gly Tyr Gly Asp Trp Leu Asn Ile Glu
    770                 775                 780

Asp Glu Thr Pro Lys Asp Val Ile Gly Thr Ala Tyr Phe Ala His Ser
785                 790                 795                 800

Ala Asp Leu Thr Ala Arg Thr Ala Glu Val Leu Gly Lys Asp Pro Gly
                805                 810                 815

Pro Tyr Arg Thr Leu Ser Gly Arg Val Arg Asp Ala Phe Arg Ala Ala
            820                 825                 830

Tyr Val Gly Asp Gly Gly Arg Val Lys Gly Asp Thr Gln Thr Ala Tyr
        835                 840                 845

Val Leu Ala Leu Ser Met Asp Leu Leu Glu Pro Gly Asp Arg Ala Pro
850                 855                 860

Ala Ala Asp Arg Leu Val Ala Leu Ile Glu Ala Lys Asp Trp His Leu
865                 870                 875                 880

Ser Thr Gly Phe Leu Gly Thr Pro Arg Leu Leu Pro Val Leu Thr Asp
                885                 890                 895

Thr Gly His Thr Asp Val Ala Tyr Arg Leu Leu Thr Arg Thr Phe
            900                 905                 910

Pro Ser Trp Gly Tyr Gln Ile Asp Arg Gly Ala Thr Thr Met Trp Glu
        915                 920                 925

Arg Trp Asp Ser Val Arg Pro Asp Gly Gly Phe Gln Asp Ala Gly Met
    930                 935                 940

Asn Ser Phe Asn His Tyr Ala Tyr Gly Ser Val Gly Glu Trp Met Tyr
945                 950                 955                 960

Ala Asn Ile Ala Gly Ile Ala Pro Ala Pro Gly Phe Arg Glu Ile
                965                 970                 975

Arg Val Arg Pro Arg Pro Gly Gly Val His Arg Ala Glu Ala Arg
            980                 985                 990

Phe Asp Ser Leu Tyr Gly Pro Val  Thr Thr Arg Trp Thr  Ser Asp Gly
        995                 1000                1005

Gly Gly  Phe Ala Leu Arg Val  Val Leu Pro Ala Asn  Thr Thr Ala
    1010                1015                1020

Glu Val  Trp Val Pro Gly  Gly Asp Gly Arg Ser  Val Arg Gly
        1025                1030                1035

Thr Ala  Val Phe Leu Arg Arg  Glu Asp Gly Cys Ala  Val Phe Ala
    1040                1045                1050
```

Ala Gly Ser Gly Ile His Arg Phe Thr Ala Pro Ala
   1055                1060                1065

<210> SEQ ID NO 48
<211> LENGTH: 1170
<212> TYPE: DNA
<213> ORGANISM: Streptomyces sp. ACTE

<400> SEQUENCE: 48

| | | | | | |
|---|---|---|---|---|---|
| atgccggagc | gtttcactcc | cactcctgag | gacaagttca | cgttcggtct | gtggaccgtg | 60 |
| ggctggcggg | gcaacgaccc | gttcggtgag | ccgacgcgtc | cggtgctgga | cccggtggag | 120 |
| tcggtcgagc | ggctggcgga | gctcggtgcg | cacggggtga | cgttccatga | cgacgacctg | 180 |
| attccgttcg | ggtcggacga | ccgtgagcgg | gcgcggctgg | tcgggcggtt | cagggaggcg | 240 |
| ctggagcgta | ccgggctcaa | ggtgccgatg | gcgacgacga | acctgttcac | gcacccggtg | 300 |
| ttcaaggacg | gcgggttcac | ctccaacgac | cgtgacgtgc | ggcggttcgc | gctgcgcaag | 360 |
| gtgatccgca | acatcgatct | cgcggtggag | ctcggcgcgc | agacgtatgt | ggcctggggc | 420 |
| gggcgtgagg | gcgccgagtc | cggtgcggcc | aaggacgtgc | ggtcggccct | ggaccggatg | 480 |
| aaggaggcct | tcgacctgct | gggcgactac | gtcaccgagc | agggctacga | cctgcggttc | 540 |
| gcgatcgagc | ccaagcccaa | cgagccccgc | ggtgacatcc | tgctgcccac | gatcgggcac | 600 |
| gcgctggcct | tcatcgagcg | cctggagcgc | cccgagctgg | tcggggtgaa | cccggagacc | 660 |
| gggcacgagc | agatggccgg | gctgaacttc | ccccacggca | tcgcgcaggc | cctgtgggcg | 720 |
| ggcaagctct | tccacatcga | cctcaacggc | cagtccggga | tcaagtacga | ccaggacttc | 780 |
| cgcttcggcg | ccggtgacct | cgccaggcg | ttctggctcg | tggacctcct | ggagacggcc | 840 |
| ggctgggacg | gctcacgcca | cttcgacttc | aagccggtac | gcaccgacgg | catcgacggg | 900 |
| gtgtgggagt | ccgcgaagaa | ctgcatgcgc | aactacctca | tcctcaagga | gcgcgccgcc | 960 |
| gccttccgcg | ccgaccccgc | cgtccaggag | gccctcaccg | cctcccgcct | cgacgaactc | 1020 |
| gcccgcccca | ccgccgacga | cggcctcaag | gcactcctcg | ccgaccgcac | cgcctacgag | 1080 |
| gacttcgacg | ccaccgccgc | cgccgaacgc | tccatggcct | tcgaagccct | cgaccagctc | 1140 |
| gccatggacc | acctcctcaa | cgtccgctga | | | | 1170 |

<210> SEQ ID NO 49
<211> LENGTH: 1968
<212> TYPE: DNA
<213> ORGANISM: Streptomyces sp. ACTE

<400> SEQUENCE: 49

| | | | | | |
|---|---|---|---|---|---|
| atgacaagcg | cgctcagggc | gacgcagggt | ttgcagtcca | cgaaccaccc | ccgtttgtcg | 60 |
| gacctcaccc | gaggagcacc | gttgagcact | gaatcccccc | gaagaagttc | ccgtctcaga | 120 |
| tggagactcg | gcccggggcg | ggccaccccgg | gccaaggcgg | tcgcgggctt | caccgcactg | 180 |
| ctgctgccgc | tcgccgcgat | ggtcggcctg | cgtccccgg | ccaggccgc | gacctcggcg | 240 |
| accgccacct | acctcaagaa | gtcggactgg | ggcagcggct | tcgagggcca | gtggacggtg | 300 |
| aagaacaccg | gcaccaccgc | cctgtcctcc | tggacgatcg | agtgggactt | ccctccggc | 360 |
| accgcggtcg | gctccgcctg | ggacgcctcc | gtgaccagct | ccggcaccca | ctggaccgcc | 420 |
| aagaacctcg | gctggaacgg | tacggtcgcc | ccgggtgcca | gcatcagctt | cggcttcaac | 480 |
| ggcaccggat | ccggctcccc | caccggctgc | aagctgaacg | gtgcctcctg | tgacggcggc | 540 |
| ggcacggtcc | ccggcgacag | cgccccgtcc | aagcccggca | cccccaccgc | gagcggcatc | 600 |

```
accgacacct cggtgaagct ctcctggagc gcagccaccg acgacaaggg catcaagaac      660
tacgacgtcc tgcgcgacgg cgccaaggtc gcgacggtca ccacgacgac gtacaccgac      720
accggcctca ccaagggcac ggactactcc tactccgtgc aggcccgcga caccgccgac      780
cagaccggac cggtcagcgg cgcggtggcc gtgcgcacca cgggcgggaa cgacaacccg      840
ggccccggca ccggcagcaa ggtcaacctc ggctacttca ccaactgggg cgtctacggg      900
cgcaactacc acgtcaagaa cctggtgacc tcgggctcgg ccgagaagat cacgcacatc      960
aactacgcct tcggcaacgt ccagggcggc aagtgcacca tcggcgactc ctacgccgac     1020
tacgacaagg cctacaccgc cgaccagtcg gtcgacggcg tcgccgacac gtgggaccag     1080
ccgctgcgcg gcaacttcaa ccagctgcgc aagctcaagg cgaagtaccc gcacatcaag     1140
gtgatctggt cgttcggcgg ctggacctgg tccggcggct tcggtgccgc ggcgcagaac     1200
ccggccgcgt tcgcccagtc ctgctacgac ctggtggagg accccgctg ggccgatgtc      1260 ttcgacggca tcgacatcga ctgggagtac cccaacgcct gcggcctgac ctgtgacacc     1320
agcggccccg ccgcgctgaa gaacctgtcc tccgcgctcc gcgccaagtt cggcgcgaag     1380
aacctggtca ccgccgcgat caccgcggac ggctcggacg gcggcaagat cgacgccgcc     1440
gactacgcgg gcgccgcgca gtccttcgac tggtacaacg tgatgacgta cgacttcttc     1500
ggcgcctggg aggcgaaggg tccgacggcc ccgcactccc cgctgaacgc gtacgccggc     1560
atcccgcagg acgcttcaa ctccgccgcc gccatcgcca gctgaaggc caagggcgtc      1620 ccggcctcga agctgctgct cggcatcggc ttctacggcc gcggctggac gggcgtgacc     1680
caggcggcac cggcggcac cgccaccggc gcggccccgg gcacgtacga ggcgggcatc     1740
gaggactaca aggtcctcaa gaccagctgc ccggccaccg gcacgatcgc cggcaccgcg     1800
tacgcgcact gcggcaccaa ctggtggagc tacgacaccc cggcgaccat cacctccaag     1860
atggcctggg cgaacagcca gggcctcggc ggtgcgttct tctgggagtt cagcggcgac     1920
accgccaacg gcgagctcgt gagcgccatg acagcggcc tcaactag                   1968
```

<210> SEQ ID NO 50
<211> LENGTH: 591
<212> TYPE: DNA
<213> ORGANISM: Streptomyces sp. ACTE

<400> SEQUENCE: 50

```
atgcggaaaa gggcaagcgc ggccgtcata ggcctggcga tcgccggcgt ctcgatgttc       60
gccaccagca gtgccagcag ccacggctac accgattccc ccatcagcag acagaagctg      120
tgtgccaacg gcaccgtcac cggctgcggc aacatccagt gggagccgca gagcgtcgag      180
ggcccgaagg gcttcccggc ggcaggtccg gcggacggca agatctgcgc cggcggaaac      240
agctccttcg ccgcgctcga cgacccgcgc gggggcaact ggcccgccac ccaggtcacc      300
ggcggccagg gctacaactt ccgctggcag ttcaccgccc gccacgccac gaccgacttc      360
cggtactaca tcaccaagga cggctgggac tccaccaagc cgctcaccag gccgccctg       420 gagtcgcagc ccttcatgac ggtgccgtac gggaaccagc agccccggc gaccctgacc       480 caccagggca ccatccccac ccagaagtcc ggcaagcaca tcatcctggc cgtctggaac      540
gtggctgaca ccgccaacgc gttctacgcg tgctcggacg tgaagttctg a                591
```

<210> SEQ ID NO 51
<211> LENGTH: 1671
<212> TYPE: DNA
<213> ORGANISM: Streptomyces sp. ACTE

<400> SEQUENCE: 51

```
gtggccgccc tcgcggccgg cgccctgacc gtgaccggtc tggtcggcac cgcacaggcg      60
gccgacatca acgtcgccaa gaacgccggg ttcgagagcg gcctcagcgg ctggacctgt     120
accggcggca gcggcgccac cgtctcctcc cccgtgcacg gcggctccgc cgccctcaag     180
gccaccccga gcggccagga caacgcgaag tgcacccaga ccgtggccgt gaagcccaac     240
tccacctatg cgctcagttc ctgggtgcag ggcgggtacg cctacctcgg ggcgagcggc     300
accggcacca ccgacgtctc cacctggacc cccggcagca ccggctggac ccagctgcgc     360
acgagcttca ccaccggccc gtccaccacc tcggtgcagg tctacaccca cggctggtac     420
ggccaggcgg cctactacgc ggacgacgtc gcggtcaccg acccgacgg cggcggcggt      480
acggaggagc ccgccccggc gatccccggc gcccccgccg gtctggccgt cggcaccacc     540
acgtcctcct cggtggccct gtcgtggaac gcggtctccg gcgccaccgg ctacaccgtc     600
taccgggacg gcaccaaggc gaccaccacc accggcacct ccgcgacggt gagcggcctg     660
gccgccgaca ccgcgtacca gttctcggtg agcgccacca acgccgccgg tgagtccgtc     720
aggtcggcga ccgtgagcgg acgtacggcc aagaaggacg agaccggccc gggcccctcg     780
acctccgtgc ccaagcacgc cgtgaccggc tactggcaga acttcaacaa cggcgcggcc     840
gtccagaagc tcagcgacgt gccgcgaac tacgacatca tcgccgtctc cttcgcggac      900
gccgccggta ccccgggtgc cgtcaccttc aacctcgact cggcgggcct gaacggctac     960
accgtcgccc agttcaaggc cgacatcaag gccaagcagg ccgcgggcaa gaacgtcatc    1020
atctccgtcg gcggcgagaa gggcaccgtc tcggtcaaca gcgacgcctc ggcgaacgcg    1080
ttcgcggact cgctgtacac gctgatccag gagtacggct tcaacggcgt cgacatcgac    1140
ctggagaacg gcctcaactc cacctacatg acgaaggccc tgcggtcgct gtcctcgaag    1200
gtgggctccg gtctcgtcat cacgatggcg ccgcagacga tcgacatgca gtcgacgtcg    1260
ggtgagtact tcaagacggc gctcaacatc aaggacatcc tgaccgtcgt caacatgcag    1320
tactacaaca gcggttcgat gctgggctgc gacggcaagg tctactcgca gggctcggtg    1380
gacttcctca ccgcgctcgc ctgcatccag ttggagggcg gcctcgcccc gtcccaggtc    1440
ggcctcggtg tgcccgcctc caccgcggc gcgggcagcg gctacgtcgc ccgtcggtc      1500
gtgaacgcgg ccctggactg cctggccaag ggcaccggct gcggttcctt caagccgtcc    1560
aggacgtacc cggacatccg tggtgcgatg acctggtcga cgaactggga cgccacggcg    1620
ggcaacgcct ggtccaacgc ggtcggcccg cacgtccacg gccttccgta a             1671
```

<210> SEQ ID NO 52
<211> LENGTH: 888
<212> TYPE: DNA
<213> ORGANISM: Streptomyces sp. ACTE

<400> SEQUENCE: 52

```
gtgatcagac gcgtcatggg cctgctcacc gcgctggccg cggtcgtcgc gacgctcgtc      60
ttcctccccg ccgccacggc ctcggcggcc acctgcgccc cggcctggaa cgcctcgtcc     120
gtgtacacgg gcgcggctc cgcctcgtac aacgggcaca ctggtcggc gaagtggtgg      180
acgcagaacg agcgtccggg cacctcggac gtctgggccg accagggcgc ctgcggttcg     240
ggcggcggcg gcaccgaccc gaaccccctcg ggcttcgtcg tcagcgaggc gcagttcaac     300
cagatgttcc cgagccggaa ctccttctac acctacagcg ggctcaccgc cgcgctgagc     360
```

```
gcctaccccg ccttcgccaa caccggcagc gacaccgtga agaagcagga ggcggcggcg      420
ttcctcgcca acgtcagcca tgagaccggc ggcctggtcc acatcgtgga gcagaacacc      480
gccaactacc cgcactactg cgacaccagc cagtcctacg gctgcccggc cggccaggcc      540
gcctactacg gccgcggccc catccagctc agctggaact tcaactacaa ggcggccggt      600
gacgccctcg gcatcgacct gctgggcaac ccctggcagg tggagcagaa cgcctccgtg      660
gcctggaaga ccggcctctg gtactggaac acccagtccg gccccggcac catgacgccc      720
cacaacgcca tcgtcaacgg ctccggattc ggtgagacca tccggtccat caacggcagc      780
atcgagtgca acggcggcaa ccccggccag gtccagagcc gcgtcaacac ctaccagtcg      840
ttcgtccaga tcctcggtac cacgcccggc tcgaacctga gctgctga                  888

<210> SEQ ID NO 53
<211> LENGTH: 1524
<212> TYPE: DNA
<213> ORGANISM: Streptomyces sp. ACTE

<400> SEQUENCE: 53
atgagacgct cacgatccgt ccgcgcgctg gtgacggcgg ccgtcaccac ggtggccgcg      60
gcaggcatgg ccgtgctggg ctccggcacc gcccaggcgg cgaccccgct gcccgaccac      120
gtcttcgccc cctacttcga gtcgtggacc ggagagagcc cggcggccat ggcggccgag      180
tccggggcga aacacctgac catggcgttc ctccagacga cggccaaggg ctcctgcacg      240
ccgtactgga acggcgacac cggcctgccg atcgcccagg cgtccttcgg cgccgacatc      300
gacacgatcc aggccggagg cggcgacgtc atcccgtcgt tcggcggcta caccgcggac      360
accaccggca cggagatcgc cgacagctgc accgacgtcg accagatcgc cgcggcctac      420
cagaaggtcg tcacgacgta cgacgtctcg cggctcgaca tggacatcga ggtcgactcc      480
ctcgacgaca ccgccgggat cgaccggcgg aacaaggcca tcaagaagct ccaggactgg      540
gcggacgcga acgccgtgaa cctggagatc tcctacacgc ttccgacgac cacccgcgga      600
ctggcctcca gcggcctcgc cgtgctgcgc aacgccgtga ccaacggggc acgggtcgac      660
gtcgtgaacc tgatgacgtt cgactactac gacaacgcgt cccacgacat ggccgccgac      720
accgagaccg ccgcccaggg cctgtacgac cagctcgcga agctgtaccc gggcaggacc      780
gccacccagc tgtggtccat ggtcggcgtc accgagatgc ccggcgtcga cgacttcggc      840
ccggccgaga ccttcacgct cgccaacgcc gcccgggtgt acgactgggc ggtggccaag      900
ggcatcaaca ccctgtcctt ctgggcgctc cagcgcgaca cggcggctg ccccggcggc      960 ccggccgccg acgactgctc cggcatccag cagaacacct gggacttcac ccgcgtcttc      1020
gcgcccttca ccagcggcac cacgcgcgcc gacgacgact tctcggtgac ggccacgccc      1080
gcctccggga cggtgaccgc gggcggttcg gccaccacca cggtgaagac cgccgtgacc      1140
aagggcgcgg cacagcaggt cggcctcacg gtcagcgggg tcccggccgg tgtcaccgcc      1200
tccctcagcc cctcctcggt gaccgcgggc ggccggtcaa cgctcaccct cgccacgacc      1260
caggccgccg tctcgggcac gtaccggatc agcgtcaccg gtacgagccc gtcgggcagc      1320
cacgcgacgg cctacacgct gaccgtcacc ggcggcaccg gcagccagtg cacggcgggg      1380
ccgtgggcgg gcgggacggt ctacaccggc ggccagcagg tctcgtacaa gggccacacc      1440
tggaaggcca agtggtggac gacgggcgag gagcccggca ccaccggtga gtggggcgtc      1500
tggcaggacc tgggcgcctg ctga                                            1524
```

<210> SEQ ID NO 54
<211> LENGTH: 1452
<212> TYPE: DNA
<213> ORGANISM: Streptomyces sp. ACTE

<400> SEQUENCE: 54

```
gtgacgcagg gaccgctcac cacggaggcc ggcgcgccgg tagccgacaa ccagaacagt      60
gagaccgcag gccccggtgg accggttctc gttcaggacc aggcgcttct ggagaagctg     120
gcccacttca accgggagcg catcccggag cgcgtcgtgc atgcccgggg agccggcgcg     180
tacggcacgt tcacgctgac ccgtgacgtc tcgcagtgga cgcgtgcgaa gttcctctcg     240
gaggtcggca aggagaccga gaccttcctg cgcttctcca ccgtcgcggg caacctcggc     300
tcggccgacg cggcgcgtga cccgcgcggc tgggcgctga agttctacac cgaagagggc     360
aactacgacc tcgtcggcaa caacaccccg gtgttcttca tcaaggacgc catcaagttc     420
cccgacttca tccacaccca gaagcgcgac ccgtacacgg gctcccagga ggcggacaac     480
gtctgggact tctggggcct gtcgccggaa tccacccacc aggtgacctg gctcttcggt     540
gaccgcggca tcccggcctc gttccgtcac atgaacggct acggctcgca cacgttccag     600
tggaacaacg aggccggcga ggtcttctgg gtcaagtacc acttcaagac cgaccagggc     660
atcaagaacc tcaccaccga ggaggccgtc cgcctctccg gcgtcgaccc ggacagccac     720
cagcgcgatc tgcgtgagtc catcgagcgc ggtgacttcc cgacctggac ggtgcaggtc     780
cagatcatgc cggcggccga ggcggccacg taccgcttca acccgttcga cctgaccaag     840
gtgtggccgc acgaggacta cccgccgatc gagatcggca agctggagct caaccgcaac     900
ccggagaaca tcttcgccga ggtcgagcag tcgatcttca gcccggcgca cttcgtaccc     960
ggcatcggcc cgtccccgga caagatgctc cagggccgcc tgttcgcgta cggcgacgcc    1020
caccgctacc gcgtcggcat caacgccgac cacctgccgg tgaaccgtcc gcacgccacc    1080
gaggcgcgta ccaacagccg tgacggctac ctgtacgacg gccggcacaa gggcacgaag    1140
aactacgagc cgaacagctt cggcggcccg gtccagaccg acaggccgct ctggcagccc    1200
gtctccgtca ccggcggtac gggcaaccac gaggccgccg tccacgcgga ggacaacgac    1260
ttcgtgcagg ccggcaatct ctaccggctg atgtcggagg acgagaaggg ccggctgatc    1320
gacaacctgg ccgggttcat cgcgaaggtg tcgcgcgacg acatcgccga tcgcgcgatc    1380
aacaacttcc gtcaggccga cgcggacttc ggcaagcggc tggaggtcgc ggtccaggcc    1440
ctgcgcggct ga                                                        1452
```

<210> SEQ ID NO 55
<211> LENGTH: 2781
<212> TYPE: DNA
<213> ORGANISM: Streptomyces sp. ACTE

<400> SEQUENCE: 55

```
gtgtatgcca tgccctccac cgccctgcg gcggtccagt ccggagagga cgctcccgtg      60
cgttcaagcc ccagacccctt cgccgccctg ctggcggcgc tcgccctgac cgcagggttg     120
tcactcatcg gaacccctgc cgtggcgcgc tccgacgagg cacctgctgc gacagaagca     180
tcggatgtgt ccatagccgc ggacacctac acctggaaga acgcccggat cgacggcggc     240
ggcttcgtcc ccgggatcgt cttcaaccgg tccgagaaga acctcgccta cgcccggacc     300
gacatcggcg cgcctaccg ctgggaccag tccggcaagc agtggaagcc cctgctggac     360
tgggtggact gggaccgctg gggctggacg ggcgtggtga gcctcgcctc cgacacggtc     420
```

```
gaccccgaca acgtgtacgc cgccgtgggg acgtacacca acagctggga cccgaccgac    480
ggcgcggtcc tgcgctcctc ggaccggggc gcctcctgga aggcggccac cctcccgttc    540
aagctcggcg gcaacatgcc cggacgcggc atggggagc ggctcgcggt cgacccgaac    600
aagaactccg tgctctacct gggcgcgccc agcggcaacg gcctctggcg gtccaccgac    660
gcgggagtca gctggtccga ggtgacggcc ttccccaacc ccgggaacta cgcgcaggac    720
ccgtcggaca ccagcggcta cggcaacgac aaccagggca tcgtctgggt gaccttcgac    780
gagcgttccg gcagcgcggg cagcgccacc caggacatct acgtcggggt cgccgacaag    840
gagaacaccg tctaccgctc cacggacggc ggcgccacct ggtcgcggat cccgggccag    900
cccaccggct acctcgcgca aagggcgta ctcgactccg cgaccggcca cctctatctg    960
acgctgagcg acacgggcgg cccctacgac ggcggcaagg gccggatctg gcggtacgac   1020
acggcgtccg gcgcctggca ggacgtcagc ccggtggcgg aggccgacgc ctactacggc   1080
ttcagcgggc tctccgtgga ccggcagaag cccggcaccc tgatggccac cgcctacagc   1140
tcctggtggc ccgacaccca gatcttccgc tccacggaca cgcgtgccac ctggacccag   1200
gcctgggact acaccggcta cccgaaccgc tccaaccgct acacgctgga cgtctcctcc   1260
gtgccgtggc tctcctgggg cgcttccccc gcaccgcccg agaccgcccc gaagctgggc   1320
tggatgacgg aggcgctgga gatcgacccg ttcgactcgg accggatgat gtacggcacc   1380
ggagcgacgg tctacggcac cgaggacctc acgtcctggg actccggcgg cacgttcagg   1440
atcaccccca tggtgaaggg gatcgaggag acggccgtca acgacctggc cagcccgccc   1500
tccggggcac cgttgctgag cgcactcggt gacatcgggg gcttccggca caccgacctc   1560
gacgccgtgc cggacctgat gtacacctcc ccgaacctcg actcgaccac cagcctggac   1620
ttcgcggaga gctcgcccgg cacggtcgtc cgggtcggca actccgacgc cgcgccccac   1680
atcggcttct ccaccgacaa cggggccaac tggttccagg gctcggagcc ttcgggcgtc   1740
accggcggcg gcacggtcgc ggcggcggcg gacggcagcg gcttcgtgtg gagcccggag   1800
ggcgcgggcg tccaccacac caccggcttc ggcacctcct ggaccgcctc caccggcatc   1860
ccggccggtg ccacggtcga gtccgaccgg aagaaccccg agaagttcta cggattcgag   1920
gcgggcacct tctacgtctc gaccgacggc ggggcgacct tcaccgccga ggccaccggg   1980
ctgcccgccg agggcaacgt ccgcttccag gcactgcccg ggacggaggg cgacatctgg   2040
ctcgcgggcg gctccgacac cggggcgtac ggtctgtggc gctccaccga ctccggggcg   2100
acgttcacga gtccgccgg cgtcgagcag gcggacagcg tgggcttcgg caaggccgcc   2160
ccgggcgcct cgtaccggac ggtgttcgtc agcgcgaaga tcggcggggt gcgcggcatc   2220
ttccggtcca ccgacgccgg ggcgagctgg accaggatca cgacgacgc ccaccagtgg   2280 ggctggaccg gcgccgcgat cacgggcgac cccagggtct acgggcgcgt ctacgtctcc   2340
accaacgggc gcgggatcca ggtgggcgag acctccgaca cgcggcggcgg aggcacggac   2400 cccggcaccg atcccggcac cgatcccggc accgatcccg gtccggagca gcccgcggac   2460
gccgcctgtg cggtgacgta cgcggtcacc aaccagtggc cggcggcttt ccaggccgat   2520
gtgacggtca ccaacacggg tgacgccgcg tacaacggct ggaagctcgg ctggtcgttc   2580
cccggcgggc agcagatcag ccagatctgg aacgcctcgc accggcagga cggggtgaag   2640
gtcaccgtca cggacgccgg ctggaacgga acgtggcgc ccggctcgtc ggcgggcttc   2700
ggcttcaccg gcagttgggc ggggagcaac gccgaaccgg ccgccttcac cctggacggc   2760
caggcctgca ccgtgggctg a                                              2781
```

<210> SEQ ID NO 56
<211> LENGTH: 1632
<212> TYPE: DNA
<213> ORGANISM: Streptomyces sp. ACTE

<400> SEQUENCE: 56

| | | | | | |
|---|---|---|---|---|---|
| atgcgcggtg | ccaagagcgc | caagtgggtc | gcgggagcgg | caatcatcgc | cctggccgcg | 60 |
| accgcctgtg | gtggcggcga | cagcgacagc | gacaacggtg | ccaagggcgc | cgtcgacgcg | 120 |
| gacggcatat | tctccgtcga | ggtcggtgag | ccgcagaacc | cgctgcagcc | ggccaacacg | 180 |
| atggagtcga | acggcagcat | cgtcaccgac | gccatcttct | cgcagctcgt | cgactacgac | 240 |
| cccgacggca | agctcgagat | gatcaacgcc | gagtccgtcg | agacgaccga | cagcaagctg | 300 |
| tggacggtca | agctcaagaa | ggactggaag | ttccacgacg | gcaccccgt | caccgccgac | 360 |
| tcctacgtca | aggcctggaa | ctgggccgcg | aacatcgaga | acgcgcagac | gaacgcctcc | 420 |
| tggttcgccg | acatcaaggg | ctacgccgac | gtccaccccg | acggcgaggg | cgccaagccg | 480 |
| aagtccgacg | ccatgtccgg | cctgaagaag | gtggacgact | acaccttcac | catcgagctc | 540 |
| aactcggccg | tcccgtactt | ctcgtacaag | ctcggctaca | cggtcttctc | gccgctgccc | 600 |
| gagtccttct | acgcggaccc | gaaggccgcc | ggtgagaagc | cggtcggcaa | cggcgcgtac | 660 |
| aagttcgtca | gctgggacca | caagaagcag | atcaaggtcg | tccgcaacga | cgactacaag | 720 |
| ggccccgaca | aggcgaagaa | cggtggtgtg | atcttcaaga | actacaccac | cctcgagacc | 780 |
| gcctacgagg | acctcaagtc | cggcaacgtc | gacgtgctcc | gccagatcgg | cccgaaggac | 840 |
| ctcccggtct | accgtgccga | cctcgaggac | cgcgccgtgg | acaaggccta | ctccgcggtt | 900 |
| cagacgctcg | gtgtcgccat | gtacaccgac | cagtggaaga | cacgcaccc | gaaggtcctc | 960 |
| cagggcctgt | cgatggccat | cgaccgggac | acgatcacca | agacggtgct | ccagggcacc | 1020 |
| cgcgagccgg | ccacggggctg | gtcgccaag | ggcgtcctcg | gttaccagga | gaacgtcgcc | 1080 |
| ggtgacgtca | ccaagtacga | cccggcgaag | gccaaggccc | tcatcaagga | gggtggcggt | 1140 |
| gttccgggca | acgagatctt | catccagttc | aacgccgacg | gcggccacaa | ggagtggatc | 1200 |
| gaggcggtct | gcaacagcat | cacgcaggcc | accgcgtca | agtgcaccgg | cgactcgaag | 1260 |
| gccgacttcc | aggccgacct | gaacgcccgc | gacgccaagc | aggtgaagtc | gttctaccgc | 1320 |
| agtggctggg | tcctcgacta | cccggtcaac | gccaacttca | tcagcgacct | gttccgcacc | 1380 |
| ggtgcggccg | caacaacgg | cttcttctcc | aacaaggacc | tcgacgcgaa | gatcaaggcc | 1440 |
| gcggactccg | ccgcgagcct | cgacgattcg | gtcaaggcct | accaggagat | cgagaaggag | 1500 |
| ctggtcaact | acatgcccag | catcccgctc | tggtactaca | aggtcaacgc | cggctactcg | 1560 |
| gagaacgtca | gaacgtgga | ctacgcgcag | gacggcgacc | cgatcctgac | cgaagtccag | 1620 |
| gtcatcaagt | aa | | | | | 1632 |

<210> SEQ ID NO 57
<211> LENGTH: 480
<212> TYPE: DNA
<213> ORGANISM: Streptomyces sp. ACTE

<400> SEQUENCE: 57

| | | | | | |
|---|---|---|---|---|---|
| atgcagggcg | accccgaggt | cctcgagttc | ctgaacgaac | agctgaccgc | cgaattgact | 60 |
| gccatcaatc | agtacttcct | gcacgcgaag | atgcaggatc | accgcggctg | gaccaagctc | 120 |
| gccaaacaca | cccgggccga | gtcgttcgac | gagatgaagc | acgcggagat | cctgaccgac | 180 |

```
cggatcctgc tgctggacgg cctgcccaac tatcagcggc tgttccacgt gcgggtgggc    240
cagaccgtca cggagatgtt ccaggccgac cggcaggtcg aggtcgaggc gatcgaccga    300
ctgcggcgcg gtgtcgatct gatgcgcgcc aagagcgaca tcacgtccgc caacatcttc    360
gaacggatcc tggaggacga ggagcaccac atcgactatc tcgacaccca gctggagctg    420
atcgagaagc tcggggagcc gctctacctc gcccaggtca tcgagcaggt cgagctctga    480
```

<210> SEQ ID NO 58
<211> LENGTH: 894
<212> TYPE: DNA
<213> ORGANISM: Streptomyces sp. ACTE

<400> SEQUENCE: 58

```
atgagcccgt acaccgccac gcgccggacc ttcctcaccg cgccctggc cgccgccacc    60 ggagtcgtcc tcggtggtac gcccgccctc gccgccccg cgagagtcct ggggacccag    120
gactggatgg gggccctcgc cgactccacc ccgctgcgac gcctcacgat ccccggcacc    180
cacaacgcgg gggcccgcta cggcggaccc tggaccgagt gccagaacac cacggtggcc    240
gagcagctcg gcagcggcat ccgcttcctg gacgtgcgct gccggatcac cggcgacgcg    300
ttcgcgatcc accacggcgc ctcgtaccag aacctgatgt cggggacgt cctcatcgcc    360 tgccgggact tcctggccgc gcacccgtcc gagacggtgc tgatgcgggt caagcaggag    420
tactcggagg agagcgacgc gcgttccgg cagatcttcg acctgtacct cgacggcaag    480
ggctggcgcc gctcttccg cctcgacccc accctgccgg acctcggcgg cgcccggggc    540
aaggtcgtgc ctcgcgga caacggcggc ctgcccgggg tccggtacgc cgacccggcg    600
gtcttcgaca tccaggacga ctacatggcc gagcccttcg gcaagtaccc caagatcgag    660
gcgcagttcc gcaaggccgc ccagcagccc ggcaagctct tcatgaacta cgtgtccacc    720
gctgccctgc tgccgccgcg ctcgaacgcc gaccggctca acccgcaggt ccacacgttc    780
ctcgacggct ccgaggcggc gggctggacc ggcctcggaa tcgtcccgct ggactatccg    840
gcgacccgcc ccggcctggt cgagtcgctg atcaggcaca cccggtggc ctga          894
```

<210> SEQ ID NO 59
<211> LENGTH: 1299
<212> TYPE: DNA
<213> ORGANISM: Streptomyces sp. ACTE

<400> SEQUENCE: 59

```
gtgagcgagc acaccaacaa cgctgtagta ctgcggtacg cgatgacga gtacacctac    60 ccggtgatcg acagcaccgt cggcgacaag ggcttcgaca tcgggaagct ccgggccaat    120
acgggcctgg tcacgctgga cagcggatac ggcaacaccg ccgcctataa atccgccatc    180
acctatctcg acggcgaaca gggcatcctg cgctaccgcg gctacccgat cgagcagctc    240
gcggagagct cgacgttcct cgaggtcgcc tacacgctga tcaacggcga ccttcccaag    300
gtcgacgagc tgtcggcctt caagaacgag atcacccagc acacgctgct gcacgaggac    360
gtcaagcgct tcttcgacgg cttcccgcgc gacgcccacc cgatggccat gctgtcctcg    420
gtcgtcagcg cgctgtccac gttctaccag gacagccaca cccgttcga cgaggagcag    480 cgtcacctct cgacgatccg gctgctggcc aagctcccga cgatcgccgc gtacgcgtac    540
aagaagtcga tcggtcaccc gttcgtctac ccgcgcaacg acctcggtta cgtcgagaac    600
ttcctgcgca tgaccttctc ggtcccgcc caggagtacg tgccggaccc gatcgtcgtc    660
tcggcgctcg agaagctgct catcctgcac gcggaccacg agcagaactg ttcgacctcc    720
```

| | |
|---|---|
| accgtgcgtc tggtcggctc ctcgcaggcc aacatgttcg cctccatctc cgccggcatc | 780 |
| tcggcgctgt ggggcccgct gcacggtggc gccaaccagt cggtgctgga gatgctggaa | 840 |
| ggcatccagg ccaacggcgg cgacgtcgac tccttcatcc agaaggtcaa gaacaaggag | 900 |
| gacggcgtcc gcctgatggg cttcggccac cgggtgtaca agtccttcga cccgcgcgcc | 960 |
| aagatcatca aggccgcggc ccacgacgtc tctcctcgc tcggcaagtc cgacgagctg | 1020 |
| ctggacatcg cgctcaagct ggaggagcac gcgctctccg acgactactt cgtctcgcgc | 1080 |
| aacctctacc ccaacgtgga cttctacacg ggcctgatct accgggccat gggcttcccg | 1140 |
| accgagatgt tcaccgtgct cttcgcgctc ggccgcctcc ccggctggat cgctcagtgg | 1200 |
| cacgagatga tcaaggagcc gggttcccgc atcggccgcc cgcgccagat ctacaccggc | 1260 |
| gaggtcctgc gcgacttcgt ccccgtcgag agccgctga | 1299 |

<210> SEQ ID NO 60
<211> LENGTH: 1584
<212> TYPE: DNA
<213> ORGANISM: Streptomyces sp. ACTE

<400> SEQUENCE: 60

| | |
|---|---|
| atgacgaaac gtgcaggcat tctggtcgca gtcggcgcca cggtcgccgg gctggtcacc | 60 |
| gcggttccgt ccgccgcgtc caccgcgccc ggggcccctg gggccgccgc ccgctgaag | 120 |
| tggaccgctt gcgggacgaa ggcgtatccg acccagcagt gcgcaaccgt tcgcgcccca | 180 |
| ctggaccatg acaggccgtc aggacggcag gtcacgctcg ccctcgcccg gatcccgcac | 240 |
| acggcgaaga cctcgcaggg tccgctgctg gtcaaccccg gcggccccgg cggcagcggg | 300 |
| ctctcgatgg ccggcttcgt ggcgtcctcg ctgccggcga agctcgccgc ccagtacgac | 360 |
| gtgatcggct tcgacccgcg cggggtcggc aggagcagcc cggcgctgga ctgcgtaccg | 420 |
| aagcacttcg acccggtacg ccccgacacc gtgcccggct cccgcgggga cgagcggacc | 480 |
| aaccgggaac gcgccgcgtc cttcgccgac gcgtgcggcg agaagcacgg ggacctgctg | 540 |
| ccgttcatgg acacggtcag caccgcgaag gacctggacg tgatccgccg ggccctcggc | 600 |
| gcacggcaga tcaactactt cggctactcc tacggcacct acctgggcgc cgtctacgcc | 660 |
| aagctgttcc cggagcgcgt gcggcgcctg gtgctcgact cgatcgtcga cccggacggc | 720 |
| gtctggtacg aggacaacct cggccaggac tacgccttcg acgcccgtca caggcgttc | 780 |
| gccgcctggg tggcgaagaa cgacgccacc taccggctcg gcaccgaccc ggcgaaggtc | 840 |
| gaagccgcct ggtaccggat gcgggccgcg gtgaagaagc accccgcggc gggcaaggtc | 900 |
| ggcccgagcg agctggagga caccttcctg cccggcggct actacaacgg ctactggccg | 960 |
| caactggccg aggcgttcgc cgcgtacgtg aacgacaagg acgaggacgc gctggccacg | 1020 |
| gcgtacgacg acttcgcggc ggtcgacgcg agcggggaca acggctactc cgtctacacg | 1080 |
| gccgtccagt gccgcgacac gggctggccg aagtcctgga ccacctggcg caacgacacc | 1140 |
| tggcaggcgc accgcaaggc gccgttcatg tcctggaaca cacctggta caacgcgccc | 1200 |
| tgcgccacct ggcccgtcgc accgctgcgg ccggtgcggg tcaccaaccg cgagatcccg | 1260 |
| ccggcgctcc tcttccaggc caccgacgac gcggcgaccc cgtacgaggg cggcctgagc | 1320 |
| atgcaccgca agctcaaggg ctcgcgcctg gtcgtcgagg agggcggcgg caaccacggc | 1380 |
| atcagcctga gcggcaacga ctgcctcgac gcgcacctga tcgcctacct caccgacggc | 1440 |
| accctgcccc gctccggcgg cagcggcgcc gacgcggtct gcgacgcgct ccccgagccg | 1500 |

```
gaggcggcgg cgaccgcgaa ggcgaaggcc gctacgggcc agaagggcag caccctgcac   1560
agcctgctcg gcttccgggg ctga                                          1584

<210> SEQ ID NO 61
<211> LENGTH: 669
<212> TYPE: DNA
<213> ORGANISM: Streptomyces sp. ACTE

<400> SEQUENCE: 61
atgaattgtc atgatcgcat caacttacgc ggctggacga cacggctgag cggtctgttc     60
gtcgccgccg tgctctgtct gctcccgtgg acgggcacgg ccgaggccca cggctcggtc    120
gtcgaccccg cgtcccgcaa ctacggctgc tggctccgct ggggcagcga cttccagaac    180
cccgccatgg cgcaggaaga ccccatgtgc tggcaggcat ggcaggccga cccgaacgcc    240
atgtggaact ggaacggcct gtaccgcaac gagtccgccg caacttccc ggcagtgatc     300 cccgacgggc agctgtgcag cggcggccgg accgagggcg ccggtacaa cgcgctggac     360 accgtgggcg cctggcaggc cacggacatc acggacgact tcaccgtgag gctggaggac    420
caggccagcc acggcgccga ctacttccgg gtgtacgtca ccgagcaggg cttcgacccc    480
actgctcagc cctgacctg gggcgcactc gacctggtgg cggagaccgg acgttacggt     540
cccagtacga gctacgagat ccccgtgagt acgtcggggt acaccggccg ccatgtcgtc    600
tacacgatct ggcaggcctc gcacatggac cagacgtact cctgtgcag tgacgtgaac    660 ttcggctga                                                           669

<210> SEQ ID NO 62
<211> LENGTH: 3198
<212> TYPE: DNA
<213> ORGANISM: Streptomyces sp. ACTE

<400> SEQUENCE: 62
gtgatcagca gaagacgact gctcagcacc accgccgcca ccgccgccct cgccgcggtc     60
tcctcgcccg ccgccgcgc cgccgcccg gccgacaccg cggccggtcg gctccgcgtc     120
accgggccga ccgtggagta cgtacgccgc ccgctcggcc tcgacgtctc ccgcccccgg    180
ctgagctggc ccctcgcctc ggaccaccg gaccacggcc agtccgccta ccaggtgcgg    240
gtcgccacct cgccggaccg cctggcccgc ccgacgtct gggacagcgg caaggtcgtg    300 tcccccgacgt cggtgctggt cccgtacgcg ggcccggcgc tggtctcccg tacgcgctac    360
cactggtcgg tgcgcgtgtg ggaccaggac ggacgcgtct cggcctggag cgagccgtcc    420
tggtgggaga ccgggctcct ggacgaggcc gactggtcgg cggggtggat cggcgcgccc    480
gccgcgctga cctcctcacc ctccctggag gcggcctcct ggatctggtt cccggagggc    540
gatccggccg tgggcgctcc ggcggccacc cggtggttcc gcggccgggt ggagatcccc    600
gagggcgtca cccgcgcccg cctggtcatg accgccgacg acggcttcac cgccctggtc    660
gacggtgtcc agtggcccg taccgagccc gacggcccg cggagaactg gcgtcgtccc     720
gtggtggtgg acgtgacggc gcacctctcc ccgggctccc gggtcgtcgc cgtgacggcc    780
accaacgcgt ggacggcccc ggccggtctg ctcggggcgc tggagctgac caccgccgac    840
ggtgcggtca cactcgccac gggaaccgga tggcgggcca ccgaccggga ccggacggg     900 gactgggcgt ccgccggcta cgacgacacc ggctgccg ccgcagcggt cctcgccccg    960
tggggttccg gccctgggg cgaggtacgg gcggccctct ccccgccac ccagctgcgc    1020 acggaattcc ggctgggccg caagcgcgtc gcgcgggccc ggctgtactc gaccgcgctc    1080
```

```
ggcctgtacg aggtgttcct gaacggcgca cgtgtcggcg aggaccggct cgcgcccggc    1140
tggaccgact accgcaagcg cgtccagtac cagacgtacg acgtgacggc actgcttcgg    1200
tccggcggca acgctctcgg ggtcaccctc gcgccggggt ggtacgccgg aacatcgcc     1260 tggttcggac cgcaccagta cggcgaacgt ccggccgtac tggcccagtt ggaggtcacc    1320
ttcaccgacg ggtcgatcga gcgggtgctg tcgggcaccg gctgggccgc cgcgaccggg    1380
cccgtcaccg ccaccgacct catggcaggc gaggagtacg acgcccggct ggagaccgac    1440
ggctggagcc gcgccggatt cgacgcgtcg gggtggctcg cggcagaagc ggtggaaggg    1500
gtcacggccg tgccggtcgc cgcggtggac ggggcctgcc gtgtcgagcg cgagctgacg    1560
gcccgcgagg tgaccgaacc cgagcccggg gtctacgtgt cgacctcgg acagaacatg     1620 gtgggcacgg tacggctcct tgtctcgggg cggcgggca cgacggtgcg gctgcgccac       1680
gccgaggtgc tgaacccgga cggcacccctc tacacggcca acctgcgcac cgcacgggcc    1740
accgacacct acacgctcag gggcggcgga ccggagacgt acgagccccg cttcaccttc    1800
cacggtttcc gctacgtcga ggtgacgggc tttccgggcc gccccgggcc ggacgcggtg    1860
gtgggccggg tcatccacac ctcggcgccg ttcaccatgg ccttctcgac cgacgtcccc    1920
atgctcgacc ggctccacag caacatcacc tgggggcagc gcggcaactt cctctccgtc    1980
ccgaccgaca cgcccgcgcg cgacgaacgc ctcggctgga ccggcgacat caacgtcttc    2040
gcgcccaccg ccgcgtacac gatggagtcg gcccgcttcc tcggcaagtg gctccaggac    2100
ctgcgcgacc accagctggc cgacggcgcc ttcccgaacg tcgccccgga cctcccgggc    2160
gtcggcagcg gggcggccgg ctggggcgac gccggggtga cggtcccgtg ggccctgtac    2220
caggcgtacg gggacgtgcg ggtgctggag cagtcctggt cgtcgatggt ggcctggctg    2280
gagtacctcc aggcgcacag cgacggtctc ctgcggccgg ccgatgggta cggggactgg    2340
ctcaacatcg aggacgagac acccaaggac gtcatcggca cggcgtactt cgcccacagc    2400
gccgacctca cggcccggac cgccgaggtg ctgggcaagg accccgggcc ctaccgcacg    2460
ctgtccggcc gggtgcgcga cgcgttccgg gcggcgtacg tgggcgacgg cgggcgggtg    2520
aagggcgaca cgcagaccgc gtacgtcctg gccctgtcga tggacctgct ggagccgggc    2580
gaccgcgcac cggctgcgga caggctggtc gcgctgatcg aggcgaagga ctggcacctg    2640
tcgacggggt cctcggcac accgcgcctg ctgccggtgc tgaccgacac cgggcacacg     2700
gacgtcgcct accggctgct gacgcggcgg acgttcccga gctgggggta ccagatcgac    2760
cggggtgcca ccacgatgtg ggagcgctgg gactccgtgc ggccggacgg cggtttccag    2820
gacgccggga tgaactcctt caaccactac gcctacgggt cggtgggcga gtggatgtac    2880
gcgaacatcg cggcatcgc cccggcgcg cccggcttcc gcgagatccg ggtgcgtccg       2940
cgtccggggg gcggggtgca ccgggccgag gcccggttcg actccctgta cgggccggtc    3000 accaccgct ggacctcgga cggggggcgg ttcgcgcttc gggtggtcct gcccgccaac      3060
acgacggccg aggtgtgggt gccgggcggt gacgggagga gctccgtccg gggcaccgcc    3120
gtgttcctgc ggcggagga cgggtgcgcg gtcttcgcgg ccggctcggg catccaccgc    3180
ttcaccgcgc cggcctga                                                   3198
```

<210> SEQ ID NO 63
<211> LENGTH: 1872
<212> TYPE: DNA
<213> ORGANISM: Artificial Sequence
<220> FEATURE:

<223> OTHER INFORMATION: CelLcc_CBM3a DNA

<400> SEQUENCE: 63

```
atgggacatc accatcatca ccatcaccat gcatccgaaa acctgtactt ccaggcgatc      60
gccatggatc cgaacaatga cgactggctg catgttgaag gtaacaaaat agtggacatg     120
tacggtaatc aggtctggct gaccggctgc aactggtttg gattcaatac cggtaccaat     180
gtgtttgacg gagtatggag ctgcaatatg agagaagccc tcaagggtat ggcggacaga     240
ggaataaatt ttttgagaat acctatttca acagaattgc tgtatcaatg gtctcaagga     300
atatatccca agcaaatgt taatgatttt gtaaatccgg agctgaaagg aaagaacagc      360
cttgagcttt ttgactttgc cgttcagtgc tgcaaagaat cggaataaaa gataatggtg     420
gatatacaca gtccggcaac agatgccatg gggcatatgt atcctttatg gtatgacggt     480
caatttacaa cagagatatg gatttcaact ttggagtggt tgacgaaaag atataaaaat     540
gatgacacaa ttcttgcact ggaccttaaa aatgagcctc acggcacccc gggcagcgaa     600
ttaatggcca atgggatgg ttccacggat ttgaacaact ggaagcatgc tgctgaaaca      660
tgcgcaaaga gaatccttgc aataaatccg aatattctta ttgtggtaga aggagtggaa     720
gtttatccaa agcctggcta tgattatacc gcagtggacg aatggggaaa agagagtaaa     780
tatttctata ctggtgggg aggaaattta agaggagtca gggattatcc cattgaccct     840
ggcaagcatc agaagcagct tgtatactca cctcacgatt acggtcccct cgtacataaa     900
caaccttggt tctatgaagg ctttaacaaa gaaactttgt ataatgattg ctggagagat     960
aactgggcat acatacacga ggaaaacatc gctcctctga tagtgggtga atggggaggt    1020
ttcatggacc gcggagacaa cgagaaatgg atgaaagcgc tgagagatta tatgattgag    1080
aataaaatat cccacacttt ttggtgctat aatgcaaatt ccggtgatac cggaggactt    1140
gtatactatg attttattac ctgggacgaa gaaaaatatg ctcttctgaa gcctgcatta    1200
tggcagacag aggacggaaa gtttataggc cttgaccatc agatacctct tggttcaaat    1260
ggaggtttaa acgcgactcc cactaaaggt gccactccta ccaatacggc gactccgact    1320
aagtcggcaa cggcaacgcc cactcgcccc agcgtaccga ccaatactcc gactaatacc    1380
ccggcgaaca ccccagtaag cggtaacctg aaggttgaat tttataactc caacccaagc    1440
gacacaacga atagcatcaa tccgcagttc aaagtcacga acactggcag ttcagctatc    1500
gatctgtcga aactgaccct tcgttactac tatacggttg atggccaaaa agatcagacc    1560
ttttggtgcg accatgcagc aatcatcggt agcaatggtt cttataacgg cattacttct    1620
aatgtaaaag gcacctttgt gaagatgtca agtagcacca acaatgctga tacctacctg    1680
gaaattagct tcacgggtgg cacacttgaa ccaggagccc acgtccagat ccagggccgt    1740
tttgcgaaaa acgattggag caactatacg caatcaaacg attatagttt caaaagcgcg    1800
tctcaattcg tagaatggga tcaggtgacc gcatatttga acggagtgct ggtttggggg    1860
aaagaaccag ga                                                        1872
```

<210> SEQ ID NO 64
<211> LENGTH: 1872
<212> TYPE: PRT
<213> ORGANISM: Artificial Sequence
<220> FEATURE:
<223> OTHER INFORMATION: CelLcc_CBM3a Amino acids

<400> SEQUENCE: 64

Ala Thr Gly Gly Gly Ala Cys Ala Thr Cys Ala Cys Cys Ala Thr Cys

-continued

```
1               5                   10                  15
Ala Thr Cys Ala Cys Cys Ala Thr Cys Ala Cys Cys Ala Thr Gly Cys
            20                  25                  30

Ala Thr Cys Cys Gly Ala Ala Ala Ala Cys Cys Thr Gly Thr Ala Cys
        35                  40                  45

Thr Thr Cys Cys Ala Gly Gly Cys Gly Ala Thr Cys Gly Cys Cys Ala
    50                  55                  60

Thr Gly Gly Ala Thr Cys Cys Gly Ala Ala Cys Ala Ala Thr Gly Ala
65                  70                  75                  80
Cys Gly Ala Cys Thr Gly Gly Cys Thr Gly Cys Ala Thr Gly Thr Thr
                85                  90                  95

Gly Ala Ala Gly Gly Thr Ala Ala Cys Ala Ala Ala Ala Thr Ala Gly
            100                 105                 110

Thr Gly Gly Ala Cys Ala Thr Gly Thr Ala Cys Gly Gly Thr Ala Ala
        115                 120                 125

Thr Cys Ala Gly Gly Thr Cys Thr Gly Gly Cys Thr Gly Ala Cys Cys
    130                 135                 140

Gly Gly Cys Thr Gly Cys Ala Ala Cys Thr Gly Gly Thr Thr Thr Gly
145                 150                 155                 160
Gly Ala Thr Thr Cys Ala Ala Thr Ala Cys Cys Gly Gly Thr Ala Cys
                165                 170                 175

Cys Ala Ala Thr Gly Thr Gly Thr Thr Thr Gly Ala Cys Gly Gly Ala
            180                 185                 190

Gly Thr Ala Thr Gly Gly Ala Gly Cys Thr Gly Cys Ala Ala Thr Ala
        195                 200                 205

Thr Gly Ala Gly Ala Gly Ala Ala Gly Cys Cys Cys Thr Cys Ala Ala
    210                 215                 220

Gly Gly Gly Thr Ala Thr Gly Gly Cys Gly Gly Ala Cys Ala Gly Ala
225                 230                 235                 240

Gly Gly Ala Ala Thr Ala Ala Ala Thr Thr Thr Thr Thr Thr Gly Ala
                245                 250                 255

Gly Ala Ala Thr Ala Cys Cys Thr Ala Thr Thr Thr Cys Ala Ala Cys
            260                 265                 270

Ala Gly Ala Ala Thr Thr Gly Cys Thr Gly Thr Ala Thr Cys Ala Ala
        275                 280                 285

Thr Gly Gly Thr Cys Thr Cys Ala Ala Gly Gly Ala Ala Thr Ala Thr
    290                 295                 300

Ala Thr Cys Cys Cys Ala Ala Ala Gly Cys Ala Ala Ala Thr Gly Thr
305                 310                 315                 320

Thr Ala Ala Thr Gly Ala Thr Thr Thr Thr Gly Thr Ala Ala Ala Thr
                325                 330                 335

Cys Cys Gly Gly Ala Gly Cys Thr Gly Ala Ala Ala Gly Gly Ala Ala
            340                 345                 350

Ala Gly Ala Ala Cys Ala Gly Cys Cys Thr Thr Gly Ala Gly Cys Thr
        355                 360                 365

Thr Thr Thr Thr Gly Ala Cys Thr Thr Thr Gly Cys Cys Gly Thr Thr
    370                 375                 380

Cys Ala Gly Thr Gly Cys Thr Gly Cys Ala Ala Ala Gly Ala Ala Thr
385                 390                 395                 400

Thr Cys Gly Gly Ala Ala Thr Ala Ala Ala Gly Ala Thr Ala Ala Thr
                405                 410                 415

Gly Gly Thr Gly Gly Ala Thr Ala Thr Ala Cys Ala Cys Ala Gly Thr
            420                 425                 430
```

Cys Cys Gly Gly Cys Ala Ala Cys Ala Gly Ala Thr Gly Cys Cys Ala
        435                 440                 445

Thr Gly Gly Gly Gly Cys Ala Thr Ala Thr Gly Thr Ala Thr Cys Cys
    450                 455                 460

Thr Thr Thr Ala Thr Gly Gly Thr Ala Thr Gly Ala Cys Gly Gly Thr
465                 470                 475                 480

Cys Ala Ala Thr Thr Thr Ala Cys Ala Ala Cys Ala Gly Ala Gly Ala
                    485                 490                 495

Thr Ala Thr Gly Gly Ala Thr Thr Cys Ala Ala Cys Thr Thr Thr
            500                 505                 510

Gly Gly Ala Gly Thr Gly Gly Thr Thr Gly Ala Cys Gly Gly Ala Ala
            515                 520                 525

Ala Gly Ala Thr Ala Thr Ala Ala Ala Ala Thr Gly Ala Thr Gly
            530                 535                 540

Ala Cys Ala Cys Ala Ala Thr Thr Cys Thr Thr Gly Cys Ala Cys Thr
545                 550                 555                 560

Gly Gly Ala Cys Cys Thr Thr Ala Ala Ala Ala Thr Gly Ala Gly
                565                 570                 575

Cys Cys Thr Cys Ala Cys Gly Gly Cys Ala Cys Cys Cys Gly Gly
            580                 585                 590

Gly Cys Ala Gly Cys Gly Ala Ala Thr Thr Ala Ala Thr Gly Gly Cys
            595                 600                 605

Cys Ala Ala Ala Thr Gly Gly Gly Ala Thr Gly Gly Thr Thr Cys Cys
    610                 615                 620

Ala Cys Gly Gly Ala Thr Thr Gly Ala Ala Cys Ala Ala Cys Thr
625                 630                 635                 640

Gly Gly Ala Ala Gly Cys Ala Thr Gly Cys Thr Gly Cys Thr Gly Ala
                    645                 650                 655

Ala Ala Cys Ala Thr Gly Cys Gly Cys Ala Ala Gly Ala Gly Ala
            660                 665                 670

Ala Thr Cys Cys Thr Thr Gly Cys Ala Ala Thr Ala Ala Ala Thr Cys
            675                 680                 685

Cys Gly Ala Ala Thr Ala Thr Thr Cys Thr Thr Ala Thr Thr Gly Thr
    690                 695                 700

Gly Gly Thr Ala Gly Ala Ala Gly Gly Ala Gly Thr Gly Gly Ala Ala
705                 710                 715                 720

Gly Thr Thr Thr Ala Thr Cys Cys Ala Ala Ala Gly Cys Cys Thr Gly
                    725                 730                 735

Gly Cys Thr Ala Thr Gly Ala Thr Thr Ala Thr Cys Cys Gly Cys
            740                 745                 750

Ala Gly Thr Gly Gly Ala Cys Gly Ala Ala Thr Gly Gly Gly Ala
            755                 760                 765

Ala Ala Ala Gly Ala Gly Ala Gly Thr Ala Ala Thr Ala Thr Thr
            770                 775                 780

Thr Cys Thr Ala Thr Ala Ala Cys Thr Gly Gly Thr Gly Gly Gly
785                 790                 795                 800

Ala Gly Gly Ala Ala Ala Thr Thr Thr Ala Ala Gly Ala Gly Ala
                    805                 810                 815

Gly Thr Cys Ala Gly Gly Gly Ala Thr Thr Ala Thr Cys Cys Ala
            820                 825                 830

Thr Thr Gly Ala Cys Cys Thr Thr Gly Gly Cys Ala Ala Gly Cys Ala
                    835                 840                 845

```
Thr Cys Ala Gly Ala Ala Gly Cys Ala Gly Cys Thr Gly Thr Ala
850                 855                 860

Thr Ala Cys Thr Cys Ala Cys Cys Thr Cys Ala Cys Gly Ala Thr Thr
865                 870                 875                 880

Ala Cys Gly Gly Thr Cys Cys Cys Thr Cys Gly Thr Ala Cys Ala
        885                 890                 895

Thr Ala Ala Ala Cys Ala Ala Cys Cys Thr Thr Gly Gly Thr Thr Cys
900                 905                 910

Thr Ala Thr Gly Ala Ala Gly Gly Cys Thr Thr Thr Ala Ala Cys Ala
        915                 920                 925

Ala Gly Ala Ala Ala Cys Thr Thr Thr Gly Thr Ala Thr Ala Ala
930                 935                 940

Thr Gly Ala Thr Thr Gly Cys Thr Gly Gly Ala Gly Ala Gly Ala Thr
945                 950                 955                 960

Ala Ala Cys Thr Gly Gly Gly Cys Ala Thr Ala Cys Ala Thr Ala Cys
        965                 970                 975

Ala Cys Gly Ala Gly Gly Ala Ala Ala Cys Ala Thr Cys Gly Cys
980                 985                 990

Thr Cys Cys Thr Cys Thr Gly Ala Thr Ala Gly Thr Gly Gly Gly Thr
995                 1000                1005

Gly Ala Ala Thr Gly Gly Gly Gly Ala Gly Gly Thr Thr Thr Cys
1010                1015                1020

Ala Thr Gly Gly Ala Cys Cys Gly Cys Gly Gly Ala Gly Ala Cys
1025                1030                1035

Ala Ala Cys Gly Ala Gly Ala Ala Ala Thr Gly Gly Ala Thr Gly
1040                1045                1050

Ala Ala Ala Gly Cys Gly Gly Cys Thr Gly Ala Gly Ala Gly Ala Thr
1055                1060                1065

Thr Ala Thr Ala Thr Gly Ala Thr Thr Gly Ala Gly Ala Ala Thr
1070                1075                1080

Ala Ala Ala Ala Thr Ala Thr Cys Cys Cys Ala Cys Ala Cys Thr
1085                1090                1095

Thr Thr Thr Thr Gly Gly Thr Gly Cys Thr Ala Thr Ala Ala Thr
1100                1105                1110

Gly Cys Ala Ala Ala Thr Thr Cys Cys Gly Gly Thr Gly Ala Thr
1115                1120                1125

Ala Cys Cys Gly Gly Ala Gly Gly Ala Cys Thr Thr Gly Thr Ala
1130                1135                1140

Thr Ala Cys Thr Ala Thr Gly Ala Thr Thr Thr Thr Ala Thr Thr
1145                1150                1155

Ala Cys Cys Thr Gly Gly Gly Ala Cys Gly Ala Ala Gly Ala Ala
1160                1165                1170

Ala Ala Ala Thr Ala Thr Gly Cys Thr Cys Thr Cys Thr Gly
1175                1180                1185

Ala Ala Gly Cys Cys Thr Gly Cys Ala Thr Thr Ala Thr Gly Gly
1190                1195                1200

Cys Ala Gly Ala Cys Ala Gly Ala Gly Gly Ala Cys Gly Gly Ala
1205                1210                1215

Ala Ala Gly Thr Thr Thr Ala Thr Ala Gly Gly Cys Cys Thr Thr
1220                1225                1230

Gly Ala Cys Cys Ala Thr Cys Ala Gly Ala Thr Ala Cys Cys Thr
1235                1240                1245

Cys Thr Thr Gly Gly Thr Thr Cys Ala Ala Ala Thr Gly Gly Ala
```

-continued

```
                1250                1255                1260

Gly  Gly  Thr  Thr  Thr  Ala  Ala  Cys  Gly  Cys  Gly  Ala  Cys  Thr
                1265                1270                1275

Cys  Cys  Cys  Ala  Cys  Thr  Ala  Ala  Ala  Gly  Gly  Thr  Gly  Cys  Cys
                1280                1285                1290

Ala  Cys  Thr  Cys  Cys  Thr  Ala  Cys  Cys  Ala  Ala  Thr  Ala  Cys  Gly
                1295                1300                1305

Gly  Cys  Gly  Ala  Cys  Thr  Cys  Cys  Gly  Ala  Cys  Thr  Ala  Ala  Gly
                1310                1315                1320

Thr  Cys  Gly  Gly  Cys  Ala  Ala  Cys  Gly  Gly  Cys  Ala  Ala  Cys  Gly
                1325                1330                1335

Cys  Cys  Cys  Ala  Cys  Thr  Cys  Gly  Cys  Cys  Cys  Ala  Gly  Cys
                1340                1345                1350

Gly  Thr  Ala  Cys  Cys  Gly  Ala  Cys  Cys  Ala  Ala  Thr  Ala  Cys  Thr
                1355                1360                1365

Cys  Cys  Gly  Ala  Cys  Thr  Ala  Ala  Thr  Ala  Cys  Cys  Cys  Gly
                1370                1375                1380

Gly  Cys  Gly  Ala  Ala  Cys  Ala  Cys  Cys  Cys  Cys  Ala  Gly  Thr  Ala
                1385                1390                1395

Ala  Gly  Cys  Gly  Gly  Thr  Ala  Ala  Cys  Cys  Thr  Gly  Ala  Ala  Gly
                1400                1405                1410

Gly  Thr  Thr  Gly  Ala  Ala  Thr  Thr  Thr  Ala  Thr  Ala  Ala  Cys
                1415                1420                1425

Thr  Cys  Cys  Ala  Ala  Cys  Cys  Ala  Ala  Gly  Cys  Gly  Ala  Cys
                1430                1435                1440

Ala  Cys  Ala  Ala  Cys  Gly  Ala  Ala  Thr  Ala  Gly  Cys  Ala  Thr  Cys
                1445                1450                1455

Ala  Ala  Thr  Cys  Cys  Gly  Cys  Ala  Gly  Thr  Thr  Cys  Ala  Ala  Ala
                1460                1465                1470

Gly  Thr  Cys  Ala  Cys  Gly  Ala  Ala  Cys  Ala  Cys  Thr  Gly  Gly  Cys
                1475                1480                1485

Ala  Gly  Thr  Thr  Cys  Ala  Gly  Cys  Thr  Ala  Thr  Cys  Gly  Ala  Thr
                1490                1495                1500

Cys  Thr  Gly  Thr  Cys  Gly  Ala  Ala  Ala  Cys  Thr  Gly  Ala  Cys  Cys
                1505                1510                1515

Cys  Thr  Thr  Cys  Gly  Thr  Thr  Ala  Cys  Thr  Ala  Cys  Thr  Ala  Thr
                1520                1525                1530

Ala  Cys  Gly  Gly  Thr  Thr  Gly  Ala  Thr  Gly  Gly  Cys  Cys  Ala  Ala
                1535                1540                1545

Ala  Ala  Ala  Gly  Ala  Thr  Cys  Ala  Gly  Ala  Cys  Cys  Thr  Thr  Thr
                1550                1555                1560

Thr  Gly  Gly  Thr  Gly  Cys  Gly  Ala  Cys  Cys  Ala  Thr  Gly  Cys  Ala
                1565                1570                1575

Gly  Cys  Ala  Ala  Thr  Cys  Ala  Thr  Cys  Gly  Gly  Thr  Ala  Gly  Cys
                1580                1585                1590

Ala  Ala  Thr  Gly  Gly  Thr  Thr  Cys  Thr  Thr  Ala  Thr  Ala  Ala  Cys
                1595                1600                1605

Gly  Gly  Cys  Ala  Thr  Thr  Ala  Cys  Thr  Cys  Thr  Ala  Ala  Thr
                1610                1615                1620

Gly  Thr  Ala  Ala  Ala  Ala  Gly  Gly  Cys  Ala  Cys  Cys  Thr  Thr  Thr
                1625                1630                1635

Gly  Thr  Gly  Ala  Ala  Gly  Ala  Thr  Gly  Thr  Cys  Ala  Ala  Gly  Thr
                1640                1645                1650
```

-continued

```
Ala Gly Cys Ala Cys Cys Ala Ala Cys Ala Ala Thr Gly Cys Thr
    1655            1660                1665
Gly Ala Thr Ala Cys Cys Thr Ala Cys Cys Thr Gly Gly Ala Ala
    1670            1675                1680
Ala Thr Thr Ala Gly Cys Thr Thr Cys Ala Cys Gly Gly Gly Thr
    1685            1690                1695
Gly Gly Cys Ala Cys Ala Cys Thr Thr Gly Ala Ala Cys Cys Ala
    1700            1705                1710
Gly Gly Ala Gly Cys Cys Cys Ala Cys Gly Thr Cys Cys Ala Gly
    1715            1720                1725
Ala Thr Cys Cys Ala Gly Gly Gly Cys Cys Gly Thr Thr Thr Thr
    1730            1735                1740
Gly Cys Gly Ala Ala Ala Ala Ala Cys Gly Ala Thr Thr Gly Gly
    1745            1750                1755
Ala Gly Cys Ala Ala Cys Thr Ala Thr Ala Cys Gly Cys Ala Ala
    1760            1765                1770
Thr Cys Ala Ala Ala Cys Gly Ala Thr Thr Ala Thr Ala Gly Thr
    1775            1780                1785
Thr Thr Cys Ala Ala Ala Gly Cys Gly Cys Gly Thr Cys Thr
    1790            1795                1800
Cys Ala Ala Thr Thr Cys Gly Thr Ala Gly Ala Ala Thr Gly Gly
    1805            1810                1815
Gly Ala Thr Cys Ala Gly Gly Thr Gly Ala Cys Cys Gly Cys Ala
    1820            1825                1830
Thr Ala Thr Thr Thr Gly Ala Ala Cys Gly Gly Ala Gly Thr Gly
    1835            1840                1845
Cys Thr Gly Gly Thr Thr Thr Gly Gly Gly Gly Ala Ala Ala
    1850            1855                1860
Gly Ala Ala Cys Cys Ala Gly Gly Ala
    1865            1870
```

METHOD AND COMPOSITIONS FOR IMPROVED LIGNOCELLULOSIC MATERIAL HYDROLYSIS

CROSS-REFERENCE TO RELATED APPLICATIONS

This application claims benefit from U.S. Provisional Application 61/579,301 filed Dec. 22, 2011 and U.S. Provisional Application 61/579,897 filed Dec. 23, 2011, both of which are incorporated herein by reference for all purposes.

STATEMENT REGARDING FEDERALLY SPONSORED RESEARCH OR DEVELOPMENT

This invention was made with government support under DE-FC02-07ER64494 awarded by the US Department of Energy and GM094584 awarded by the National Institutes of Health. The government has certain rights in the invention.

BACKGROUND

Cellulose is the most abundant organic polymer on Earth and represents a vast source of renewable energy. Most of this energy is stored in the recalcitrant polysaccharide cellulose, which is difficult to hydrolyze because of the highly crystalline structure, and in hemicellulose, which presents challenges because of its structural diversity and complexity. Plant cell walls are approximately composed in pinewood of lignin (30% by weight), hemicellulose (glucomannan, 20%, arabinoxylan, 10%), and crystalline cellulose (40%), which presents a major barrier to efficient use. In terrestrial ecosystems, cellulolytic microbes help drive carbon cycling through the deconstruction of biomass into simple sugars. The deconstruction is largely accomplished through the action of combinations of secreted glycoside hydrolases (GHs), carbohydrate esterases (CEs), polysaccharide lyases (PLs), and carbohydrate binding modules (CBMs) (Baldrian and Valaskova, 2008; Cantarel, et al., 2009; Lynd, Weimer, et al., 2002; Schuster and Schmoll, 2010). Consequently, organisms from many lignocellulose-rich environments and their enzymes are being studied for new insights into overcoming this barrier.

In order to obtain the hydrolysis of crystalline cellulose, enzymes must cleave three types of glycosidic bonds. These enzymes are endocellulases, which cleave beta-1,4 glycosidic bonds that reside within intact cellulose strands in the crystalline face, non-reducing-end exocellulases, which remove cellobiose units from the non-reducing end of cellulose strands, and reducing-end exocellulases, which remove glycosyl units from the reducing-end of a cellulose strand. The endocellulolytic reaction is essential because it creates the non-reducing and reducing ends that serve as the starting point for exocellulolytic reactions. The exocellulolytic reactions are essential because they remove glycosyl groups in a processive manner from the breakages in the cellulose strand introduced by the endocellulases, thus amplifying the single initiating reaction of the endocellulases.

*Trichoderma reesei* and *Clostridium thermocellum* are well-characterized cellulose-utilizing organisms (Merino and Cherry, 2007; Bayer et al., 2008; Wilson, 2011). *T. reesei* is a slow-growing eukaryote fungus that secretes enzymes containing glycoside hydrolase (GH) domains fused to carbohydrate binding domains, while *C. thermocellum* is a strictly anaerobic prokaryote that predominantly assembles GHs and carbohydrate-binding molecules (CBMs) into a large complex called the cellulosome. Enzymes from these free-living organisms cleave polysaccharides using general acid-base catalyzed hydrolytic reactions (Vuong and Wilson, 2010). Moreover, fungal and microbial communities associated with termites (Scharf et al., 2011) shipworms (Luyten et al., 2006), and rumen (Hess et al., 2011) contribute these types of hydrolytic enzymes to their respective anaerobic niches.

Some free-living aerobes such as *Cellvibrio japonicus* (Ueda 107) (DeBoy et al., 2008), *Streptomyces* (Schlochtermeier et al., 1992; Wilson, 1992; Forsberg et al., 2011), *Thermoascus aurantiacus* (Langston et al., 2011; Quinlan et al., 2011) and *Serratia marcescens* (Vaaje-Kolstad et al., 2010) also grow on biomass polysaccharides. Recent work with some of these organisms has identified that the structurally related fungal GH61 (Langston et al., 2011; Quinlan et al., 2011) and bacterial CBM33 (Forsberg et al., 2011) families of proteins catalyze a previously unrecognized oxidative breakage of glycosidic bonds. This reaction is thought to be an endo-cleavage, with the oxidation reaction yielding gluconate and keto-sugars instead of the typically observed reducing and non-reducing sugars obtained from hydrolytic cellulases.

Actinobacteria in the genus *Streptomyces* are an ecologically important group, especially in soil environments, where they are considered to be vital players in the decomposition of cellulose and other biomass polymers (Cantarel et al., 2009; Crawford et al., 1978; Goodfellow and Williams, 1983; McCarthy and Williams, 1992). *Streptomyces* are able to utilize a wide range of carbon sources, form spores when resources are depleted, and produce antimicrobial secondary metabolites to reduce competition (Goodfellow and Williams, 1983; Schlatter et al., 2009).

Although a large number of *Streptomyces* species can grow on biomass, only a small percentage (14%) have been shown to efficiently degrade crystalline cellulose (Wachinger, Bronnenmeier, et al., 1989). Furthermore, the secreted cellulolytic activities of only a few species have been biochemically characterized, and still fewer species have been examined to identify key biomass degrading enzymes (Ishaque and Kluepfel, 1980; Semedo et al., 2004). *Streptomyces reticuli* is one of the best-studied cellulose- and chitin-degrading soil-dwelling *Streptomyces*; functional analyses of several important cellulases and other hydrolytic enzymes have been reported (Wachinger, Bronnenmeier, et al., 1989; Schlochtermeier, Walter, et al., 1992; Walter and Schrempf, 1996).

Furthermore, polysaccharide monooxygenase (PMO) activity with cellulose was identified using the CBM33 protein from *Streptomyces coelicolor* (Forsberg, et al., 2011), which suggests *Streptomyces* may use both hydrolytic and oxidative enzymes to deconstruct biomass. With the tremendous amount of sequence data collected in the past few years, and despite the view that *Streptomyces* make important contributions to cellulose degradation in the soil, genome-wide analyses of cellulolytic *Streptomyces* have not been reported.

In addition to their putative roles in carbon cycling in the soil, *Streptomyces* may also potentiate biomass deconstruction in insects through symbiotic associations (Bignell, Anderson, et al., 1991; Pasti and Belli, 1985; Pasti, Pometto, et al., 1990; Schafer, et al., 1996). Recent work has identified cellulose degrading *Streptomyces* associated with the pine-boring woodwasp *Sirex noctilio*, including *Streptomyces* sp. SirexAA-E (ActE) (Adams, et al., 2011). *S. noctilio* is a highly destructive wood-feeding insect that is found throughout forests in Eurasia and North Africa and is spreading invasively in North America and elsewhere (Bergeron, et al., 2011). While the wasp itself does not produce cellulolytic enzymes, evidence supports the role of a symbiotic microbial community that secretes biomass-degrading enzymes to facilitate nutrient acquisition for developing larvae in the pine tree (Kukor and Martin, 1983).

The white rot fungus, *Amylostereum areolatum*, is the best-described member of this community, and the success of *Sirex* infestations is thought to arise from the insect's association with this cellulolytic fungal mutualist. However, work with pure cultures has suggested that ActE and other *Sirex*-associated *Streptomyces* are more cellulolytic than *A. areolatum* (Adams, et al., 2011).

Optimal activity in the CBM33 enzymes apparently requires the addition of a transition metal ion such as Cu(II), Fe(III), or Mn(II) and an external reducing agent. In the laboratory, the reducing agent can be provided by ascorbate. In natural systems, the reducing function is most likely provided by another redox active protein such as cellobiose dehydrogenase (Langston et al., 2011; Quinlan et al., 2011) or some other presently unknown protein.

Needed in the art are improved compositions and organisms for digestion of lignocellulosic materials.

BRIEF SUMMARY

The invention relates generally to methods and compositions for digesting lignocellulosic material and more particularly to methods that involve exposing the material to secretome derived from *Streptomyces* sp. ActE.

In a first aspect, the present invention is summarized as a method of digesting a lignocellulosic material comprising the step of exposing the material to an effective amount of *Streptomyces* sp. ActE secretome preparation such that at least partial lignocellulosic digestion occurs.

In some embodiments of the first aspect, the preparation is a supernatant preparation obtained from a *Streptomyces* sp. ActE culture. In some embodiments of the first aspect, the preparation is obtained from *Streptomyces* sp. ActE grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass and chitin. In some embodiments of the first aspect, the lignocellulosic material is selected from the group consisting of materials that comprise at least 75% cellulose, cellulose/hemicelluloses, xylose, biomass and chitin.

In a second aspect, the present invention is summarized as a purified preparation comprising the *Streptomyces* sp. ActE secretome.

In some embodiments of the second aspect, the preparation is a supernatant preparation obtained from a *Streptomyces* sp. ActE culture. In some embodiments of the second aspect, *Streptomyces* sp. ActE is grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass and chitin.

In a third aspect, the present invention is summarized as a composition useful for digesting lignocellulosic material comprising SActE_0237 (GH6) (SEQ ID NO:1) gene or expression product thereof.

In a fourth aspect, the present invention is summarized as a composition useful for digesting lignocellulosic material comprising SActE_0236 (GH48) (SEQ ID NO:2) gene or expression product thereof.

In a fifth aspect, the present invention is summarized as a composition useful for digesting lignocellulosic material comprising SActE_3159 (CBM33) (SEQ ID NO:3) gene or expression product thereof.

In a sixth aspect, the present invention is summarized as a composition useful for digesting lignocellulosic material comprising SActE_0482 (GH5) (SEQ ID NO:4) gene or expression product thereof.

In a seventh aspect, the present invention is summarized as a composition useful for digesting lignocellulosic material comprising SActE_0265 (GH10) (SEQ ID NO:5) gene or expression product thereof.

In a eighth aspect, the present invention is summarized as a composition useful for digesting lignocellulosic material comprising SActE_2347 (GH5) (SEQ ID NO:6) gene or expression product thereof.

In a ninth aspect, the present invention is summarized as a composition useful for digesting lignocellulosic material comprising SActE_0237 (GH6) (SEQ ID NO:1), SActE_0236 (GH48) (SEQ ID NO:2), SActE_3159 (CBM33)(SEQ ID NO:3), SActE_0482 (GH5) (SEQ ID NO:4) and gene or expression product thereof.

In some embodiments of the third, fourth, fifth, sixth, seventh, eighth, and ninth aspects, the composition is optimized for cellulose utilization. In these embodiments the composition can additionally comprise at least one member selected from SActE_0265 (GH10) (SEQ ID NO:5) and SActE_2347 (GH5) (SEQ ID NO:6) genes or expression products thereof. In a preferred embodiment, the composition comprises at least three or four of the genes or expression products.

In some embodiments of the third, fourth, fifth, sixth, seventh, eighth, and ninth aspects, the composition is optimized for xylan release. By "release," we mean degradation, such as hydrolysis, and release of an important or desired product. In these embodiments the composition can additionally comprise at least one member selected from SActE_0265 (GH10) (SEQ ID NO:5), SActE_0358 (GH11) (SEQ ID NO:8), SActE_0357 (CE4) (SEQ ID NO:7), SActE_5978 (PL1)(SEQ ID NO:16) and SActE_5230 (xylose isomerase) genes or expression products thereof. In a preferred embodiment, the composition comprises at least three or four of the genes or expression products.

In some embodiments of the third, fourth, fifth, sixth, seventh, eighth, and ninth aspects, the composition is optimized for chitin release. In these embodiments the composition can additionally comprise at least one member selected from SActE_4571 (GH18), SActE_2313 (CBM33), SActE_4246 (GH18), SActE_3064 (GH19) and SActE_5764 (GH18) genes or expression products thereof. In a preferred embodiment, the composition comprises at least three or four of the genes or expression products.

In some embodiments of the third, fourth, fifth, sixth, seventh, eighth, and ninth aspects, the composition is optimized for biomass degradation. In these embodiments the composition can additionally comprise SActE_5457 (GH46) (SEQ ID NO:14) gene or expression products thereof.

In some embodiments of the third, fourth, fifth, sixth, seventh, eighth, and ninth aspects, the composition is optimized for mannan release. In these embodiments the composition can additionally comprise SactE_2347 (GH5) (SEQ ID NO:6) gene or expression products thereof.

In some embodiments of the third, fourth, fifth, sixth, seventh, eighth, and ninth aspects, the composition is optimized for beta-1,3-glucan release. In these embodiments the composition can additionally comprise at least one member selected from SActE_4755 (GH64) (SEQ ID NO:13) and SActE_4738 (GH16) (SEQ ID NO:12) genes or expression products thereof. In a preferred embodiment, the composition comprises both of the genes or expression products.

In some embodiments of the third, fourth, fifth, sixth, seventh, eighth, and ninth aspects, the composition is optimized for pectin cleavage. In these embodiments the composition can additionally comprise SActE_1310 (PL3) (SEQ ID NO:9) gene or expression products derived thereof.

In some embodiments of the third, fourth, fifth, sixth, seventh, eighth, and ninth aspects, the composition is optimized for alginate release. In these embodiments the composition can additionally comprise SActE_4638 (SEQ ID NO:11) gene or expression products derived thereof.

In some embodiments of the third, fourth, fifth, sixth, seventh, eighth, and ninth aspects, the composition is optimized for galactose release. In these embodiments the composition can additionally comprise SactE_5647 (GH87) (SEQ ID NO:15) gene or expression products derived thereof.

In a tenth aspect, the present invention is summarized as a composition useful for xylan degradation comprising SActE_0265 (GH10) (SEQ ID NO:5) and SActE_0358 (GH11) (SEQ ID NO:8) gene or expression products thereof.

In some embodiments of the tenth aspect, the composition additionally comprises SActE_0265 (GH10) (SEQ ID NO:5), SActE_0358 (GH11) (SEQ ID NO:8), SActE_0357 (CE4) (SEQ ID NO:7), SActE_5978 (PL1) (SEQ ID NO:16), and SActE_5230 (xylose isomerase) genes or expression products thereof. In a preferred embodiment, the composition comprises at least three or four of the genes or expression products.

In an eleventh aspect, the present invention is summarized as a composition useful for biomass degradation comprising SActE_0237 (GH6) (SEQ ID NO:1), SActE_0482 (GH5) (SEQ ID NO:4), SActE_3159 (CBM33)(SEQ ID NO:3), SActE_0236 (GH48) (SEQ ID NO:2), SActE_3717 (GH9) (SEQ ID NO:10), SActE_0265 (GH10) (SEQ ID NO:5), SActE_0358 (GH11) (SEQ ID NO:8), SActE_2347 (GH5) (SEQ ID NOs:6) and SActE_1310 (PL1) genes or expression products thereof. In a preferred embodiment, the composition comprises at least three or four of the genes or expression products.

In a twelfth aspect, the present invention is summarized as a composition useful for cellulose degradation comprising SActE_0237 (GH6) (SEQ ID NO:1), SActE_0482 (GH5) (SEQ ID NO:4), SActE_3159 (CBM33) (SEQ ID NO:3) SActE_0236 (GH48) (SEQ ID NO:2), SActE_2347 (GH5) (SEQ ID NO:6), and SActE_0265 (GH10) (SEQ ID NO:5) genes or expression products thereof. In a preferred embodiment, the composition comprises at least three or four of the genes or expression products.

In a thirteenth aspect, the present invention is summarized as a method for digesting a lignocellulosic material, comprising exposing the material to a sufficient amount of a composition of any one of the third to eighth aspects of the invention, wherein the exposed material is at least partially digested.

In a fourteenth aspect, the present invention is summarized as a purified preparation of *Streptomyces* sp. ActE, wherein the *Streptomyces* sp. ActE has been grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass, and chitin.

In a fifteenth aspect, the present invention is summarized as a purified preparation of *Streptomyces* sp. ActE, wherein the *Streptomyces* sp. ActE has been grown on a substrate wherein at least 40%, preferably 85%, of *Streptomyces* sp. ActE's carbon in the substrate is derived from pretreated lignocellulosic material.

In some embodiments of the fifteenth aspect, the pretreated material has been exposed to pretreatment selected from the group consisting of acid hydrolysis, steam explosion, ammonia fiber expansion (AFEX), organosolve, sulfite pretreatment to overcome recalcitrance of lignocellulose (SPORL), ionic liquids, metal-catalyzed hydrogen peroxide, alkaline wet oxidation and ozone pretreatment. In some embodiments of the fifteenth aspect, the pretreated material is wood.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIG. 1 is a set of pictures showing growth of ActE in minimal medium containing filter paper as the sole carbon source. (A) Growth of ActE, *Streptomyces coelicolor*, and *Streptomyces griseus* in minimal medium for 7 days at 30° C. and pH 6.9. The expanded image shows small colonies of *S. coelicolor* and *S. griseus* forming on the surface of the paper. (B) Growth of ActE and *Trichoderma reesei* Rut-C30 for 7 days at 30° C. and pH 6.0.

FIG. 8 a set of diagrams showing temperature and pH profiles of the ActE secretome obtained from growth on AFEX-treated corn stover. (A) The effect of temperature on the deconstruction of AFEX-treated switchgrass (AFEX-SG) and ionic liquid-treated switchgrass (IL-SG). The relative activity of the ActE secretome was compared to the maximal rates determined for reaction with AFEX-SG (blue star), and IL-SG (red star) at pH 6.0. (B) The effect of pH on the AFEX-SG and IL-SG deconstruction activities in the indicated ActE secretomes. The maximal rates observed for AFEX-SG and IL-SG were at pH 7.0 (blue star) and pH 8 (red star), respectively. Reactions were carried out at 40° C. and the 0.1 M buffers used were citrate (pH 4.5), phosphate (pH 6-8), CHES (pH 9-10), and CAPS (pH 11). The reaction was performed for 20 h and the reducing sugar content was measured by DNS assay.

FIG. 15 is a diagram with a table showing expression of 167 predicted CAZy genes in ActE, highlighting group 2 genes. These genes showed no signal above the average genomic expression intensity (log 2=10.5). (A) Clustering of genes with similar expression profiles. (B) Additional information on group 2 genes including expression profile, SACTE_locus ID, CAZy family, and annotated function.

FIG. 16 is a diagram with a table showing expression of 167 predicted CAZy genes in ActE, highlighting group 3 genes. (A) Clustering of genes with similar expression profiles. (B) Additional information on group 3 genes including expression profile, SACTE_locus ID, CAZy family, and annotated function.

FIG. 17 is a table illustrating proteins separated by ion exchange chromatography and identified by mass spectrometry.

FIG. 18 is a table showing spectra count of proteins identified on each substrate, where top 95% spectra covered were highlighted green, light purple, purple, blue, orange, pink, light blue and yellow on glucose, cellobiose, cellulose, xylan, switchgrass, AFEX-SG, IL-SG and chitin, respectively.

FIG. 19 shows the nucleic acid sequences of the ActE genes.

FIG. 20 shows the amino acid sequences of the ActE genes.

FIG. 21 is a graph illustrating a comparison of specific activities of *Streptomyces* sp. ActE secretomes with Spezyme CP. FIG. 21A depicts relative specific activity of ActE secretomes prepared from growth on cellulose or xylan and Spezyme CP (100%) for reducing sugar release from xylan or mannan. FIG. 21B depicts relative activity (pH 6.0, 40° C.) of ActE cellulose secretome and CelLcc_CBM3a, an engineered *C. thermocellum* endo/exoglucanase, compared to Spezyme CP. Total amounts of protein included in all reactions were equivalent.

FIG. 22 illustrates nucleotide (SEQ ID NO:63) and amino acid (SEQ ID NO:64)sequence of CelLcc_CBM3a. Construct described in US Patent Application Publication No.: US2010/037094 (Fox and Elsen).

FIG. 25 illustrates synergy of recombined fractions from ion exchange chromatography. All reactions were prepared to contain the same total amount of protein.

FIG. 26 is a set of graphs illustrating mannanase activity demonstrated in fractions containing various naturally truncated versions of SACTE_2347 (GH5). FIGS. 26A-B depict proteins found in previous assayed fractions. FIG. 26C depicts Coomassie Blue staining of 12% polyacrylamide gel (PAGE) separation of different mannanase isoforms. Three polypeptide bands corresponding to SACTE_2347 (GH5) with molecular masses of ~57, ~45, and ~37 kDa. FIG. 26D depicts a zymogram performed in the presence of 0.5% mannan. The strong clearing zone in fraction F1 associated with the ~37 kDa isoform demonstrates how size reduction can increase the specific activity of a protein.

FIG. 27 is a set of graphs illustrating ion exchange fractionation of *Streptomyces* sp. ActE secretome.

FIG. 28 is a SDS-PAGE graph and a list illustrating mass spectral assignment of polypeptides from the *Streptomyces* sp. ActE secretome separated by ion exchange chromatography. FIG. 28B depicts information on the identified proteins including gene locus, function, CAZy GH and CBM assignments, number of amino acid (AA) residues, and best BLAST result for relationship to another known enzyme. The reactivity of fractions marked with stars is also described in FIG. 25A.

FIG. 29 is a SDS-PAGE graph and a table that demonstrates the existence of xylanases from *Streptomyces* sp. ActE. Five ActE proteins were produced using cell-free translation as described in US Patent Application Publication No.: US2010/037094 (Fox and Elsen). FIG. 29A depicts a stain-free gel image of proteins produced by wheat germ cell-free translation (indicated by asterisks). FIG. 29B depicts a summary of protein information, expression and secretion data, and diagnostic assay results. Small molecule assays (MUG, methylumbelliferyl glucoside; MUC, methylumbelliferyl cellobioside; MUM, methylumbelliferyl mannoside and MUX2, methylumbelliferyl xylobioside) were performed in 0.1 M phosphate buffer, pH 6.0, at 30° C. SACTE_0265 and SACTE_0358, highly expressed and secreted proteins during growth on xylan, are confirmed by these assays to be xylanases. Results from three other non-secreted ActE enzymes are provided as controls.

FIG. 34 is a set of Venn diagrams representing 95% of total proteins identified in LC-MS/MS analyses generated using VennMaster-0.37.5 (Kestler et al., 2008). FIG. 8A depicts secretomes obtained from growth on glucose, Sigmacell™, and xylan. FIG. 8B depicts secretomes obtained from growth on switchgrass, ammonia fiber expansion (AFEX)-SG, and IL-SG. For clarification, glucose ∩ Sigmacell)=4 represents the intersection of the two sets, while glucose/(Sigmacell ∪ xylan)=117 represents the proteins uniquely associated with growth on glucose as compared to Sigmacell. Other results are interpreted in a similar manner.

Figure 2:
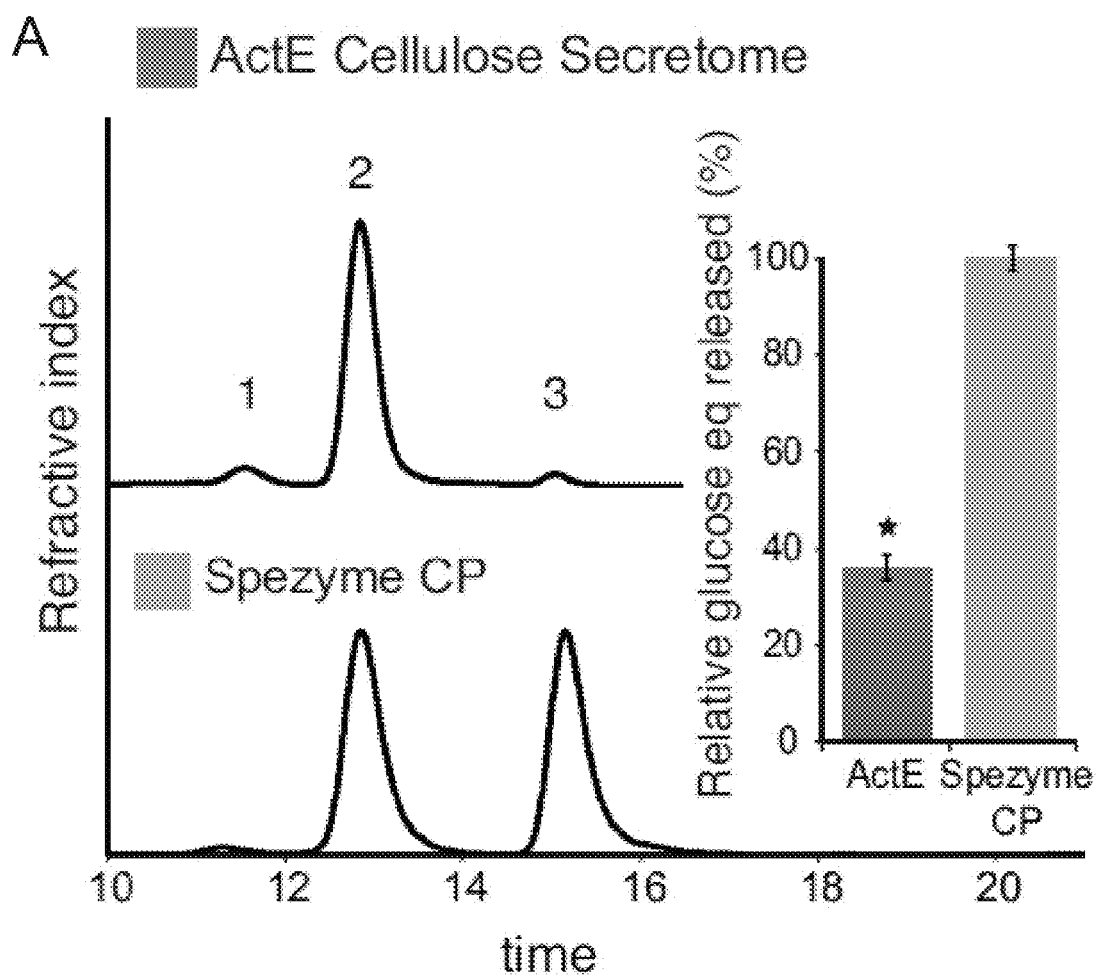
FIG. 2 is a set of graphs demonstrating reactions of ActE secretomes and Spezyme CP. (A) HPLC of sugars released from cellulose (1, cellotriose; 2, cellobiose; 3, glucose) and quantification of glucose equivalent (insert). (B) Reducing sugars released from xylan and mannan by the secretomes of ActE grown on cellulose and xylan. (C) Total reducing sugar released from ionic liquid-switchgrass (IL-SG) or AFEX-switchgrass (AFEX-SG) in reactions of the ActE cellulose, AFEX-SG, and IL-SG secretomes and Spezyme CP. Data represent the mean±s.d. from three experiments; * indicates P<0.01 compared with Spezyme CP.
Figure 2:
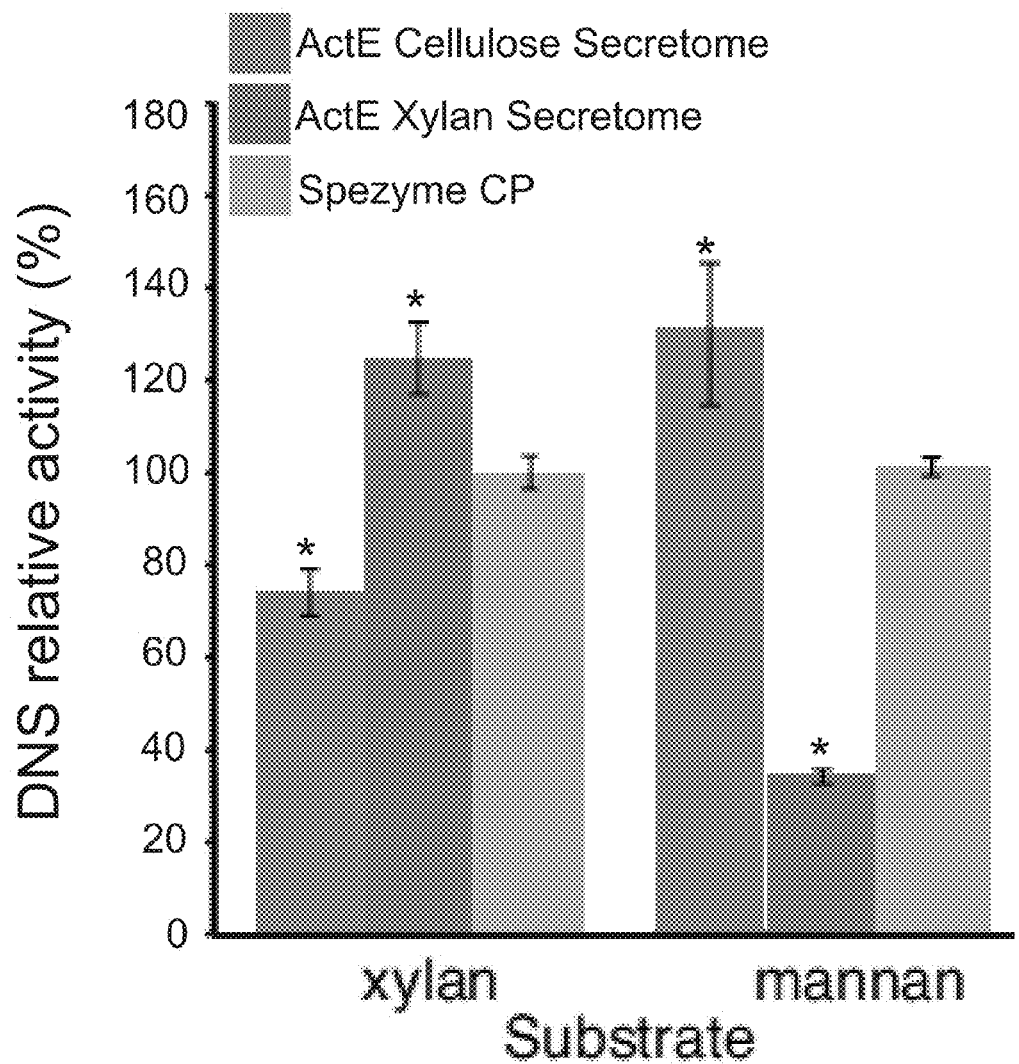
Figure 2:
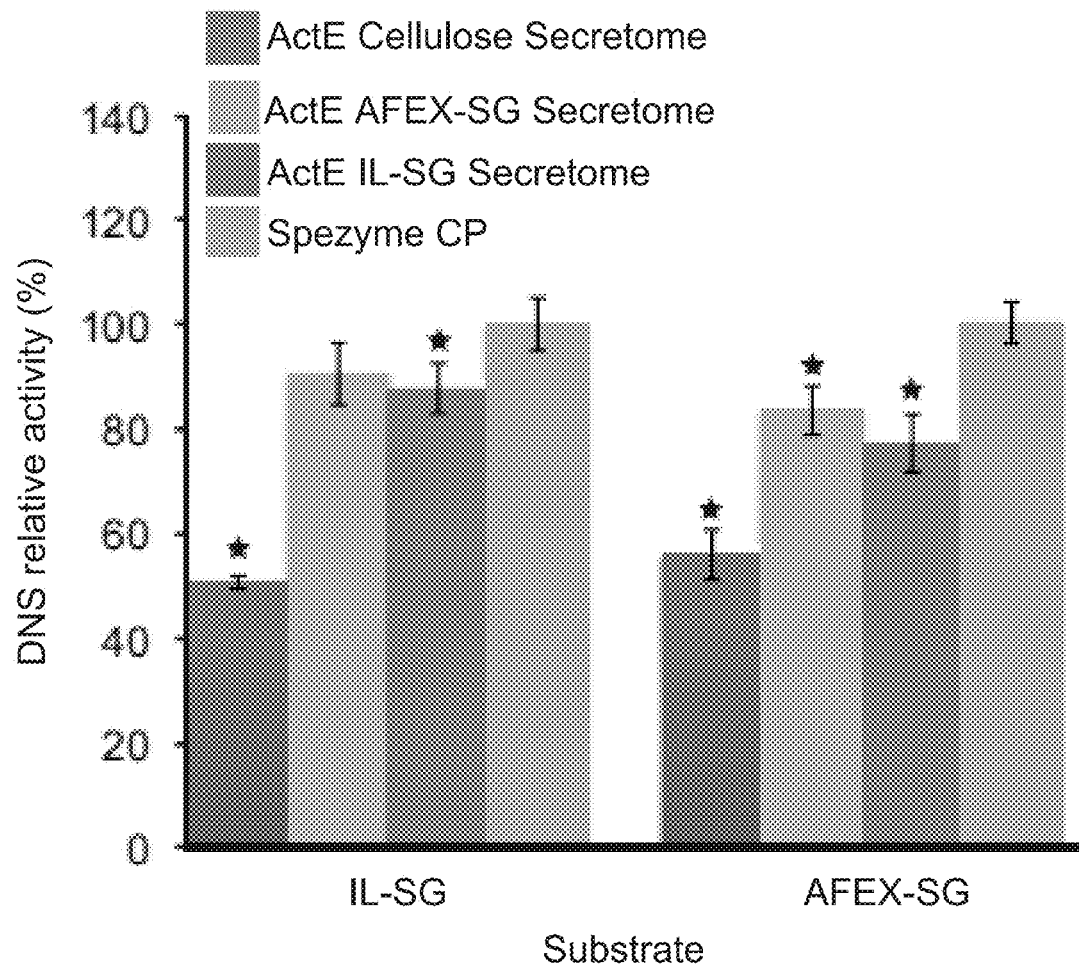

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

In General

The present invention comprises many embodiments. In one embodiment, the invention is a method of digesting a lignocellulosic material, comprising the step of exposing the material to an effective amount of *Streptomyces* sp. ActE secretome preparation such that at least partial lignocellulosic digestion occurs. In one embodiment of that method, the preparation is a supernatant preparation obtained from a *Streptomyces* sp. ActE culture. In another embodiment of that method, the preparation is obtained from *Streptomyces* sp. ActE grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass, and chitin. In another embodiment of that method, the lignocellulosic material is selected from the group consisting of materials that comprise at least 75% cellulose, cellulose/hemicelluloses, xylose, biomass and chitin.

In one embodiment, the invention is a purified preparation comprising the *Streptomyces* sp. ActE secretome. In one embodiment, the preparation is a supernatant preparation obtained from a *Streptomyces* sp. ActE culture. In another embodiment of the preparation, *Streptomyces* sp. ActE is grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass, and chitin.

In one embodiment, the invention is a composition useful for digesting lignocellulosic material comprising one gene or expression product thereof selected from the group consisting of SActE_0237 (GH6) (SEQ ID NO:1), SActE_0236 GH48) (SEQ ID NO:2), SActE_3159 (CBM33) (SEQ ID NO:3), SActE_0482 (GH5) (SEQ ID NO:4), SActE_0265 (GH10) (SEQ ID NO:5), and SActE_2347 (GH5) (SEQ ID NO:6) genes or expression products thereof. In one embodiment, the composition additionally comprises at least one member selected from the group consisting of SActE_0357 (CE4) (SEQ ID NO:7), SActE_0358 (GH11) (SEQ ID NO:8), SActE_1310 (PL3) (SEQ ID NO:9), SActE_3717 (GH9) (SEQ ID NO:10), SActE_4638 (SEQ ID NO:11), SActE_4738 (GH16) (SEQ ID NO:12), SActE_4755 (GH64) (SEQ ID NO:13), SActE_5457 (GH46) (SEQ ID NO:14), SActE_5647 (GH87) (SEQ ID NO:15), and SActE_5978 (PL1) (SEQ ID NO:16) genes or expression products derived thereof.

In one embodiment, the invention is a composition useful for cellulose degradation comprising SActE_0236 (GH48) (SEQ ID NO:2), SActE_3159 (CBM33) (SEQ ID NO:3), SActE_0482 (GH5) (SEQ ID NO:4) and SActE_0237 (GH6) (SEQ ID NO:1) genes or expression product thereof. In one embodiment, the composition additionally comprises at least one member selected from the group consisting of SActE_0357 (CE4) (SEQ ID NO:7), SActE_0358 (GH11) (SEQ ID NO:8), SActE_1310 (PL3) (SEQ ID NO:9), SActE_3717 (GH9) (SEQ ID NO:10), SActE_4638 (SEQ ID NO:11), SActE_4738 (GH16) (SEQ ID NO:12), SActE_4755 (GH64) (SEQ ID NO:13), SActE_5457 (GH46) (SEQ ID NO:14), SActE_5647 (GH87) (SEQ IDNO:15), and SActE_5978 (PL1) (SEQ ID NO:16) genes or expression products derived thereof.

In one embodiment, the invention is a method for digesting a lignocellulosic material, comprising exposing the material to a sufficient amount of a composition of any combinations of genes or expression products derived thereof as disclosed above, wherein the exposed material is at least partially digested.

In one embodiment, the invention is a purified preparation of *Streptomyces* sp. ActE, wherein the *Streptomyces* sp. ActE has been grown on a substrate wherein at least 40%, preferably 85%, of *Streptomyces* sp. ActE's carbon source in the substrate is derived from a material selected from the group consisting of cellulose, cellulose/hemicelluloses mixture, hemicelluloses, xylan, non-wood biomass, wood biomass and chitin.

In one embodiment, the invention is a purified preparation of *Streptomyces* sp. ActE, wherein the *Streptomyces* sp. ActE has been grown on a substrate wherein at least 40%, preferably 85%, of *Streptomyces* sp. ActE's carbon in the substrate is derived from pretreated lignocellulosic material. In one embodiment of the preparation, the pretreated material has been exposed to pretreatment selected from the group consisting of acid hydrolysis, steam explosion, ammonia fiber expansion (AFEX), organosolve, sulfite pretreatment to overcome recalcitrance of lignocellulose (SPORL), ionic liquids (IL), metal-catalyzed hydrogen peroxide treatment, alkaline wet oxidation and ozone pretreatment. In another embodiment of the preparation, the pretreated material is wood.

Specific Embodiments

Applicants have been interested in insects that utilize plant biomass and their associated microbial and fungal communities. *Sirex noctilio*, a wood boring wasp, is found in pine forests throughout Eurasia and North Africa and is spreading throughout North America and elsewhere (Bergeron et al., 2011). Although the destructive nature of the *Sirex* infestation is generally considered to arise from a symbiotic relationship between *S. noctilio* and *Amylostereum areolatum*, a white rot basidiomycete (Kukor and Martin, 1983; Klepzig et al., 2009; Bergeron et al., 2011), the role of cellulolytic microbes has not been previously considered in the context of the infestation or symbiosis. *Streptomyces* sp. SirexAA-E [*Streptomyces* sp. ActE, also referred to herein as "ActE" (Adams et al., ISME J. 5:1321-1231, 2011)], was isolated from the ovipositor mycangium of *S. noctilio* (Adams et al., 2011). Applicants hypothesized that ActE is inoculated into insect feeding tunnels upon infestation along with the symbiotic fungus. Thus, Applicants were interested to learn how ActE might contribute to the *Sirex* community.

The present invention will be more fully understood upon consideration of the following non-limiting Examples. All papers and patents disclosed herein are hereby incorporated by reference as if set forth in their entirety.

As used herein, the term "ActE" refers to *Streptomyces* sp. SirexAA-E, as described in Adams et al., ISME J. 5:1321-1231, 2011. A representative sample of *Streptomyces* sp. ActE has been deposited according to the Budapest Treaty for the purpose of enabling the present invention. The repository selected for receiving the deposit is the American Type Culture Collection (ATCC) having an address at 10801 University Boulevard, Manassas, Va. USA, Zip Code 20110. The ATCC repository has assigned the patent deposit designation PTA-12245 to the *Streptomyces* sp. ActE strain.

As used herein, the term "secretome" refers to the plurality of secreted enzymes. For example, ActE secretome refers to the secreted enzymes from *Streptomyces* sp. SirexAA-E.

As used herein, the term "lignocellulosic material" refers to any material that is composed of cellulose, hemicellulose, and lignin, wherein the carbohydrate polymers (cellulose and hemicelluloses) are tightly bound to the lignin.

As used herein, the term "biomass" refers to a renewable energy source, is biological material from living or recently living organisms. As an energy source, biomass can either be used directly, or converted into other energy products such as biofuel. Biomass includes plant or animal matter that can be converted into fibers or other industrial chemicals, including biofuels. Industrial biomass can be grown from numerous types of plants, including miscanthus, switchgrass, hemp, corn, poplar, willow, sorghum, sugarcane, bamboo, and a variety of tree species, ranging from eucalyptus to oil palm (palm oil). Thus, biomass can include wood biomass and non-wood biomass.

The present invention has multiple embodiments. All embodiments are related to Applicants' discovery of improved lignocellulosic digestion and utilization using proteins and genes obtained from the Streptomyces sp. ActE secretome.

ActE Isolates and Secretomes

Streptomyces sp. SirexAA-E may be isolated from ovipositor mycangia of S. noctilio. In Adams, et al, S. noctilio were collected from a population in Pennsylvania, USA. Infested trees were cut and transported to USDA Pest Survey, Detection, and Exclusion Lab in Syracuse, N.Y., USA (Zylstra et al. (2010) Agric. Forest. Entomol. in press). Four adult females and six larvae from the Pennsylvania population were sampled, and cultures of bacteria derived from these insect samples were screened for cellulose degradation.

Prior to sampling for bacteria, all insects were typically surface sterilized in 95% ethanol for 1 minute and then rinsed twice in sterile phosphate-buffered solution (1×PBS). Larval guts and adult ovipositors and mycangia were removed surgically. These segments and the body were ground separately in 1 ml 1×PBS using a sterilized mortar and pestle. 50 µl of three 100-fold dilutions of each insect part were plated onto yeast and malt extract agar (Becton, Dickinson and Company, Sparks, Md., USA), acidified yeast malt extract agar (for gut dissections only), 10% tryptic soy agar (Becton, Dickinson and Company, Sparks, Md., USA), and agar supplemented with chitin (MP Biomedicals, Solon, Ohio). Petri dishes were stored at room temperature in darkness for at least three days until visible colonies formed, except for Petri dishes with chitin agar that were stored for at least one month.

All isolates were typically screened for production of cellulolytic enzymes on carboxymethyl cellulose (CMC) (Teather R M, Wood P J (1982); incorporated herein by reference as if set forth in its entirety). Isolates that tested positive on CMC were then studied further. Assays on CMC, AFEX-treated corn stover at three pH levels, and microcrystalline cellulose were typically performed to assess growth and degradation ability of each insect-derived bacterial isolate. Isolates capable of degrading CMC were further analyzed genomically to identify isolates with high CAZy content relative to one another and relative to known organisms. Streptomyces sp. ActE was selected based on its CMC degradation and CAZy gene profile.

In one embodiment, secretomes from ActE would be used alone in a first reaction to convert biomass into a hydrolyzed solution of sugars that would be used in a second reaction with a fermentation organism to convert the sugars into usable biofuels. The first and second reaction could occur simultaneously.

In a second embodiment, secretomes from ActE would be combined with secretomes from other organisms, or with enzymes or enzyme compositions, such as Spezyme CP, to increase the activity of both preparations by synergy of the enzymes contained in each preparation.

Preferably, the ActE secretomes would be prepared as supernatants from ActE preparations.

In one embodiment, the supernatant is prepared by centrifugation of the ActE culture for 10 min at 3,000×g, which will pellet the remaining insoluble polysaccharide and adhered ActE cells. The supernatant fraction is filter-sterilized, preferably using a 0.22 µm filter, in order to remove any remaining cells. The supernatant is concentrated, preferably using a 3 kDa cut-off ultrafiltration membrane. The concentration of total protein is determined by Bradford assay (Bradford, 1976). In one preferred embodiment, the proteomic composition of the ActE secretome is that described in FIG. 3 or FIG. 18.

The secretomes obtained from growth on specific lignocellulosic materials, such as cellulose, xylan, cellulosic hemi-cellulosic biomass, and chitin, will have distinct compositions of individual enzymes and also distinct reactivity with different polysaccharides. The cellulosic hemi-cellulosic biomass may be non-wood biomass or wood biomass. For example, the secretome prepared from ActE grown on cellulose has unique enzymes and enhanced reactivity with cellulose and mannan. Also, the secretome prepared from ActE grown on xylan possesses high xylan degradation activity, whereas the secretome from ActE grown on chitin possesses uniquely high chitin degradation activity. Example A discloses the specific secretomes.

When ActE is grown on switchgrass, AFEX-pretreated switchgrass or ionic liquid pretreated switchgrass, the secretome has a protein composition that partially matches that obtained from growth on either cellulose or xylan. However, switchgrass, AFEX-pretreated switchgrass or ionic liquid pretreated switchgrass elicit the appearance of new proteins in the secretome that enhance the degradative ability of the secretome for the plant biomass materials. Applicants envision that the present invention would also apply to other pretreatment methods comprising acid hydrolysis, steam explosion, organosolve, sulfite pretreatment to overcome recalcitrance of lignocellulose (SPORL), metal-catalyzed hydrogen peroxide treatment, alkaline wet oxidation and ozone pretreatment.

The inventors' preliminary data shows synergistic filter paper degrading activity between the ActE secretome and other cellulases from a different organism. Also, addition of a beta-glucosidase to the secretome helps to break down the oligosaccharides (e.g., cellotetraose, cellotriose and cellobiose) released from filter paper into simpler sugars.

Preferably, the secretome would be prepared as a concentrated solution by ultrafiltration. The concentrated material would be mixed with the substrate at weight percentages varying from 0.1% to 20% w/w, with the remainder of the solution containing a buffer substance that controls pH. Trace metals would be added to the reaction. The material would be incubated at the appropriate temperature to allow the reaction to occur, with mixing of the reaction materials. The sample might be equilibrated with air or $O_2$ gas throughout the reaction time period.

The secretome obtained from growth of ActE on cellulose provides all necessary enzymes for most efficient breakdown of cellulose to cellobiose and mannan to mannose. Weak reaction is observed for breakdown of xylan to xylose and a mixture of mannobiose and mannose.

The secretome obtained from growth of ActE on xylan provides all necessary enzymes for most efficient breakdown of xylan to xylobiose and xylose. Weak reaction is observed for breakdown of cellulose to cellobiose and for breakdown of mannan to mannose.

The secretome obtained from growth of ActE on chitin provides all necessary enzymes for most efficient breakdown of chitin to N-acetylglucosamine. Weak reaction is observed for breakdown of xylan to xylose. Weak reaction is observed for breakdown of cellulose to cellobiose and for breakdown of mannan to mannose.

The secretome obtained from growth of ActE on switchgrass biomass provides all of the necessary enzymes for breakdown of cellulose, xylan, and mannan contained in switchgrass to the constituent monosaccharides and disaccharides. Growth of ActE on switchgrass exposed to different chemical pretreatments changes the composition of enzymes present, which alters the rate of production and yield of the constituent monosaccharides and disaccharides.

The secretome obtained from growth of ActE on cellulose provides the necessary enzymes for breakdown of cellulose to cellobiose. ActE uses cellobiose as the growth substrate, so no enzymes are present to convert cellobiose to glucose.

In order to obtain glucose, a cellobiase or beta-glucosidase would be added. This is a standard practice in biofuels enzymology.

In order to convert cellobiose to glucose, a cellobiase or beta-glucosidase would be added. Addition of cellulases from other organisms can improve the rate of hydrolysis of cellulose, e.g., addition of CelLcc_CBM3a, an engineered enzyme from C. thermocellum covered in Fox and Elsen Patent Application No.: PCT/US2010/037094.

The secretome obtained from growth of ActE on cellulose provides all of the necessary enzymes for breakdown of cellulose to cellobiose in a soluble form. One skilled in the art might purify these proteins directly from the secretome without use of tags or recombinant approaches.

As previously noted, the dominance of cellobiose as a product of cellulose deconstruction by ActE might help to channel cellulolytic activity to only a subset of the diverse microbes found in the *Sirex* community. Exploiting this community interaction, along with establishing control of the highly regulated patterns of gene expression observed in ActE provides the basis for a new biotechnological route for lignocellulosic digestion. For example, use of ActE secretomes to produce cellobiose will restrict the use of cellulose as a fermentation substrate to only those organisms capable of cellobiose uptake followed by intracellular conversion to glucose and subsequent glycolytic pathway intermediates. This might be achieved by coupling ActE enzymes with a yeast fermentation strain engineered to contain a specific cellobiose transporter and an intracellular cellobiose phosphorylase, leading to the intracellular production of glucose and glucose-1-phosphate.

ActE secretomes can be mixed with cellulosic biomass to convert it to cellobiose and xylose, as in the biofuels industry. For example, one might (1) mix the secretome with paper waste to convert it to a mixture of readily fermentable oligo-, di-, and monosaccharides; (2) mix with animal feeds to increase the digestibility of the biomass to promote animal growth; (3) mix with cotton-based textiles for smoothing or other refinements; (4) mix with waste from the shrimp industry to process solid chitin to soluble constituents; (5) mix with mannan-enriched materials to convert them to mannose and mannobiose. One would also find the secretome useful for commercial food processing or treatment of cellulosic bezoar found in the human stomach.

One embodiment of the present invention is an isolation or purified preparation of *Streptomyces* sp. ActE.

An isolation of ActE was originally reported by Adams et al., (2011) ISME j doi:10.1038/ismej.2011.14, where it was stated that "*Sirex noctilio* were collected from infested scots pine, *Pinus sylvestris* L, in Onondaga County, N.Y., USA in 2008", and "Microbial isolates were obtained from four adult females and six larvae collected in 2008, and were screened for cellulase activity." These isolates were screened for cellulolytic ability by growing them on CMC, AFEX-treated corn stover, and microcrystalline cellulose.

Applicants envision that one would wish to prepare ActE isolates on specific nutrient sources for optimization for particular digestion profiles. Therefore, one may wish to prepare ActE on substrates wherein at least 40%, preferably 85% of *Streptomyces* sp. ActE's carbon source in the substrate is derived from a material selected from the group consisting of cellulose, cellulose/hemicelluloses mixture, hemicelluloses, xylan, non-wood biomass, wood biomass, and chitin.

In a preferred embodiment, ActE would be grown aerobically to maximize the secretion of enzymes that include both oxidative and hydrolytic enzymes capable of the rapid deconstruction of biomass. Since ActE cannot utilize mannose for growth, but efficiently liberates mannose from biomass, mannose would become available for growth of the inoculum of a fermentation organism in co-culture. The likely fact that ActE produces at least one antibiotic that would help maintain culture sterility is another possible advantage to establishment of an effective co-culture.

The high capacity for mannan hydrolysis coupled with the inability of ActE to use mannose as a growth substrate offers unique potential opportunity for expansion of deconstruction enzymology to the use of woody substrates. The deconstruction of woody substrates is considered to be more challenging for biofuels production despite the fact that woody substrates are also considerably more highly enriched in mannan than grass substrates. This unique potential opportunity will be enhanced by ongoing plant engineering research efforts to redefine the proportion of xylan and mannan in plant hemicellulose. The availability of plant material enriched in mannan will be coupled to vigorous conversion to mannose by ActE secretomes, providing a targeted, simply fermented C6 sugar for exclusive use by the fermentation organism.

When sufficient titer of enzymes and fermentation organism have been achieved, facilitated by the vigorous, obligate aerobic growth of ActE and corresponding deconstruction of biomass, the fermentation could be initiated by removal of the air source from the culture vessel. In the anoxic conditions, ActE would cease to grow, and perhaps even lyse to become a protein source for the fermentation organism, which will continue to grow on biomass that is simultaneously being deconstructed by the loading of highly active hydrolytic enzymes originally produced by ActE during the aerobic growth phase.

Applicants envision adding an ActE isolate directly to biomass slurry. More preferably an ActE isolate would be added to the pretreated biomasses in the enzyme hydrolysis step, because ActE is able to grow at wide range of pH. ActE can be genetically modified so that the proteolysis proof secretome will be achieved. Growth on switchgrass elicits the appearance of new proteins in the secretome that enhance the degradative ability of the secretome for the plant biomass materials. Applicants envision that the present invention would apply to the biomasses pretreated by many pretreatment methods comprising AFEX, ionic liquid pretreated, acid hydrolysis, steam explosion, organosolve, sulfite pretreatment to overcome recalcitrance of lignocellulose (SPORL), metal-catalyzed hydrogen peroxide, alkaline wet oxidation and ozone pretreatment.

In one preferred embodiment of the present invention, at least one key enzyme in the secretome can be overexpressed by genetic modification of the ActE strain. Table 1 provides various combinations of genes that can be overexpressed. For example, one may wish to overexpress core cellulose deconstructing enzymes, SACTE_0237, SACTE_0482, SACTE_0236, or SACTE_3159 together with one or more of SACTE_2347, and SACTE_0265. One may wish to overexpress core xylan deconstructing enzymes, SACTE_0265, SACTE_0358, SACTE_0357, SACTE_5978, and SACTE_5230. One may wish to overexpress core mannan deconstruction enzymes, such as SACTE_2347. Additionally, SACTE_4755 and SACTE_4738 may be overexpressed for beta-1,3-glucan deconstruction. One may also overexpress all or some of the aforementioned genes for efficient biomass deconstruction.

In another embodiment of the present invention, at least one key enzyme in the secretome can be overexpressed and secreted by genetic modification of a different microbial host such as *Streptomyces lividans*, which is used for industrial secretion of proteins (Anne and Van Mellaert. (1993)), or *T. reesei*, which is used for secretion of enzymes in the biofuels industry (Saloheimo and Pakula, Microbiology, Epub date 2011 Nov. 5).

In another embodiment of the present invention, at least one key enzyme in the secretome can be overexpressed by genetic modification of a different microbial host such as *S. cerevisiae* or *E. coli* such that the expressed protein will be retained inside of the host cell. The host cells would then be harvested and used as a delivery agent without need for purification of the entrained enzyme, as described in (Wood et al., 1997. This version of the invention may be useful in the enzymatic pretreatment of agricultural crop materials for consumption by ruminant animals.

Combinations of ActE Genes and Expression Products

Selected minimal genes in each subset were chosen based on the combination of genomic, transcriptomic and secretomic results (See Examples and Table 1). For example, in the cellulose minimal gene set, expression of these genes was relatively enriched in cellulose grown cells, compared to glucose grown cells, also corresponding proteins were highly secreted in response to the cellulose in culture medium. Elected minimal genes were annotated to have cellulose utilization function. A larger set of genes for cellulose utilization were selected based on the enrichment of gene expression in cellulose-grown cells relative to glucose-grown cells, and a functional annotation supports cellulose utilization of these genes. Additionally, neighborhood genes to these selected genes on genome were included as genes regulated under same promoter. Similarly, both minimal and a large set of genes for xylan, chitin, and biomasses were elected.

In one embodiment, the present invention is a composition useful for digesting lignocellulosic material comprising genes or expression products thereof selected from the group consisting of: (a) SActE_0237 (SEQ ID NO:1), SActE_0236 (SEQ ID NO:2), SActE_3159 (SEQ ID NO:3), SActE_0482 (SEQ ID NO:4), SActE_0265 (SEQ ID NO:5), and SActE_2347 (SEQ ID NO:6), and (b) SActE_0357 (CE4) (SEQ ID NO:7), SActE_0358 (GH11) (SEQ ID NO:8), SActE_1310 (PL3) (SEQ ID NO:9), SActE_3717 (GH9) (SEQ ID NO:10), SActE_4638 (SEQ ID NO:11), SActE_4738 (GH16) (SEQ ID NO:12), SActE_4755 (GH64) (SEQ ID NO:13), SActE_5457 (GH46) (SEQ ID NO:14), SActE_5647 (GH87) (SEQ ID NO:15), and SActE_5978 (PL1) (SEQ ID NO:16). In a preferred embodiment, the composition comprises at least three or four of the genes or expression products.

In one embodiment, one would use at least one member of (a) to digest a preferred lignocellulosic material.

In another embodiment, one would use at least the first four members [SActE_0237 (SEQ ID NO:1), SActE_0236 (SEQ ID NO:2), SActE_3159 (SEQ ID NO:3), and SActE_0482 (SEQ ID NO:4)] of (a) to digest a preferred lignocellulosic material.

In another embodiment, one would use at least one member of (a) and at least one member from (b), to digest a preferred lignocellulosic material.

In a preferred embodiment, one would use all the members of (a) and (b), to digest a preferred lignocellulosic material.

In other embodiments, the combination of genes or expression products thereof in the present invention is dependent on the specific lignocellulosic material to be digested. In one embodiment, a composition optimized for cellulose utilization may include any combinations of ActE genes and expression products disclosed above with at least one member selected from SActE_0265 (GH10) (SEQ ID NO:5) and SActE_2347 (GH5) (SEQ ID NO:6) genes or expression products thereof.

In another embodiment, a composition optimized for xylan utilization may include any combinations of ActE genes and expression products disclosed above with at least one member selected from SActE_0265 (GH10) (SEQ ID NO:5), SActE_0358 (GH11) (SEQ ID NO:8), SActE_0357 (CE4) (SEQ ID NO:7), SActE_5978 (PL1) (SEQ ID NO:16) and SActE_5230 (xylose isomerase) genes or expression products thereof. In a preferred embodiment, the composition comprises at least three or four of the genes or expression products.

In another embodiment, a composition optimized for chitin utilization may include any combinations of ActE genes and expression products disclosed above with at least one member selected from SActE_4571 (GH18), SActE_2313 (CBM33), SActE_4246 (GH18), SActE_3064 (GH19), and SActE_5764 (GH18) genes or expression products thereof. In a preferred embodiment, the composition comprises at least three or four of the genes or expression products.

In another embodiment, a composition optimized for biomass utilization may include any combinations of ActE genes and expression products disclosed above with SActE_5457 (GH46) (SEQ ID NO:14) genes or expression products thereof.

In another embodiment, a composition optimized for mannan utilization may include any combinations of ActE genes and expression products disclosed above with SactE_2347 (GH5) (SEQ ID NO:6) genes or expression products thereof.

In another embodiment, a composition optimized for beta-1,3-glucan utilization may include any combinations of ActE genes and expression products disclosed above with at least one member selected from SActE_4755 (GH64) (SEQ ID NO:13) and SActE_4738 (GH16) (SEQ ID NO:12) genes or expression products thereof.

In another embodiment, a composition optimized for pectin release utilization may include any combinations of ActE genes and expression products disclosed above with SActE_1310 (PL3) (SEQ ID NO:9) gene or expression products derived thereof.

In another embodiment, a composition optimized for alginate release utilization may include any combinations of ActE genes and expression products disclosed above with SActE_4638 (SEQ ID NO:11) gene or expression products derived thereof.

In another embodiment, a composition optimized for galactose release utilization may include any combinations of ActE genes and expression products disclosed above with SactE_5647 (GH87) (SEQ ID NO:15) gene or expression products derived thereof.

In another embodiment, the present invention is summarized as a composition useful for xylan degradation comprising SActE_0265 (GH10) (SEQ ID NO:5) and SActE_0358 (GH11) (SEQ ID NO:8) genes or expression products thereof.

In another embodiment, the present invention is summarized as a composition useful for xylan degradation comprising SActE_0265 (GH10) (SEQ ID NO:5), SActE_0358 (GH11) (SEQ ID NO:8), SActE_0265 (GH10) (SEQ ID NO:5), SActE_0358 (GH11) (SEQ ID NO:8), SActE_0357 (CE4) (SEQ ID NO:7), SActE_5978 (PL1) (SEQ ID NO:16), and SActE_5230 (xylose isomerase) genes or expression products thereof. In a preferred embodiment, the composition comprises at least three or four of the genes or expression products.

In another embodiment, the present invention is summarized as a composition useful for biomass degradation comprising SActE_0237 (GH6) (SEQ ID NO:1), SActE_0482 (GH5) (SEQ ID NO:4), SActE_3159 (CBM33) (SEQ ID NO:3), SActE_0236 (GH48) (SEQ ID NO:2), SActE_3717 (GH9) (SEQ ID NO:10), SActE_0265 (GH10) (SEQ ID NO:5), SActE_0358 (GH11) (SEQ ID NO:8), SActE_2347 (GH5) (SEQ ID NO:6) and SActE_1310 (PL1) genes or expression products thereof. In a preferred embodiment, the composition comprises at least three or four of the genes or expression products.

In one embodiment, the present invention is a composition useful for digesting lignocellulosic material comprising genes or expression products thereof selected from the group consisting of: (a) SActE_0237 (SEQ ID NO:1), SActE_0236 (SEQ ID NO:2), SActE_3159 (SEQ ID NO:3), SActE_0482 (SEQ ID NO:4), SActE_0265 (SEQ ID NO:5), and SActE_2347 (SEQ ID NO:6) (for cellulose); (b) SActE_0265 (SEQ ID NO:5), SActE_0357 (SEQ ID NO:7), SActE_0358 (SEQ ID NO:8), SActE_5230 and SActE_5978 (for xylan); (c) SActE_2313, SActE_3064, SActE_4246, SActE_4571 and SActE_5764 (for chitin); (d) SActE_2347 (for mannan); and (e) SActE_0236 (SEQ ID NO:2), SActE_0237 (SEQ ID NO:1), SActE_0265 (SEQ ID NO:5), SActE_0358, SActE_1310, SActE_2347 and SActE_3159 (for biomass). In a preferred embodiment, the composition comprises at least three or four of the genes or expression products.

In one embodiment, one would use at least two members of (a), (b), (c), (d) or (e) to digest a preferred lignocellulosic material.

In another embodiment, one would use at least three members.

In a preferred embodiment, one would use all members of (a), (b), (c), (d) or (e).

In another embodiment, one would add gene expression products from the list in Table 1 to a substrate to be digested. For example, for preferred cellulose digestion, one would select at least two members of (a), as described above, and at least one member of the "additional useful genes" in Table 1.

In the case of cellulose degradation, the inventors believe SACTE_3159, SACTE_0237, SACTE_0482, and SACTE_0236 act cooperatively to create nicks and hydrolyze cellobiose units from crystalline cellulose.

ActE key genes can be transferred into known cellulolytic organisms in order to enhance the cellulolytic ability of these organisms. A cellulolytic fungus, *T. reesei*, has been studied for industrial applications, and can be genetically modified. Applicants' data support synergism of cellulolytic ability of enzymes from different species. A chromosomal gene transfer can be performed into *T. reesei* by protoplast transformation with a high copy plasmid carrying one or more of the ActE cellulolytic key genes.

A chromosomal or a non-chromosomal gene transfer can be made into a yeast species such as *Saccharomyces cerevisiae*. For non-chromosomal gene transfer, a high copy plasmid carrying a cassette of five minimal genes (SACTE_0236, SACTE_0237, SACTE_0482, SACTE_3717 and SACTE_3159) would be used to confer cellulolytic and mannanolytic capability to the yeast strain. Similar approaches could be used to confer xylanolytic and chitinolytic capability using combinations of the genes described herein.

One might wish to recombinantly express the disclosed enzymes in *E. coli* in order to achieve high yield of each enzyme. As is shown in the synergistic result in Example 18, cellulose degradation can be improved by combination of ActE enzymes to enzymes from other organisms.

FIG. 18 shows Spectra count of proteins identified on each substrate, where top 95% most abundant proteins were highlighted green, light purple, purple, blue, orange, pink, light blue and yellow on glucose, cellobiose, cellulose, xylan, switchgrass, AFEX-SG, IL-SG and chitin, respectively.

Applicants envision that one would use a composition comprising at least one member of the abundant proteins, e.g., those highlighted proteins in FIG. 18, for digesting the corresponding lignocellulosic materials. For example, to digest a cellulose material, one would choose at least one gene or expression products thereof selected from the group consisting of SACTE_0237, SACTE_0236, SACTE_2347, SACTE_3159, SACTE_0482, SACTE_0265, SACTE_0357, SACTE_4439, SACTE_0562, SACTE_0358, SACTE_4343, SACTE_1546, SACTE_1310, SACTE_4638, SACTE_5668, SACTE_3717, SACTE_3590, SACTE_2172, SACTE_4571, SACTE_5978, SACTE_6428, SACTE_2313, and SACTE_0366. In a preferred embodiment, the composition comprises at least three or four of the genes or expression products.

In one preferred embodiment, one would use all the highlighted proteins for digesting the corresponding lignocellulosic materials.

In another embodiment, one would add gene expression products from the list in Table 1 to a substrate to be digested. For example, for preferred cellulose digestion, one would select at least one member of the abundant proteins, as described above, and at least one member of the "additional useful genes" in Table 1.

TABLE 1

ActE genes or expression products useful for lignocellulosic degradation.

| Gene or Expression Product Combinations | Preferred subsets | Additional Useful Genes |
|---|---|---|
| SACTE_0236, SACTE_0237, SACTE_3159, SACTE_0482 SACTE_2347, and SACTE_0265. | Cellulose degradation | SACTE_0229, SACTE_0230, SACTE_0231, SACTE_0232, SACTE_0233, SACTE_0234, SACTE_0235, SACTE_0480, SACTE_0481, SACTE_0483, SACTE_0562, SACTE_0563, SACTE_0733, SACTE_0734, SACTE_2286, SACTE_2287, SACTE_2288, SACTE_2289, SACTE_3158, SACTE_4737, and SACTE_6428 |
| SACTE_0265, SACTE_0357, SACTE_0358, SACTE_5230 and SACTE_5978 | Xylan degradation | SACTE_0364, SACTE_0365, SACTE_0366, SACTE_0368, SACTE_0369, SACTE_0370, SACTE_0527, SACTE_0528, SACTE_5227, SACTE_5228, SACTE_5229, SACTE_5858, and SACTE_5859 |
| SACTE_2313, SACTE_3064, SACTE_4246, SACTE_4571 and SACTE_5764 | Chitin degradation | SACTE_0080, SACTE_0081, SACTE_0844, SACTE_0846, SACTE_0860, SACTE_3063, SACTE_4858, SACTE_6493 and SACTE_6494 |
| SACTE_2347 | Mannan degradation | |
| SACTE_1310 | Pectin degradation | |
| SACTE_4638 | Alginate release | |
| SACTE_5647 | Galactose release | SACTE_5648 |
| SACTE_4738 and SACTE_4755 | Beta-1,3-glucan degradation | SACTE_4737, SACTE_4739 and SACTE_4756 |
| SACTE_0236, SACTE_0237, SACTE_0265, SACTE_0358, SACTE_0482, SACTE_1310, SACTE_2347, SACTE_3159 and SACTE_3717 | Cellulose and hemicelluloses degradation | SACTE_3065, SACTE_4730, SACTE_4755, and SACTE_5166 |

In one embodiment, the present invention is a method for digesting a lignocellulosic material, comprising exposing the material to a sufficient amount of a composition of enzymes, wherein the exposed material is at least partially digested. The enzymes may be ActE secretomes, and ActE secretomes may be prepared and isolated using the methods described above.

In another embodiment, the composition of enzymes for a method for digesting a lignocellulosic material may include ActE secretomes in a combination with secretomes from other organisms, or with enzymes or enzyme compositions, such as Spezyme CP, to increase the activity of both preparations by synergy of the enzymes contained in each preparation.

In another embodiment, the composition of enzymes for a method for digesting a lignocellulosic material may be any combinations of ActE genes and expression products as described above.

EXAMPLES

Materials and Methods

Genome Analysis. The complete genome sequence of Streptomyces sp. SirexAA-E (ActE, taxonomy ID 862751) was determined by the Joint Genome Institute, project ID 4086644. Gene annotation models were predicted using Prodigal (Hyatt, et al., 2010), examined using Artemis (Rutherford, et al., 2000), and are available at NCBI with the following accession numbers, GenBank: CP002993.1; RefSeq: NC_015953.1. Carbohydrate-active enzymes were annotated by comparison of all translated open-reading frames to the CAZy database (Cantarel, et al., 2009). We collected CAZy annotated genes from the CAZy database (www.cazy.org). We then used BLASTP to compare all ActE protein-coding sequences to the CAZy database and to the pfam database (ftp://ftp.ncbi.nih.gov/pub/mmdb/cdd/little_endian/Pfam_LE.tar.gz). These two annotations were then crosschecked, and proteins annotated by both databases were identified as our final CAZy annotation. Secreted proteins were identified by SignalP, TatP, and SecretomeP analyses. BLAST was used to identify sequence orthologs in other organisms. Secondary metabolite gene clusters were identified by AntiSmash analysis (Medema, et al., 2011). CebR boxes were identified by using BLAST comparison of the S. griseus CebR box sequence to the ActE genome (Marushima, Ohnishi, et al., 2009). Networks of expression and functional categories were visualized using Cytoscape (Shannon, et al., 2003)

Biomass Substrates. Switchgrass and AFEX-treated switchgrass were obtained from Great Lakes Bioenergy Research Center. Extensively washed ionic liquid-treated switchgrass was the generous gift of Dr. Masood Hadi (Joint BioEnergy Institute). Wood kraft pulp preparations were the generous gift of Dr. Xuejun Pan (University of Wisconsin Department of Biosystems Engineering).

The complete genome sequence of Streptomyces sp. SirexAA-E (ActE, taxonomy ID 862751) was determined by the Joint Genome Institute, project ID 4086644. Gene annotation models were predicted using Prodigal (Hyatt, et al., 2010), examined using Artemis (Rutherford, et al., 2000), and are available at NCBI with the following accession numbers, GenBank: CP002993.1; Ref Seq: NC_015953.1. Carbohydrate-active enzymes were annotated by comparison of all translated open-reading frames to the CAZy database (Cantarel, et al., 2009). We collected CAZy annotated genes from the CAZy database (See CAZy's website for detail information). We then used BLASTP to compare all ActE protein-coding sequences to the CAZy database and to the pfam database (the pfam database can be found in the website of the National Institute of Health (NIH)). These two annotations were then crosschecked, and proteins annotated by both databases were identified as our final CAZy annotation. Secreted proteins were identified by SignalP, TatP, and SecretomeP analyses. BLAST was used to identify sequence orthologs in other organisms. Secondary metabolite gene clusters were identified by AntiSmash analysis (Medema, et al., 2011). CebR boxes were identified by using BLAST comparison of the S. griseus CebR box sequence to the ActE genome (Marushima, Ohnishi, et al., 2009). Networks of expression and functional categories were visualized using Cytoscape (Shannon, et al., 2003)

RNA microarray. ActE was grown in minimal medium plus the indicated substrate for 7 days. The cell pellet was separated from the culture medium by centrifugation for 10 min at 3000×g. Microarray experiments were carried out as reported previously (Riederer, et al., 2011). The total RNA was extracted from the cell pellet and purified. The University of Wisconsin Gene Expression Center carried out the syntheses of cDNA and array hybridizations. Four-plex arrays were constructed by Nimblegen and hybridized with 10 μg of labeled cDNA. ArrayStar (v4.02, DNASTAR, Madison, Wis.) was used to quantify and visualize data. All analyses were based on three or more biological replicates per carbon source. Quantile normalization and robust multiarray averaging (RMA) were applied to the entire data set. Unless otherwise specified, expression levels are based on log 2 values and statistical analysis of the datasets were performed using the moderated t-test.

Preparation of Secretomes. Supernatants obtained from different culture media were prepared by centrifugation of the culture medium for 10 min at 3000×g, which removed the remaining insoluble polysaccharide and adhered cells. The supernatant fraction was then passed through a 0.22-μm filter in order to remove any remaining cells. For enzymatic assays, the secretomes were concentrated using a 3-kDa cut off ultrafiltration membrane. The concentration of secretome protein was determined by Bradford assay, and the typical yield was ~150-300 mg of total secreted protein per liter of culture medium.

Extracellular Protein Profiles. Extracellular proteins from culture secretomes were precipitated with trichloroacetic acid (TCA), resuspended in denaturing sample buffer (SDS and 2-mercaptoethanol), and separated by SDS-PAGE in 4-20% gels. Protein bands of interest were excised from the gel, digested with trypsin, desalted with C18 pipette tips (Millipore, Billerica, Mass.) and identified by MALDI-TOF (MDS SCIEX 4800 MALDI TOF/TOF, Applied Biosystems, Foster City, Calif.). Additional samples from the same culture secretomes were analyzed by LC-MS/MS to identify highly abundant proteins in the sample.

Ion exchange separation of the ActE secretome. The ActE cellulose secretome was diluted with cold deionized water until the ionic strength was less than 50 mS. The diluted sample was loaded onto an AKTApürifier™ chromatography station equipped with a 16/10 MonoQ FF ion exchange column. The column was washed with 100 mL of 10 mM phosphate, pH 6.0, to remove unbound proteins. The bound proteins were eluted in a linear, 200 mL gradient of NaCl from 0 to 0.8 M in the same buffer. Fractions from the gradient elution were collected and separated by SDS PAGE. The proportional contribution of individual proteins in each fraction was estimated from SDS PAGE. Individual protein bands from each fraction were cut from the gel and submitted for LC-MS/MS analysis to confirm their identities.

LC-MS/MS Analyses. These experiments were performed at the University of Wisconsin Biotechnology Center. Samples were prepared by TCA precipitation of 100 ng of total secreted protein from 7-day old culture supernatants. Protein samples were digested with trypsin (sequencing grade trypsin, Promega, Madison, Wis.) and were desalted using C18 pipette tips (Millipore, Billerica, Mass.). High-energy collision dissociation (HCD) MS analyses employing a capillary LC-MS/MS were performed on an electrospray ionization FT/ion-trap mass spectrometer (LTQ Orbitrap XL, Thermo Fisher Scientific, San Jose, Calif.). The MS and MS/MS spectra were searched against the spectra obtained from the ActE proteome by using Scaffold (Scaffold_3_00_06, Proteome Software, Portland, Oreg.).

Enzyme Activity Measurements. Reducing sugar assays were carried out by mixing secretome preparations with polysaccharide-containing substrates including cellulose (either Whatman #1 filter paper or Sigmacell-20 as indicated), xylan, chitin, mannan, switchgrass, AFEX pretreated switchgrass, or ionic-liquid pretreated switchgrass[24]. After incubation in 0.1 M sodium phosphate, pH 6 at 40° C. for 20 h, the reducing sugar content was detected by dinitrosalicylic acid assay (Miller, 1959) and calibrated by using glucose, xylose, or mannose as standards. Purified polysaccharide preparations had negligible background response in the absence of added enzymes. Cellobionic and gluconic acids were assayed by a coupled enzyme assay (K-GATE system, Megazyme, Bray Ireland). Spezyme CP was obtained from Genencor with batch number #4901522860. The distributions of soluble sugar oligomers obtained from secretome reactions were determined using a Shimadzu Liquid Chromatograph HPLC system (Shimadzu Scientific Instruments, Columbia, Md.) equipped with a refractive index detector (RID-10A) and a Phenomenex Rezex RPM-monosaccharide column. The temperature was maintained at 85° C. and Milli-Q water was used as the mobile phase at 0.6 mL min$^{-1}$ flow rate. Glucose, cellobiose, cellotriose, cellotetraose, cellopentaose, and cellohexaose (Sigma) were used as standards. The integrated areas of peaks were analyzed by EZ start 7.2 SP1 software (Shimadzu).

Fractions obtained from the ion exchange separation of the ActE cellulose secretome were combined as unary, binary, ternary, and quaternary assemblies where the total protein concentration was fixed and the individual fractions contributed all, halves, thirds, or quarters of the total protein. The most active fraction was assembled from a ternary combination of fractions containing the following enzymes: fraction 1, SACTE_3159 (CBM33/CBM2 oxidative endocellulase, 95%) and SACTE_4738 (GH16 β-1,3 endoglucanase, 5%); fraction 2, SACTE_0237 (GH6 exocellulase, 60%), SACTE_0482 (GH5 endocellulase, 25%), SACTE_0237 (β-1,3 glucanase, 10%) and SACTE_3159 (oxidative endocellulase, <5%); and fraction 3, SACTE_0236 (GH48 exocellulase, 75%), SACTE_3717 (GH9 endocellulase, 20%) and SACTE_5457 (GH46 chitinase, 5%).

Cellobionic and gluconic acids were assayed by a coupled enzyme assay (K-GATE system, Megazyme, Bray Ireland), either with or without the addition of a large excess of β-glucosidase (Cat. No. 31571, Lucigen, Middleton, Wis.).

Two lots of Spezyme CP were obtained from Genencor (#4900901244, Jan. 27, 2010 and #4901522860, Sep. 2, 2011). The specific activity of these two preparations was indistinguishable.

HPLC Analysis. The distributions of soluble sugar oligomers obtained from secretome reactions without and with the addition of excess β-glucosidase (Lucigen) were determined using a Shimadzu Liquid Chromatograph HPLC system (Shimadzu Scientific Instruments, Columbia, Md.) equipped with a refractive index detector (RID-10A) and a Phenomenex Rezex RPM-monosaccharide column. The temperature was maintained at 85° C. and milli-Q water was used as the mobile phase at 0.6 mL min$^{-1}$ flow rate. Glucose, cellobiose, cellotriose, cellotetraose, and cellopentaose (Sigma) were used as standards. The integrated areas of peaks were analyzed by EZ start 7.2 SP1 software (Shimadzu).

For the experiments shown in FIG. 21, the ActE secretome (1 μg total protein); CelLcc_CBM3a (1 μg); ActE secretome (0.5 μg) and CelLcc_CBM3a (0.5 μg); or Spezyme CP (1 μg total protein) were used. The products of the enzyme reactions detected by HPLC were: ActE secretome, 95% cellobiose, 5% glucose; CelLcc_CBM3a reaction, 90% cellobiose, 10% glucose; ActE & CelLcc_CBM3a, 5% cellotetraose, 80% cellotriose, 15% cellobiose; Spezyme CP, 33% cellobiose, 67% glucose. All products could be converted to glucose in the presence of excess β-glucosidase.

CelLcc_CBM3a. The nucleotide and amino acid sequence of CelLcc_CBM3a is shown in FIG. 22. CelRcc_CBM3a is an engineered exoglucanase composed of the catalytic core of *C. thermocellum* CelL (Cthe_0405, residues 32 to 429) fused to a *C. thermocellum*-derived linker sequence and the CBM3a domain from Cthe_3077, the CipA scaffoldin. This construct was created to better understand the performance of enzymes that are normally targeted to the clostridial cellulosome. The replacement of the dockerin domain in Cthe_0405 with the CBM3a domain abrogates the need for a cellulosomal attachment to obtain maximal catalytic activity from CelLcc_CBM3a on solid substrates. The indicated nucleotide sequence was sub-cloned into wheat germ cell-free translation (Makino et al., 2010) and *E. coli* expression vectors (Blommel et al., 2009) for protein production. CelLcc_CBM3a was purified by standard immobilized metal (Ni$^{2+}$) chromatography. There was no difference in the specific activity of the protein prepared by these two methods.

Example 1

ActE Exhibits High Cellulolytic Activity Relative to other Cellulolytic Organisms Prokaryotes such as *Streptomyces* are often easier to grow than eukaryotes (i.e., fungi such as *T. reesei*), and aerobes are often easier and more energetically efficient to grow than anaerobes. *Streptomyces* may also have an advantage of producing antibiotics that limit the ability of other organisms to contaminate the culture medium during growth (Galm et al., 2011; Susi et al., 2011). This may be of advantage during large-scale culture with non-sterile biomass materials such as will be encountered in the biofuels industry.

Figure 6:
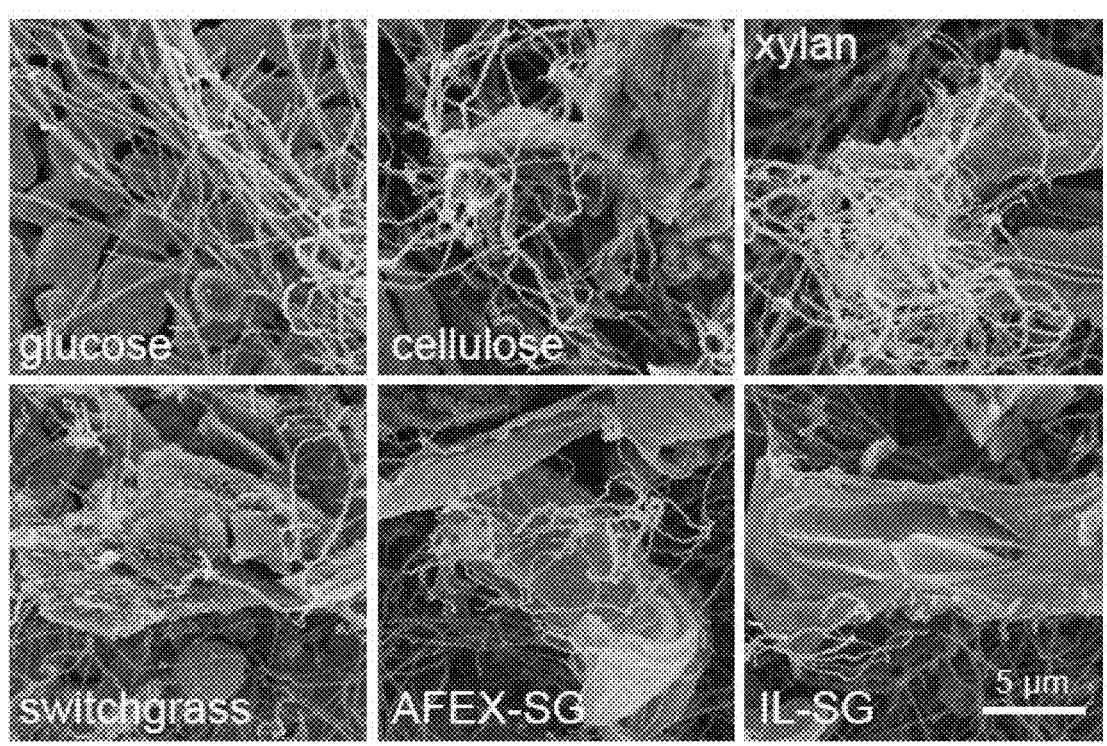
FIG. 6 is a set of scanning electron microscopy (SEM) images showing ActE grown on different carbon sources including glucose, cellulose, xylan, switchgrass, ammonia fiber expansion-treated switchgrass (AFEX-SG) and ionic liquid-treated switchgrass (IL-SG). ActE cells were grown in minimum medium with the indicated substrate as a sole carbon source for 7 days at 30° C. The scale bar indicates 5 μm.

When compared to other cellulolytic organisms (FIG. 1 and FIG. 6), ActE grows well on pure cellulose substances including amorphous cellulose (cellulose treated with phosphoric acid so as to remove all crystalline structure), filter paper (containing a mixture of amorphous and crystalline cellulose) and Sigmacell (primarily in the crystalline state as determined by X-ray powder diffraction), as well as other polysaccharides such as beta-1,3-glucan (callose), xylan, and chitin. ActE also grows well on biomass samples such as corn stover, ammonia-fiber expansion pretreated corn stover, switchgrass, ammonia-fiber expansion pretreated switchgrass, ionic liquids pretreated switchgrass, bleached spruce wood kraft pulp, and unbleached lodgepole pine kraft pulp.

FIG. 1 compares the ability of ActE, *S. coelicolor* A3(2) (NCBI taxonomy ID 100226) and *S. griseus* (NCBI CP002993.1; RefSeq: NC_015953.1) to grow in minimal medium containing filter paper as the only carbon and energy source. These images demonstrate the considerably different capabilities of the three ostensibly cellulolytic organisms. Thus ActE completely destroys the filter paper and achieves high cell density, while the two other, reputedly highly cellulolytic strains are only capable of weak colony formation attached to the filter paper. This result establishes that ActE has uniquely high cellulolytic capacity relative to other *Streptomyces* strains reported to also have this capability (Forsberg et al., 2011). In fact, the images of FIG. 1 and FIG. 6 demonstrate ActE has cellulolytic capacity rivaling that of *T. reesei* strain Rut-C30, which is widely acknowledged to be the industrial benchmark for cellulolytic capacity (Merino and Cherry, Adv. Biochem. Eng. Biotechnol. 108:95-120, 2007).

Example 2

Pretreatments Useful for Generating Fermentable Sugars

In the biofuels arena, the desired cellulose fractions of plant biomass are protected by the crystalline packing of the individual cellulose strands, and by the surrounding coating of hemicellulose and lignin. In order to most efficiently access the cellulose, chemical pretreatments are required to "loosen up" the plant cell wall structure. In this context, "loosen up" may mean removal of the lignin fraction, partial hydrolysis of feruloyl and acetyl esters present in hemicellulose, and changes in the crystallinity of the cellulose. An optimal pretreatment retains all fractions of biomass (i.e., lignin, hemicellulose and cellulose) in physical states that can be subsequently used by microbes and enzymes as substrates.

Ammonia-fiber expansion is a pretreatment that uses a combination of ammonia gas, low pressure, and low temperature to effect the loosening process (Balan et al., 2009; Chundawat et al., 2011; International Patent Publication No.: WO 2010/125679). It is particularly effective with grasses, and retains all fractions of the biomass for subsequent valorization without introducing water or salts into the biomass. Ionic liquids pretreatment comprises mixing a charged chemical substance (i.e., the ionic liquid) in equal mass proportions with the biomass material. Interactions between the ionic liquid substance and the biomass cause the crystalline structure of cellulose to convert to an amorphous state (Cheng et al., 2011; Li et al., 2011) but the biomass also becomes heavily contaminated with the ionic liquid during this pretreatment, requiring extensive washing with water, a valuable resource in many localities. Kraft pulping is a method for production of paper from wood that involves treatment of the biomass material with strong alkali, sodium sulfite and moderate temperature, resulting in destruction of the lignin and hemicellulose from the desired cellulose fraction; the final biomass material is also heavily contaminated with salts that also requires extensive washing with water to remove. Acid pretreatments retain the lignin and cellulose but destroy the hemicellulose fraction, and in doing so create toxic substances derived from the decomposition of hemicellulose. Because of the need to neutralize the acid, this pretreatment generates a large contamination of salt that also requires extensive washing with water. SPORL is an acidic pretreatment that uses sulfuric acid, elevated temperature, and sodium bisulfite to effect the pretreatment (Wang et al., 2009; Tian et al., 2011). In SPORL, the lignin and hemicellulose are destroyed and cellulose is recovered, but the cellulose is again heavily contaminated with salts and toxic substances derived from chemical decomposition of hemicellulose.

ActE secretomes are highly effective for degradation of lignocellulosic material pre-treated with AFEX. ActE secretomes are also effective for degrading lignocellulosic material pretreated with ionic liquids, Kraft pulping, acid or SPORL and for degrading untreated lignocellulosic material.

Example 3

ActE Genome has High Content of Genes Encoding Carbohydrate Active enZymes (CAZy) Relative to other Cellulolytic Organisms Protein-coding sequences of the ActE genome (Hyatt et al., 2010) were analyzed by BLAST comparison (Altschul et al., 1990) to the Carbohydrate Active enZyme (CAZy) database (Cantarel et al., 2009).

Table 2 compares the genomic characteristics of ActE with well-known soil-isolated *Streptomyces* that produce antibiotics and with two model cellulolytic bacteria, *Clostridium thermocellum* and *Cellvibrio japonicas* (Lynd, Weimer, et al., 2002; Deboy, et al., 2008; Riederer, et al., 2011). Putative biomass-degrading protein-coding sequences from ActE were identified by BLAST analysis of the finished genome to the Carbohydrate Active enZyme (CAZy) database. Among the 6357 predicted protein-coding genes, 167 have one or more domains assigned to CAZy families, including 119 glycoside hydrolases (GHs), 29 carbohydrate esterases (CEs), 6 polysaccharide lyases (PLs) and 85 carbohydrate binding modules (CBMs). ActE contains 45 different types of GH families, 4 PL families, 7 CE families, and 21 CBM families. The number of total CAZy domains and diversity of CAZy families is comparable to other highly cellulolytic organisms.

TABLE 2

Comparison of genomic composition.

|  | ActE | S. coelicolor | S. griseus | C. thermocellum | C. japonicus |
|---|---|---|---|---|---|
| Genome size (nt) | 7414440 | 8667507 | 8545929 | 3843301 | 4576573 |
| Proteome size | 6357 | 8153 | 7136 | 3173 | 3750 |
| Total CAZy Proteins | 167 | 221 | 132 | 103 | 183 |
| % CAZy Proteins[a] | 2.6% | 2.7% | 1.8% | 3.2% | 4.9% |
| Total GH[b] | 119 | 154 | 80 | 70 | 124 |
| Total PL[c] | 6 | 11 | 4 | 6 | 14 |
| Total CE[d] | 29 | 36 | 23 | 20 | 28 |
| Total CBM[e] | 85 | 98 | 68 | 121 | 134 |
| antiSMASH clusters[f] | 22 | 24 | 37 | 3 | 4 |
| Genes in clusters | 620 | 718 | 1139 | 89 | 111 |
| % antiSMASH | 9.8% | 8.8% | 16.0% | 2.8% | 3.0% |

[a]Proteins classified as Carbohydrate Active Enzymes (CAZy).
[b]GH, glycoside hydrolase.
[c]PL, pectate lyase.
[d]CE, carbohydrate esterase.
[e]CBM, carbohydrate binding module.
[f]Putative antibiotic producing gene cluster.

Nearly all publically available *Streptomyces* genomes encode a relatively high percentage of genes for putative cellulolytic enzymes. Interestingly, ActE and the antibiotic producing *Streptomyces*, *S. griseus* and *S. coelicolor*, shown in Table 2 have similar numbers and compositions of CAZy families, but substantially different genome sizes. However, these antibiotic-producing *Streptomyces* are not highly cellulolytic (FIG. 1). Relative to *S. griseus* and *S. coelicolor*, the ActE genome contains two unique CAZy families but does not possess 16 CAZy families present in these species. However, ActE contains more representatives in 13 CAZy families. Enrichment of certain CAZy families was observed in other highly cellulolytic organisms. For example, *C. thermocellum* contains 16 genes in the GH9 family alone. It is interesting to consider whether the reduction in total genome size and differences in CAZy composition between ActE and other closely related soil-dwelling *Streptomyces* might have arisen from evolutionary specialization of ActE, perhaps driven by association with the *Sirex*-fungal symbiosis.

Figure 3:
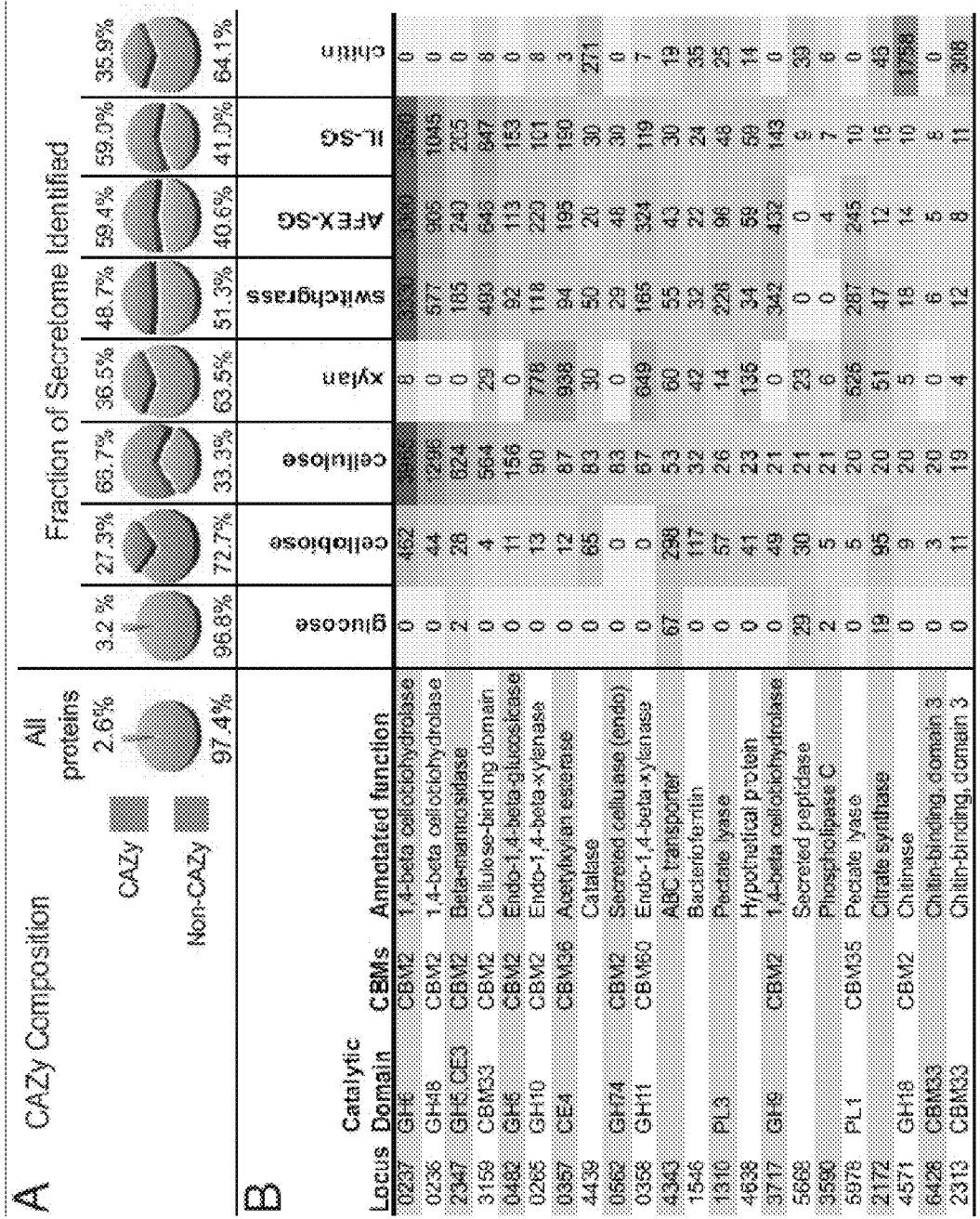
FIG. 3 is a table illustrating composition of ActE secretomes identified by LC-MS/MS. (A) CAZy genes account for 2.6% of the 6357 predicted protein-coding sequences in the ActE genome. (B) Identity of most abundant proteins in the cellulose secretome proteins is sorted according to decreasing spectral counts (accounting for 95% of total spectral counts); corresponding spectral counts from other secretomes are also shown.

ActE contained 12 CAZy families not found in the other model cellulolytic organisms shown in FIG. 3, including GHs, CBMs, and PLs. Seven other CAZy categories, primarily hemicellulases, were shared only with *T. reesei*. ActE had 23 GH, 10 CBM and 2 PL not found in *Thermobifida fusca*, another cellulolytic *Actinomycetales*, which had only 1 GH and 1 CBM not found in ActE. The genome sequence revealed *C. japonicus* (strain Ueda 107) is highly enriched in GH43 enzymes required for hemicellulose utilization, but is missing a key reducing end exocellulase (bacterial GH48) required for robust growth on cellulose [e.g., see page 5459 of (DeBoy et al., 2008)]; both of these enzyme families are present in highly cellulolytic ActE. Furthermore, ActE also contained 6 genes from the CBM33 family, recently shown to catalyze oxidative cleavage of chitin (Vaaje-Kolstad et al., 2010) and cellulose (Forsberg et al. 2011). Thus, ActE has genomic composition overlapping other cellulolytic organisms, but with notable expansion in the CAZy composition for both hydrolytic and oxidative enzymes and the presence of the complete set of enzymes required for efficient cellulose deconstruction.

Example 4

Genome-wide Gene Expression Analysis of ActE CAZy Gene

Figure 4:
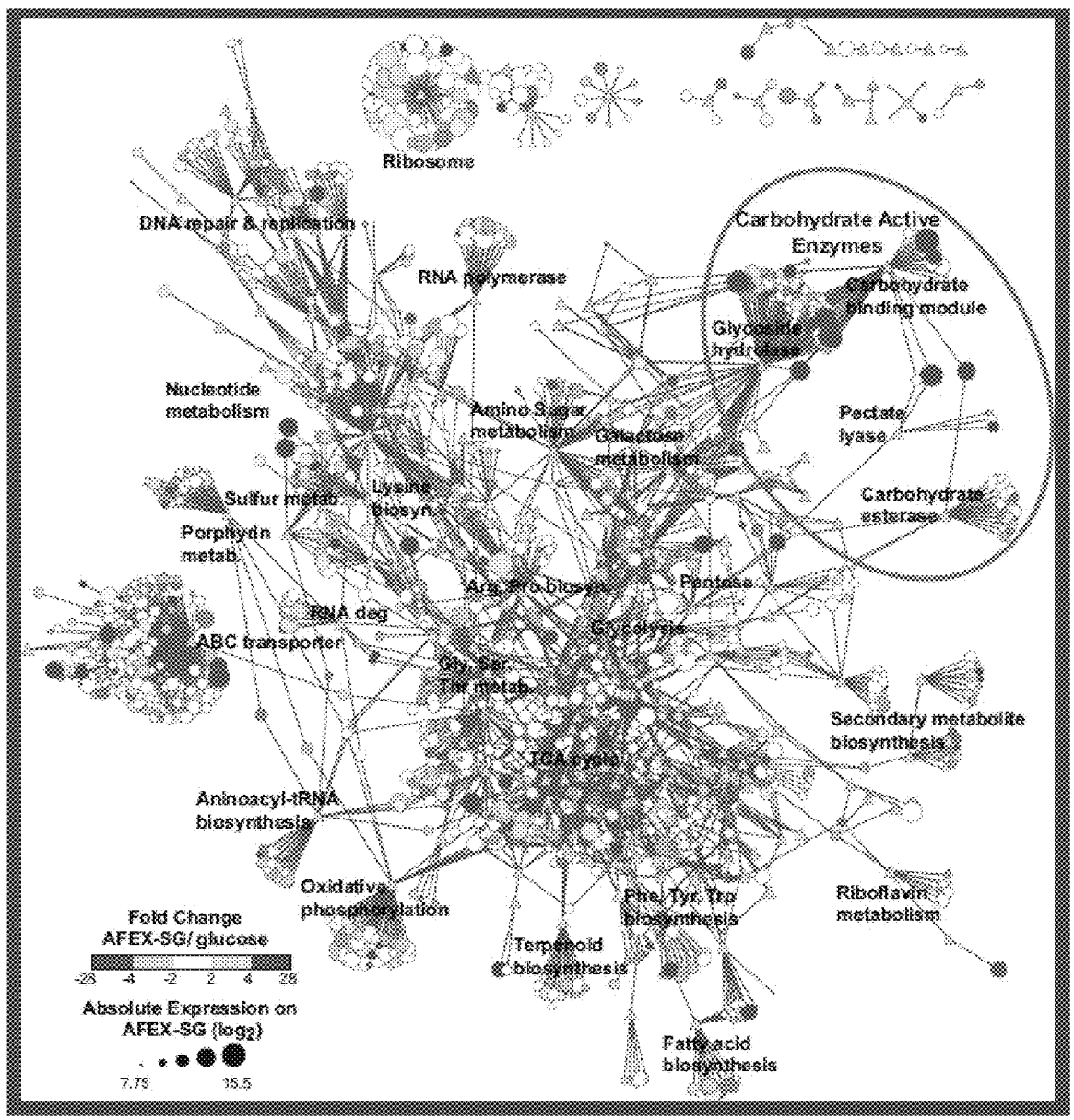
FIG. 4 is a systematic diagram showing genome-wide changes in expression during growth of ActE on AFEX-treated switchgrass (AFEX-SG) versus glucose. Nodes are genes (circles) or KEGG/CAZy functional categories (yellow triangles); edges indicate that the gene belongs to the indicated functional group as defined by either KEGG or CAZy analysis. Gene node sizes reflect expression intensity determined by microarray from growth on AFEX-SG as a $\log_2$ ratio, where the genome-wide average transcriptional intensity was ~10.5 for both substrates. Node colors represent expression changes as the $\log_2$ ratio of AFEX-SG/glucose transcript intensities.

Gene expression profiles were determined for ActE grown on purified polysaccharides and plant biomass by whole genome microarrays (FIGS. 4 and 5, FIGS. 9 to 14). Genome-wide gene expression was analyzed as a functional annotation network composed of ActE genes (circles) connected to predicted functional groups (triangles; KEGG or CAZy). In FIG. 4, the network was annotated with genome-wide microarray expression data to indicate genes that were differentially expressed when ActE was grown on either AFEX-SG or glucose, and further annotated to indicate normalized expression levels observed during growth on AFEX-SG. While many aspects of metabolism are modestly changed in response to these different carbon sources, the CAZy and ABC transporter categories were substantially enriched in differentially expressed genes (FIG. 4, green circles). Furthermore, pentose sugar metabolism, sulfur metabolism, and some amino acid biosynthesis pathways (e.g., aromatic amino acids) were also highly induced during growth on AFEX-SG relative to other carbon sources (FIGS. 9-14). In contrast, ribosomal, secondary metabolite, and DNA repair genes showed little change in expression across the conditions examined. Within the CAZy functional group, there was a large induction of genes that contained both a GH domain and a CBM2 domain. Among the 11 genes in the ActE genome that contain a CBM2 domain, 6 were induced greater than 4-fold during growth on AFEX-SG. Furthermore, 9 of the 11 CBM2 containing proteins were identified in the secreted proteome (FIG. 3).

Example 5

ActE CAZy Gene Expression is Dependent on ActE Growth Substrate

Figure 5:
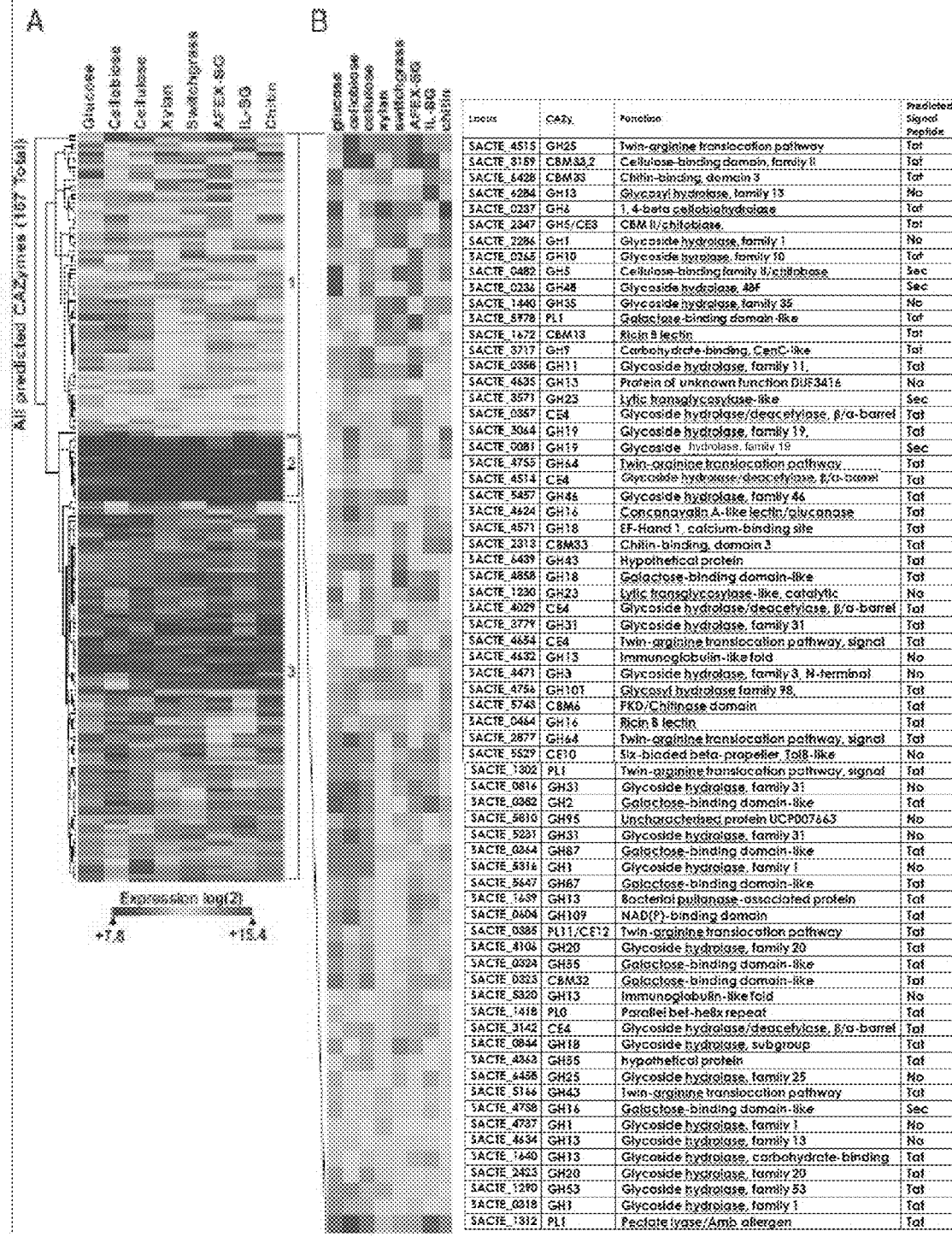
FIG. 5 is a diagram with a table showing expression of ActE CAZy genes on various carbon sources. (A) Hierarchical clustering of expression for 167 CAZy genes from the ActE genome during growth on the indicated substrates. (B) Identity of CAZy genes with distinct changes in expression observed in group 1 CAZy genes during growth in different carbon sources.

Given the large number of differentially expressed CAZy genes identified in the network analysis, Applicants analyzed the expression of this group of genes in cultures grown on different carbon sources (FIG. 5, FIG. 15 and FIG. 16). As with other cellulolytic organisms, there was strong correlation between the content of the secreted proteomes and the most highly expressed genes. Of the 167 ActE genes containing CAZy domains, 68 genes (FIG. 5, group 1) showed distinct increases in expression when grown on different polymeric substrates, 14 genes (FIG. 15, group 2) did not show any appreciable level of expression, and 85 genes (FIG. 16, group 3) showed moderate changes in expression with the different substrates. A significant fraction of these genes contained translocation signals for either the Sec or twin-arginine translocation pathways, and genes encoding structural polypeptides for these translocation pathways were also highly expressed. Besides correlation with secreted proteins, the transcriptomic studies also gave insight into co-regulated gene clusters that potentially encode functional units for utilization of different polysaccharides by ActE. In the following, the 130 genes with normalized expression intensities in the top 2% of all genes are described.

During growth on cellulose, four CAZy genes (SACTE_0236, SACTE_0237, SACTE_3159, and SACTE_0482) showed >15-fold increase in transcript abundance (FIG. 5), and the corresponding proteins were highly enriched in the secreted proteome. None of these four were obviously placed in a gene cluster, and the two most highly expressed genes, SACTE_0236 and SACTE_0237, while adjacent on the chromosome, were transcribed in opposite directions. Nevertheless, these four most highly expressed genes and three others that showed >5-fold increase in transcript abundance (SACTE_3717, SACTE_6428, SACTE_2347, Table 3) were associated with a conserved 14 bp palindromic promoter sequence, TGGGAGCGCTCCCA (the CebR binding element). CebR proteins are LacI/GalR-like transcriptional regulators shown to provide transcriptional control of gene expression in response to the presence of cellobiose or other small oligosaccharides in *S. griseus, S. reticuli*, and *Thermobifida fusca* (Marushima, Ohnishi, et al., 2009; Water and Schrempf, 1996; Deng and Fong, 2010). Likewise, the genes (SACTE_2285 to SACTE_2289) encoding a CebR regulator (SACTE_2285), a GH1 protein (β-glucosidase), a two-protein cellobiose transporter system, and an extracellular solute binding protein were associated with a CebR binding element and were also among the most highly expressed genes during growth on cellulose. These latter five genes have 75% or greater sequence identity with the cellobiose utilization operon identified in *S. griseus* and *S. reticuli* (Marushima, Ohnishi, et al., 2009; Schlosser and Schrempf, 1996). There were only 15 genes annotated as hypothetical or domain of unknown function (12%) up-regulated during growth on cellulose, a considerably smaller percentage of these than in the entire genome (27%).

TABLE 3

Analysis of upstream DNA sequence elements in ActE genes upregulated during growth on cellulose.

| Locus | Catalytic domain | CBM | Annotated function | Sequence[a] | Rank[b] | Fold change[b] |
|---|---|---|---|---|---|---|
| SACTE_0236 | GH48 | CBM2 | 1,4-beta cellobiohydrolase | TGGGAGCGCTCCCA | 1 | 21.7 |
| SACTE_0237 | GH6 | CBM2 | 1,4-beta cellobiohydrolase | TGGGAGCGCTCCCA | 2 | 17.3 |

TABLE 3-continued

Analysis of upstream DNA sequence elements in ActE genes upregulated during growth on cellulose.

| Locus | Catalytic domain | CBM | Annotated function | Sequence[a] | Rank[b] | Fold change[b] |
|---|---|---|---|---|---|---|
| SACTE_3159 | CBM33 | CBM2 | Cellulose-binding domain | TGGGAGCGCTCCCA | 3 | 16.2 |
| SACTE_0482 | GH5 | CBM2 | Endo-1,4-beta-glucosidase | TGGGAGCGCTCCCA | 4 | 15.4 |
| SACTE_2288 | | | Transport systems inner membrane component | TGGGAGCGCTCCCA | 5 | 11.2 |
| SACTE_3717 | GH9 | CBM2 | 1,4-beta cellobiohydrolase | TGGGAGCGCTCCCA | 6 | 9.7 |
| SACTE_6428 | CBM33 | | Chitin-binding, domain 3 | GGGAGCGCTCCA | 9 | 7.9 |
| SACTE_2347 | GH5 | CBM2 | Beta-mannosidase | TGGGAGCGCTCCCA | 11 | 5.0 |
| SACTE_2287 | | | Transport systems inner membrane component | TGGGAGCGCTCCCA | 15 | 4.3 |
| SACTE_2289 | | | Family 1 extracellular solute-binding protein | TGGGAGCGCTCCCA | 19 | 3.9 |
| SACTE_0352 | | | GCN5-related N-acetyltransferase | TGGGAGCGCTCCCA | 22 | 3.6 |
| SACTE_2286 | GH1 | | Glycoside hydrolase 1 | GGGAGCGCTCCA | 27 | 3.4 |
| SACTE_0483 | | CBM2 | Cellulose-binding family protein | GGGAGCGCTCCA | 503 | 1.6 |
| SACTE_0562 | GH74 | CBM2 | Secreted cellulase (endo) | TGGGAGCGCTCCCA | 5759 | 0.7 |
| SACTE_2285 | | | LacI family transcriptional regulator (CebR) | TGGGAGCGCTCCCA | 6229 | 0.6 |

[a] Predicted binding sequence element found upstream from gene locus.
[b] Ranking and fold change in expression intensity detected by microarray for ActE genes when grown on cellulose relative to glucose.

Several characteristics distinguished expression during growth on either xylan or chitin. First, unique sets of genes were induced, as there was only 14% and 10% overlap, respectively, when compared to cellulose. Second, ~33% of the top 2% of genes expressed during growth on either xylan or chitin were annotated as hypothetical or domain of unknown function, which greatly exceeds the unknown fraction in the cellulose secretome. During growth on xylan, two clusters of genes were up-regulated. One extended from SACTE_0357 to SACTE_0370, encoding proteins from the GH11, GH13, GH42, GH43, GH78, GH87, and CE4 families, a LacI-like transcriptional regulator, a secreted peptidase, and two sets of inner membrane transporters and associated solute binding proteins. Alternatively, during growth on chitin, three CBM33 proteins were up-regulated (SACTE_0080, SACTE_2313, SACTE_6493), and two of these had an immediately adjacent gene encoding a GH18 (SACTE_6494) or GH19 (SACTE_0081) that was up-regulated.

When ActE was grown on biomass samples, 14 additional CAZy genes were uniquely up regulated, and the corresponding proteins were identified in the proteomic analysis of biomass secretomes (FIGS. 3 and 4). A gene cluster extending from SACTE_5858 to SACTE_5864 was uniquely up regulated during growth on biomass. Among these genes, SACTE_5860 and SACTE_5862 are annotated as a twin-arginine translocation pathway protein and an ABC transporter, respectively, while the rest are annotated either as hypothetical protein or as domain of unknown function.

Eight CAZy genes were >4-fold up-regulated during growth on cellulose, including endoglucanases, reducing and non-reducing end exoglucanases, xylanase and CBM33 proteins (FIG. 5, Table 4). During growth on xylan, eight CAZy genes were elevated >4-fold relative to glucose, including exoglucanase, xylanase, pectate lyase and other hemicellulases (Table 4). Furthermore, chitin-grown cells contained 2 up-regulated genes from CAZy families including chitinase (SACTE_4571) and a CBM33 protein [SACTE_2313, an ortholog of oxidative chitin oxidase from S. marcescens (Vaaje-Kolstad et al., 2010)]. Thus on a genome-wide basis ActE selectively expresses small, distinct sets of CAZy genes during growth on pure polysaccharides, which is distinct from the larger numbers of CAZy genes expressed by *T. reesei* (Herpoel-Gimbert et al., 2008), *C. thermocellum* (Raman et al., 2009; Riederer et al., 2011), and *T. fusca* (Chen and Wilson, 2007).

TABLE 4

*Streptomyces* sp. ActE genes with >4-fold expression increase during growth on pure polysaccharides.

| | CAZy | Annotation | Fold increase | | |
| --- | --- | --- | --- | --- | --- |
| | | | Sigmacell: glc | xylan: glc | chitin: glc |
| Sigmacell | | | | | |
| SACTE_6428 | CBM33 | Chitin-binding, domain 3 | 7.06 | 1.64 | 1.81 |
| SACTE_3159 | CBM33, 2 | Cellulose-binding domain, family II, bacterial type | 13.03 | 1.90 | 1.29 |
| SACTE_0358 | GH11, CBM60, 36 | Glycoside hydrolase, family 11, active site | 6.28 | 4.01 | 2.12 |
| SACTE_0236 | GH48, CBM2, 37 | Glycoside hydrolase, 48F | 19.00 | 4.93 | 3.91 |
| SACTE_0482 | GH5, CBM2 | Cellulose-binding family II/chitobiase, carbohydrate-binding domain | 11.84 | 3.01 | 2.00 |
| SACTE_2347 | GH5, CE3, CBM2, 37 | Cellulose-binding family II/chitobiase, carbohydrate-binding domain | 4.46 | 1.17 | 0.99 |
| SACTE_0237 | GH6, CBM2 | 1,4-beta cellobiohydrolase | 15.33 | 1.12 | 0.77 |
| SACTE_3717 | GH9, CBM4, 2 | Carbohydrate-binding, CenC-like | 8.03 | 2.61 | 1.55 |
| SACTE_2288 | | Binding-protein-dependent transport systems inner membrane component | 11.05 | 4.76 | 3.26 |
| SACTE_0168 | | Transcription regulator LuxR, C-terminal | 7.55 | 1.53 | 1.37 |
| SACTE_0169 | | Glyceraldehyde 3-phosphate dehydrogenase, active site | 5.01 | 0.75 | 1.08 |
| SACTE_3594 | | Peptidase S1C, HrtA/DegP2/Q/S | 4.52 | 3.36 | 2.70 |
| SACTE_5228 | | Binding-protein-dependent transport systems inner membrane component | 4.20 | 4.35 | 3.24 |
| Xylan | | | | | |
| SACTE_4029 | CE4 | Glycoside hydrolase/deacetylase, beta/alpha-barrel | 1.07 | 4.35 | 2.22 |
| SACTE_0358 | GH11, CBM60, 36 | Glycoside hydrolase, family 11, active site | 6.28 | 4.01 | 2.12 |
| SACTE_0382 | GH2, CBM42 | Galactose-binding domain-like | 1.79 | 4.18 | 2.46 |
| SACTE_1230 | GH23 | Lytic transglycosylase-like, catalytic | 1.29 | 5.64 | 3.70 |
| SACTE_0816 | GH31 | Glycoside hydrolase, family 31 | 1.53 | 4.51 | 3.27 |
| SACTE_0236 | GH48, CBM2, 37 | Glycoside hydrolase, 48F | 19.00 | 4.93 | 3.91 |
| SACTE_1290 | GH53, CBM61 | Galactose-binding domain-like | 1.43 | 4.73 | 2.40 |
| SACTE_5978 | PL1, CBM35 | Galactose-binding domain-like | 2.00 | 6.86 | 2.12 |
| SACTE_5325 | | Binding-protein-dependent transport systems inner membrane component | 1.78 | 8.26 | 3.76 |
| SACTE_6023 | | Galactose-binding domain-like | 1.92 | 7.84 | 3.34 |
| SACTE_1834 | | Alkaline phosphatase D-related | 1.78 | 7.73 | 3.98 |
| SACTE_6100 | | Sulfate transporter | 2.07 | 7.45 | 4.75 |
| SACTE_5361 | | hypothetical protein | 1.77 | 7.20 | 3.94 |
| SACTE_5163 | | Lambda repressor-like, DNA-binding | 1.47 | 6.89 | 3.29 |
| SACTE_6365 | | Isocitrate lyase/phosphorylmutase | 1.88 | 6.82 | 4.01 |
| SACTE_0254 | | Thiolase-like | 2.13 | 6.76 | 5.02 |
| SACTE_6478 | | FAD-dependent pyridine nucleotide-disulfide oxidoreductase | 2.00 | 6.72 | 4.46 |
| SACTE_3570 | | hypothetical protein | 1.61 | 6.71 | 3.72 |
| SACTE_0590 | | Polyketide cyclase/dehydrase | 1.55 | 6.67 | 4.42 |
| SACTE_3152 | | Twin-arginine translocation pathway, signal sequence | 1.41 | 6.60 | 2.98 |

TABLE 4-continued

*Streptomyces* sp. ActE genes with >4-fold expression increase during growth on pure polysaccharides.

| CAZy | Annotation | Fold increase | | |
|---|---|---|---|---|
| | | Sigmacell: glc | xylan: glc | chitin: glc |
| SACTE_5285 | Bacterial bifunctional deaminase-reductase, C-terminal | 1.71 | 6.54 | 3.33 |
| SACTE_1383 | Glycerophosphoryl diester phosphodiesterase | 1.08 | 6.50 | 3.51 |
| SACTE_4333 | Binding-protein-dependent transport systems inner membrane component | 1.37 | 6.46 | 3.58 |
| SACTE_3876 | hypothetical protein | 1.21 | 6.42 | 2.73 |
| SACTE_6340 | Monooxygenase, FAD-binding | 2.82 | 6.27 | 3.69 |
| SACTE_4237 | hypothetical protein | 1.82 | 6.27 | 2.91 |
| SACTE_5136 | NAD(P)-binding domain | 2.20 | 6.27 | 2.87 |
| SACTE_6561 | hypothetical protein | 2.92 | 6.06 | 5.65 |
| SACTE_0686 | Transcription regulator AsnC-type | 0.88 | 6.04 | 2.72 |
| SACTE_0817 | NUDIX hydrolase, conserved site | 1.96 | 6.03 | 3.19 |
| SACTE_3004 | Type II secretion system F domain | 1.67 | 6.01 | 4.18 |
| SACTE_1835 | DoxX | 1.66 | 5.97 | 3.30 |
| SACTE_1933 | hypothetical protein | 0.93 | 5.96 | 2.77 |
| SACTE_6290 | Glyoxalase/bleomycin resistance protein/dioxygenase | 1.86 | 5.95 | 4.10 |
| SACTE_5583 | hypothetical protein | 1.33 | 5.87 | 4.56 |
| SACTE_0586 | hypothetical protein | 1.40 | 5.81 | 2.90 |
| SACTE_0046 | NADH: flavin oxidoreductase/NADH oxidase, N-terminal | 2.48 | 5.75 | 4.56 |
| SACTE_1096 | Mandelate racemase/muconate lactonizing enzyme, N-terminal | 1.19 | 5.73 | 3.32 |
| SACTE_2897 | hypothetical protein | 1.18 | 5.73 | 3.81 |
| SACTE_5359 | Rhs repeat-associated core | 1.30 | 5.70 | 2.41 |
| SACTE_0200 | hypothetical protein | 1.34 | 5.67 | 3.64 |
| SACTE_0018 | hypothetical protein | 1.67 | 5.63 | 3.58 |
| SACTE_5542 | hypothetical protein | 2.03 | 5.61 | 3.52 |
| SACTE_3137 | hypothetical protein | 1.46 | 5.61 | 3.91 |
| SACTE_0017 | DNA helicase, UvrD/REP type | 2.32 | 5.58 | 4.26 |
| SACTE_0672 | hypothetical protein | 1.53 | 5.54 | 3.20 |
| SACTE_1393 | Urease, beta subunit | 2.08 | 5.53 | 3.67 |
| SACTE_0064 | Transcription regulator PadR N-terminal-like | 2.17 | 5.52 | 3.07 |
| SACTE_1168 | Peptidase S1/S6, chymotrypsin/Hap | 0.98 | 5.51 | 3.36 |
| SACTE_6371 | hypothetical protein | 1.37 | 5.51 | 3.44 |
| SACTE_4334 | Binding-protein-dependent transport systems inner membrane component | 1.46 | 5.50 | 3.35 |
| SACTE_2457 | CDP-glycerol glycerophosphotransferase | 1.07 | 5.48 | 3.79 |
| SACTE_4734 | Binding-protein-dependent transport systems inner membrane component | 1.21 | 5.44 | 3.31 |
| SACTE_3661 | hypothetical protein | 1.76 | 5.44 | 3.25 |
| SACTE_0036 | hypothetical protein | 1.75 | 5.43 | 2.99 |
| SACTE_6005 | Citrate synthase-like, core | 1.01 | 5.38 | 2.90 |
| SACTE_6562 | hypothetical protein | 2.34 | 5.36 | 3.37 |
| SACTE_1937 | Major facilitator superfamily MFS-1 | 0.88 | 5.34 | 3.02 |
| SACTE_6220 | Dodecin flavoprotein | 2.13 | 5.32 | 5.08 |
| SACTE_0778 | FMN-binding split barrel | 1.13 | 5.28 | 2.72 |
| SACTE_5672 | Acyltransferase 3 | 1.33 | 5.28 | 3.09 |
| SACTE_5989 | Cysteine-rich domain | 1.40 | 5.24 | 3.11 |
| SACTE_5296 | HTH transcriptional regulator, MarR | 1.42 | 5.22 | 2.96 |
| SACTE_2021 | hypothetical protein | 1.44 | 5.17 | 2.54 |
| SACTE_1845 | Transposase, IS4-like | 1.69 | 5.16 | 3.30 |
| SACTE_1771 | Phage T4-like virus tail tube gp19 | 1.55 | 5.10 | 1.71 |
| SACTE_2583 | hypothetical protein | 1.38 | 5.10 | 3.11 |

TABLE 4-continued

*Streptomyces* sp. ActE genes with >4-fold expression increase during growth on pure polysaccharides.

| CAZy | Annotation | Fold increase | | |
|---|---|---|---|---|
| | | Sigmacell: glc | xylan: glc | chitin: glc |
| SACTE_5957 | Helix-turn-helix, HxlR type | 2.38 | 5.09 | 3.95 |
| SACTE_4642 | hypothetical protein | 1.31 | 5.08 | 3.05 |
| SACTE_3695 | Aminoglycoside/hydroxyurea antibiotic resistance kinase | 1.41 | 5.03 | 3.76 |
| SACTE_0079 | ATPase-like, ATP-binding domain | 2.21 | 5.01 | 2.98 |
| SACTE_0727 | hypothetical protein | 2.54 | 5.00 | 3.88 |
| SACTE_0019 | hypothetical protein | 1.37 | 5.00 | 2.40 |
| SACTE_6422 | *Streptomyces* cyclase/dehydrase | 2.40 | 4.99 | 3.57 |
| SACTE_4348 | Bacterial extracellular solute-binding protein, family 5 | 1.60 | 4.97 | 3.06 |
| SACTE_5318 | Forkhead-associated (FHA) domain | 1.50 | 4.93 | 2.84 |
| SACTE_5413 | Urease accessory protein UreF | 1.94 | 4.93 | 2.52 |
| SACTE_5434 | Glutathione S-transferase, C-terminal-like | 2.41 | 4.93 | 2.96 |
| SACTE_6061 | Glyoxalase/bleomycin resistance protein/dioxygenase | 1.61 | 4.92 | 2.18 |
| SACTE_0025 | hypothetical protein | 1.58 | 4.92 | 4.22 |
| SACTE_5552 | Transposase, IS4-like | 1.94 | 4.92 | 3.26 |
| SACTE_4156 | HTH transcriptional regulator, LysR | 1.57 | 4.86 | 2.81 |
| SACTE_5600 | hypothetical protein | 1.78 | 4.83 | 2.01 |
| SACTE_5331 | Conserved hypothetical protein CHP03086 | 1.56 | 4.82 | 2.96 |
| SACTE_0784 | hypothetical protein | 1.43 | 4.80 | 2.65 |
| SACTE_0045 | NAD(P)-binding domain | 1.74 | 4.78 | 3.35 |
| SACTE_5426 | Twin-arginine translocation pathway, signal sequence | 0.80 | 4.77 | 2.68 |
| SACTE_2654 | 4Fe—4S ferredoxin, iron-sulfur binding domain | 1.30 | 4.77 | 2.68 |
| SACTE_2288 | Binding-protein-dependent transport systems inner membrane component | 11.05 | 4.76 | 3.26 |
| SACTE_2324 | Membrane insertion protein, OxaA/YidC, core | 0.91 | 4.75 | 2.58 |
| SACTE_0142 | Amidohydrolase 2 | 1.28 | 4.71 | 2.65 |
| SACTE_0787 | hypothetical protein | 1.66 | 4.70 | 2.93 |
| SACTE_5790 | hypothetical protein | 1.28 | 4.69 | 2.83 |
| SACTE_6291 | hypothetical protein | 1.25 | 4.68 | 3.13 |
| SACTE_6499 | hypothetical protein | 1.66 | 4.67 | 3.29 |
| SACTE_6548 | Lytic transglycosylase-like, catalytic | 1.97 | 4.66 | 3.20 |
| SACTE_3087 | Major facilitator superfamily MFS-1 | 1.30 | 4.66 | 3.26 |
| SACTE_5512 | hypothetical protein | 1.79 | 4.64 | 3.48 |
| SACTE_0491 | hypothetical protein | 2.44 | 4.63 | 2.71 |
| SACTE_0312 | Thiamine pyrophosphate enzyme, C-terminal TPP-binding | 2.32 | 4.60 | 3.49 |
| SACTE_6130 | hypothetical protein | 1.47 | 4.55 | 2.64 |
| SACTE_3787 | Helix-turn-helix type 3 | 1.38 | 4.53 | 2.73 |
| SACTE_0040 | hypothetical protein | 1.64 | 4.52 | 4.80 |
| SACTE_2461 | Macrocin-O-methyltransferase | 1.07 | 4.51 | 3.00 |
| SACTE_5041 | hypothetical protein | 1.50 | 4.49 | 3.25 |
| SACTE_5540 | Transposase, IS204/IS1001/IS1096/IS1165 | 1.79 | 4.49 | 2.99 |
| SACTE_0776 | Protein of unknown function DUF6, transmembrane | 1.34 | 4.48 | 2.52 |
| SACTE_0785 | Bacterial TniB | 1.67 | 4.43 | 2.93 |
| SACTE_0360 | Binding-protein-dependent transport systems inner membrane component | 1.70 | 4.43 | 2.39 |
| SACTE_3569 | Protein of unknown function DUF1023 | 1.00 | 4.42 | 2.78 |
| SACTE_2986 | hypothetical protein | 1.62 | 4.42 | 2.96 |
| SACTE_4732 | Twin-arginine translocation pathway, signal sequence | 2.08 | 4.41 | 2.72 |

TABLE 4-continued

*Streptomyces* sp. ActE genes with >4-fold expression increase during growth on pure polysaccharides.

| CAZy | Annotation | Fold increase | | |
|---|---|---|---|---|
| | | Sigmacell: glc | xylan: glc | chitin: glc |
| SACTE_5228 | Binding-protein-dependent transport systems inner membrane component | 4.20 | 4.35 | 3.24 |
| SACTE_0406 | Binding-protein-dependent transport systems inner membrane component | 1.34 | 4.35 | 2.52 |
| SACTE_6516 | Binding-protein-dependent transport systems inner membrane component | 2.24 | 4.34 | 3.41 |
| SACTE_1781 | hypothetical protein | 1.16 | 4.34 | 2.56 |
| SACTE_5936 | Radical SAM | 1.43 | 4.33 | 2.23 |
| SACTE_0819 | Protein of unknown function DUF962 | 1.50 | 4.33 | 2.83 |
| SACTE_4539 | NERD | 1.42 | 4.32 | 3.98 |
| SACTE_0532 | Binding-protein-dependent transport systems inner membrane component | 3.47 | 4.31 | 2.42 |
| SACTE_3300 | hypothetical protein | 1.68 | 4.31 | 2.59 |
| SACTE_6277 | hypothetical protein | 2.24 | 4.31 | 3.11 |
| SACTE_0941 | Twin-arginine translocation pathway, signal sequence | 1.32 | 4.30 | 2.63 |
| SACTE_1115 | GntR, C-terminal | 1.57 | 4.29 | 2.63 |
| SACTE_6105 | Fatty acid hydroxylase | 1.63 | 4.29 | 2.78 |
| SACTE_4407 | Spherulation-specific family 4 | 1.19 | 4.29 | 4.15 |
| SACTE_5387 | hypothetical protein | 1.24 | 4.27 | 3.08 |
| SACTE_5053 | NmrA-like | 1.23 | 4.27 | 3.05 |
| SACTE_5562 | Amino acid ABC transporter, permease protein, 3-TM domain, His/Glu/Gln/Arg/opine family | 1.37 | 4.26 | 3.75 |
| SACTE_5522 | Galactose-binding domain-like | 1.82 | 4.26 | 2.62 |
| SACTE_5484 | Transcription regulator, TetR-like, DNA-binding, bacterial/archaeal | 1.45 | 4.21 | 3.24 |
| SACTE_6526 | Restriction endonuclease, type IV-like, Mrr | 2.31 | 4.20 | 2.40 |
| SACTE_4164 | hypothetical protein | 1.06 | 4.19 | 2.48 |
| SACTE_4979 | Transcription regulator, TetR-like, DNA-binding, bacterial/archaeal | 1.20 | 4.19 | 2.34 |
| SACTE_0952 | hypothetical protein | 1.33 | 4.18 | 2.02 |
| SACTE_1785 | hypothetical protein | 1.25 | 4.17 | 1.94 |
| SACTE_3454 | hypothetical protein | 1.46 | 4.16 | 2.32 |
| SACTE_1271 | Class II aldolase/adducin, N-terminal | 1.77 | 4.16 | 2.65 |
| SACTE_1760 | hypothetical protein | 1.38 | 4.13 | 2.07 |
| SACTE_0035 | hypothetical protein | 1.93 | 4.13 | 3.13 |
| SACTE_0247 | Protein of unknown function DUF2241 | 1.30 | 4.10 | 2.77 |
| SACTE_3796 | F420-dependent enzyme, PPOX class, family Rv2061, putative | 1.43 | 4.10 | 3.33 |
| SACTE_4641 | hypothetical protein | 1.43 | 4.09 | 2.60 |
| SACTE_4816 | Peptidase S26, conserved region | 1.17 | 4.09 | 2.77 |
| SACTE_2331 | Major facilitator superfamily MFS-1 | 1.15 | 4.08 | 2.20 |
| SACTE_1666 | hypothetical protein | 1.44 | 4.07 | 2.46 |
| SACTE_5867 | Mammalian cell entry, mce1C | 1.79 | 4.07 | 2.92 |
| SACTE_2705 | AMP-binding, conserved site | 1.38 | 4.07 | 2.75 |
| SACTE_6014 | Binding-protein-dependent transport systems inner membrane component | 0.89 | 4.07 | 2.51 |
| SACTE_2018 | Putative DNA binding domain | 1.05 | 4.06 | 2.63 |
| SACTE_5690 | Gluconate transporter | 1.00 | 4.05 | 2.29 |
| SACTE_3243 | hypothetical protein | 0.91 | 4.05 | 2.23 |
| SACTE_0786 | Polynucleotidyl transferase, ribonuclease H fold | 1.81 | 4.03 | 2.98 |
| SACTE_6450 | Rhamnose isomerase related | 2.72 | 4.02 | 2.90 |
| SACTE_0097 | Beta-lactamase-related | 1.70 | 4.02 | 2.52 |

TABLE 4-continued

*Streptomyces* sp. ActE genes with >4-fold expression increase during growth on pure polysaccharides.

|  | CAZy | Annotation | Fold increase | | |
|---|---|---|---|---|---|
|  |  |  | Sigmacell: glc | xylan: glc | chitin: glc |
| SACTE_6341 |  | FMN-binding split barrel, related | 1.82 | 4.01 | 2.45 |
| SACTE_1483 |  | hypothetical protein | 0.82 | 4.01 | 2.75 |
| SACTE_0754 |  | Uncharacterised protein family UPF0060 | 1.21 | 4.00 | 2.51 |
| SACTE_5308 |  | Winged helix-turn-helix transcription repressor DNA-binding | 1.33 | 4.00 | 1.56 |
| SACTE_5862 |  | ABC transporter, conserved site | 1.87 | 4.00 | 3.05 |
| Chitin |  |  |  |  |  |
| SACTE_2313 | CBM33 | Chitin-binding, domain 3 | 1.08 | 1.24 | 4.77 |
| SACTE_4571 | GH18, CBM57, 2 | EF-Hand 1, calcium-binding site | 0.88 | 1.37 | 4.08 |
| SACTE_5381 |  | hypothetical protein | 1.31 | 3.09 | 10.06 |
| SACTE_5386 |  | hypothetical protein | 0.96 | 1.59 | 8.49 |
| SACTE_1949 |  | Peptidase M4, thermolysin | 1.30 | 2.16 | 7.57 |
| SACTE_6519 |  | Binding-protein-dependent transport systems inner membrane component | 2.00 | 3.04 | 7.36 |
| SACTE_0243 |  | Protein kinase-like domain | 1.68 | 2.55 | 6.89 |
| SACTE_6520 |  | ABC transporter, conserved site | 1.03 | 1.18 | 6.25 |
| SACTE_5384 |  | hypothetical protein | 1.16 | 2.39 | 5.99 |
| SACTE_6463 |  | hypothetical protein | 1.28 | 2.52 | 5.85 |
| SACTE_6561 |  | hypothetical protein | 2.92 | 6.06 | 5.65 |
| SACTE_5383 |  | hypothetical protein | 1.06 | 1.69 | 5.28 |
| SACTE_6518 |  | hypothetical protein | 1.66 | 1.91 | 5.21 |
| SACTE_4797 |  | hypothetical protein | 2.22 | 0.34 | 5.19 |
| SACTE_6170 |  | Domain of unknown function DUF1996 | 1.47 | 3.49 | 5.12 |
| SACTE_6220 |  | Dodecin flavoprotein | 2.13 | 5.32 | 5.08 |
| SACTE_0254 |  | Thiolase-like | 2.13 | 6.76 | 5.02 |
| SACTE_2678 |  | Protein of unknown function DUF397 | 1.40 | 1.13 | 5.02 |
| SACTE_5968 |  | hypothetical protein | 1.58 | 1.31 | 4.90 |
| SACTE_4757 |  | Acetyl-coenzyme A carboxyltransferase, C-terminal | 1.64 | 0.59 | 4.86 |
| SACTE_0040 |  | hypothetical protein | 1.64 | 4.52 | 4.80 |
| SACTE_6100 |  | Sulfate transporter | 2.07 | 7.45 | 4.75 |
| SACTE_1833 |  | Twin-arginine translocation pathway, signal sequence | 1.64 | 1.56 | 4.64 |
| SACTE_5583 |  | hypothetical protein | 1.33 | 5.87 | 4.56 |
| SACTE_0046 |  | NADH: flavin oxidoreductase/NADH oxidase, N-terminal | 2.48 | 5.75 | 4.56 |
| SACTE_5398 |  | hypothetical protein | 1.45 | 1.73 | 4.55 |
| SACTE_6144 |  | Twin-arginine translocation pathway, signal sequence | 1.21 | 1.13 | 4.52 |
| SACTE_6478 |  | FAD-dependent pyridine nucleotide-disulfide oxidoreductase | 2.00 | 6.72 | 4.46 |
| SACTE_0590 |  | Polyketide cyclase/dehydrase | 1.55 | 6.67 | 4.42 |
| SACTE_2112 |  | Homeodomain-like | 1.44 | 1.33 | 4.40 |
| SACTE_0017 |  | DNA helicase, UvrD/REP type | 2.32 | 5.58 | 4.26 |
| SACTE_5841 |  | Protein of unknown function, ATP binding | 1.90 | 3.09 | 4.24 |
| SACTE_0025 |  | hypothetical protein | 1.58 | 4.92 | 4.22 |
| SACTE_3004 |  | Type II secretion system F domain | 1.67 | 6.01 | 4.18 |
| SACTE_4407 |  | Spherulation-specific family 4 | 1.19 | 4.29 | 4.15 |
| SACTE_0307 |  | Protein of unknown function DUF320, *Streptomyces* species | 1.13 | 1.79 | 4.15 |
| SACTE_6290 |  | Glyoxalase/bleomycin resistance protein/dioxygenase | 1.86 | 5.95 | 4.10 |
| SACTE_5286 |  | hypothetical protein | 1.33 | 3.34 | 4.07 |
| SACTE_5953 |  | Protein of unknown function, ATP binding | 1.35 | 2.11 | 4.05 |

TABLE 4-continued

Streptomyces sp. ActE genes with >4-fold expression increase during growth on pure polysaccharides.

| CAZy | Annotation | Fold increase | | |
|---|---|---|---|---|
| | | Sigmacell: glc | xylan: glc | chitin: glc |
| SACTE_6365 | Isocitrate lyase/phosphorylmutase | 1.88 | 6.82 | 4.01 |

Example 6

Composition of ActE Secretome is Dependent on ActE Growth Substrate

To identify secreted proteins, supernatants from ActE cultures grown on glucose, cellobiose, cellulose, xylan, chitin, switchgrass, AFEX-SG, and IL-SG were analyzed by LC-MS/MS (FIG. 3 and FIG. 18). The proteins were sorted into a descending rank according to spectral counts, and sets whose spectral counts summed to 95% of the total protein in each secretome are shown. FIG. 3A summarizes the percentages of CAZy families in the detected proteins. The glucose secretome had a protein concentration of ~0.03 g/L of culture medium, and among the 136 proteins identified only 3% had a CAZy annotation. Indeed, the majority (>90%) likely originated from cell lysis. In contrast, the polysaccharide secretomes had a protein concentration of ~0.3 g/L of culture medium, a ~10-fold increase from the glucose secretome. Pectate lyase (SACTE_1310), chondroitin/alginate lyase (SACTE_4638), an extracellular solute binding protein (SACTE_4343), bacterioferritin (SACTE_1546), and catalase (SACTE_4439) were observed in all polysaccharide secretomes. The first two proteins, SACTE_1310 and SACTE_4638, have signal peptides and are thus secreted as part of the response needed for growth on polysaccharides.

FIG. 3 and FIG. 18 further demonstrate that 22 proteins accounted for 95% of the total spectral counts during growth on cellulose; two-thirds were from CAZy families. The five most abundant proteins, in order and representing ~85% of the total spectral counts, were reducing and non-reducing exoglucanases (SACTE_0236 and SACTE_0237), a CBM33 polysaccharide monooxygenase (SACTE_3159), an endoglucanase (SACTE_0482), and a β-mannosidase (SACTE_2347). The first four proteins encode a non-redundant set of enzymes that likely provide the essential activities required for utilization of crystalline cellulose (Deboy, et al., 2008). Among the 22 most abundant proteins, there were representatives from 9 different GH families, two CE families, two PL families, and two additional CMB33 proteins. Collectively, these secreted proteins represent ~20% of the CAZy composition in the ActE genome.

There were substantial differences in the composition of the xylan and chitin secretomes as compared to the cellulose secretome (FIG. 3 and FIG. 18). In the xylan secretome, 92 proteins comprise 95% of the detected spectral counts. Twenty GHs from 18 different CAZy families were included, along with 1 CE4 and 2 PL family proteins. Thus, growth on xylan elicits secretion of representatives from half of the total CAZy families found in the ActE genome. The broad distribution of hemicellulytic enzymes in the xylan secretome contrasts with the considerably less diverse composition of the chitin secretome, which consists of 7 representatives from GH18 (e.g., chitinase, endo beta-N-acetyl-glucosaminidase), 2 from GH19 (e.g., chitinase, lysozyme), and 1 chitinolytic CBM33 (FIG. 18). While chitinolytic CAZy families account for two-thirds of the proteins secreted during growth on chitin, they represent only ~6% of the diversity of CAZy families found in the genome. These results document the substantially different substrate-specific responses of ActE during growth on different polysaccharides.

The secretomes isolated from cells grown on switchgrass, AFEX-SG, and IL-SG contained the highly abundant secreted proteins identified in the purified cellulose and xylan experiments and some additional proteins. These additional proteins likely reflect cellular response to the more complex composition of polysaccharides present in the biomass samples. The increased diversity of proteins present in the biomass secretome also increased the efficiency of reaction with plant biomass (FIG. 2C). In total, the biomass secretomes contained 31 different CAZy families that contributed to the total spectral counts (~70% of the CAZy families present in the ActE genome), thus representing coordinated and extensive use of CAZyme families present in the ActE genome for biomass utilization.

The gene loci of the 117 proteins observed only in the glucose secretome are: SACTE_0494; SACTE_0514; SACTE_0541; SACTE_0548; SACTE_0604; SACTE_0669; SACTE_0687; SACTE_0800; SACTE_0810; SACTE_0899; SACTE_1006; SACTE_1045; SACTE_1068; SACTE_1069; SACTE_1111; SACTE_1201; SACTE_1240; SACTE_1285; SACTE_1328; SACTE_1344; SACTE_1368; SACTE_1419; SACTE_1426; SACTE_1506; SACTE_1522; SACTE_1586; SACTE_1650; SACTE_1861; SACTE_1888; SACTE_1934; SACTE_2036; SACTE_2049; SACTE_2068; SACTE_2238; SACTE_2403; SACTE_2431; SACTE_2468; SACTE_2558; SACTE_2645; SACTE_2729; SACTE_2755; SACTE_2756; SACTE_2801; SACTE_2819; SACTE_3012; SACTE_3037; SACTE_3067; SACTE_3086; SACTE_3088; SACTE_3097; SACTE_3219; SACTE_3327; SACTE_3361; SACTE_3371; SACTE_3385; SACTE_3389; SACTE_3392; SACTE_3414; SACTE_3438; SACTE_3511; SACTE_3604; SACTE_3716; SACTE_3896; SACTE_3948; SACTE_3955; SACTE_3956; SACTE_3960; SACTE_3961; SACTE_3989; SACTE_3995; SACTE_4030; SACTE_4031; SACTE_4038; SACTE_4039; SACTE_4073; SACTE_4081; SACTE_4083; SACTE_4145; SACTE_4191; SACTE_4194; SACTE_4205; SACTE_4224; SACTE_4281; SACTE_4283; SACTE_4376; SACTE_4397; SACTE_4399; SACTE_4415; SACTE_4462; SACTE_4501; SACTE_4550; SACTE_4565; SACTE_4566; SACTE_4567; SACTE_4568; SACTE_4591; SACTE_4610; SACTE_4616; SACTE_4618; SACTE_4652; SACTE_4718;

SACTE_4768; SACTE_4791; SACTE_4795; SACTE_4830; SACTE_4860; SACTE_4873; SACTE_4926; SACTE_4959; SACTE_5028; SACTE_5081; SACTE_5192; SACTE_5267; SACTE_5482; SACTE_5519; SACTE_5983; and SACTE_6342.

The gene loci of the 9 proteins observed only in the Sigmacell secretome are: SACTE_0236; SACTE_0482; SACTE_0562; SACTE_2313; SACTE_2347; SACTE_3590; SACTE_3717; SACTE_4571; and SACTE_6428.

The gene loci of the 46 proteins observed only in the xylan secretome are: SACTE_0081; SACTE_0169; SACTE_0365; SACTE_0379; SACTE_0383; SACTE_0464; SACTE_0528; SACTE_0549; SACTE_0634; SACTE_0880; SACTE_1003; SACTE_1130; SACTE_1239; SACTE_1324; SACTE_1325; SACTE_1356; SACTE_1364; SACTE_1367; SACTE_1603; SACTE_1680; SACTE_1858; SACTE_1949; SACTE_2768; SACTE_3064; SACTE_4231; SACTE_4246; SACTE_4363; SACTE_4459; SACTE_4483; SACTE_4515; SACTE_4607; SACTE_4612; SACTE_4624; SACTE_4730; SACTE_4755; SACTE_4858; SACTE_5166; SACTE_5230; SACTE_5231; SACTE_5418; SACTE_5457; SACTE_5630; SACTE_5647; SACTE_5682; SACTE_5751; and SACTE_6439.

In the xylan secretome, five proteins accounted for half of the total secreted protein. These were xylanases (GH10 and GH11, respectively; SACTE_0265, 9.7% and SACTE_0358, 8.1%), extracellular xylose isomerase (SACTE_5230, 12.7%), acetyl xylan esterase (CE4; SACTE_0357, 11.7%), and pectate lyase (PL1, SACTE_5978, 6.6%). Among the remaining 98 proteins, there were numerous GH families. Given the complexity of hemicellulose, which is enriched in xylan but also contains many other sugars and many different bonding linkages between these sugars, it is noted that these additional proteins represent many GH families associated with unique hemicellulolytic activities.

Although not analyzed in FIG. 34, the chitin secretome contained ten proteins from the chitinase GH18 (49% of total protein) and GH19 (21%) families. In addition, the CBM33 protein SACTE_2313, having 50% primary sequence identity with the CBP21 chitin oxygenase from *S. marcescens*, was also detected (3.9%). Insect molt and fungal hyphae provide abundant chitin, likely accounting for the utility of these enzymes in the natural environment. There were 50 other proteins (63 total) that comprised 95% of the chitin secretome. Relative to the glucose, Sigmacell, and xylan secretomes, the following 15 proteins were observed only in the chitin secretome: SACTE_0746, SACTE_0844, SACTE_0860, SACTE_1702, SACTE_2033, SACTE_2059, SACTE_2062, SACTE_2384, SACTE_3685, SACTE_4468, SACTE_4472, SACTE_4727, SACTE_5330, SACTE_5764, and SACTE_6494

The gene loci of the 19 proteins observed only in the switchgrass secretome are: SACTE_0642; SACTE_1130; SACTE_1250; SACTE_1858; SACTE_2033; SACTE_3012; SACTE_3777; SACTE_4198; SACTE_4571; SACTE_4624; SACTE_4669; SACTE_4676; SACTE_4718; SACTE_4738; SACTE_5220; SACTE_5418; SACTE_5685; SACTE_5751; and SACTE_5880.

The gene loci of the 8 proteins observed only in the IL-SG secretome are: SACTE_0132; SACTE_0880; SACTE_2556; SACTE_4246; SACTE_4515; SACTE_4702; SACTE_5231; and SACTE_5330.

There were no proteins observed only in the AFEX-SG secretome when compared to either the switchgrass or IL-SG secretomes.

Example 7

Minimized Size of ActE Enzymes Increases Specific Activity

Figure 23:
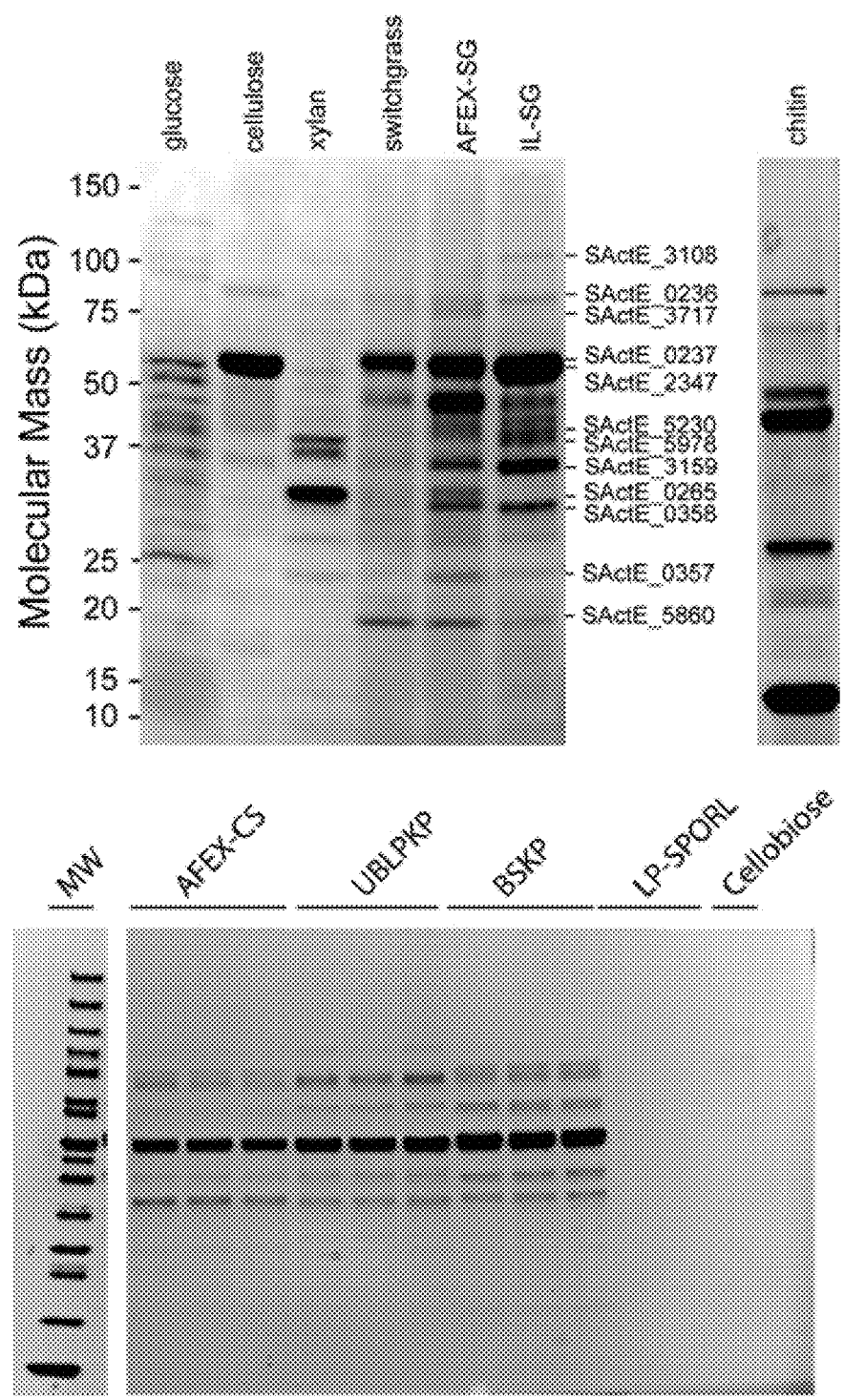
FIG. 23 is a graph illustrating SDS-PAGE of *Streptomyces* sp. ActE secretomes obtained from growth on minimal medium containing different substrates (SG, switchgrass; CS, corn stover; UBLPKP, unbleached lodgepole pine kraft pulp; BSKP, bleached spruce kraft pulp; LP-SPORL, lodgepole pine pretreated by sulfite pretreatment to overcome recalcitrance of lignocellulose (SPORL)). Culture secretomes were separated after 7 days of growth at 30° C. by centrifugation and concentrated by ultrafiltration. Sample loading was normalized to total protein. The identities of proteins were determined from samples extracted from the SDS-PAGE gel. Among the 162 proteins accounting for 95% of spectral counts from the glucose secretome, most were intracellular proteins originating from cell lysis during growth, and were not detected in the polysaccharide secretomes.

When ActE is grown on Sigmacell, AFEX-SG, IL-SG, AFEX-CS, unbleached lodgepole pine kraft pulp (UBLPKP) or bleached spruce wood kraft pulp (BSKP), the characteristic secretome consists of the proteins that permit deconstruction of these substrates into sugars that can be used for growth (FIG. 23). Interestingly, ActE is not capable of growing on lodgepole pine pretreated by SPORL, indicating this pretreatment produces toxins that inhibit the growth of highly cellulolytic microbes. When ActE is grown on cellobiose, which it does readily and rapidly, it produces a secretome that is distinct from those obtained from ActE grown on cellulose, xylan or biomass substrates, demonstrating that ActE has highly specific responses to different polymeric substances that are present in biomass. This behavior is distinct from that observed for *T. fusca*, another cellulolytic *Actinomycete*, and from *C. thermocellum*, where each organism produced similar sets of secreted proteins during growth on either cellulose or cellobiose (Chen and Wilson, 2007; Riederer et al., 2011). This result indicates ActE contains a unique regulatory mechanism for controlling cellulose deconstruction genes that can provide exquisite control of their production under desired circumstances.

For a single enzyme from a secretome, (Segel, Enzyme kinetics: behavior and analysis of rapid equilibrium and steady state enzyme systems. Wiley, New York, 1993) the specific activity (μmol/min/mg) is defined as mol of product formed per unit time (i.e., μmol/min) per unit mass of enzyme (i.e., mg). Specific activity is the parameter that must be used in making comparisons of catalytic properties between enzymes with different molecular masses. If two enzyme isoforms yield the same μmol/min, the isoform with the smaller molecular weight will, by definition, have the higher specific activity. In this application, it is relevant to consider the implications of a 10% or more reduction in the mass of an enzyme required to treat gigatonnes of biomass.

In the cellulose secretome, five proteins contributed ~85% of the total spectral counts. These were reducing and non-reducing end exoglucanases, endoglucanases, and CBM33 (SACTE_0237, SACTE_0236, SACTE_2347, SACTE_0482 and SACTE_3159); xylanase, another endoglucanase, and another CBM33 were also abundant (SACTE_0265, SACTE_3717 and SACTE_6428). According to the definition provided above, size minimization is a way to achieve the desired increases in specific activity. Interestingly, the set of ActE enzymes described above are on average 10% smaller in mass than their closest orthologs from *T. fusca* (Chen and Wilson, 2007), suggesting size minimization may have occurred in ActE (Table 5). These enzymes also provide all of the requisite catalytic reactions needed for the deconstruction of crystalline cellulose.

TABLE 5

ActE cellulose secretome proteins and corresponding best match in *T. fusca*. The single protein SACTE_0237 is the best match to both Cel6A and Cel6B suggesting one protein from ActE might replace two proteins from another organism.

| ActE Gene locus | CAZy | residues | MW | identity | coverage | T fusca Gene locus | Protein name | residues | MW |
|---|---|---|---|---|---|---|---|---|---|
| SACTE_0237 | GH6 | 586 | | 49 | 80 | Tfu_1074 | Cel6A | 441 | 45844 |
| SACTE_0237 | GH6 | 586 | 61062 | 62 | 93 | Tfu_0620 | Cel6B | 596 | 63548 |
| SACTE_0236 | GH48 | 954 | 100726 | 57 | 95 | Tfu_1959 | Cel48A | 984 | 107127 |
| SACTE_2347 | GH8 | 562 | 57753 | 45 | 23 | Tfu_2176 | Cel9A | 880 | 95203 |
| SACTE_3159 | CBM33 | 362 | 37787 | 42 | 71 | Tfu_1665 | E8 | 438 | 46808 |
| SACTE_0482 | GH5 | 456 | 47654 | 51 | 97 | Tfu_0901 | Cel5A | 466 | 49807 |
| SACTE_0265 | GH10 | 458 | 47683 | 44 | 95 | Tfu_2923 | Xyl10A | 491 | 53185 |
| SACTE_3717 | GH9 | 909 | 96338 | 61 | 82 | Tfu_1627 | Cel9B | 998 | 107045 |
| SACTE_6428 | CBM33 | 222 | 24668 | 62 | 99 | Tfu_1268 | E7 | 222 | 25372 |
| Average identity, coverage | | | | 53 | 82 | | | | |
| Sum ActE | | 4509 | 473671 | | | with Cel6A | | 4920 | 530391 |
| | | 4509 | 473671 | | | with Cel6B | | 5075 | 548095 |
| Percentage with Cel6A | | 92% | 89% | | | with Cel6A, B | | 5516 | 593939 |
| Percentage with Cel6B | | 89% | 86% | | | | | | |
| Percentage with Cel6A, B | | 82% | 80% | | | | | | |

Example 8

ActE Secretome Specific Activity is Comparable to that of Spezyme CP™

The enzymatic activities of ActE secretomes were compared with a commercial secretome, Spezyme CP. The enzyme cocktail of Spezyme CP was prepared from *T. reesei* Rut-C30, thus providing a useful, routinely available reference point for the capabilities of other cellulolytic organisms. HPLC analysis showed that the ActE cellulose secretome released cellobiose as the primary product during reaction with cellulose (FIG. 2A, 95% of products), which is distinct from the higher proportion of glucose produced by the *T. reesei* secretome. Similarly, the primary products from xylan and mannan were xylobiose and mannobiose, respectively. Upon accounting for total glucose equivalents released, the ActE secretome obtained from growth on pure cellulose had specific activity that was about half of that provided by Spezyme CP (FIG. 2A, inset). Interestingly, the ActE secretome obtained from growth on pure cellulose had higher specific activity for deconstruction of pure mannan than Spezyme CP (FIG.2B). Additionally, the ActE secretome obtained from growth on pure xylan had higher specific activity for reaction with pure xylan than Spezyme CP. Cellulose, xylan, and mannan are all abundant in pinewood, thus accounting for the necessity of each of the major catalytic activities detected.

Figure 7A:
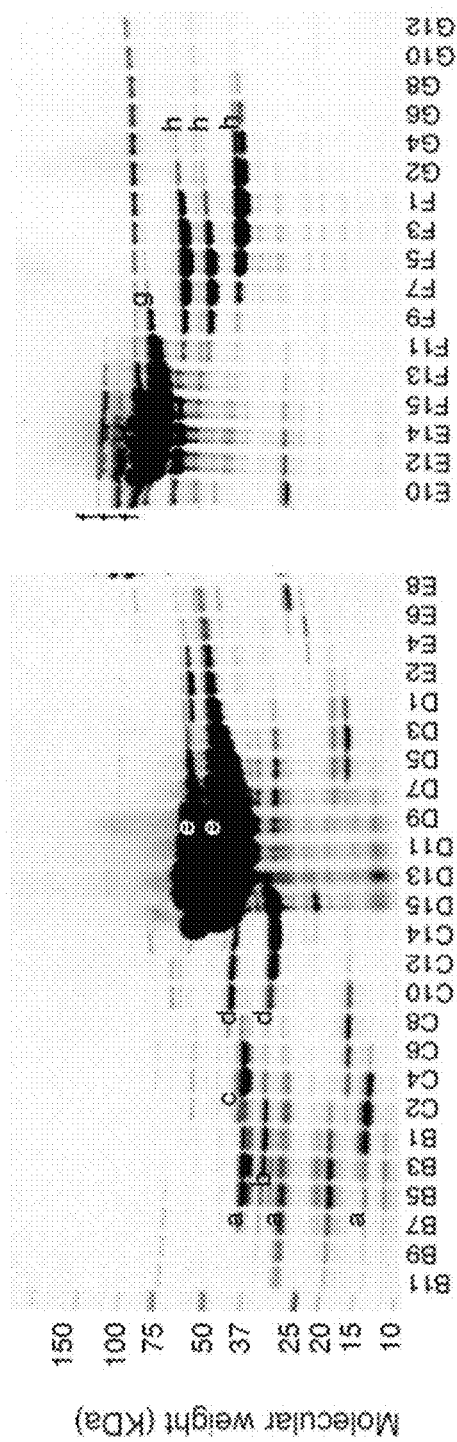
FIG. 7 is a set of graphs demonstrating fractionation of the ActE cellulose secretome and assays of reactions with different polysaccharides. (A) Anion exchange chromatography was performed using the ActE cellulose secretome, and fractions were collected and analyzed by SDS-PAGE. Lowercase letters indicate protein identified by MALDI-TOF MS shown in FIG. 17. (B) Results from hydrolysis assays for reaction with filter paper (FP), xylan, mannan and beta-1,3 glucan as detected by DNS assay of each fraction. The percentage reactivity relative to the maximum activity observed for each substrate is shown. Error bars indicate the standard deviation, with n=3 for technical replicates.
Figure 7B:
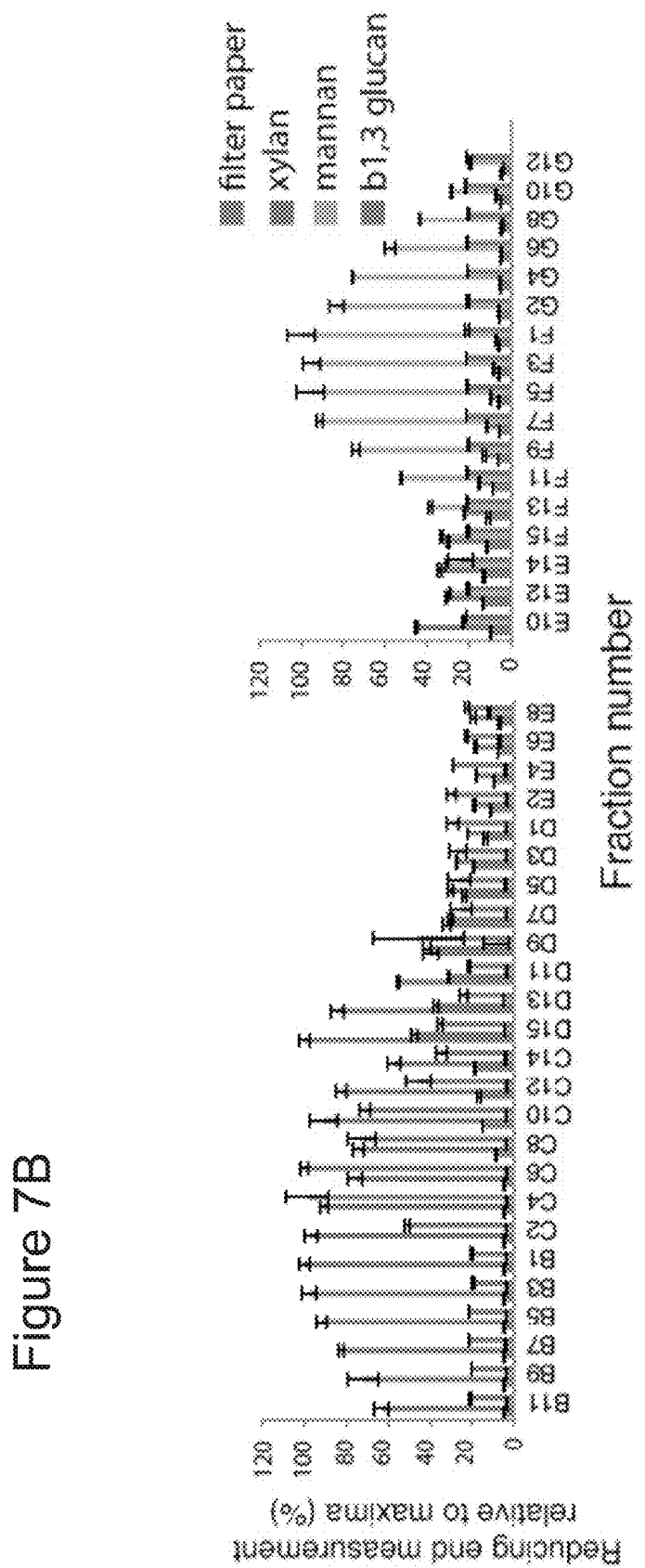
Figure 9:
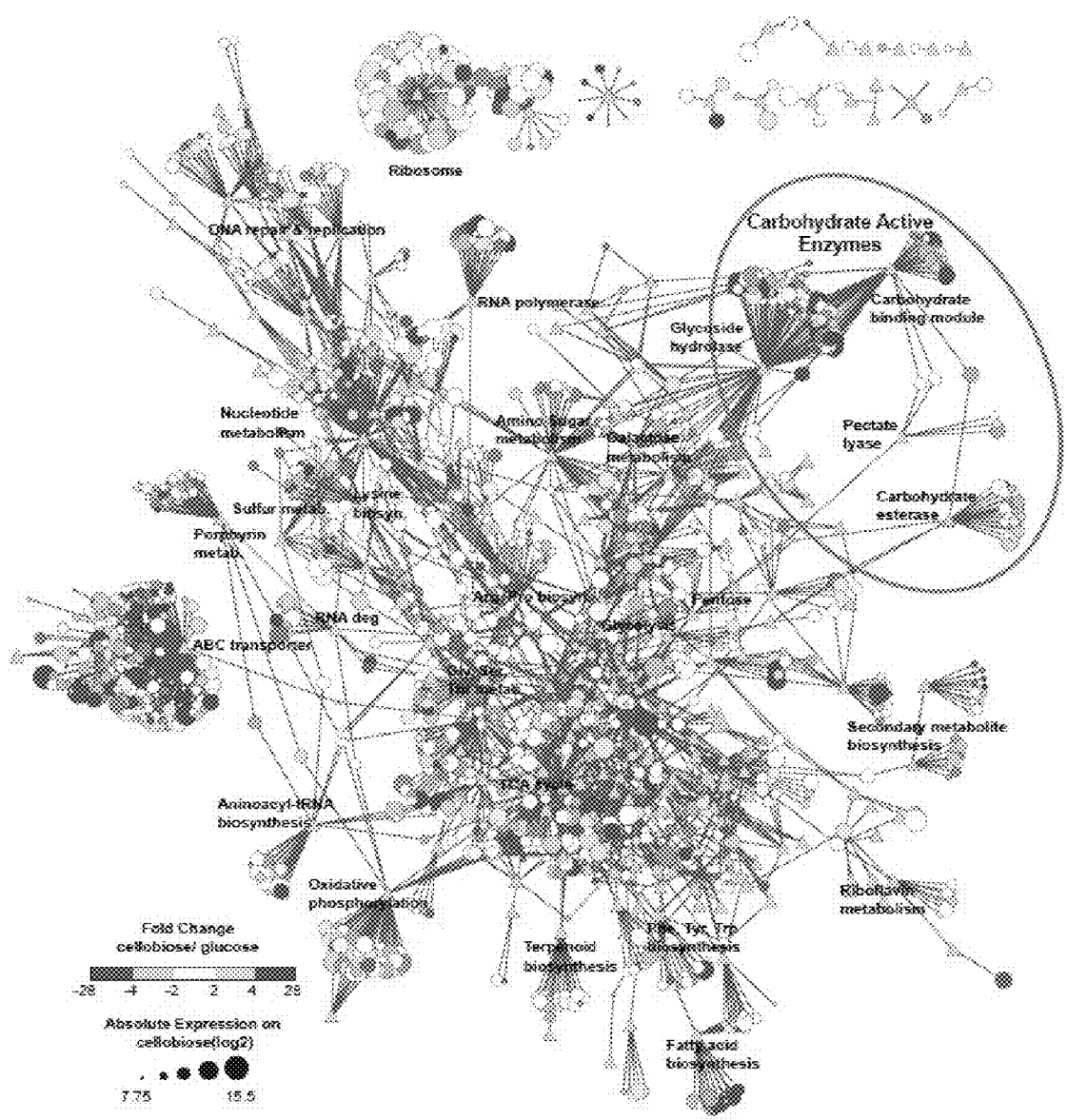
FIG. 9 is a systematic diagram showing genome-wide changes in expression during growth of ActE on substrate cellobiose versus glucose visualized as a Cytoscape interaction network. Nodes are genes (circles) or KEGG/CAZy functional categories (yellow triangles); edges indicate that the gene belongs to the indicated functional group as defined by either KEGG or CAZy analysis. Gene node sizes reflect expression intensity determined by microarray from growth on substrate as a log 2 ratio. Node colors represent expression changes as the log 2 ratio of substrate/glucose transcript intensities, where the genome-wide average transcriptional intensity was ~10.5 for both substrate and glucose. Transcripts with less than two-fold changes in expression intensity are colored white; transcripts with greater than two-fold increase in expression intensity during growth on substrate are shown as a red gradient; transcripts with greater than two-fold increase in expression intensity during growth on glucose are shown as a blue gradient.
Figure 10:
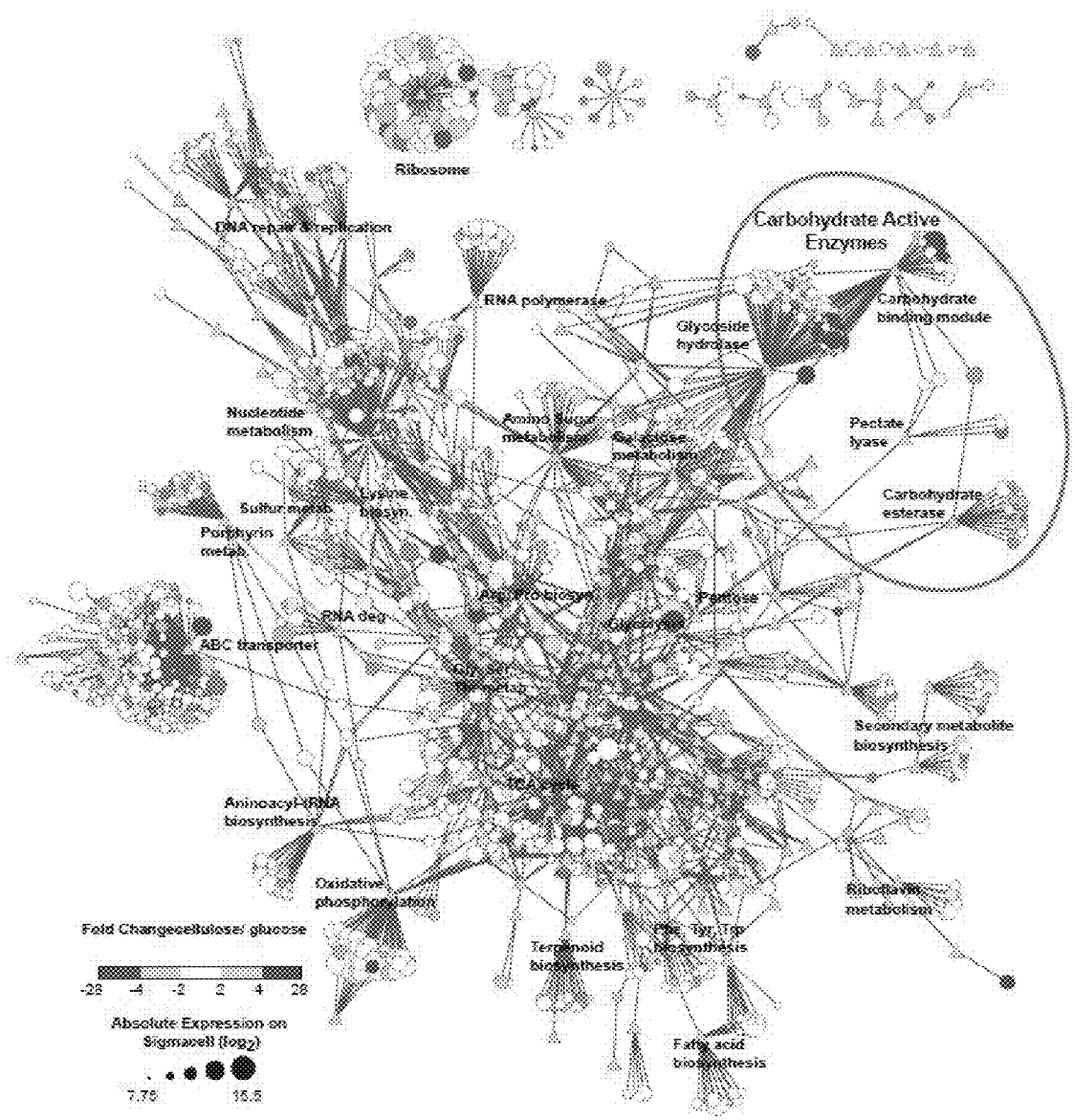
FIG. 10 is a systematic diagram showing genome-wide expression changes for growth on the substrate cellulose versus glucose visualized as a Cytoscape interaction network. Other information is the same as that described in FIG. 9.
Figure 11:
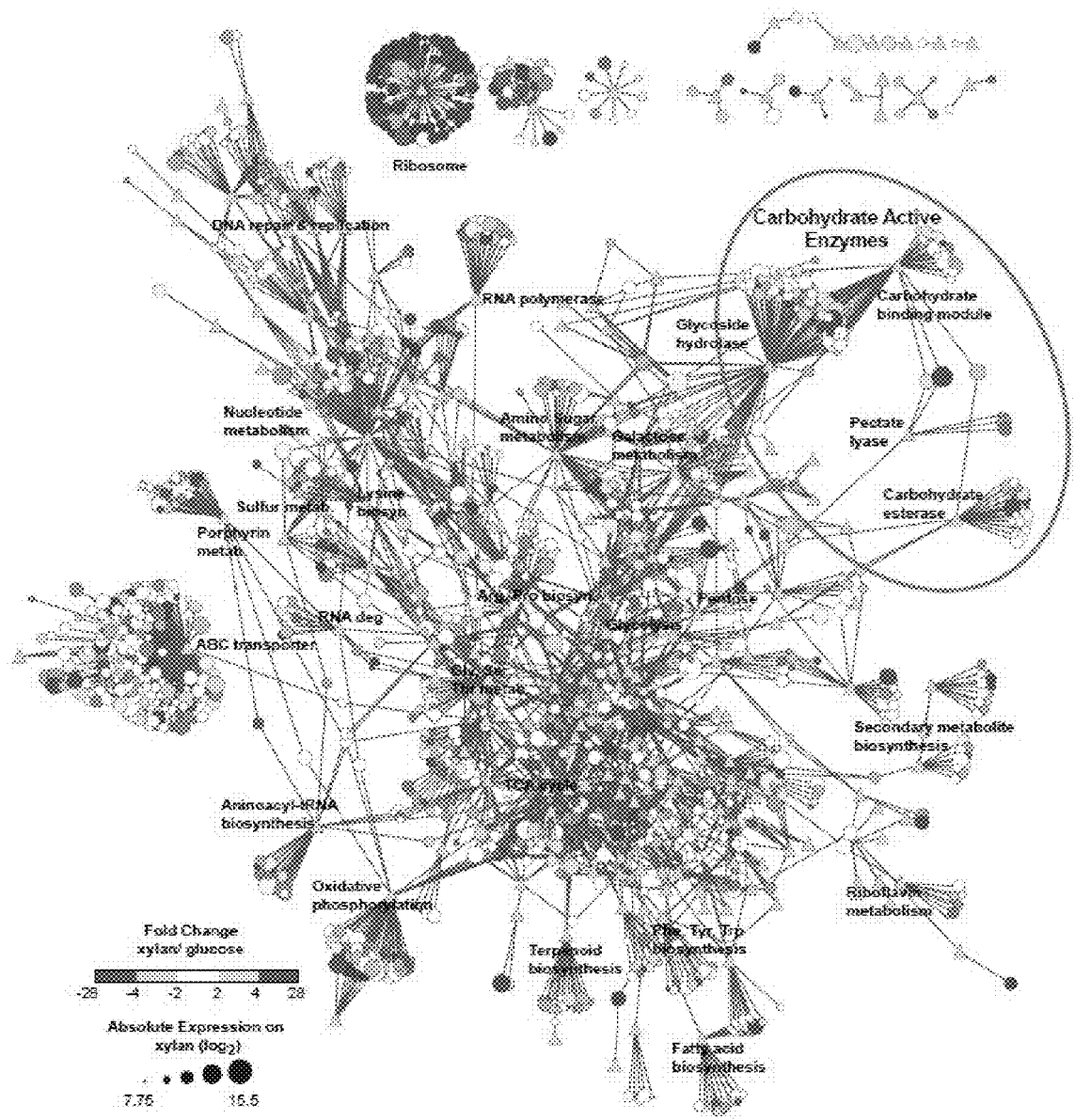
FIG. 11 is a systematic diagram showing genome-wide expression changes for growth on the substrate xylan versus glucose visualized as a Cytoscape interaction network. Other information is the same as that described in FIG. 9.
Figure 12:
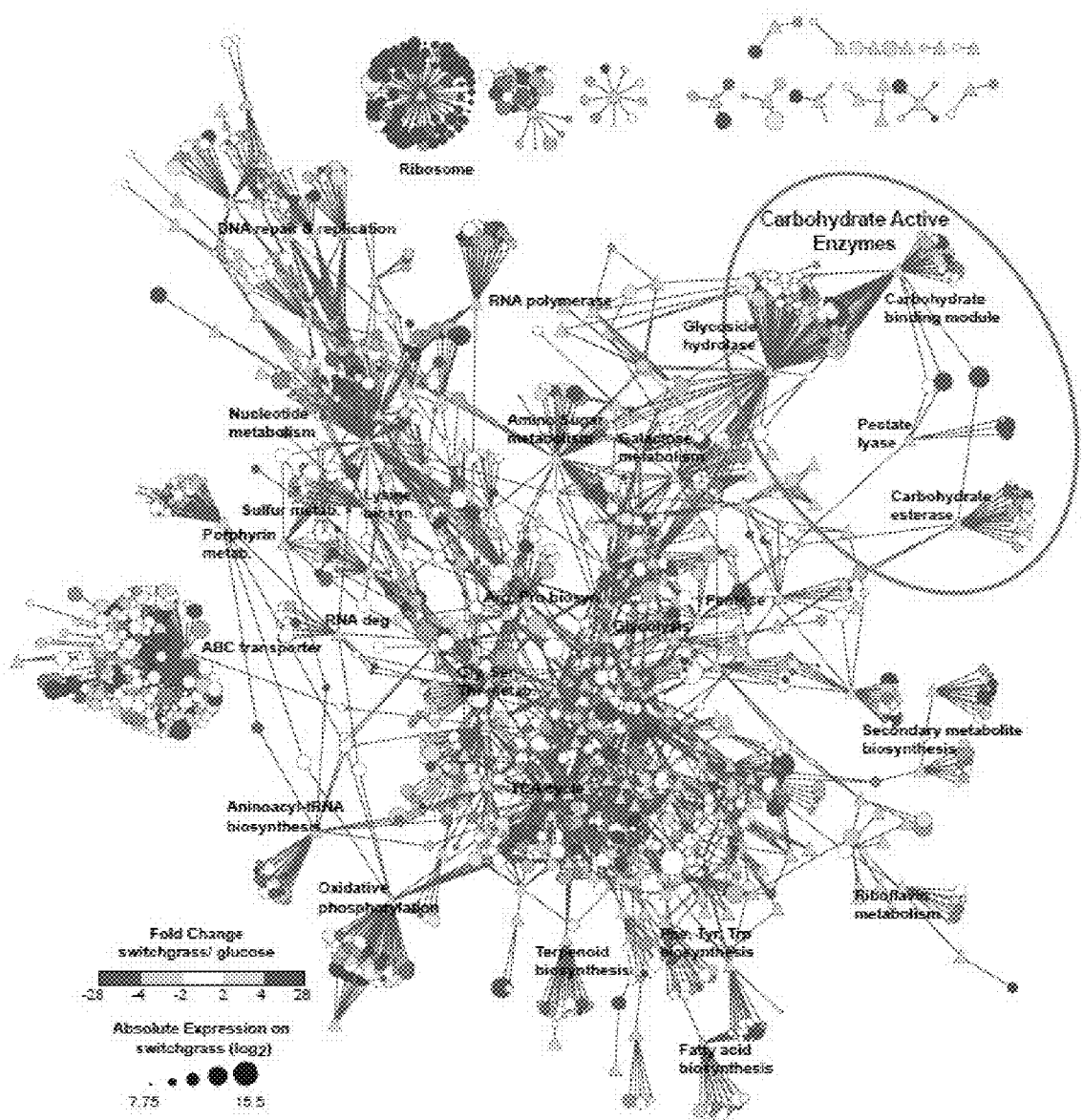
FIG. 12 is a systematic diagram showing genome-wide expression changes for growth on the substrate switchgrass versus glucose visualized as a Cytoscape interaction network. Other information is the same as that described in FIG. 9.
Figure 13:
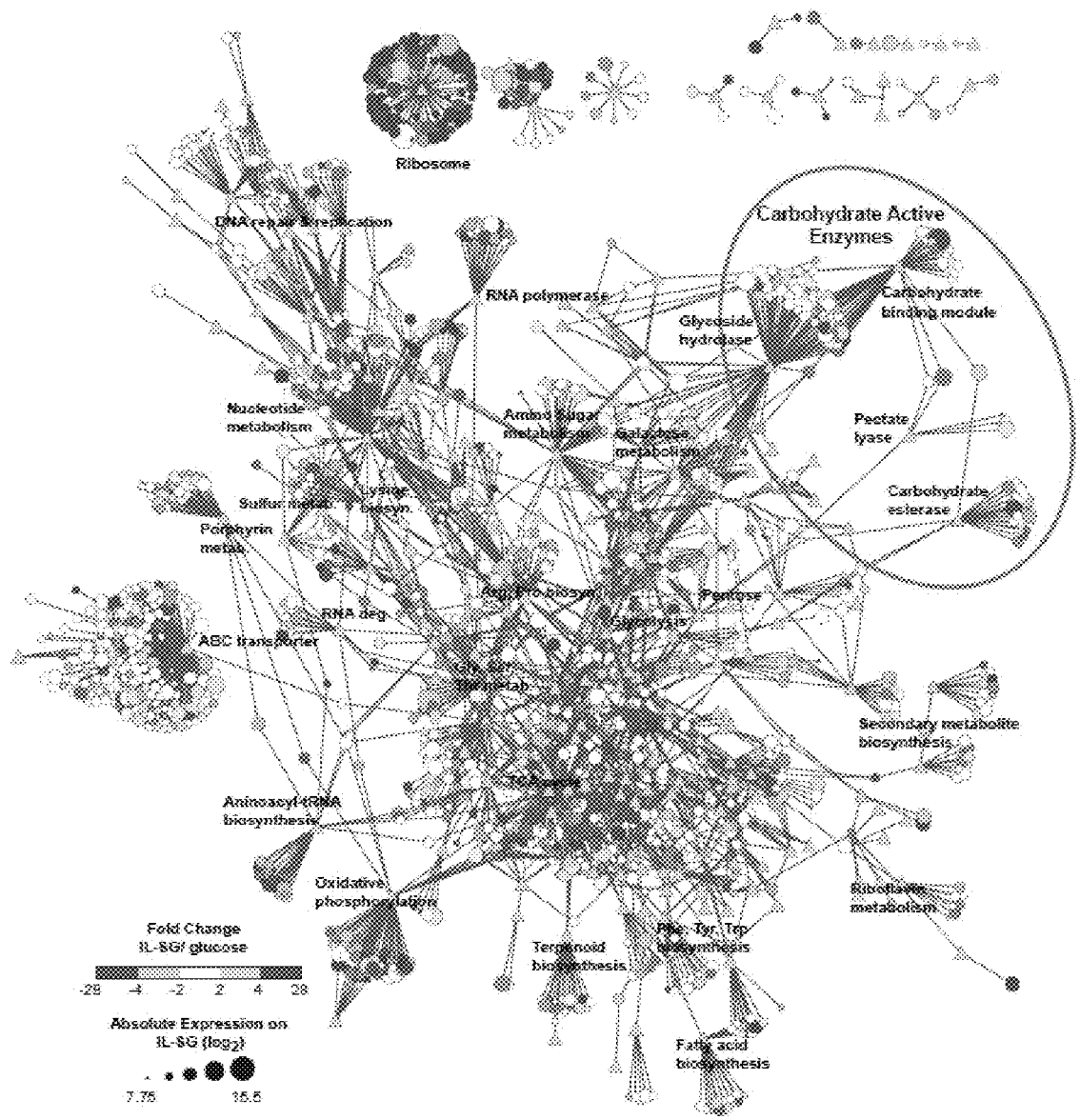
FIG. 13 is a systematic diagram showing genome-wide expression changes for growth on the substrate IL-treated switchgrass versus glucose visualized as a Cytoscape interaction network. Other information is the same as that described in FIG. 9.
Figure 14:
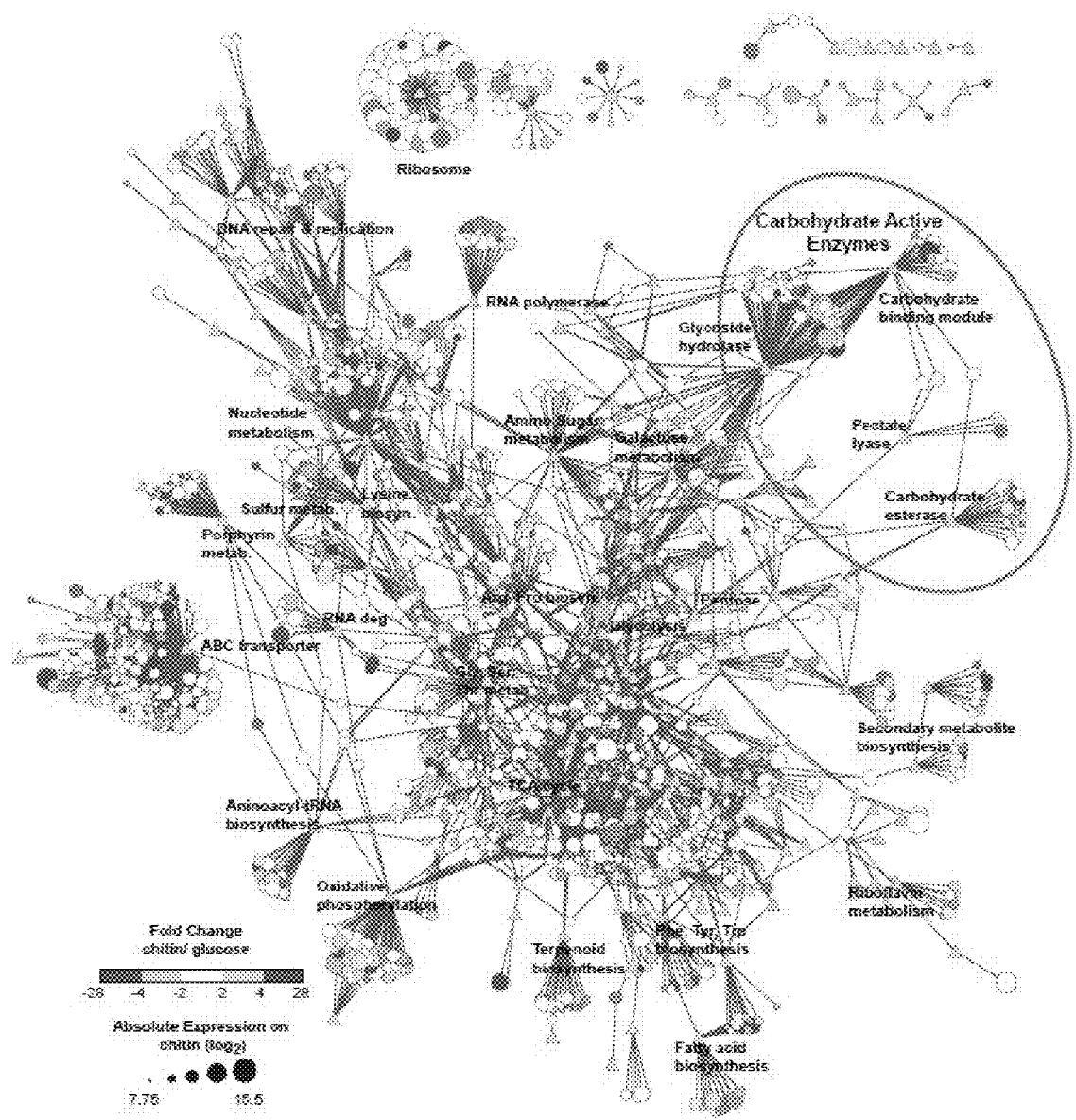
FIG. 14 is a systematic diagram showing genome-wide expression changes for growth on the substrate chitin versus glucose visualized as a Cytoscape interaction network. Other information is the same as that described in FIG. 9.

Anion exchange chromatography was performed to fractionate the ActE secretome obtained from cells grown on cellulose as the sole carbon source. We identified fractions that hydrolyzed pure polysaccharides by biochemical assays (FIG. 7), and confirmed the identity of the protein or proteins contained in these fractions by mass spectrometry (FIG. 17). Where multiple polypeptides were present, the identity of each was confirmed by mass spectrometry to correspond to the indicated gene locus. In several cases, these most likely arise from proteolysis of a single protein found in the secretome. Fractions containing the maximum cellulase activity were highly enriched in SACTE_0236 and SACTE_0237, reducing and non-reducing end cellobiohydrolases from the GH6 and GH48 families, respectively. SACTE_0265 and SACTE_2347 were identified as the major proteins present in fractions associated with xylan and mannan hydrolysis, respectively. A CBM33 polysaccharide monooxygenase (SACTE_3159) was also identified in the ion exchange profile. Moreover, beta-1,3 glucanase activity was identified in fractions that were enriched in SACTE_4755.

When ActE was grown on either ammonia fiber expansion-treated switchgrass (AFEX-SG) (Li, C. et al., 2011) or ionic liquid-treated switchgrass (IL-SG), the secretomes had ~2-fold increase in specific activity relative to the cellulose secretome and were equivalent to Spezyme CP for reaction with both the AFEX- and IL-treated biomass (FIG. 2C) (Li, C. et al., 2011). The ActE secretomes retained greater than 60% of maximal activity for the hydrolysis of AFEX- and IL-SG from 30 to 55° C. and 35 to 47° C., respectively, which is comparable to recent reports on the temperature profile of secretomes from thermophilic biomass-degrading fungi (Tolonen et al., 2011) (FIG. 8A). The secretomes showed a pH optimum of ~7 for reaction with AFEX-SG and a pH optimum of ~8 for reaction with IL-SG. Moreover, these secretomes retained greater than 60% of maximal activity over the ranges of pH 4.5 to 8.0, and pH 7.0 to 8.0, respectively (FIG. 8B). These optimal pH values are considerably higher than observed for Spezyme CP.

Example 9

ActE Produces Cellobiose as the Primary Extracellular Product of Cellulose Utilization The isolated ActE secretomes contained substantial ability to release reducing sugars from pure polysaccharides. Cellobiose accounted for ~95% of soluble sugar released from pure cellulose and glucose represented the remainder; cellotriose and cellobionic acid were not detected. Neither cellobiosidase nor β-glucosidase was detected in the ActE secretome. Thus ActE produces cellobiose as the primary extracellular product of cellulose utilization and also grows vigorously on this. Dominance of cellobiose may help to channel cellulolytic activity to only a subset of the *Sirex* community. Since genes encoding cellobiose oxidase and cellobiose dehydrogenase (Eastwood et al., 2011; Langston et al., 2011) were not present in ActE, biological reduction systems for the CBM33 proteins may be provided by other members of the *Sirex* community, in analogy to that described for the heterologous complex of *T. aurantiacus* GH61 and *Humicola insolens* cellobiose dehydrogenase (Langston et al., 2011).

Example 10

Figure 24:
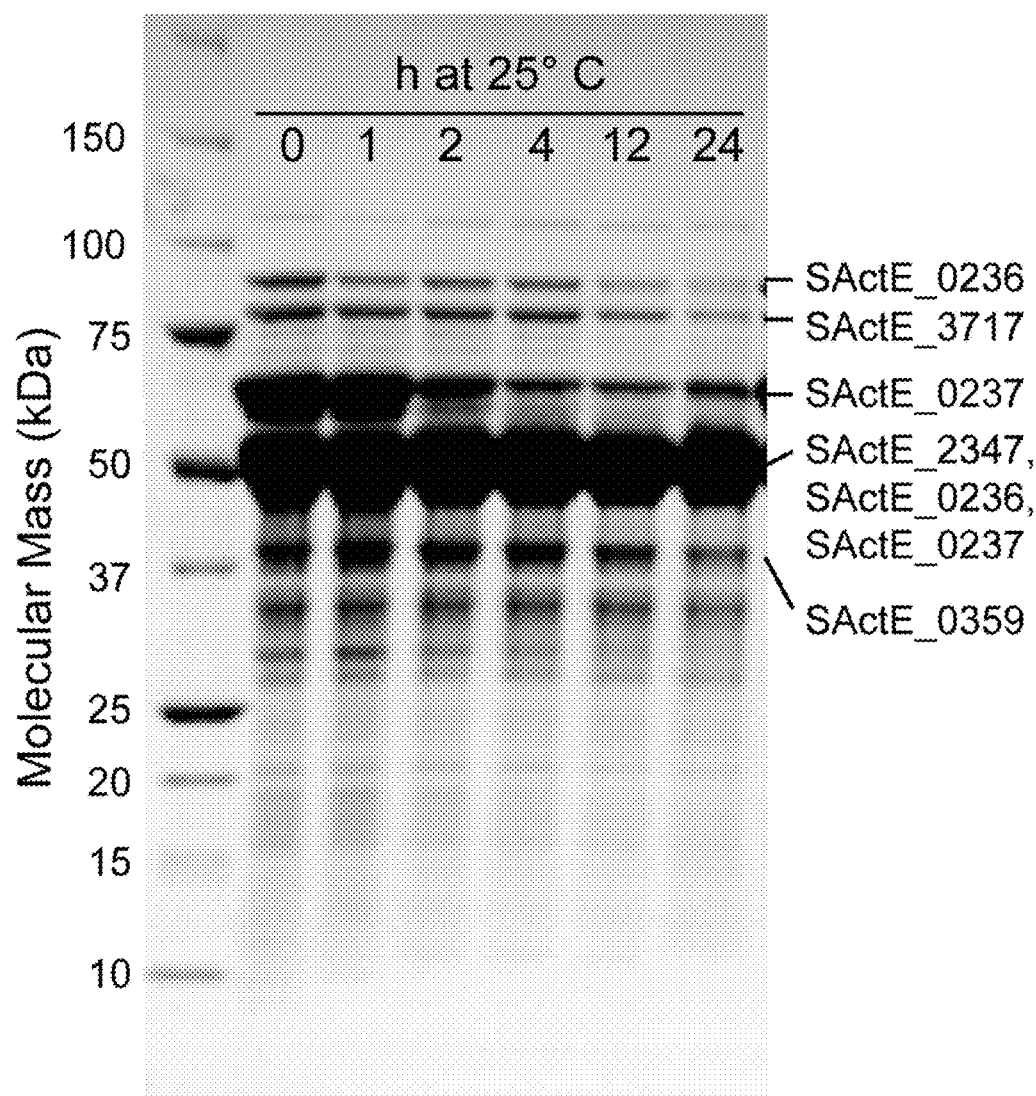
FIG. 24 is a graph illustrating SDS-PAGE of time-dependent changes in the *Streptomyces* sp. ActE secretome obtained from growth on minimal medium containing cellulose. Culture secretomes were collected after 7 days by centrifugation and concentrated by ultrafiltration. The concentrated secretomes were incubated at 25° C. for the indicated times and analyzed. Protein bands with time-dependent decrease in intensity were excised from the gel and identified by LC-MS/MS.

Enzymatic Activity of the ActE Secretome can be Improved by Adding One or More Enzymes from other Organisms or Sources In the ActE secretome, enzymes SACTE_0236, SACTE_0237, and SACTE_3717 (GH48, GH6, and GH9, respectively) showed decreases in content of the native forms over a 24 h period, and SACTE_0236 and SACTE_0237 were converted into ~50 kDa fragments (FIG. 24). SACTE_0359 (CBM33) also showed a time-dependent decrease. The reactions could be slowed but not eliminated by addition of phenylmethylsulfonyl fluoride (1 mM), a possible inhibitor of serine proteases (Turini et al., 1969), but not by EDTA (10 mM), a possible inhibitor of metallo-proteases (Trop and Birk, 1970).

SACTE_5668, a serine protease, was detected in all pure polysaccharide secretomes (FIG. 3), while another metallo-peptidase, SACTE_3389 annotated as peptidase M24B, X-Pro dipeptidase/aminopeptidase P, was detected in all secretomes at low level (0.026%). The protease SACTE_5530 (peptidase S1/S6, chymotrypsin/Hap, 0.1%) was also present in all polysaccharide and biomass samples. The proteases SACTE_5668 (annotated secreted peptidase, 0.3%) and SACTE_4231 (serine/cysteine peptidase, trypsin-like, 0.039%) were also detected in all pure polysaccharide secretomes, and the protease SACTE_6303 (serine/cysteine peptidase, trypsin-like, 0.039%) was also present in all biomass samples. Elimination of one or more of these proteases may impart stabilization of the enzymatic activity in the secreted proteome.

Addition of CelLcc_CBM3a (SEQ ID Nos:63 and 64), an engineered exoglucanase (FIG. 22) that produces cellobiose with low specific activity alone (FIG. 21), gave a synergistic increase in the activity of the ActE cellulose secretome. This result demonstrates the potential for heterologous supple-mentation of the ActE secretome to improve its performance by replacing an enzyme activity that is lost to proteolysis.

Example 11

ActE Cellulolytic Activity Requires a Minimal Set of Enzymes

When the ActE secretome obtained from growth on cellulose was fractionated by ion exchange chromatography (FIG. 7), several fractions were obtained that could be tested in unary, binary, ternary and quaternary combinations for reconstitution of cellulose hydrolysis and other enzymatic activities (FIG. 25). SDS PAGE and LC-MS/MS analysis showed that these fractions contained the following poly-peptides in the approximate weight percentages: fraction 1, SACTE_3159 (CBM33/CBM2 oxidative endocellulase, 95%) and SACTE_4738 (GH16 β-1,3 endoglucanase, 5%); fraction 2, SACTE_0237 (GH6 non-reducing end exocellu-lase, 60%), SACTE_0482 (GH5 endocellulase, 25%), SACTE_4755 (GH64 β-1,3 glucanase, 10%) and SACTE_3159 (oxidative endocellulase, <5%); and fraction 3, SACTE_0236 (GH48 reducing end exocellulase, 75%), SACTE_3717 (GH9 endocellulase, 20%) and SACTE_5457 (GH46 chitinase, 5%). These results demonstrate that SACTE_3159 (oxidative endocellulase) provides a comple- mentary activity to SACTE_0482 and SACTE_3717 (hy-drolytic endocellulolytic activity). Evidently, the oxidative reaction provides breaks in the cellulose strands that can be readily used by non-reducing and reducing end exocellu-lases also present in the secretome to processively decon-struct the polymeric material.

According to the current understanding of reactions required for hydrolysis of crystalline cellulose, SACTE_3159 (CBM33/CBM2 oxidative endocellulase), SACT_0482 (GH5), and SACTE_3717 provide endocel-lulolytic activities, while SACTE_0237 (GH6) provides non-reducing end exocellulase reaction and SACTE_0236 (GH48) provides reducing end exocellulase activity.

FIG. 16 shows that the secretome contains beta-1,3 endo-glucanase activity. The majority of this activity corresponds to the fractions containing SACTE_4738 and SACTE_4755. These enzymes hydrolyze callose, a cellulose-like material that is typically produced by plants in respond to wounding by invasive insects and other trauma.

The proteins described here constitute a naturally evolved and matched set specialized for the hydrolysis of cellulosic substrates.

Example 12

ActE Mannanase Specific Activity Increases as Mannanase Molecular Weight Decreases FIG. 26 shows that the mannanase activity present in the ActE secretome is associated with fractions containing vari-ous naturally truncated variants of SACTE_2347 (GH5) with molecular weights of ~57, ~45, and ~37 kDa. Fractions F9 through F1 from ion exchange chromatographic separa-tion of the ActE secretome were examined for mannan-deconstruction activity by Zymogram assay. The basis of the Zymogram assay is as follows: Congo Red stain interacts with the polysaccharide fraction (mannan) incorporated into the gel and imparts a red color. When an enzyme's activity hydrolyzes the mannan, the interaction of Congo Red with the polysaccharide is broken and the gel takes on a dark grey appearance. Of note, the strongest mannanase activity was observed in fraction F1, which primarily contains the 37 kDa truncated variant. Corresponding to the definition of specific activity given above, the 37 kDa variant has an ~35% increase in specific activity relative to the 57 kDa variant. This provides a naturally produced example of how size reduction may contribute to increased specific activity of enzymes.

Example 13

Figure 27A:
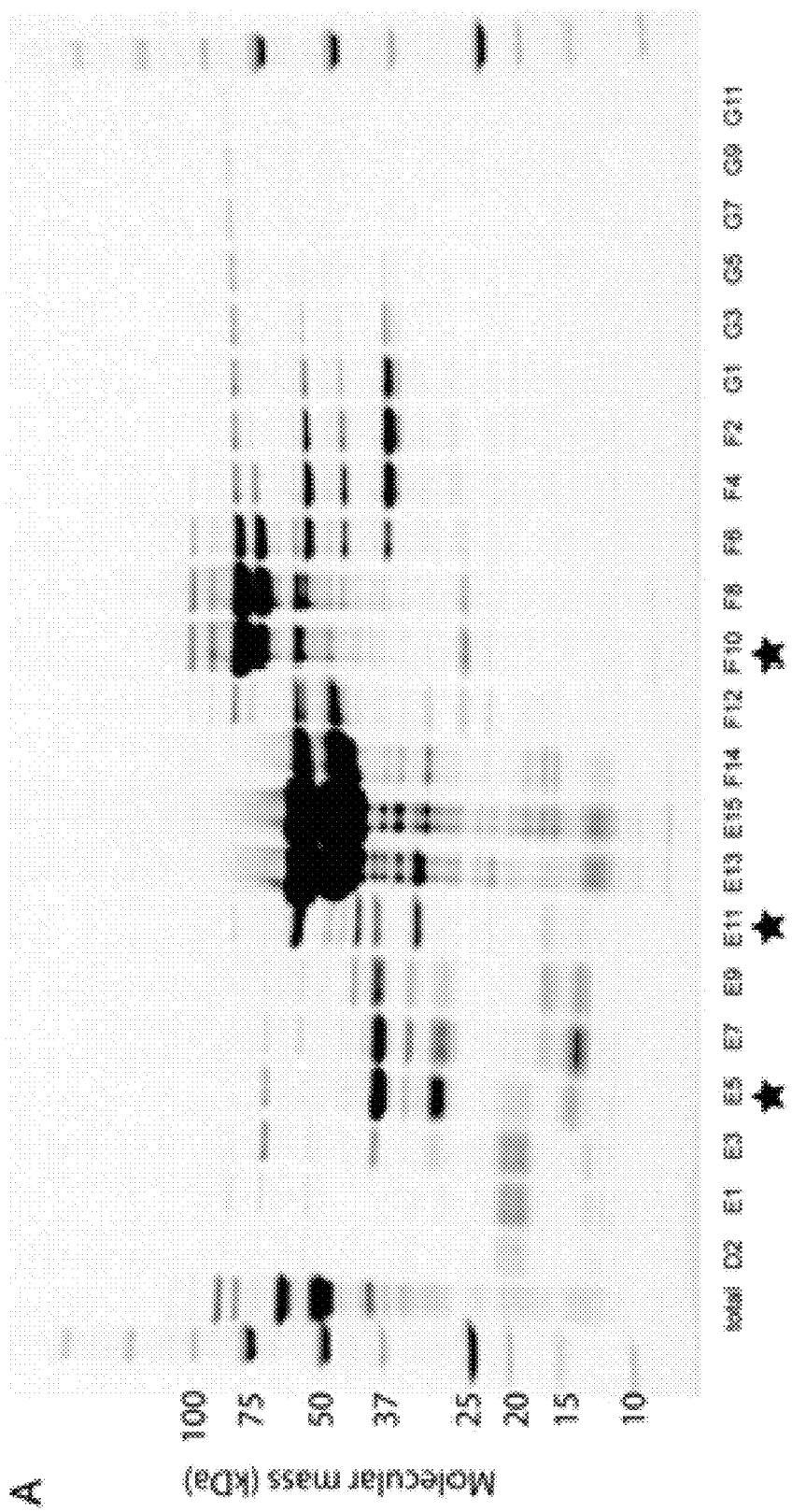
FIG. 27A depicts an SDS-PAGE analysis of the fractionation of an ActE secretome by ion exchange chromatography.
Figure 27B:
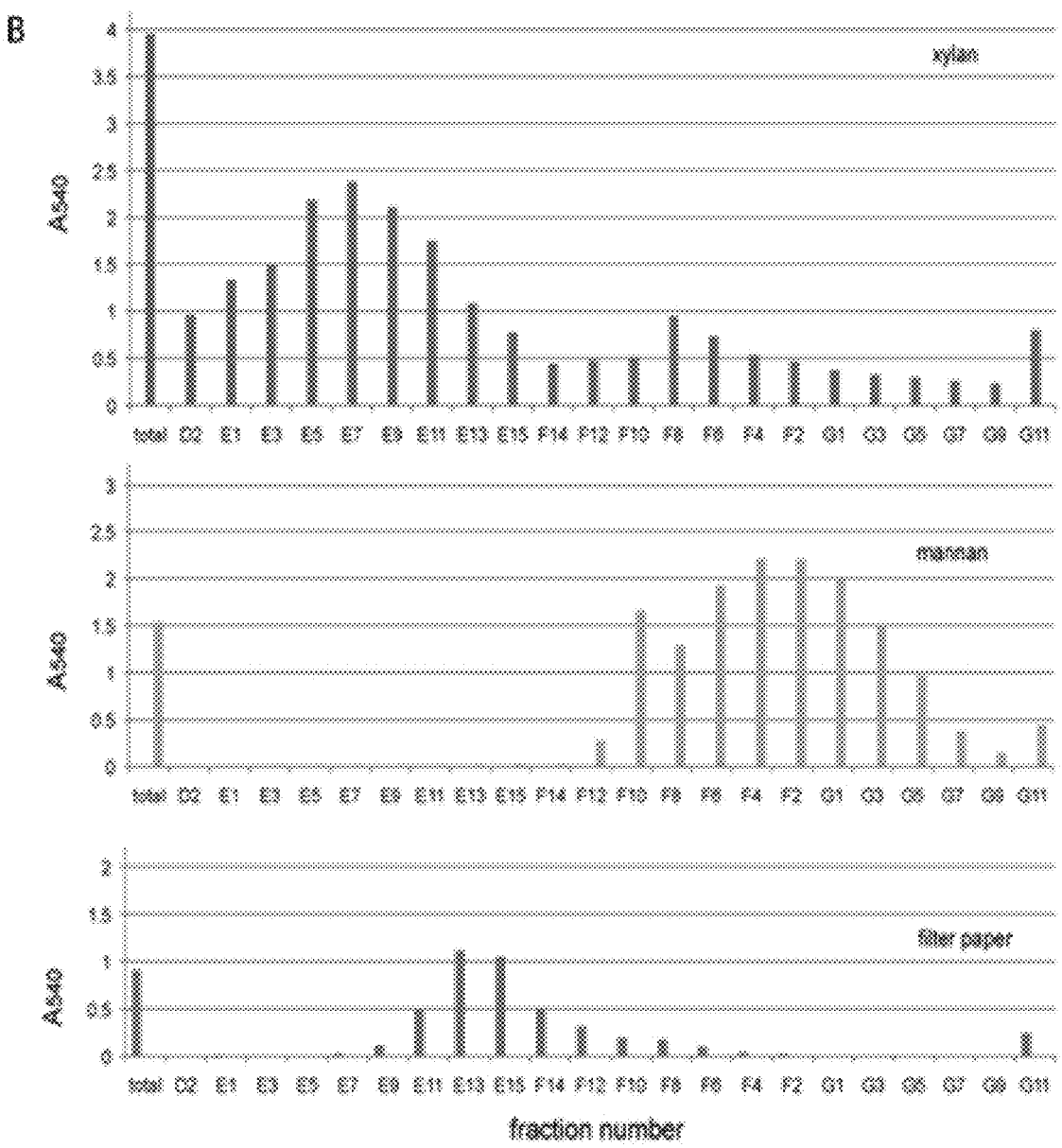
FIG. 27B depicts catalytic assays of the separate fractions at 40° C. for 20 h in 0.1 M phosphate buffer, pH 6.0, showing different enzymes are capable of reacting with xylan, mannan, and cellulose. The reactivity of fractions marked with stars is also described in FIG. 25A.
Figure 28A:
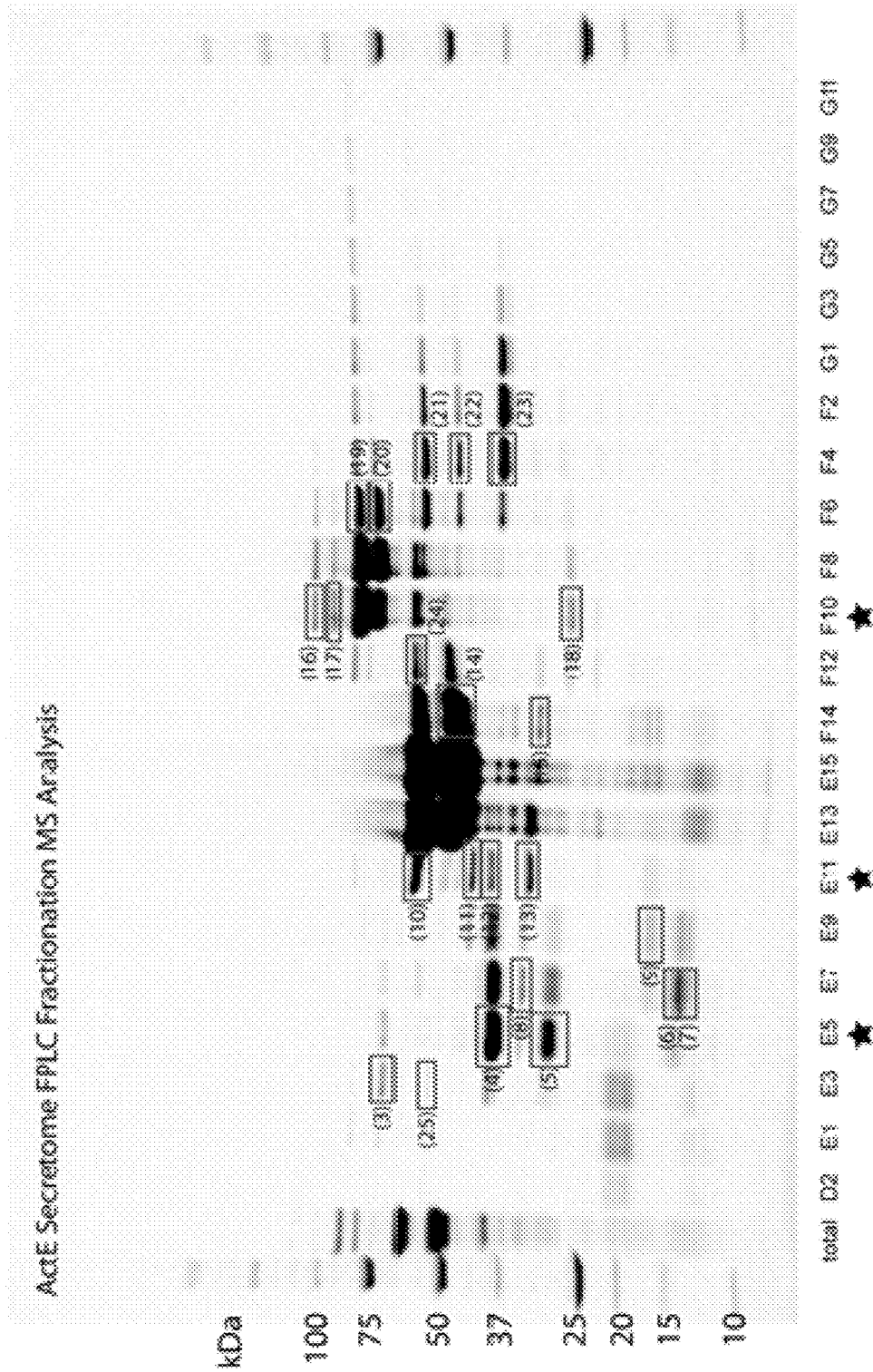
FIG. 28A depicts an SDS PAGE of separated fractions annotated with identities of polypeptides determined by LC-MS analysis.

Recombination of ActE Secretome Fractions Provides Synergistic Cellulolytic Activity FIG. 25 shows synergy of reaction obtained by recom-bining fractions obtained from ion exchange fractionation. In FIG. 25A, reactions were obtained from combinations of the fractions indicated by stars in FIG. 27 and FIG. 28. Combination of fractions E5 (oxidative endocellulase) and E11 (hydrolytic endo- and exocellulases) gave a ~30% increase in product yield over that expected from the arith-metic sum of reactions of E5 and E11 alone, i.e., synergy in reaction. Combination of fractions E5, E11 and F10 (hydro-lytic endo- and exocellulases) gave ~60% increase in reac-tivity. In FIG. 25B, reactions were obtained from recombin-ing fractions shown in FIG. 16. Titration of fraction B1 (full-length oxidative endocellulase) into D15 (hydrolytic endo- and exocellulases) shows an optimal reactivity at ~1:1 ratio of proteins from the two fractions, while an excess of B1 relative to D15 causes decrease in reaction because of depletion of required exocellulase activities. Titration of fraction C4 (truncated oxidative endocellulase and beta-1,3-endocellulase) with D15 gave maximal stimulation (62% increase) at an 80:20 proportion. These results indicate both forms of oxidative endocellulase SACTE_3159 are catalytically active, with the smaller form providing a higher synergistic response, again corresponding to a specific activity increase associated with size minimization.

Example 14

The Function of ActE Xylanases can be Assigned by Functional Assay of Proteins Produced by Using Cell-free Translation FIG. 29 shows that both of the xylanases identified in the fractions of ActE secretomes obtained from ion exchange chromatography can also be expressed using cell-free translation and demonstrated to be xylanases by catalytic activity assays. These proteins are SACTE_0265 and SACTE_0358. Other proteins that are not secreted were successfully expressed (SACTE_2548, SACTE_2286, SACTE_437) as control proteins, and as expected from their predicted intracellular localization, none of these controls exhibited xylanase activity. The negative result with the control proteins also demonstrates that the wheat germ extract used for cell-free translation of novel cellulolytic enzymes does not have an endogenous xylanase activity, as established in US Patent Application Publication No.: US2010/037094 (Fox and Elsen).

Example 15

Total Protein Secreted by ActE can be Increased

A minimal set of enzymes for biomass deconstruction can be defined by combining the additional enzymes whose expression is elicited during growth on biomass (Table 1) with enzymes uniquely expressed during growth on cellulose and xylan.

Figure 30:
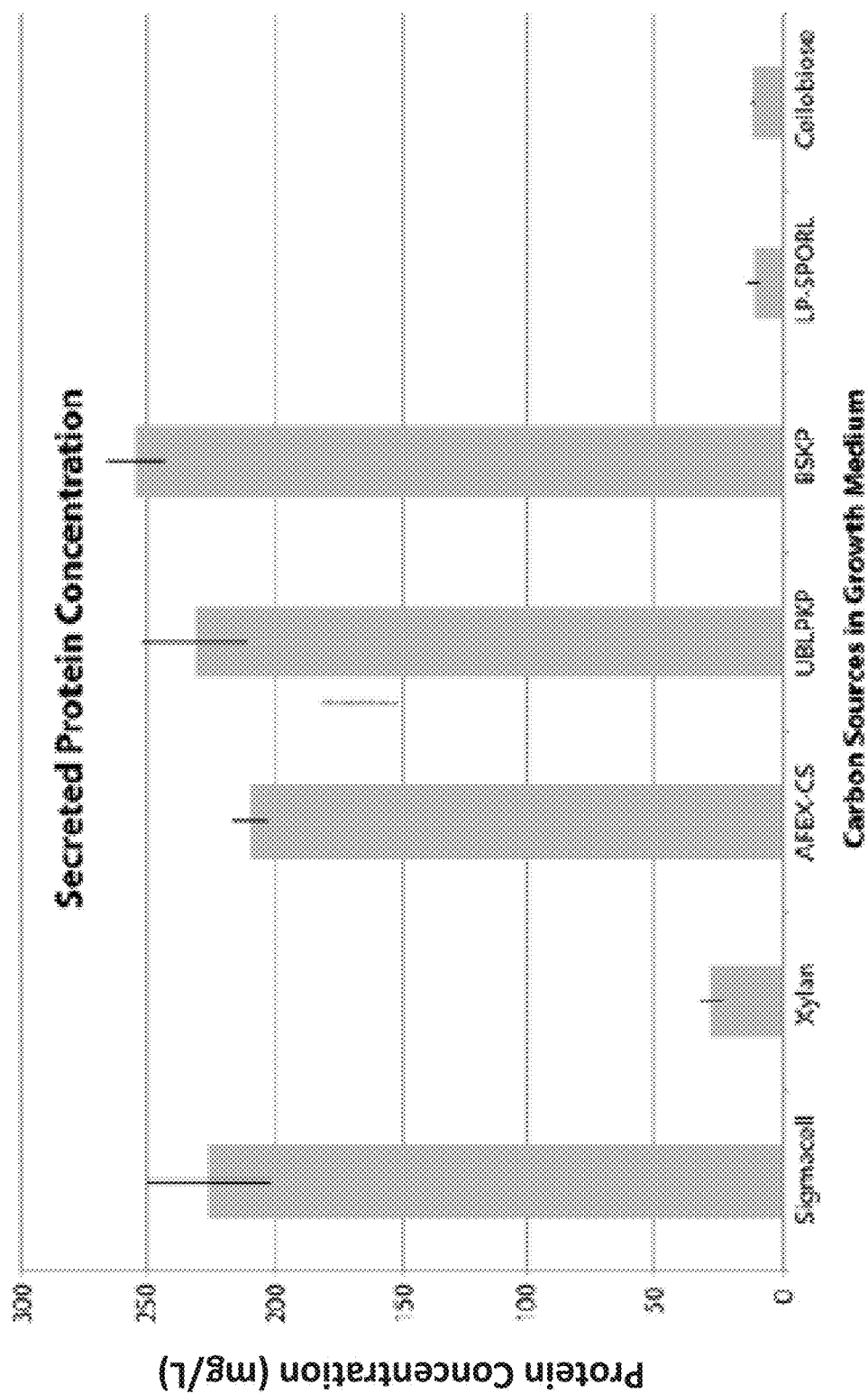
FIG. 30 is a graph illustrating quantification of total secreted protein obtained from *Streptomyces* sp. ActE grown on different substrates (AFEX-CS, AFEX corn stover; UBLPKP, unbleached lodgepole pine kraft pulp; BSKP, bleached spruce kraft pulp; LP-SPORL, lodgepole pine pretreated by SPORL).

Besides assembling the proper enzymatic constituents, the level of total protein secreted is an important biotechnological constraint for industrial enzyme production. FIG. 30 shows the non-optimized level of secreted protein obtained from growth of ActE on different biomass substrates. By use of lignocellulosic substrates for growth, secreted protein levels up to 0.25 g per liter of culture medium can be readily obtained. Growth on non-polymeric substrates such as cellobiose does not elicit a secreted protein response. FIG. 15, FIG. 16 and Table 1 indicate that the twin-arginine pathway (Tat) is used during growth, thus identifying this pathway as playing a key role in the secretion of enzymes required for extracellular deconstruction of biomass polysaccharides (Natale et al., 2008; Chater et al., 2010). Methods to increase the titer of secreted proteins are known, and have been highly effectively when applied to *Streptomyces* and other organisms (Cereghino et al., 2002; Zhang et al., 2006; Nijland and Kuipers, 2008; Chater et al., 2010; Schuster and Schmoll, 2010). These established methods can be applied to ActE to obtain more concentrated secretome preparations.

Example 16

Figure 31:
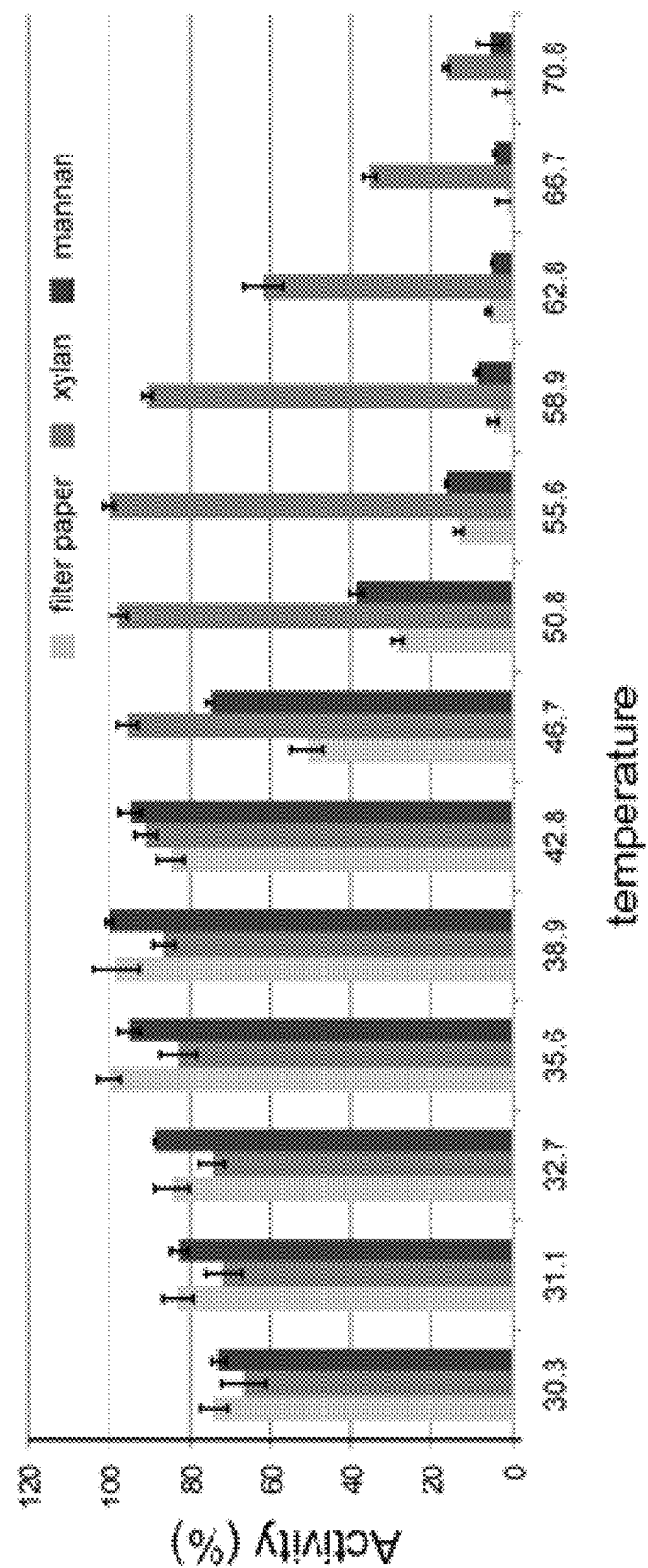
FIG. 31 is a graph illustrating the temperature versus activity profile of the *Streptomyces* sp. ActE secretome obtained from growth on cellulose. Hydrolysis activities were measured by DNS assay. Greater than 80% of maximal rates for cellulase and mannase activity were observed at the range of 31-43° C., while greater than 80% of maximal rate for xylanase activity was observed in the range of 35-59° C.

ActE Enzymatic Activity Corresponds with Optimal Growth Conditions of Fermentation Organisms FIG. 31 shows the temperature versus activity profile for ActE secretomes for reaction with cellulose, xylan and mannan. These profiles are well matched to the growth optima range for mesophilic fermentation organisms such as *Saccharomyces cerevisiae, Zymomonas mobilis, Escherichia coli* or others (Jarboe et al., 2010; Peralta-Yahya and Keasling, 2010), which are widely used for ethanol production from sugar hydrolysates. These hydrolysates are produced from biomass by the enzymatic action of highly cellulolytic secretomes, such as those described here from ActE. These optima are also well matched with the conditions found in the rumen, where the efficiency of conversion of animal feed, which is a biomass material, can be improved by addition of enzymes.

Figure 32:
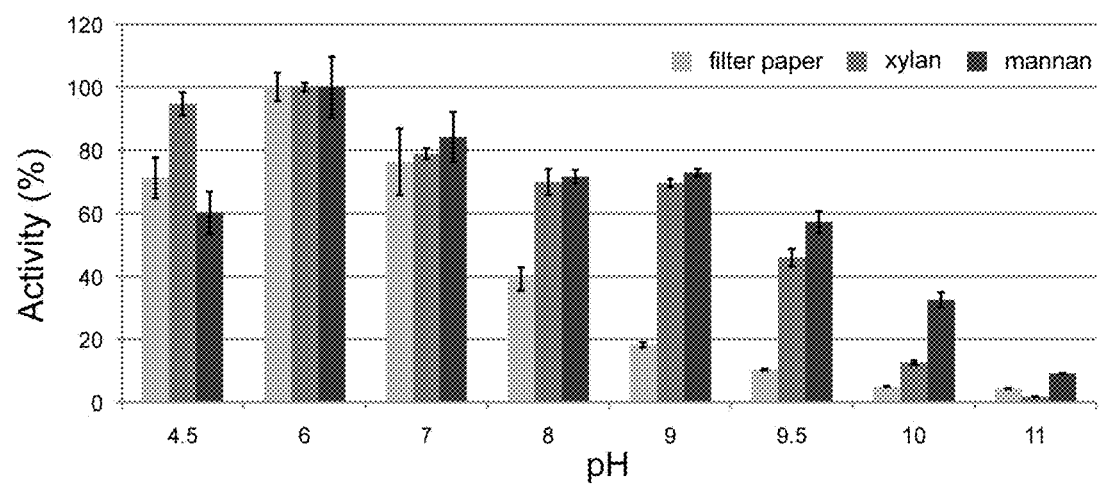
FIG. 32 is a graph illustrating the pH versus activity profile of the *Streptomyces* sp. ActE secretome obtained from growth on cellulose. The maximal rate was observed at approximately pH 6. Buffers used in this study were 0.1 M citrate (pH 4.5), phosphate (pH 6-8), CHES (pH 9-10) and CAPS (pH 11).

FIG. 32 shows the pH versus activity profiles for ActE secretomes for reaction with cellulose, xylan and mannan. These profiles are well matched to the growth optima range for fermentation organisms such as *S. cerevisiae, Z. mobilis, E. coli* or other organisms (Jarboe et al., 2010; Peralta-Yahya and Keasling, 2010) which are widely used for ethanol production from sugar hydrolysates such as might be produced from biomass by a highly cellulolytic secretome, such as those described here from ActE. These optima are also well matched with the conditions found in the rumen, where the efficiency of conversion of animal feed, which is a biomass material, can be improved by addition of enzymes. The ActE secretome retains high specific activity (>80% of maximal) at pH 7, which closely approximates that of the rumen. Sectetomes from fungi such as *T. reesei* are considerably less active at neutral pH, rendering them less effective at neutral pH.

The high cellulolytic capacity of ActE, and its corresponding secretomes, coupled with the temperature and pH optima described above permit assembly of two-part systems to effect the simultaneous deconstruction of biomass and fermentation to fuels.

Example 17

ActE Induction in Medium Containing Various Percentages of Cellulose

Figure 33:
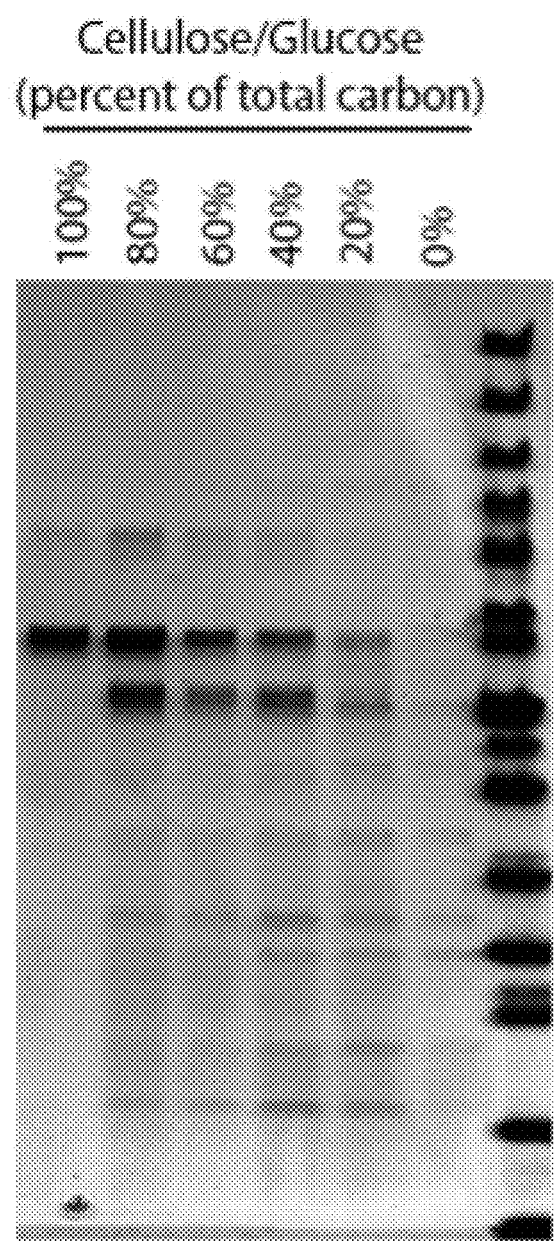
FIG. 33 is a SDS-PAGE graph illustrating ActE induction in medium containing as little as 20% cellulose.

To determine ActE's growth profile on cellulose as a carbon source ActE was grown in M63 media plus 5 g/L carbon. The carbon source ratio was adjusted from 100% cellulose to 100% glucose, total carbon in each culture was equal. Cells were grown for 6 days at 30 degrees. Supernatant was harvested, filtered, and separated by 4-20% SDS-PAGE. Results suggest that ActE is induced in media containing as little as 20% cellulose, with optimal induction in medium containing between 80%-100% cellulose (FIG. 33).

Example 18

Discussion

The work presented here provides the first genome-wide insight into how an aerobic microbe deconstructs polysaccharides. ActE achieves efficient utilization of cellulose by a simple combination of well-understood hydrolytic reactions with newly identified oxidative reactions. The two required exoglucanases are each encoded by a single gene, which also represents the only example of their respective GH families in the genome. The proteins encoded by these genes provide reactions that are complementary to the reactions of other enzymes in the secretome, and provide cellobiose as the major product of reaction. We have discovered that many of the highly abundant enzymes secreted by ActE during growth on cellulose have reduced size relative to their orthologs from closely related organisms. This novel finding suggests natural evolution to improve specific activity has already occurred in ActE in response to growth in the highly specialized insect association. Additional specializations of ActE were identified by demonstrating the secretion of a unique set of proteins in response to biomass. In addition, this work defines how simple new combinations of improved biomass deconstruction enzymes can be assembled according to the propensities of the naturally evolved system.

The present work also indicates that insect-associated microbes such as ActE are important contributors to the vigorous attack on biomass by insects. The 'highly invasive' designation given to *Sirex* has been generally attributed to the combined action of wasp and fungus (Tabata and Abe, 2000; Bergeron et al., 2011). Species convergence is now recognized in the microbial communities associated with insects (Suen et al., 2010; Hulcr et al., 2011). Given the ubiquitous presence of *Streptomycetes* in these communities, the enzymatic properties described here also contribute a potential risk to pine forests, including those used for industrial purposes.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

REFERENCES

1. Baldrian, P. & Valaskova, V. *FEMS Microbiol Rev* 32, 501-521 (2008).
2. Cantarel, B. L. et al. *Nucleic Acids Res* 37, D233-238 (2009).
3. Schuster, A. & Schmoll, M. *Appl Microbiol Biotechnol* 87, 787-799 (2010).
4. Crawford, D. L. *Appl Environ Microb* 35, 1041-1045 (1978).
5. Goodfellow, M. & Williams, S. T. *Annu Rev Microbiol* 37, 189-216 (1983).
6. McCarthy, A. J. & Williams, S. T. *Gene* 115, 189-192 (1992).
7. Schlatter, D. et al. *Microb Ecol* 57, 413-420 (2009).
8. Wachinger, G., Bronnenmeier, K., Staudenbauer, W. L. & Schrempf, H. *Appl Environ Microb* 55, 2653-2657 (1989).
9. Ishaque, M. & Kluepfel, D. *Can J Microbiol* 26, 183-189 (1980).
10. Semedo, L. T. et al. *Int J Syst Evol Microbiol* 54, 1323-1328, (2004).
11. Schlochtermeier, A., Walter, S., Schroder, J., Moorman, M. & Schrempf, H. *Mol Microbiol* 6, 3611-3621 (1992).
12. Walter, S. & Schrempf, H. *Appl Environ Microb* 62, 1065-1069 (1996).
13. Forsberg, Z. et al. *Protein Science* 20, 1479-1483 (2011).
14. Bignell, D. E., Anderson, J. M. & Crosse, R. *Fems Microbiol Ecol* 85, 151-159 (1991).
15. Pasti, M. B. & Belli, M. L. *Fems Microbiol Lett* 26, 107-112 (1985).
16. Pasti, M. B., Pometto, A. L., Nuti, M. P. & Crawford, D. L. *Appl Environ Microb* 56, 2213-2218 (1990).
17. Schafer, A. et al. *J Appl Bacteriol* 80, 471-478 (1996).
18. Adams, A. S. et al. *ISME Journal* 5, 1323-1331 (2011).
19. Bergeron, M. J. et al. *Fungal Biol* 115, 750-758 (2011).
20. Kukor, J. J. & Martin, M. M. *Science* 220, 1161-1163 (1983).
21. Lynd, L. R., Weimer, P. J., van Zyl, W. H. & Pretorius, I. S. *Microbiol Mol Biol Rev* 66, 506-577 (2002).
22. Deboy, R. T. et al. *J Bacteriol* 190, 5455-5463 (2008).
23. Riederer, A. et al. *Appl Environ Microb* 77, 1243-1253 (2011).
24. Marushima, K., Ohnishi, Y. & Horinouchi, S. *J Bacteriol* 191, 5930-5940 (2009).
25. Walter, S. & Schrempf, H. *Mol Gen Genet* 251, 186-195 (1996).
26. Deng, Y. & Fong, S. S. *Appl Environ Microb* 76, 2098-2106 (2010).
27. Li, C. et al. *Bioresour Technol* 102, 6928-6936 (2011).
28. Tolonen, A. C. et al. *Mol Syst Biol* 6, 461 (2011).
29. Hyatt, D. et al. *BMC Bioinformatics* 11, 119 (2010).
30. Rutherford, K. et al. *Bioinformatics* 16, 944-945 (2000).
31. Medema, M. H. et al. *Nucleic Acids Res* 39, W339-346 (2011).
32. Shannon, P. et al. *Genome Res* 13, 2498-2504 (2003).
33. Miller, G. L. *Anal Chem* 31, 426-428 (1959).
34. Merino and Chemy, *Adv. Biochem. Eng. Biotechnol.* 108:95-120, 2007
35. Bayer et al., *Chem. Rec.* 8:364-377, 2008
36. Wilson, *Curr. Opin. Microbiol.* 14:259-263, 2011
37. Vuong and Wilson, *Biotechnol. Bioeng.* 107:195-205, 2010
38. Scharf et al., *PLoS One* 6: e21709, 2011
39. Luyten et al., *App. Environ. Microbiol.* 72:412-417, 2006
40. Hess et al., *Science* 331:463-467, 2011
41. Schlochtermeier et al., *App. Environ. Microbiol.* 58:3240-3248, 1992
42. Wilson, *Crit. Rev. Biotechnol.* 12:45-63; 1992
43. Langston et al., *App. Environ. Microbiol.* 77:7007-7015, 2011
44. Quinlan et al., *PNAS* 108:15079-15084, 2011
45. Vaaje-Kolstad et al., *Science* 330:219-222, 2010
46. Klepzig et al., *Environ. Entomol.* 38: 67-77, 2009
47. Teather R M, Wood P J (1982) *Appl Environ Microbiol* 43:777-780
48. Bradford, *Anal. Biochem.* 72:248-254 (1976)
49. Anne and Van Mellaert. *FEMS Microbiol. Lett.*, 114; 121-8 (1993)
50. Saloheimo and Pakula, *Microbiology*, Epub date 2011 Nov. 5
51. Wood et al., *Biotechnol. Bioeng.* 55:547-55 (1997)
52. Balan et al., *Meth. Mol. Biol.* 581:61-77; 2009

53. Makino et al., *Meth. Microbiol.* 607:127-134, 2010
54. Blommel et al., *Meth. Mol. Biol.* 498:55-73, 2009
55. Galm et al., *J. Nat. Prod.* 74:526-536, 2011;
56. Susi et al. *J. Environ. Manage.* 92:1681-1689, 2011
57. Balan et al., *Meth. Mol. Biol.* 581:61-77, 2009
58. Chundawat et al., *J. Am. Chem. Soc.* 133:11163-11174, 2011
59. Cheng et al., *Biomacromol.* 12:933-941, 2011
60. Wang et al., *Biotechnol. Progress* 25:1086-1093, 2009
61. Tian et al., *Biotechnol. Progress* 27: 419-427, 2011
62. Altschul et al., *J. Mol. Biol.* 215:403-410, 1990
63. Herpoel-Gimbert et al., *Biotechnol. Biofuels* 1:18; 2008
64. Raman et al., *PLoS One* 4:e5271, 2009
65. Chen and Wilson, *J. Bacteriol.* 189:6260-6265, 2007
66. Eastwood et al., *Science* 333:762-765, 2011
67. Langston et al., *App. Environ. Microbiol.* 77:7007-7015, 2011
68. Turini et al., *J. Pharmacol. Exper. Therapeu.* 167:98-104, 1969
69. Trop and Birk, *Biochem. J.* 27:419-427, 1970
70. Natale et al., *Biochim. Biophys. Acta* 1778:1735-1756, 2008
71. Chater et al., *FEMS Microbiol. Rev.* 34:171-198, 2010
72. Cereghino et al., *Curr. Opin. Biotechnol.* 13:329-332, 2002
73. Zhang et al., *Nat. Biotechnol.* 24:100-104, 2006
74. Nijland and Kuipers, *Recent Pat. Biotechnol.* 2:79-87, 2008
75. Jarboe et al., *J. Biomed. Biotechnol.* 761042, 2010
76. Peralta-Yahya and Keasling, *Biotechnol. J.* 5:147-162, 2010
77. Tabata and Abe, *Mycoscience* 41:585-539, 2000
78. Suen et al., *PLoS Gen.* 6: e1001129, 2010
79. Hulcr et al., *Micro. Ecol.* 61:759-768, 2011
80. Kestler et al., *BMC Bioinform.* 9:67, 2008

We claim:

1. A method for digesting a non-wood biomass lignocellulosic material, wherein the method comprises:
   recombinantly expressing in a non-native microbial host cell SActE_0237 (GH6) (SEQ ID NO: 1), SActE_0265 (GH10) (SEQ ID NO: 5) and SActE_0236 GHQ48) (SEQ ID NO: 2),
   isolating SActE_0237 (GH6) (SEQ ID NO: 1), SActE_0265 (GH10) (SEQ ID NO: 5) and SActE_0236 (GH48) (SEQ ID NO: 2) from the host cell, and
   exposing the non-wood biomass lignocellulosic material to a sufficient amount of a composition comprising the isolated SActE_0237, SActE_0265, and SActE_0236, wherein the exposed lignocellulosic material is at least partially digested.

2. The method of claim 1, wherein the microbial host is selected from the group consisting of *Streptomyces lividans*, *Trichoderma reesei*, and *Escherichia coli*.

3. The method of claim 1, wherein the method additionally comprises recombinantly expressing in a microbial host at least one member selected from the group consisting of SActE_0357 (CE4) (SEQ ID NO:7), SActE_0358 (GH11) (SEQ ID NO:8), SActE_1310 (PL3) (SEQ ID NO:9), SActE_3717 (GH9) (SEQ ID NO:10), SActE_4638 (SEQ ID NO:11), SActE_4738 (GH16) (SEQ ID NO:12), SActE_4755 (GH64) (SEQ ID NO:13), SActE_5457 (GH46) (SEQ ID NO:14), SActE_5647 (GH87) (SEQ ID NO:15), and SActE_5978 (PL1) (SEQ ID NO:16) to produce a composition comprising isolated SActE_0237, SActE_0265, SActE_0236, and the at least one member, and exposing the at least 85% non-wood biomass lignocellulosic material to a sufficient amount of the composition comprising isolated SActE_0237, SActE_2065, SActE_0236, and the at least one member.

4. A method for digesting a non-wood biomass lignocellulosic material, wherein the method comprises:
   genetically modifying an ActE strain to overexpress SActE_0237 (GH6) (SEQ ID NO:1). SActE_0265 (GH10) (SEQ ID NO:5), and SActE_0236 (GH48) (SEQ ID NO:2), and
   exposing the non-wood biomass lignocellulosic material to the genetically modified ActE strain,
   wherein the exposed lignocellulosic material is at least partially digested.

5. The method of claim 4, wherein the ActE strain is further genetically modified to overexpress least one member selected from the group consisting of SActE_0357 (CE4) (SEQ ID NO:7), SActE_0358 (GH11) (SEQ ID NO:8), SActE_1310 (PL3) (SEQ ID NO:9), SActE_3717 (GH9) (SEQ ID NO:10), SActE_4638 (SEQ ID NO:11), SActE_4738 (GH16) (SEQ ID NO:12), SActE_4755 (GH64) (SEQ ID NO:13), SActE_5457 (GH46) (SEQ ID NO:14), SActE_5647 (GH87) (SEQ ID NO:15), and SActE_5978 (PL1) (SEQ ID NO:16).

6. A method for enzymatically pretreating agricultural crop materials for consumption by ruminant animals, wherein the method comprises:
   recombinantly expressing in a non-native microbial host cell SActE_0237 (GH6) (SEQ ID NO:1), SActE_0265 (GH10) (SEQ ID NO:5) and SActE_0236 (GH48) (SEQ ID NO:2),
   harvesting said host cells, and
   exposing agricultural crop materials for consumption by ruminant animals to the host cells,
   wherein the agricultural crop materials are at least partially digested.

7. The method of claim 6, wherein the host cell is *Saccharomyces cerevisiae* or *Escherichia coli*.

* * * * *

UNITED STATES PATENT AND TRADEMARK OFFICE
CERTIFICATE OF CORRECTION

Page 1 of 2

PATENT NO. : 10,214,758 B2
APPLICATION NO. : 13/709971
DATED : February 26, 2019
INVENTOR(S) : Brian Grant Fox et al.

It is certified that error appears in the above-identified patent and that said Letters Patent is hereby corrected as shown below:

In the Specification

Under EXAMPLES

Column 22, Lines 63-67, and Column 23, Lines 1-21, "Genome Analysis. The complete genome sequence of *Streptomyces* sp. SirexAA-E (ActE, taxonomy ID 862751) was determined by the Joint Genome Institute, project ID 4086644. Gene annotation models were predicted using Prodigal (Hyatt, et al., 2010), examined using Artemis (Rutherford, et al., 2000), and are available at NCBI with the following accession numbers, GenBank: CP002993.1; RefSeq: NC_015953.1. Carbohydrate-active enzymes were annotated by comparison of all translated open-reading frames to the CAZy database (Cantarel, et al., 2009). We collected CAZy annotated genes from the CAZy database (See CAZy's website for detail information). We then used BLASTP to compare all ActE protein-coding sequences to the CAZy database and to the pfam database (the pfam database can be found in the website of the National Institute of Health (NIH)). These two annotations were then crosschecked, and proteins annotated by both databases were identified as our final CAZy annotation. Secreted proteins were identified by SignalP, TatP, and SecretomeP analyses. BLAST was used to identify sequence orthologs in other organisms. Secondary metabolite gene clusters were identified by AntiSmash analysis (Medema, et al., 2011). CebR boxes were identified by using BLAST comparison of the *S. griseus* CebR box sequence to the ActE genome (Marushima, Ohnishi, et al., 2009). Networks of expression and functional categories were visualized using Cytoscape (Shannon, et al., 2003)" should read --Growth of Organisms. ActE, *S. coelicolor*, *S. griseus* and *T.reesei* RUT-C30 were grown at pH 6.0 and ActE was also grown at pH 6.9 in M63 minimal medium, where 1 L contains: 10.72 g $K_2HPO_4$; 5.24 g $KH_2PO_4$; 2 g $(NH_4)_2SO_4$; 0.5 mL iron sulfate (1 mg/mL in 0.01 M HCl); 1 mL 1 M $MgSO_4$; 1 mL thiamine solution (1 mg/mL) supplemented with glucose, cellulose (either Whatman #1 filter paper or Sigmacell-20, Sigma/Aldrich, St. Louis, MO as indicated), xylan, chitin, switchgrass, AFEX-treated switchgrass (Balan et al., 2009), or ionic liquid-treated switchgrass as the sole carbon source (0.5% w/v). Cultures were incubated for 7 days at 30 °C with shaking. In this medium at pH 6.9, ActE has doubling times of 2.5 h for growth on xylan and switchgrass, 8 h for glucose and 13 h for cellulose as determined by time-dependent increases in total protein present in the culture medium.--

Signed and Sealed this
Twenty-first Day of May, 2019

Andrei Iancu
*Director of the United States Patent and Trademark Office*

Under REFERENCES

Column 54, Line 41, "Chemy" should be --Cherry--

Column 54, Line 43, "Chem" should be --Cehm--